(12) United States Patent
Fiset

(10) Patent No.: US 10,939,812 B2
(45) Date of Patent: *Mar. 9, 2021

(54) CLEANING DEVICE SYSTEM TO CLEAN A SURGICAL SCOPE, WHICH CLEANING DEVICE SYSTEM INCLUDES AN ATTACHMENT ELEMENT TO ATTACH THE CLEANING DEVICE, BEING POSITIONED OUTSIDE THE BODY OF A PATIENT, TO A TROCAR

(71) Applicant: Claude Fiset, Ojai, CA (US)

(72) Inventor: Claude Fiset, Ojai, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/391,682

(22) Filed: Apr. 23, 2019

(65) Prior Publication Data

US 2019/0343703 A1 Nov. 14, 2019

Related U.S. Application Data

(60) Division of application No. 16/164,420, filed on Oct. 18, 2018, now abandoned, and a continuation-in-part of application No. 16/110,035, filed on Aug. 23, 2018, now Pat. No. 10,575,722, which is a continuation of application No. 14/966,622, filed on Dec. 11, 2015, now Pat. No. 10,080,488.

(60) Provisional application No. 62/720,534, filed on Aug. 21, 2018, provisional application No. 62/091,466, filed on Dec. 12, 2014.

(51) Int. Cl.
*A61B 1/12* (2006.01)
*A61B 90/70* (2016.01)
*A61B 17/34* (2006.01)
*A61B 1/00* (2006.01)
*A61B 1/313* (2006.01)

(52) U.S. Cl.
CPC ............ *A61B 1/126* (2013.01); *A61B 1/0014* (2013.01); *A61B 1/121* (2013.01); *A61B 1/127* (2013.01); *A61B 1/313* (2013.01); *A61B 17/3417* (2013.01); *A61B 2090/701* (2016.02)

(58) Field of Classification Search
CPC ............................... A61B 1/126; A61B 1/127
USPC ................................. 600/104, 133, 157, 169
See application file for complete search history.

(56) References Cited

U.S. PATENT DOCUMENTS 3,521,332 A * 7/1970 Kramer ..................... F16B 2/22
                                                    403/188
4,392,485 A   7/1983 Hiltebrandt
(Continued)

*Primary Examiner* — Matthew J Kasztejna

(57) ABSTRACT

A cleaning device system to clean a surgical scope, which cleaning device system includes an attachment element to attach the cleaning device, being positioned outside the body of a patient, to a trocar. The abstract of the disclosure is submitted herewith as required by 37 C.F.R. § 1.72(b). As stated in 37 C.F.R. § 1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

15 Claims, 119 Drawing Sheets

(56) References Cited

U.S. PATENT DOCUMENTS

| | | | |
|---|---|---|---|
| 4,707,906 A * | 11/1987 | Posey | A61G 7/0503 128/DIG. 26 |
| 5,115,542 A * | 5/1992 | Gehres | F16L 3/2235 24/339 |
| 5,382,297 A | 1/1995 | Valentine | |
| 5,910,106 A | 6/1999 | Morgan | |
| 5,993,379 A | 11/1999 | Ouchi | |
| 6,394,285 B1 * | 5/2002 | Arthurs | A47L 15/505 211/41.9 |
| 6,477,744 B1 * | 11/2002 | Miles | B43K 23/002 24/3.1 |
| 6,503,192 B1 | 1/2003 | Ouchi | |
| 7,080,641 B2 | 7/2006 | Gomez | |
| 7,179,223 B2 | 2/2007 | Motoki | |
| 7,198,599 B2 | 4/2007 | Goto | |
| 7,311,660 B2 | 12/2007 | Gomez | |
| 7,803,109 B2 | 9/2010 | Gomez | |
| 7,922,650 B2 | 4/2011 | McWeeney | |
| 7,927,330 B2 | 4/2011 | Platt | |
| 7,955,330 B2 | 6/2011 | Platt | |
| 8,148,667 B2 | 4/2012 | Faries, Jr. | |
| 8,152,717 B2 | 4/2012 | Gomez | |
| 8,185,997 B2 | 5/2012 | Heck | |
| 8,353,815 B2 | 1/2013 | Okada | |
| 8,452,068 B2 | 5/2013 | Averbuch et al. | |
| 8,454,645 B2 | 6/2013 | Criscuolo et al. | |
| 8,467,589 B2 | 6/2013 | Averbuch et al. | |
| 8,517,918 B2 | 8/2013 | Smith | |
| 8,535,220 B2 | 9/2013 | Mondschein | |
| 8,540,745 B2 | 9/2013 | Criscuolo et al. | |
| 8,696,552 B2 | 4/2014 | Whitman | |
| 8,721,529 B2 | 5/2014 | Hess | |
| 8,727,969 B2 | 5/2014 | Leiner | |
| 8,870,752 B2 | 10/2014 | Avitsian et al. | |
| 9,060,676 B2 | 6/2015 | Blackhurst | |
| 9,078,694 B2 | 7/2015 | Hartoumbekis | |
| 10,080,488 B2 * | 9/2018 | Fiset | A61B 1/126 |
| 2002/0022762 A1 | 2/2002 | Beane | |
| 2007/0142702 A1 * | 6/2007 | Haller | A61B 1/313 600/102 |
| 2008/0277853 A1 * | 11/2008 | Menn | A61B 1/0014 269/87 |
| 2010/0168520 A1 | 7/2010 | Poll et al. | |
| 2012/0184897 A1 | 7/2012 | Poll | |
| 2012/0197084 A1 | 8/2012 | Drach et al. | |
| 2013/0060086 A1 | 3/2013 | Talbert et al. | |
| 2016/0135673 A1 | 5/2016 | Miller | |
| 2016/0166135 A1 * | 6/2016 | Fiset | A61B 1/126 600/101 |

* cited by examiner

SECTION A-A
SCALE 4 : 1

SECTION A-A
SCALE 3 : 1

606.1

608

608

608

608

615 →

SECTION A-A
SCALE 3.5 : 1

R0.991±0.381

615

617

620

SECTION A-A
SCALE 6 : 1

621

FLAT PATTERN

619

SECTION A-A
SCALE 12 : 1
ENERGY DIRECTOR DETAIL

SECTION B-B
SCALE 3.5 : 1

612

602

602

SECTION C-C
SCALE 22 : 1

SECTION C-C
SCALE 12 : 1

CLEANING DEVICE SYSTEM TO CLEAN A SURGICAL SCOPE, WHICH CLEANING DEVICE SYSTEM INCLUDES AN ATTACHMENT ELEMENT TO ATTACH THE CLEANING DEVICE, BEING POSITIONED OUTSIDE THE BODY OF A PATIENT, TO A TROCAR

CONTINUING APPLICATION DATA

The present application is a divisional of U.S. patent application Ser. No. 16/164,420, filed Oct. 18, 2018. U.S. patent application Ser. No. 16/164,420 claims benefit of U.S. Provisional Patent Application No. 62/720,534, filed Aug. 21, 2018. The present application also claims benefit of U.S. Provisional Patent Application No. 62/720,534, filed Aug. 21, 2018. The present application is a continuation-in-part of U.S. patent application Ser. No. 16/110,035, filed Aug. 23, 2018. U.S. patent application Ser. No. 16/110,035 is a continuation of U.S. patent application Ser. No. 14/966,622, filed Dec. 11, 2015. U.S. patent application Ser. No. 14/966,622 claims benefit of U.S. Provisional Patent Application No. 62/091,466, filed Dec. 12, 2014.

BRIEF DESCRIPTION OF THE DRAWINGS

The present application is explained in greater detail below with reference to the accompanying drawings.

DESCRIPTION OF EMBODIMENT OR EMBODIMENTS

Figure 1:
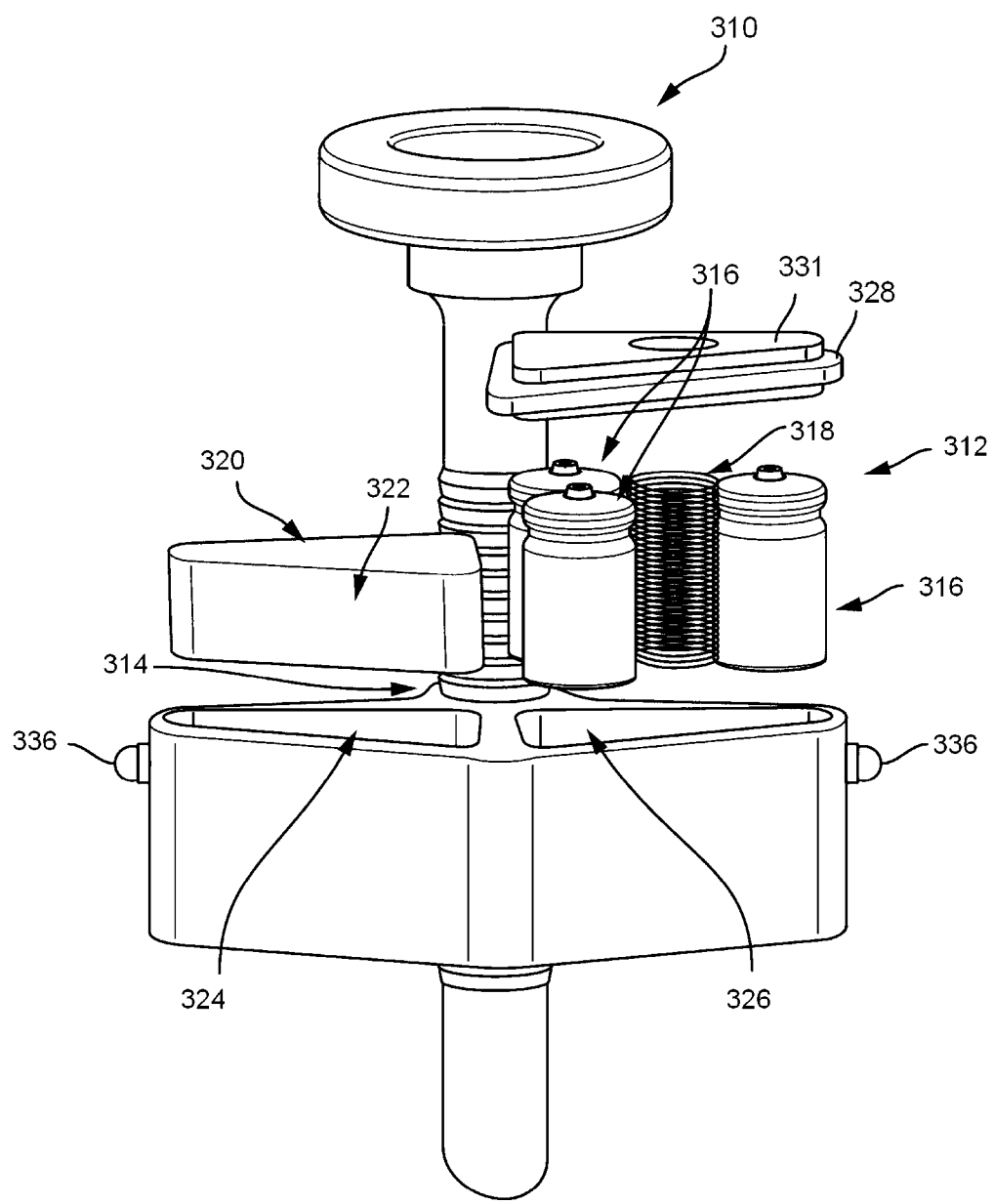
FIG. 1 shows an exploded front view of an exemplification of a cleaning device and a trocar used in at least minimally invasive surgery.

The present application relates to a cleaning device for cleaning a scope, laparoscope, or microscope used in surgery or other medical procedures, and a method of using the device during surgical or other medical procedures. The present application further relates to a cleaning kit for cleaning a trocar and a scope, laparoscope, or microscope, used in surgery or other medical procedures, and a method of using the kit during surgical or other medical procedures.

During minimally invasive surgeries, such as laparoscopic surgery, trocars are used to permit access into a patient's body. Trocars are medical devices or instruments that comprise hollow tubes or hollow portions. During surgery, such as laparoscopic surgery, a trocar may be inserted through an incision into a patient's body, such as into the abdominal or pelvic cavity of a patient. The trocar acts as a passageway for other surgical tools or devices, such as scopes, laparoscopes, microscopes, knives, graspers, scissors, staplers, and more, to enter the body for use during surgery.

During such surgical procedures, the lenses of viewing devices inserted into the body through the trocar, such as scopes, laparoscopes, and/or microscopes, may become clouded or the view therethrough may become partially or completely obscured. The view can be obscured, either partially or completely, if the lenses are smeared with bodily fluids or the like, or if the lenses become clouded or fogged over due to the humidity within the body of the patient. In addition, the interior of the trocars should also be kept clean.

An object of the present application may be to provide a cleaning device for a trocar and surgical scopes, which cleaning device may be utilized during surgery. The cleaning device also may be used to defog lenses or optics of a surgical scope.

When minimally invasive surgeries are performed using trocars, the scopes and/or microscopes used during surgery, which often are inserted into the body of the patient, may become smeared with bodily fluids or the like. This may cause the lens of the scope or microscope to become obscured or clouded because of smearing and/or the humidity or moisture within the body of the patient. Embodiments of the cleaning device and method described herein address these problems. There may be other applications for the scope or microscope which create the same problems as with minimally invasive surgery, and embodiments of the device and method described below may be appropriate to address those problems as well.

An exemplification of the cleaning device according to the present application may be configured for cleaning a surgical scope during minimally invasive surgery. The cleaning device may comprise a casing which houses a sponge and a heating element, and an attachment element connected to an outer surface of the casing and configured to removably attach the casing to the trocar, wherein the casing is configured to allow a lens of the surgical scope to access the sponge and the heating element. In an embodiment, the casing may comprise a first depression formed in an upper surface of the casing and configured to receive the sponge therein, and a second depression formed in an upper surface of the casing and configured to receive the heating element therein. In an embodiment, the sponge may be impregnated with a cleaning medium. In an embodiment, the cleaning device may include a snap member that is configured to removably attach the casing to the trocar.

In an embodiment, the heating element may be comprised of a heating coil and at least one battery operatively connected to the heating coil, wherein the heating coil is configured to warm the lens of the surgical scope when the surgical scope is positioned in proximity to the heating coil. In an embodiment, the cleaning device may further comprise at least one light operatively connected to the at least one battery.

In an embodiment, the heating element may be comprised of a chemical pack.

An embodiment of the cleaning device described herein may comprise a cover and a wiping element, wherein the cover is disposed over the second depression, wherein the cover comprises a first hole, wherein a wiping element comprises a second hole, and wherein the wiping element is disposed over the cover so that the first hole and the second hole are oriented to allow the surgical scope to access the heating element. In an embodiment, the wiping element may be comprised of a microfiber material.

Another embodiment disclosed herein is a cleaning kit for use during minimally invasive surgery, comprising a container housing a sponge and configured to removably attach to the trocar; a cover comprising a scope access hole configured to permit a surgical scope to access the sponge; the cover positioned on an upper surface of the container; and a cannula cleaner comprising an elongated body having a first end having a cleaning tip disposed thereon and a second end, the cannula cleaner configured to be removably supported by at least one of the container and cover when not in use, wherein the cannula cleaner is configured for insertion in a cannula of a trocar and the cleaning tip is configured to contact the cannula when the cannula cleaner is inserted into the cannula. An embodiment of the cleaning kit may include a cannula cleaner wherein the elongated body further comprises a solution container configured to receive a cleaning medium, and a valve disposed on the second end of the elongated body, wherein the valve is configured to dispense the cleaning medium during surgery. In an embodiment, the cleaning kit may comprise at least one wiping element disposed on the cover, wherein the at least one wiping element is configured to allow the surgical scope to access the sponge through the scope access hole. In an embodiment, the cleaning kit may further comprise a snap member configured to attach the container to the trocar.

In an embodiment, the cleaning kit may further comprise a heater disposed in the container, wherein the heater is configured to warm the surgical scope inserted through the scope access hole. In an embodiment, the heater is configured to border a substantial portion of a perimeter of the sponge. In an embodiment, the heater comprises a heating coil and at least one battery operatively connected to the heating coil, and the heating coil is configured to warm the lens of the surgical scope during surgery. In an embodiment, the heater may comprise a chemical pack.

In an embodiment, the cleaning kit may further comprise one or more lights operatively connected to at least one battery.

Another embodiment is directed to a method of cleaning a surgical scope during minimally invasive surgery comprising inserting a trocar into a patient, attaching a cleaning device to the trocar, heating a heating element of the cleaning device to a desired temperature, inserting the surgical scope into the trocar, removing the surgical scope from the trocar, wiping the lens of the surgical scope on the wiping element, and heating the lens of the surgical scope with the heating element. In an embodiment, this method further may comprise wiping the lens on the sponge.

One feature or aspect of an embodiment is using a cleaning device for cleaning laparoscopes used in a medical procedure, the cleaning device comprising a body with a snap device attached to the body, which snap device is configured to attach to a trocar. The body comprises an isosceles triangular shape with a longer side connecting the equal sides of the isosceles triangle with the snap device being attached to the middle of said longer side of the isosceles triangle, and the body comprising two hollowed out portions, one of said hollowed out portions being disposed on each side of said snap arrangement. A first hollowed out portion being configured to house a sponge impregnated with a cleaning solution, which cleaning solution is configured to clean off the tip portion of a laparoscope, where a lens is disposed, which tip portion is configured to be inserted into the trocar and into the body of the patient. A second hollowed out portion being configured to house a heating arrangement, which heating arrangement comprises a chemical heat pack and/or a battery-operated electric heating arrangement and a cover for the heating arrangement being disposed to form a closing side of said second hollowed out portion and being configured to provide an enclosure for the heating arrangement disposed in said second hollowed out portion. The cover comprising at least one of: a heat chamber cover; a microfiber holder; and a microfiber covering layer. The cover further comprises a hole therein being configured to receive a tip of a laparoscope. The procedure comprising: wetting said sponge by impregnating said sponge with cleaning solution, and disposing said impregnated sponge in said first hollowed out portion of said cleaning device; inserting said heating arrangement in said second hollowed out portion of said cleaning device; snapping said cleaning device onto the trocar and orienting said cleaning device toward a surgeon such that the apex of said isosceles triangle is disposed towards the surgeon or in some other direction than the apex being disposed towards said surgeon; heating the heating arrangement to a predetermined temperature; initially inserting a laparoscope into the trocar and into the body of a patient; proceeding with surgery until the lens portion of the laparoscope at its tip becomes smeared with the patient's bodily components or until the lens of the laparoscope is unusable because of condensation on the lens; removing the laparoscope from the trocar and wiping the lens on said impregnated sponge until the bodily components or condensate has been removed; inserting the tip of the laparoscope with its lens through said hole in said heat chamber cover; raising the temperature of the laparoscope tip sufficiently to minimize condensation on the laparoscope lens during a next phase of the surgical procedure; removing the tip of the laparoscope from said heating chamber and inserting the tip of the laparoscope into the trocar; continuing the surgical procedure with a cleaned laparoscope; and repeating the above cleaning operation when required.

Another feature or aspect of an embodiment is a cleaning device for cleaning laparoscopes during a medical procedure for performing laparoscopic surgery, said cleaning device comprising a body with a snap device attached to said body, which snap device is configured to attach to a trocar. The body comprises an isosceles triangular shape with a longer side connecting the equal sides of the isosceles triangle with the snap device being attached to the middle of said longer side of the isosceles triangle and the body comprising two hollowed out portions, one of said hollowed out portions being disposed on each side of said snap arrangement. A first hollowed out portion being configured to house a sponge impregnated with a cleaning solution, which cleaning solution is configured to clean off the tip portion of a laparoscope, where a lens is disposed, which tip portion is configured to be inserted into the trocar and into the body of the patient. A second hollowed out portion being configured to house a heating arrangement, which heating arrangement comprises a chemical heat pack and/or a battery-operated electric heating arrangement and a cover for the heating arrangement being disposed to form a closing side of said second hollowed out portion and being configured to provide an enclosure for the heating arrangement disposed in said second hollowed out portion. The cover comprising at least one of: a heat chamber cover; a microfiber holder; and a microfiber covering layer. The cover further comprises a hole therein being configured to receive a tip of a laparoscope. According to another embodiment, a cleaning device configured for cleaning a surgical tool prior to insertion of the tool into a body of a patient during minimally invasive surgery includes a housing having at least one opening for accessing an interior of the housing; a sponge and a heater assembly positioned in the interior of the housing; and a connector. The connector includes a first arm and a second arm extending from an outer surface of the housing. An inner surface of the first arm and an inner surface of the second arm define at least a first recess sized to receive a sidewall of a first tubular body having a first diameter, and a second recess sized to receive a sidewall of a second tubular body having a second diameter, different than the first diameter. The connector is configured to removably attach the housing to the sidewall of the first tubular body or to the sidewall of the second tubular body, thereby supporting the housing relative to the first tubular body or the second tubular body.

According to another embodiment, a trocar assembly for introducing a surgical scope to a body during a minimally invasive surgery includes: a trocar having a tubular body with a sidewall having a first maximum outer diameter; and a cleaning device configured to removably mount to the sidewall of the tubular body of the trocar. The cleaning device includes: a housing having at least one opening for accessing an interior of the housing; a sponge and a heater assembly positioned in the interior of the housing; and a connector. The connector includes a first arm and a second arm extending from an outer surface of the housing. An inner surface of the first arm and an inner surface of the second arm define at least a first recess sized to receive the sidewall of the tubular body of the trocar and a second recess sized to receive a sidewall of a tubular body of a trocar having a second diameter which is smaller than the first diameter. The connector is configured to removably attach the housing to the trocar to support the housing relative to the trocar.

Examples of the present application will now be described in the following numbered clauses:

Clause 1: A cleaning device configured for cleaning a surgical tool prior to insertion of the tool into a body of a patient during minimally invasive surgery, the cleaning device comprising: a housing comprising at least one opening for accessing an interior of the housing; a sponge and a heater assembly positioned in the interior of the housing; and a connector comprising a first arm and a second arm extending from an outer surface of the housing, wherein an inner surface of the first arm and an inner surface of the second arm define at least a first recess sized to receive a sidewall of a first tubular body having a first diameter, and a second recess sized to receive a sidewall of a second tubular body having a second diameter, different than the first diameter, and wherein the connector is configured to removably attach the housing to the sidewall of the first tubular body or to the sidewall of the second tubular body, thereby supporting the housing relative to the first tubular body or the second tubular body.

Clause 2: The cleaning device of clause 1, wherein the tubular body comprises a tubular portion of a surgical trocar.

Clause 3: The cleaning device of clause 1 or clause 2, wherein the connector supports the housing, such that a central longitudinal axis of a portion of the first tubular body received within the first recess or of the second tubular body received within the second recess of the connector is spaced apart from the interior of the housing.

Clause 4: The cleaning device of any of clauses 1 to 3, wherein the connector supports the housing, such that a line normal to a bottom surface and passing through the opening of the housing is parallel to and a fixed distance from a central longitudinal axis of the portion of the first tubular body received within the first recess or of the second tubular body received within the second recess of the connector.

Clause 5: The cleaning device of any of clauses 1 to 4, wherein the at least one opening is sized such that a lens of the surgical tool can be inserted through the at least one opening to access the sponge and/or the heater assembly.

Clause 6: The cleaning device of any of clauses 1 to 5, wherein the first arm and the second arm of the connector are configured to deflect radially outwardly from the first recess and/or the second recess to receive the first or second tubular body and to move radially inwardly to engage a portion of a sidewall of the first or second tubular body upon insertion of the tubular body into the first recess and/or the second recess.

Clause 7: The cleaning device of any of clauses 1 to 6, wherein the first arm and the second arm comprise a first end mounted to a portion of an outer surface of the housing and a free second end opposite the first end, the free second end comprising a protrusion comprising an inwardly angled outer surface configured to direct the sidewall of the first or second tubular body into the first recess and/or the second recess.

Clause 8: The cleaning device of clause 7, wherein an inwardly facing surface of the protrusion is configured to engage the sidewall of the first tubular body of the first diameter to maintain the first tubular body within the first recess.

Clause 9: The cleaning device of clause 7 or clause 8, wherein the first recess is accessible through a space between the protrusion of the first arm and the protrusion of the second arm, and wherein the second recess is accessible from the first recess through a space between portions of the first arm and the second arm other than the protrusions.

Clause 10: The cleaning device of any of clauses 1 to 9, wherein the first diameter is from about 6.0 mm to about 18.0 mm and the second diameter is from about 1.0 mm to about 6.0 mm.

Clause 11: The cleaning device of any of clauses 1 to 10, wherein an inner surface of the first arm and an inner surface of the second arm each comprise a first curved portion having a first radius sized such that the first curved portion engages a sidewall of the first tubular body, and a second curved portion having a radius sized such that the second curved portion engages a sidewall of the second tubular body.

Clause 12: The cleaning device of any of clauses 1 to 11, wherein the first arm and/or the second arm further define at least one third recess sized to receive and engage a sidewall of a third tubular body having a third diameter, which is less than the first diameter or the second diameter, and wherein the third recess is accessible through a space between the inner surface of the first arm and the inner surface of the second arm which forms a portion of the second recess.

Clause 13: The cleaning device of any of clauses 1 to 12, wherein portions of the first arm and/or the second arm configured to contact a sidewall of the first tubular body and/or the second tubular body comprise textured regions configured to enhance a frictional engagement between the sidewall of the tubular body and the inner surface of the first arm and/or the second arm.

Clause 14: The cleaning device of clause 13, wherein the textured regions comprise a plurality of longitudinally extending ribs extending radially inwardly from inner surfaces of the first arm and/or the second arm.

Clause 15: The cleaning device of any of clauses 1 to 14, further comprising a cloth wiping element adhered to a portion of an outer surface of the housing for wiping fluid from a lens of the surgical tool.

Clause 16: The cleaning device of any of clauses 1 to 15, wherein the housing comprises: a base integrally formed with the connector; a cover comprising an open bottom connected to the base, a partially closed top, and an annular sidewall extending therebetween, wherein the at least one opening of the housing extends through the top of the cover; and a tubular fluid reservoir comprising an open top accessible through the at least one opening of the cover and a closed bottom mounted to the base.

Clause 17: The cleaning device of clause 16, wherein the at least one sponge is held in an interior of the fluid reservoir by a frictional engagement between an inner sidewall of the fluid reservoir and an outer annular surface of the at least one sponge.

Clause 18: The cleaning device of clause 16, wherein the heater assembly comprises a conductive film wrapped around at least a portion of a sidewall of the fluid reservoir; an insulating film wrapped around at least a portion of the conductive film of the conductive film; and a thermostat electrically connected between the conductive film and a power source, configured to disconnect the conductive film from the power source when the thermostat measures a temperature above a target value.

Clause 19: The cleaning device of any of clauses 16 to 18, wherein the base further comprises at least one battery terminal, configured to receive at least one battery for powering the heater assembly, and wherein the battery terminal holds the battery in a position, in which a longitudinal axis of the battery is parallel to a longitudinal axis of a portion of the tubular body received by the connector.

Clause 20: A trocar assembly for introducing a surgical scope to a body during a minimally invasive surgery, the assembly comprising: a trocar comprising a tubular body comprising a sidewall having a first maximum outer diameter; and a cleaning device configured to removably mount to the sidewall of the tubular body of the trocar, the cleaning device comprising: a housing comprising at least one opening for accessing an interior of the housing; a sponge and a heater assembly positioned in the interior of the housing; and a connector comprising a first arm and a second arm extending from an outer surface of the housing, wherein an inner surface of the first arm and an inner surface of the second arm define at least a first recess sized to receive the sidewall of the tubular body of the trocar, and a second recess sized to receive a sidewall of a tubular body of a trocar having a second diameter which is smaller than the first diameter, and wherein the connector is configured to removably attach the housing to the trocar to support the housing relative to the trocar.

For purposes of the description hereinafter, the spatial orientation terms and derivatives thereof shall relate to the exemplification as it is oriented in the drawing figures. However, it is to be understood that the present application may assume various alternative variations, except where expressly specified to the contrary. It is also to be understood that the specific devices illustrated in the attached drawings, and described in the following specification, are simply exemplary exemplifications. Hence, specific dimensions and other physical characteristics related to the exemplifications disclosed herein are not to be considered as limiting.

These and other features and characteristics of the present application, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation an object, the term "proximal" refers to portions of the device nearest to a center or center of mass of the object. The term "distal" refers to a portion of the object farthest away from the center or center of mass of the device. For example, for a scope cleaning device, portions of the device located in the interior of the device housing are "proximal" relative to portions of the device connected to and extending from an outer surface of the device housing. When used in connection with a tool, such as a surgical or medical device, such as a surgical scope or trocar, the term "proximal" refers to the portion of the device configured to be handled by a user. The term "distal" refers to portions of the device opposite the proximal side of the device (e.g., portions of the device farthest away from the portions of the device handled by the user). It is also to be understood, however, that the specific devices and processes illustrated in the attached drawings, and described in the following specification, are simply exemplary exemplifications of the disclosure. Hence, specific dimensions and other physical characteristics related to the exemplifications disclosed herein are not to be considered as limiting.

FIG. 1 shows a trocar 310 used in minimally invasive surgery. The trocar 310 has a cleaning device 312 removably connected thereto. The cleaning device 312, as shown, is snapped onto the trocar 310 using a snap member 314. However, this is not to be construed as limiting the present disclosure as any suitable attachment element, such as a hook-and-loop fabric, buckles, clips, tape, etc., configured to securely and removably attach the cleaning device 312 to the trocar 310 may be utilized.

An exemplification of cleaning device 312 is depicted in FIG. 1 in an exploded view. The cleaning device 312 comprises a casing 315 having the snap member 314 attached to an outside rear surface thereof. A first depression 324 may be formed in an upper surface of the casing 315 of cleaning device 312 to receive a sponge 320. In one example, the sponge 320 may be impregnated with a cleaning medium 322. The casing 315 may further include a second depression 326 formed in an upper surface thereof and disposed opposite the first depression 324. The second depression 326 may be configured to receive a heating element therein. In one example, the heating element can comprise batteries 316 and a heating coil 318 operatively connected to the batteries 316. The heating coil 318 may be configured to warm a microscope, laparoscope, or other surgical scope (not shown) so that the scope is ready for reinsertion in the trocar 310 and ready for reinsertion into the body of the patient being operated upon. Instead of batteries 316 and heating coil 318, a chemical pack housing chemicals that combine in an exothermic reaction, such as is used by skiers in their gloves to keep their hands warm while skiing, may be used as the heating element.

In one exemplary use of the cleaning device 312, the scope being utilized in a surgical procedure is removed from the trocar 310. It is first wiped off on the sponge 320, thereby to remove matter from the patient which has built up during the surgical procedure or which has condensed upon the scope during the surgical procedure. The heating element is then used to heat the front of the scope, thereby heating the front of the scope above the temperature of the patient to discourage the formation of condensate on the front of the scope when the scope is within the body of the patient. One or more lights 336, such as light emitting diode (LED), may be positioned on casing 315 and used to provide illumination for the trocar 310 and the site where the trocar 310 is inserted into a patient. The lights may be operatively connected to batteries 316.

Figure 2:
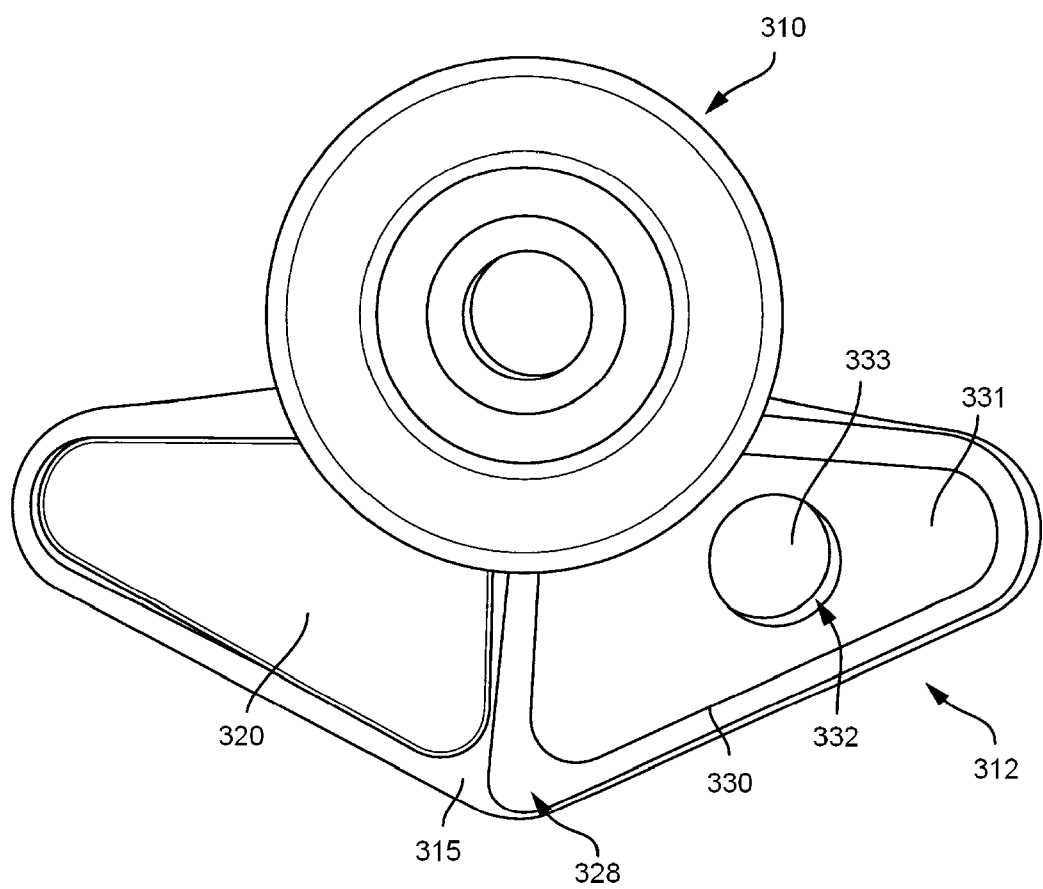
FIG. 2 is a top view of an exemplification of a cleaning device attached to a trocar.

FIG. 2 shows a top view of cleaning device 312 attached to trocar 310. The second depression 326 may further include a heating chamber cover 328 positioned over the top thereof to provide protection for the heating element. The heating chamber cover 328 may further include a microfiber holder 330 formed therein configured to hold a microfiber cover 331. The heating chamber cover 328 and the microfiber cover 331 may be configured with at least one scope access hole 332 which permit the microscope or other scope to be inserted into heating chamber 333 to be warmed by heating coil 318, a heating pack, or some other manner known in the art. Microfiber cover 331 may be used by surgical staff to wipe debris and/or fluids from a scope in order to clean the optics thereof prior to inserting the scope into the scope access hole 332 to be heated. In an exemplification, microfiber cover 331 may be disposed on heating chamber cover 328 within the holder 330 in order to provide easy access to surgical staff.

With further reference to FIG. 2, in one example, casing 315 may have a substantially isosceles triangular shape when viewed from above, with the two sides of the triangle that are not of equal length not adjacent to the trocar 310. Such a configuration may have the benefit of optimizing placement of the heating coil 318 and batteries 316 in casing 315 next to sponge 320. This configuration also may have the benefit of providing easy access to cleaning device 312 while minimizing interference of the device with access to the surgical site while the cleaning device 312 is attached to the trocar 310 during a surgical procedure.

Figure 3:
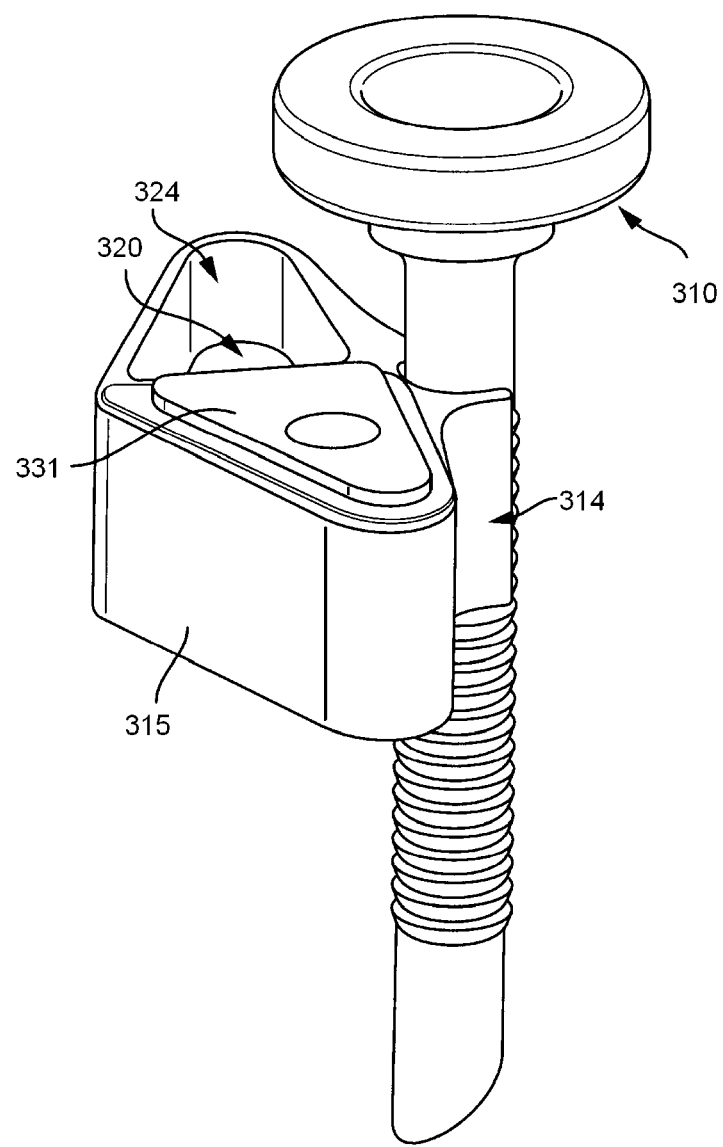
FIG. 3 shows a perspective view of an exemplification of a cleaning device attached to a trocar by a snap member.

In FIG. 3, the trocar 310 is shown again with the cleaning device 312 attached thereto by snap member 314. A possible advantage of such an exemplification is that it places cleaning device 312 in close proximity to trocar 310, and thereby provides easy access to surgical staff. Such an exemplification also has the possible advantage that cleaning device 312 does not need to be set on a separate tray.

Figure 4:
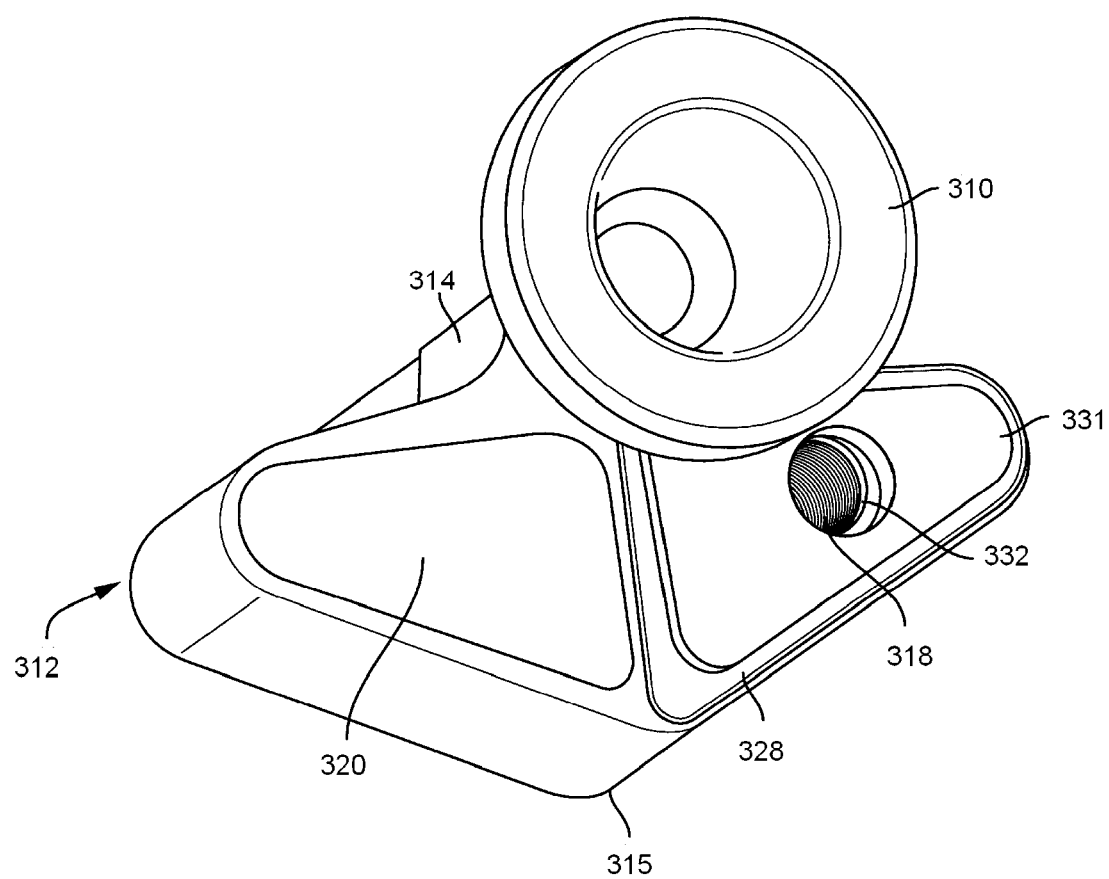
FIG. 4 shows a perspective view of an exemplification of a cleaning device and trocar.

With reference to FIGS. 3 and 4, sponge 320 is shown in its installed position in first depression 324 in casing 315. Sponge 320 may be comprised of any material known in the art. Sponge 320 may be used for cleaning debris and/or fluid from a scope. Sponge 320 also may be impregnated with cleaning medium 322, such as a cleaning and/or defogging fluid. In an exemplification, cleaning medium 322 and/or sponge 320 may be sterile.

FIG. 4 shows the trocar 310 with an exemplification of cleaning device 312 from a different angle than the previous figures. Holes in microfiber cover 331 and heating chamber cover 328 create the scope access hole 332, which allows a scope to access heating chamber 333 in second depression 326, where heating coil 318 may warm and aid in defogging a scope. Debris may be wiped from a scope's optical components by surgical staff on microfiber cover 331 and/or sponge 320, which may be impregnated with cleaning medium 322.

Figure 5:
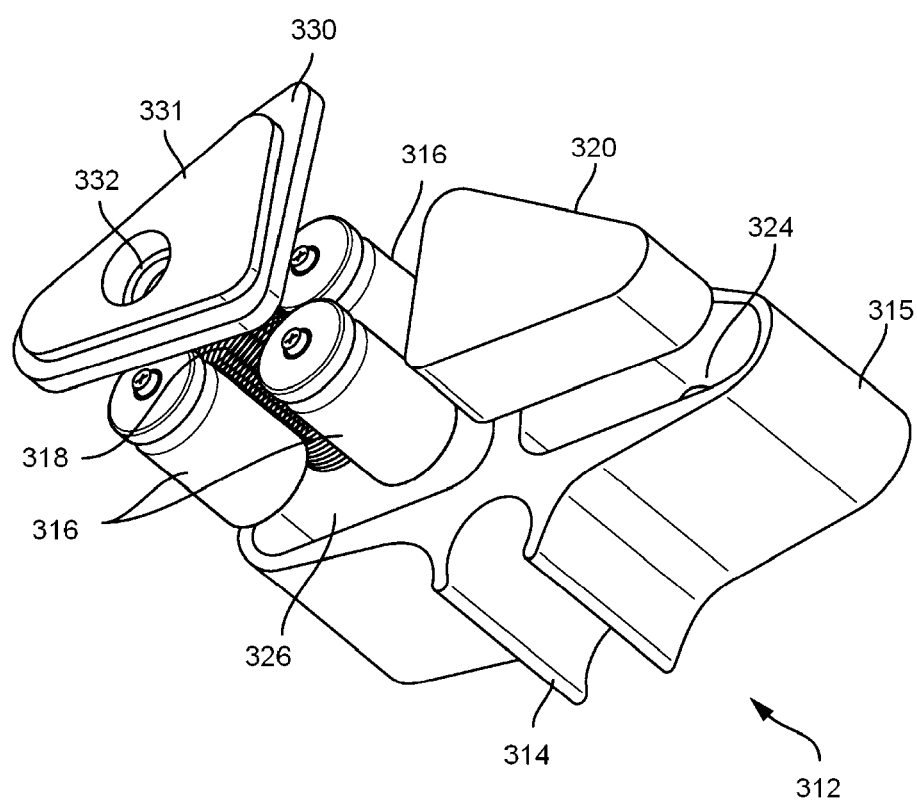
FIG. 5 shows an exploded view of an exemplification of a cleaning device.

FIG. 5 is another exploded view of the cleaning device 312 having the casing 315. The casing 315 comprises an attaching mechanism, such as snap member 314, which is configured to attach to a trocar 310. Snap member 314 is configured to removably attach to trocar 310. Other exemplifications of casing 315 may be configured to attach to trocar 310 with tape, a friction fit, or through another mechanism otherwise known in the art.

The casing 315 also comprises a first depression 324, which is configured to hold a sponge 320. The sponge 320 may be at least partially moistened with cleaning medium 322. The casing 315 also comprises second depression 326 which is configured to hold batteries 316 and heating coil 318 or a defogger, and forms heating chamber 333. Second depression 326 may hold one or more batteries 316, which in an exemplification includes three lithium batteries. In other exemplifications, other types of batteries 316 may be used or adapted for use, and other numbers of batteries may be used. In another exemplification, another heating source other than an electrical or battery-powered heating source could be utilized, such as a chemical heat source or chemical heat pack, which would avoid the use and ultimate disposal of batteries, which can present challenges due to the potential environmental impact of battery waste.

The second depression 326 and heating chamber 333 of the casing 315 may be at least partially covered by heating chamber cover 328. The heating chamber cover 328 may comprise the microfiber holder 330 and scope access hole 332. A scope or microscope may be inserted into the scope access hole 332 and through the heating coil 318 or defogger. The scope or microscope may be wiped on the microfiber cover 331 disposed in the holder 330 before or after insertion into the scope access hole 332.

In at least one possible exemplification, a structure or material, such as double-sided adhesive tape, could be connected or attached to the casing 315, such as the side or underside, to allow the casing 315 to be connected or attached to a support structure.

Figure 6:
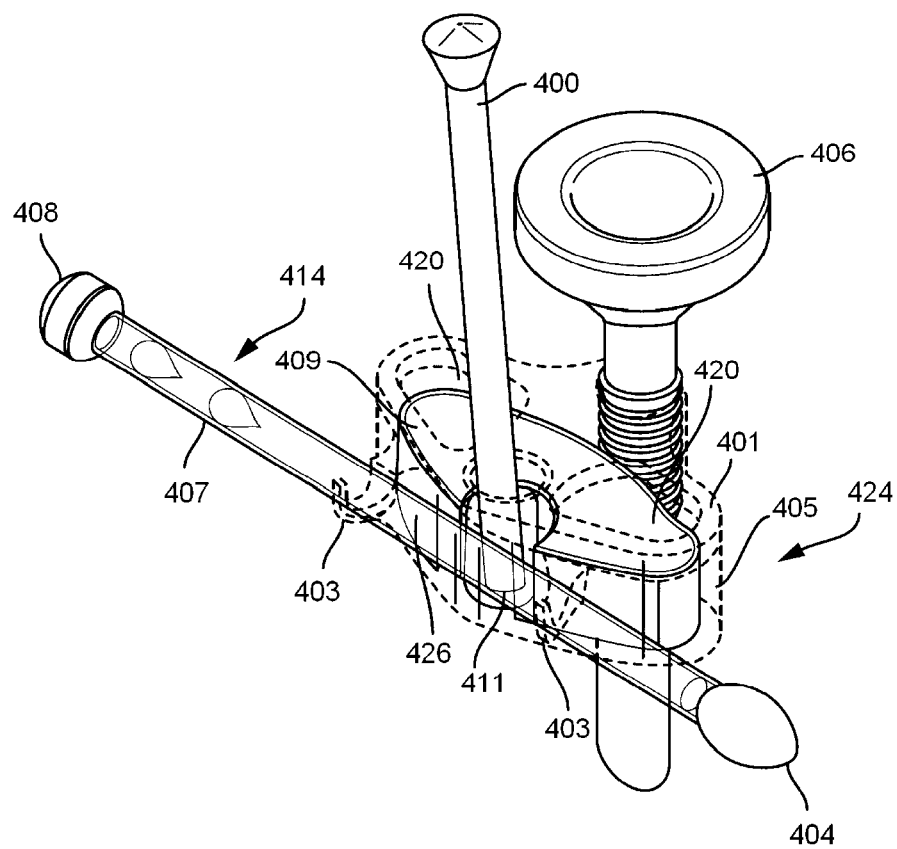
FIG. 6 shows a partially transparent perspective view of an exemplification of a cleaning kit attached to a trocar or cannula.

FIG. 6 shows a partially transparent view of an exemplification of a cleaning kit 424 attached to a trocar 406. The kit 424 includes a container 105 that may house a sponge 410, which may be impregnated with a cleaning solution, and a heater 409. A cover 401 is located on top of the container 405. The cover 401 has an opening therein into which can be inserted a surgical viewing device 400, such as a scope, laparoscope, or microscope, such that the scope lens 411 is inside the container 405. In an exemplification, cover 401 may include one or more recesses 420, at least one of which contains a microfiber wipe or cleaner 402. Also shown is a cannula cleaner 414, which is held by two cannula cleaner tube holders 403. Holders 403 may removably secure the cannula cleaner 414 to the container 405 when it is not in use during a surgical procedure. Cannula cleaner 414 may be secured by a friction fit, or in some other manner otherwise known in the art. In addition, the cover 401 may have one or more projections 426 that project out above the cannula cleaner 414 to further secure the cannula cleaner 414 in place in a secured position on container 405.

An exemplification of cannula cleaner 414 may include an elongated body with a cleaning tip 404 disposed at one end. In an exemplification, the body of the cannula cleaner 414 may comprise a tube that also functions as a solution container 407. On the end opposite the cleaning tip 404 is located a solution dispensing valve 408. Either the valve 408 or the solution container 407 may be squeezed, pinched, or pressed in to cause an amount of a cleaning or defogging solution, or some other liquid known in the art, to be dispensed. The solution may be dispensed into the container 405. By containing the solution in the cannula cleaner 414, a supply of cleaning solution is readily available to be dispensed into the container 405, and is in easy reach for a user of the trocar 406 and cleaning kit 424, such as by a surgeon or other medical professional. By mounting the cannula cleaner 414 on the container 405, the cannula cleaner 414 is easy to reach for use in cleaning or clearing out the trocar 406. The design of the cannula cleaner 414, therefore, combines a cleaning device with a cleaning solution supply, so as to facilitate keeping the trocar 406 and viewing instruments clean during a surgical procedure. However, it should be understood that other exemplifications of cannula cleaner 414 may exist, such as an exemplification that does not hold solution and lacks a solution dispensing valve 408. Another exemplification may include cleaning tips 404 at both ends of the cleaning device 414. In such an exemplification, the cleaning tips 404 may be of the same size or of different sizes. Cannula cleaning tip 404 may be comprised of a sponge, foam, microfiber, or some material otherwise known in the art.

Figure 7:
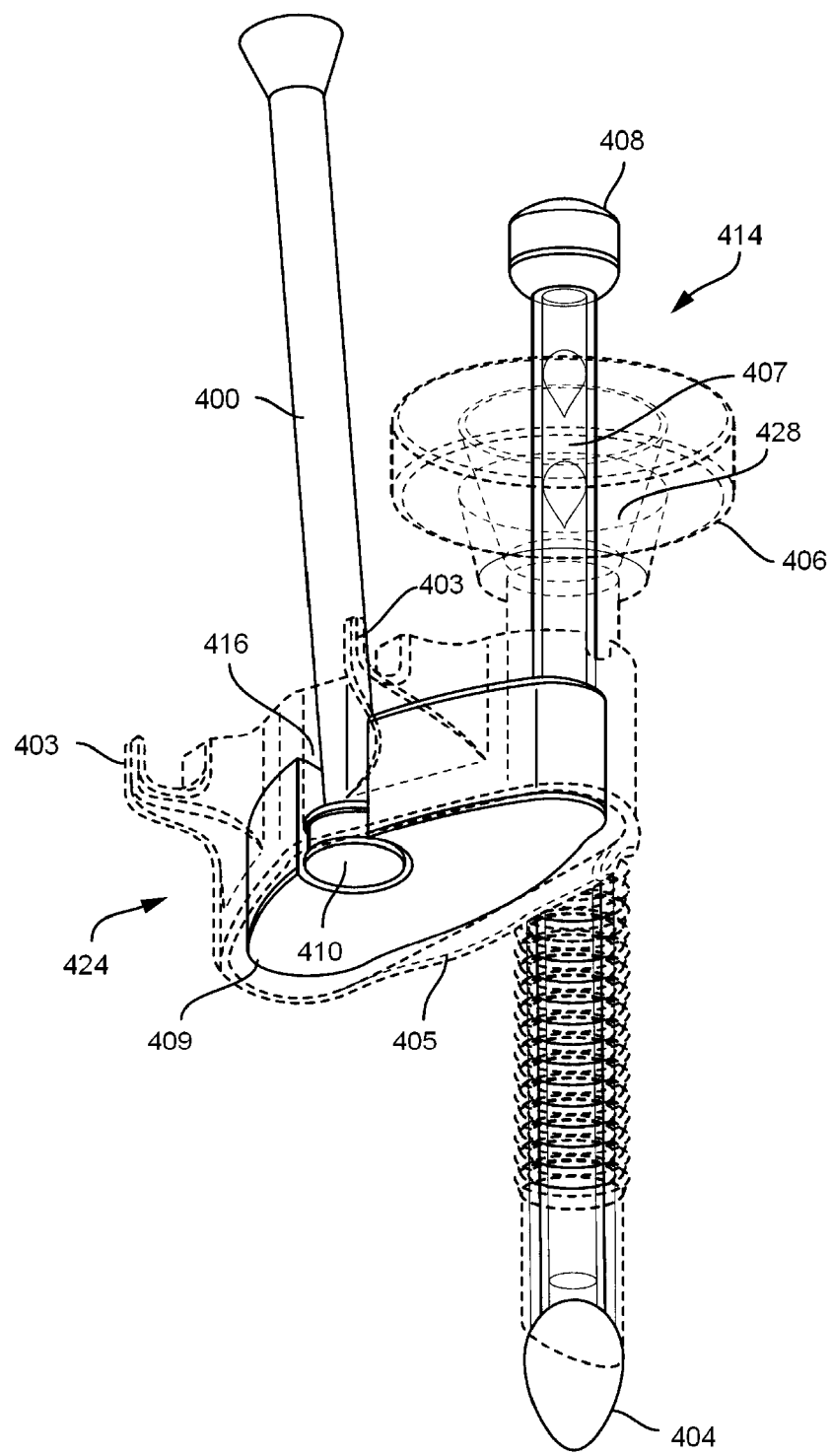
FIG. 7 shows another view of an exemplification of the cleaning kit shown in FIG. 6.

FIG. 7 shows another view of the cleaning kit 424 shown in FIG. 6. In FIG. 7, container 405 is shown as transparent in order to demonstrate how scope 400 may be inserted through scope access hole 416, so that the optics thereof may contact sponge 410. However, it should be understood that not all exemplifications of container 405 need be transparent. FIG. 7 also depicts how scope 400 may interact with an exemplification of heater 409. In an exemplification, heater 409 may be configured to surround or partially surround scope 400, and may substantially border the perimeter or part of the perimeter of sponge 410. Heater 409 and sponge 410 may be configured to create a substantially cylindrical space, where the lens 411 of a scope 400 may be inserted for cleaning and/or defogging, which may be possible to engage exemplifications of scopes 400 that are substantially cylindrically-shaped. In an exemplification, sponge 410 may be configured to maximize efficient contact with lens 411 of scope 400. In an exemplification, sponge 410 may be substantially circular in shape. Exemplifications of heater 409 may comprise other shapes. Exemplifications of heater 409 may use electrical or chemical processes to generate heat, or may do so using another manner known in the art.

With further reference to FIG. 7, cannula cleaner 414 may be inserted into a cannula 428 of trocar 406 to clean the cannula 428 of fluids, condensates, and/or debris. In an exemplification, cannula cleaning tip 404 may be inserted into cannula 428. In an exemplification, cannula cleaning tip 404 may have a diameter that is substantially the same or larger than the diameter of the cannula 428. Cannula cleaning tip 404 may be comprised of a deformable material, and deform to fit into cannula 428 while contacting the walls of the cannula 428. Cannula cleaning tip 404 may be sufficiently absorptive to absorb fluids and/or condensate present in trocar 406. Trocar 406 is shown as transparent in order to better illustrate the insertion of cannula cleaner 414 therein; however, it should be understood that exemplifications of trocar 406 need not be transparent.

Figure 8:
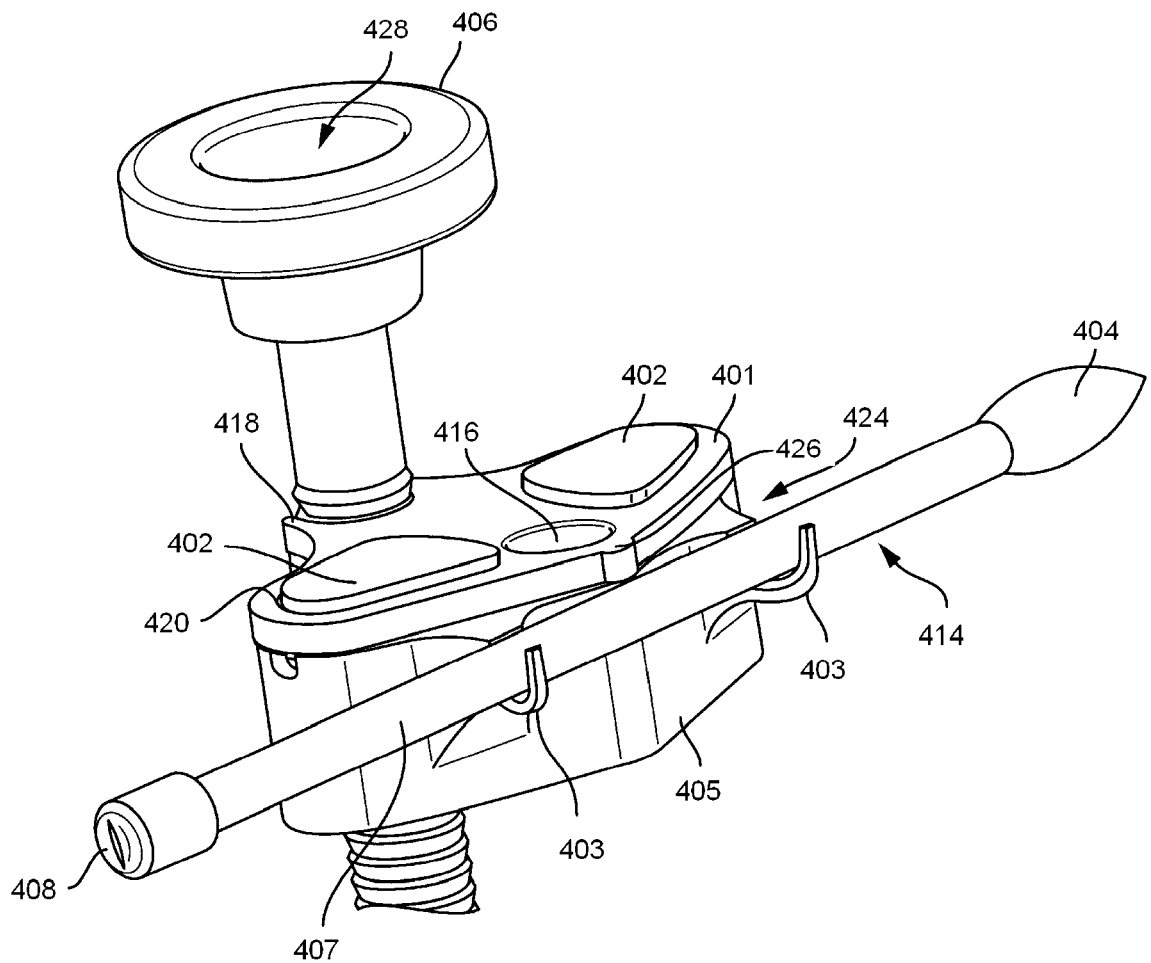
FIG. 8 shows another view of an exemplification of the cleaning kit shown in FIG. 6.

FIG. 8 shows a perspective view of the cleaning kit 424 depicted in FIG. 6. Cannula cleaner 414 is shown disposed on cannula holders 403, which are configured to contain cannula cleaning device 414 against container 405 during a surgical procedure when cannula cleaner 414 is not in use. In an exemplification, cover 401 of cleaning kit 424 may include projection 426 that is configured to further constrain cannula cleaner 414 when not in use. Cover 401 may include one or more microfiber wipes 402 disposed thereon to further aid in cleaning debris or condensate from a scope 400. While the exemplification shown in FIG. 8 shows a configuration wherein two microfiber wipes 402 are positioned on cover 401 roughly on either side of scope access hole 416, it should be understood that other configurations or numbers of wipes 402 may be used. It also should be understood that exemplifications of cover 401 need not include microfiber wipes 402, and that other materials or wiping elements otherwise known in the art may be used to wipe debris from the lens 411 of a scope 400. Wipes 402 may be disposed in one or more recesses 420 in cover 401. Cleaning kit 424 may removably attach to trocar 406 by a snap member 418, or another manner known in the art.

Figure 9:
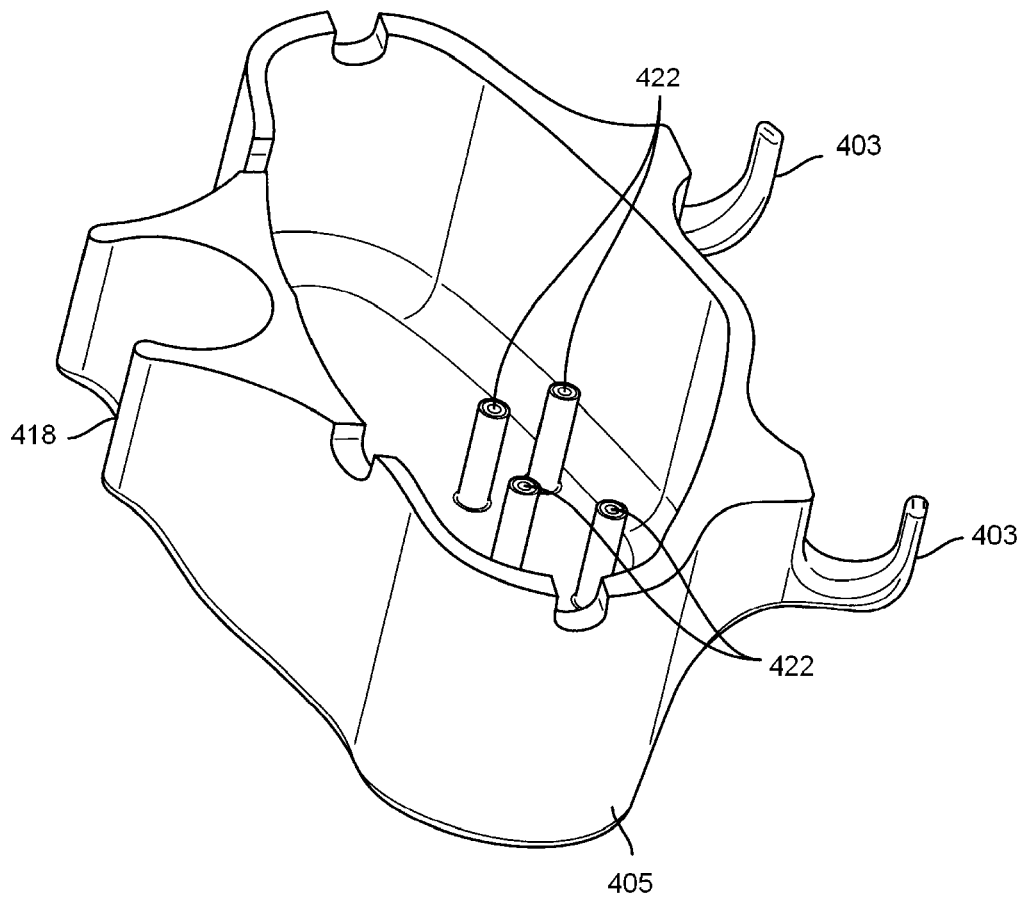
FIG. 9 shows a view of a container of an exemplification of the cleaning kit shown in FIG. 6.

FIG. 9 shows a perspective view of a portion of the container 405 of the cleaning kit 424 shown in FIG. 6. An exemplification of container 405 may be integrally molded with snap member 418 and/or one or more cannula cleaning device holder 403. The interior of container 405 may comprise a single chamber, or multiple chambers. The at least one chamber may include one or more support posts 422. Support posts 422 may provide support for cover 401, and may provide support for configurations of heater 409. In exemplifications of heater 409, posts 422 may support configurations of batteries, a heating coil, chemical packs, or other components of a heater 409 otherwise known in the art.

Figure 10:
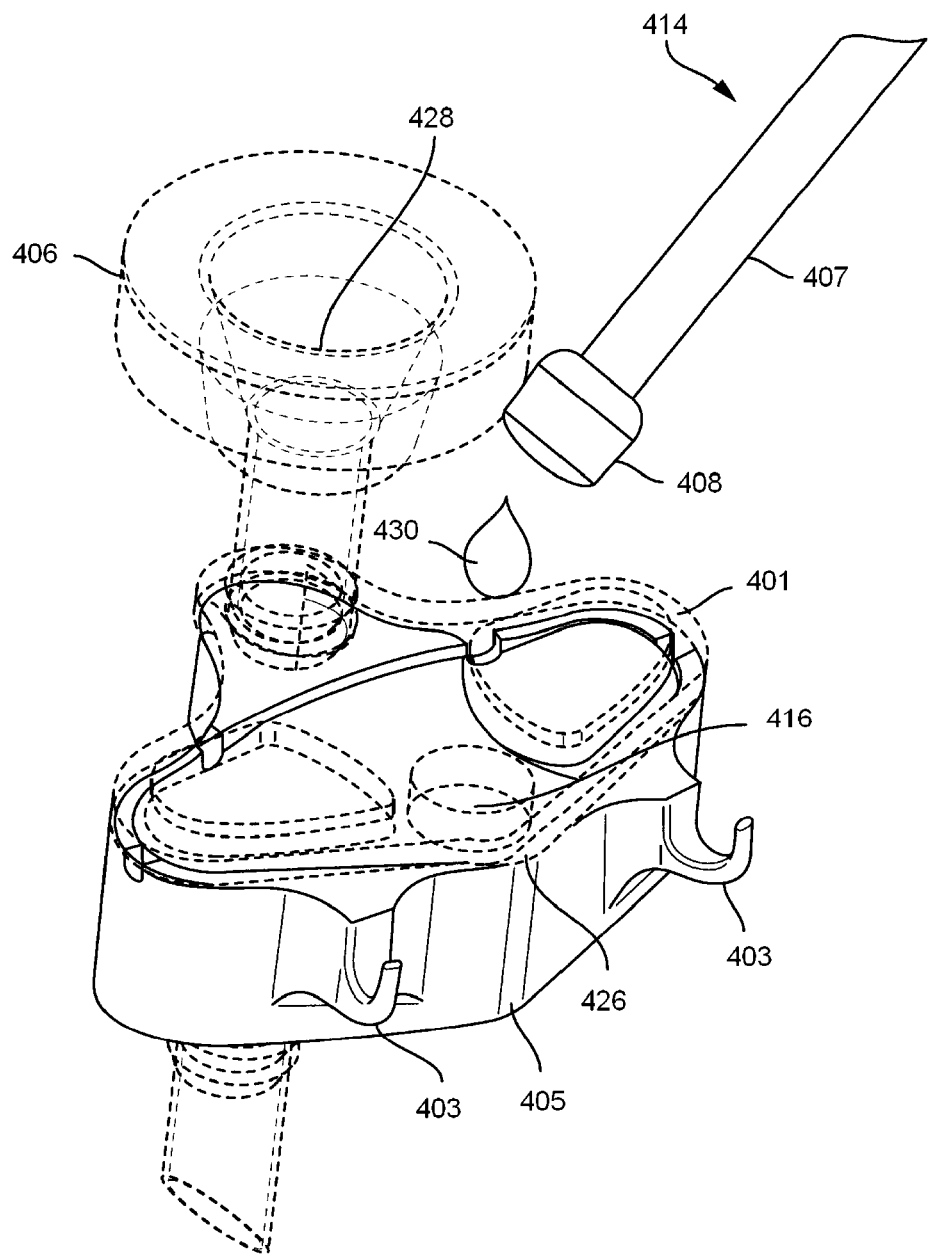
FIG. 10 shows another view of the exemplification of the cleaning kit shown in FIG. 6, with a cannula cleaner being used to dispense a cleaning medium.

FIG. 10 shows another view of the cleaning kit 424. In an exemplification, cannula cleaner 414 may be used to dispense cleaning and/or defogging solution into container 405 through scope access hole 416. In an exemplification, solution may exit solution container 407 of cannula cleaner 414 through solution dispensing valve 408. When solution—represented by a droplet of cleaning solution 430—enters through scope access hole 416, it may contact and be absorbed by sponge 410. A scope may then be inserted into container 405 through scope access hole 416 and contact impregnated sponge 410, which may aid in cleaning and/or defogging the scope 400.

Figure 11:
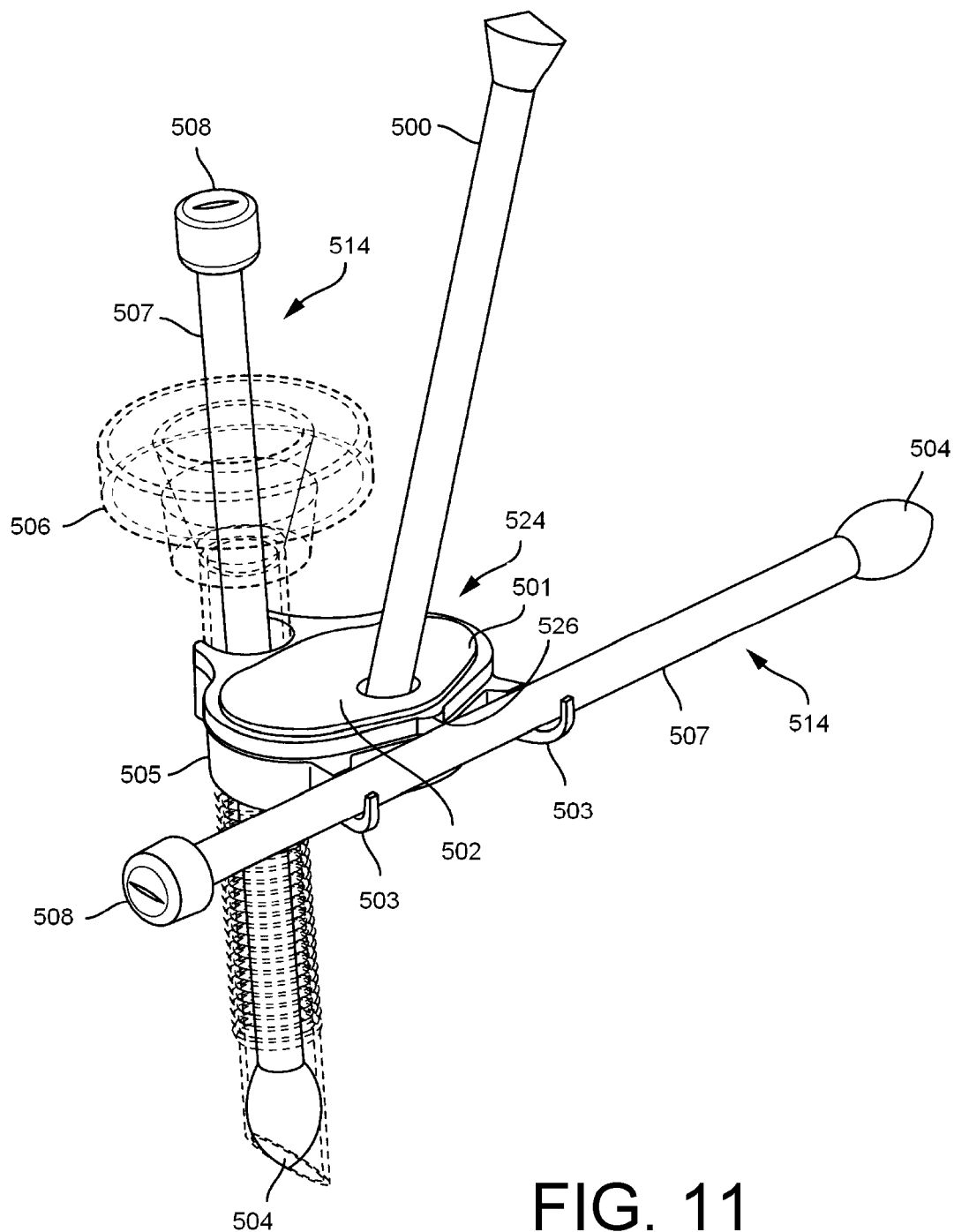
FIG. 11 shows an exemplification of a cleaning kit.
Figure 12:
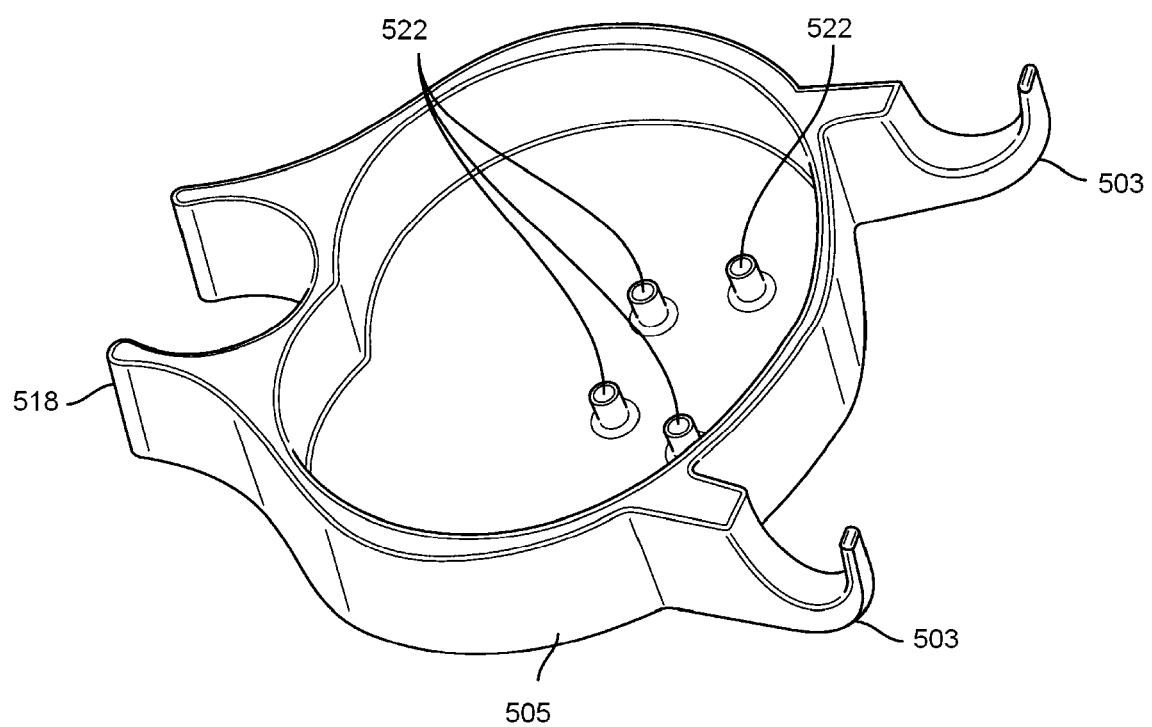
FIG. 12 shows a view of a container of an exemplification of the cleaning kit shown in FIG. 11.

With reference to FIGS. 11 and 12, an alternative exemplification of a cleaning kit 524 is illustrated. Cleaning kit 524 is configured to clean lens 511 of a scope 500 and may include a container 505 that is shorter or thinner than the exemplification of the container 405 shown in FIG. 6. In the example in FIG. 11, no batteries are utilized, so a shorter or thinner container 505 can be utilized. In an exemplification, the kit may use no heating device or heating medium. In another exemplification, a chemical heating medium or chemical heating pack may be used which takes up less space than batteries. Cover 501 also may include a microfiber wipe or cleaner 502 that spans most or all of the surface area of cover 501. FIG. 11 depicts two cannula cleaners 514 in order to demonstrate both insertion into trocar 506, and placement in cleaner tube holders 503. However, it should be understood that not all exemplifications of cleaning kit 524 require more than one cannula cleaner 514. Each of the cannula cleaners may include a cannula cleaning tip 504 at a first end thereof, a solution container 507 extending between the first end and second end thereof, and a solution dispensing valve 508 positioned at the second end.

FIG. 12 shows a view of container 505 of the exemplification of the cleaning kit 524 shown in FIG. 11. In an exemplification, snap member 518 and one or more cannula cleaner holders 503 may be integrally molded with container 505. The container 505 may comprise a chamber, and may include one or more internal supports 522. In one example, internal supports 522 may be used to support cover 501, or constrain a heater and/or sponge.

With reference to FIGS. 13-19, another exemplification of cleaning device 710 configured for cleaning a surgical tool, such as a surgical scope, prior to insertion of the tool into a body of a patient during minimally invasive surgery, is illustrated. As described herein, the cleaning device 710 includes a connector 712, such as a snap fit connector, which is configured to removably mount the cleaning device 710 to tubular or cylindrical objects having different maximum outer diameters without needing to adjust or reposition the connector 712 to accept and engage the different sized structures. As used herein, the cleaning device 710 is described as being connected to trocars used in surgical procedures. However, it is understood that the connector 712 can also be used for mounting the cleaning device 710 to other tubular bodies and structures including, for example, rods, posts, railings, pieces of furniture, as well as other medical devices and tools located at a surgical scene.

Figure 18:
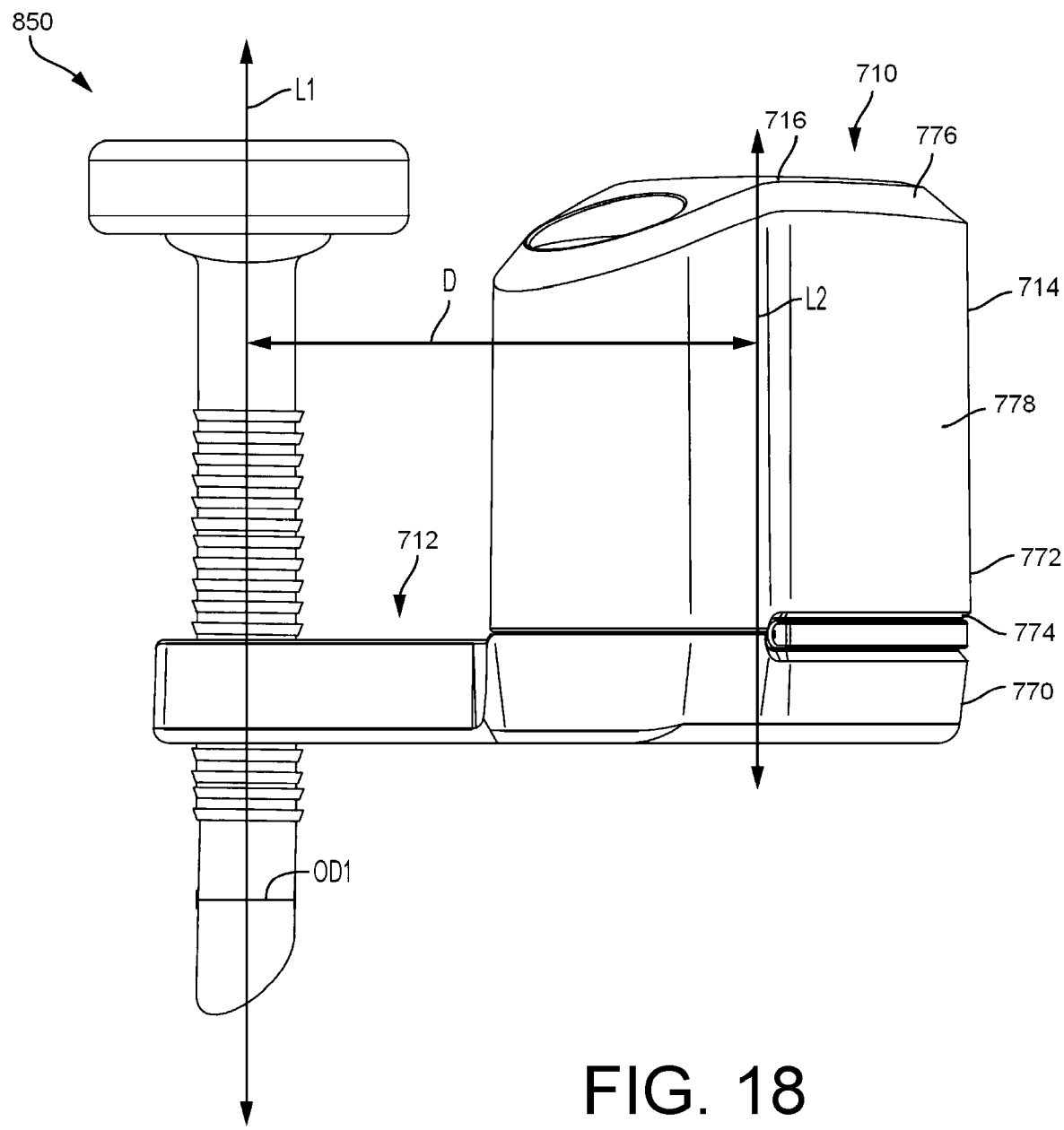
FIG. 18 is a side view of the scope cleaning device of FIG. 13 connected to a trocar having a first diameter.
Figure 19:
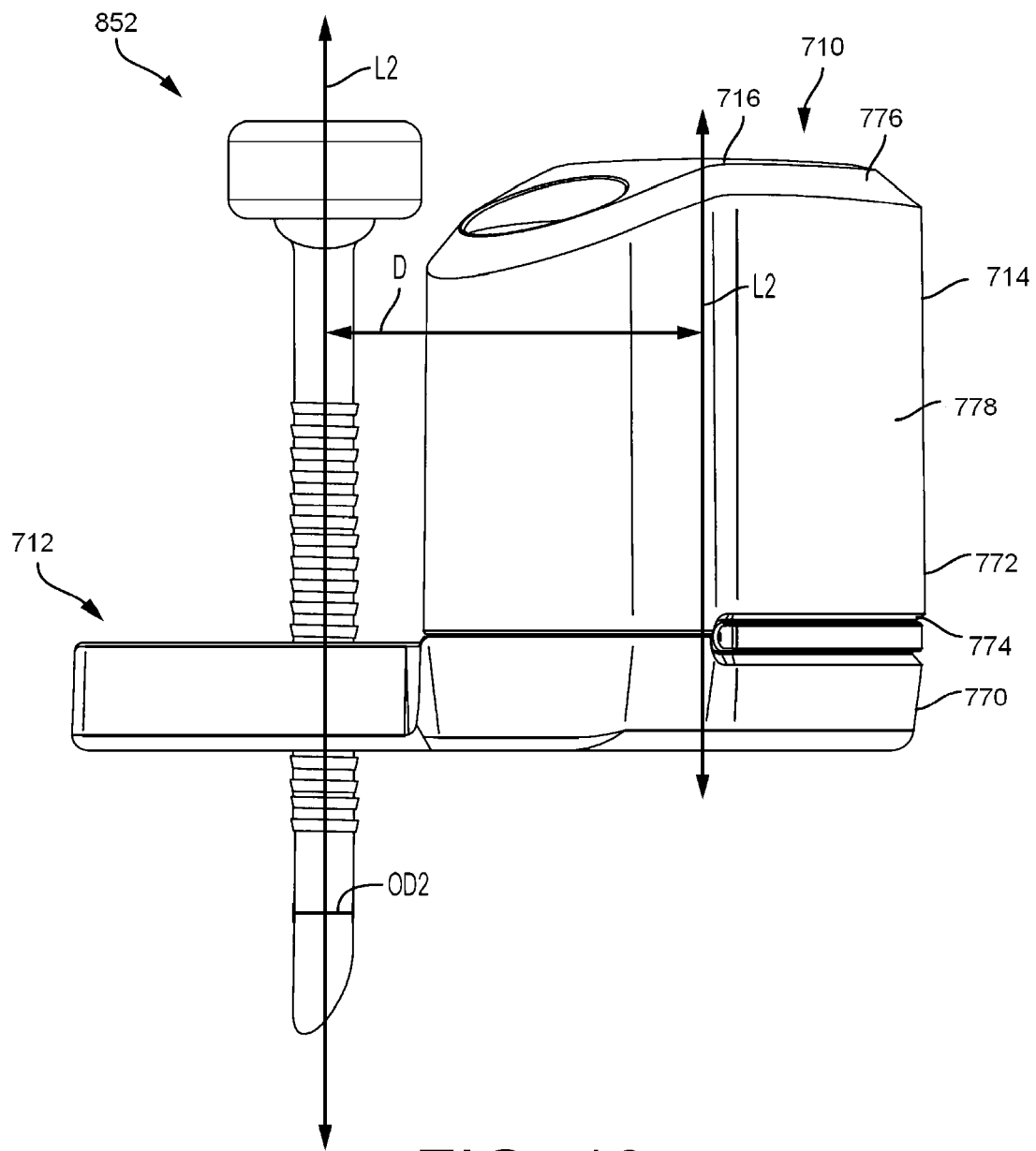
FIG. 19 is a side view of the scope cleaning device of FIG. 13 connected to a trocar having a second diameter.

In some examples, the connector 712 can be configured to removably attach the cleaning device 710 to two different standard sized surgical trocars 850, 852 (shown in FIGS. 18 and 19). For example, the connector 712 can be configured to receive a large diameter trocar 850 (shown in FIG. 18), such as a trocar having a maximum outer diameter OD1 of from 6.0 mm to 18.0 mm, in one possible exemplification having a maximum outer diameter of about 8.0 mm. The connector 712 can also be configured to receive a smaller diameter trocar 852 (shown in FIG. 19), such as trocar having an outer maximum diameter OD2 of from 1.0 mm to 6.0 mm, in one possible exemplification about 4.0 mm. The connector 712 is configured to connect to one trocar at a time (either the single small (e.g., 4.0 mm) diameter trocar or the single large diameter (e.g., 8.0 mm) trocar). While the connector 712 may connect to other similar sized trocars (e.g., trocars having a maximum outer diameter within 5% or 10% of the designated size), the connector 712 is not designed to connect to a wide range of different trocar sizes. For example, the connector 712 is not designed to be adjusted or reconfigured for use with a range of trocar diameters. Desirably, portions of the connector 712 are naturally biased or sized to frictionally engage the trocar to hold the connector 712 and cleaning device 710 in place relative to the trocars 850, 852. Therefore, as described herein, the user does not need to, for example, tighten the connector 712 to secure the connector 712 to the trocar, cinch down a portion of the connector against the trocar, or perform some other action for adjusting the connector 712 to receive different sized trocars. Instead, the user need only insert the tubular portion of the trocar of either size (e.g., either 4.0 mm trocar or the 8.0 mm trocar) into the connector 712 to removably attach the cleaning device 712 to the trocar.

In some examples, the cleaning device 710 includes a protective outer structure such as a housing 714, casing, or other enclosure having at least one opening 716 for accessing an interior 718 of the housing 714. The housing 714 can be formed from any suitable rigid and substantially fluid tight material, such as plastic, rubber, ceramics, glass, or metal. Desirably, the housing 714 is lightweight and can be supported by a surgical tool, such as the trocar, without damaging the housing 714 or cleaning device 710. Accordingly, such housings are often formed from rigid lightweight plastics (e.g., polyesters, copolyesters, polyethylene terephthalate (PET), polystyrene, high-density polyethylene, polycarbonate, or similar materials).

As in previous exemplifications, the cleaning device 710 also includes a sponge 720 (shown in FIG. 15) immersed in a defogging solution and a heater assembly 722 (shown in FIG. 15) in an interior 718 of the housing 714. For example, the sponge 720 can be a circular or cylindrical sponge having an outer diameter OD3 (shown in FIG. 15) of from about 15 mm to about 25 mm. The housing 714 and housing interior 718 are generally sized to receive a lens of a surgical tool, such as a laparoscope, endoscope, or cytoscope. Accordingly, dimensions of the housing 714 and interior 718 are selected so that the lens of the scope can be easily inserted into the interior 718 through the opening 716 to contact the sponge 720 and/or to be brought into proximity to the heater assembly 722. For example, the housing 714 can be from about 40 mm to 60 mm in height H1 and about 50 mm to about 70 mm in width W1.

The cleaning device 710 further includes the connector 712, which is configured to removably attach the housing 714 to the trocar, thereby supporting the housing 714 relative to the trocar. For example, the connector 712 can be configured to support the housing 714, such that a central longitudinal axis L1 (shown in FIGS. 18 and 19) of a portion of the trocar 850, 852 received by the connector 712 is spaced apart from the interior 718 of the housing 714. Similarly, the connector 712 can be configured to support the housing 714, such that a line L2 (shown in FIGS. 18 and 19) normal to a bottom surface and passing through the opening 716 of the housing 714 is parallel to and a fixed distance D1 (shown in FIGS. 18 and 19) from the central longitudinal axis L1 of the trocar 850, 852.

With specific reference to FIGS. 13-17, features of an exemplary connector 712 configured to receive the different sized trocars will now be discussed in detail. The connector 712 can include a first arm 724 and a second arm 726 extending from an outer surface 728 of the housing. The arms 724, 726 can be integrally formed with other portions of the housing 714. For example, the housing 714 and arms 724, 726 can be formed together by a suitable plastic molding process, such as injection molding. In other examples, the arms 724, 726 can be formed separately from other portions of the housing 714 and mounted to the outer surface 728 of the housing 714 by a suitable adhesive, fastener, or combination thereof. As described herein, the arms 724, 726 are sized to receive the different sized trocars and to hold the cleaning device 710 in a fixed position relative to the trocar. In order to receive the trocar, an inner surface 730 of the first arm 724 and an inner surface 732 of the second arm 726 may define at least a first recess 734, shown by circle C1 in FIGS. 16-17, sized to receive a trocar having a first diameter. The arms 724, 726 may also define at least one second recess 736, shown by circle C2 in FIGS. 16 and 17, sized to receive a trocar having a smaller diameter.

In order to permit mounting the cleaning device 710 to the trocar, the first arm 724 and the second arm 726 of the connector 712 can be configured to deflect radially outwardly, in a direction of arrow A1 (shown in FIGS. 16 and 17) from the first recess 734 and/or the second recess 336 to receive the trocar. The arms 724, 726 are also configured to move radially inwardly, in a direction of arrow A2 (shown in FIGS. 16 and 17) to engage the trocar.

In some examples, the first arm 724 and the second arm 726 include a first end 738, 740 mounted to a portion of the outer surface 728 of the housing 714 and a free second end opposite the first end 738, 740. In order to secure the trocar within the recess 734, 736, the arms 724, 726 can include a protrusion 742, 744 positioned at the free end of each arm 724, 726. The protrusions 742, 744 can include an inwardly angled outer surface 746 configured to direct the trocar into the first recess 734 and/or into the second recess 736. The protrusions 742, 744 can also include an inner surface 748 configured to engage the trocar to retain the trocar within the first recess 734. For example, the inner surface 748 can have a curvature which matches the curvature of the trocar.

The trocar enters the first recess 734 through a space 750 between the opposing protrusion 742 of the first arm 724 and the protrusion 744 of the second arm 726. For example, the user may press the trocar in a direction of arrow A3 through the space 750 and into the first recess 734. If the trocar is small enough (e.g., has a maximum outer diameter of less than about 6.0 mm) to pass from the first recess 734 into the second recess 736, the user can advance the trocar in a direction of arrow A4 into the second recess 736 through a second space 752 between portions of the first arm 724 and the second arm 726.

In some examples, the recesses 734, 736 are formed by curved portions or regions of the first arm 724 and the second arm 726. For example, the inner surface 730 of the first arm 724 and the inner surface 732 of the second arm 726 may each include a first curved portion 754 having a first radius R1 sized such that the first curved portion 754 engages a trocar of the first diameter OD1 (shown in FIG. 18). The arms 724, 726 can also include a second curved portion 756 having a radius R2, sized such that the second curved portion 756 engages a trocar with the second diameter OD2 (shown in FIG. 19).

In some examples, portions of the first arm 724 and/or the second arm 726 configured to contact the trocar can include textured or high friction surfaces 758 configured to enhance the frictional engagement between the trocar and the inner surface 730, 732 of the first arm 724 and/or the second arm 726. For example, the textured surface 758 can include a plurality of longitudinally extending ribs 760 extending radially inwardly from inner surfaces 730, 732 of the first arm 724 and/or the second arm 726.

In some examples, the connector 712 can also include a third recess 762 (shown by the circle C3 in FIGS. 16 and 17) for connecting the device 710 to a trocar of a third diameter, which is smaller than the first diameter or the second diameter. For example, the third recess 762 can be sized to receive a trocar with a maximum outer diameter of about 2.0 mm or less. The third recess 762 can be accessible through a space 764 between the portions of the arms 724, 726 that form the second recess 736.

Figure 13:
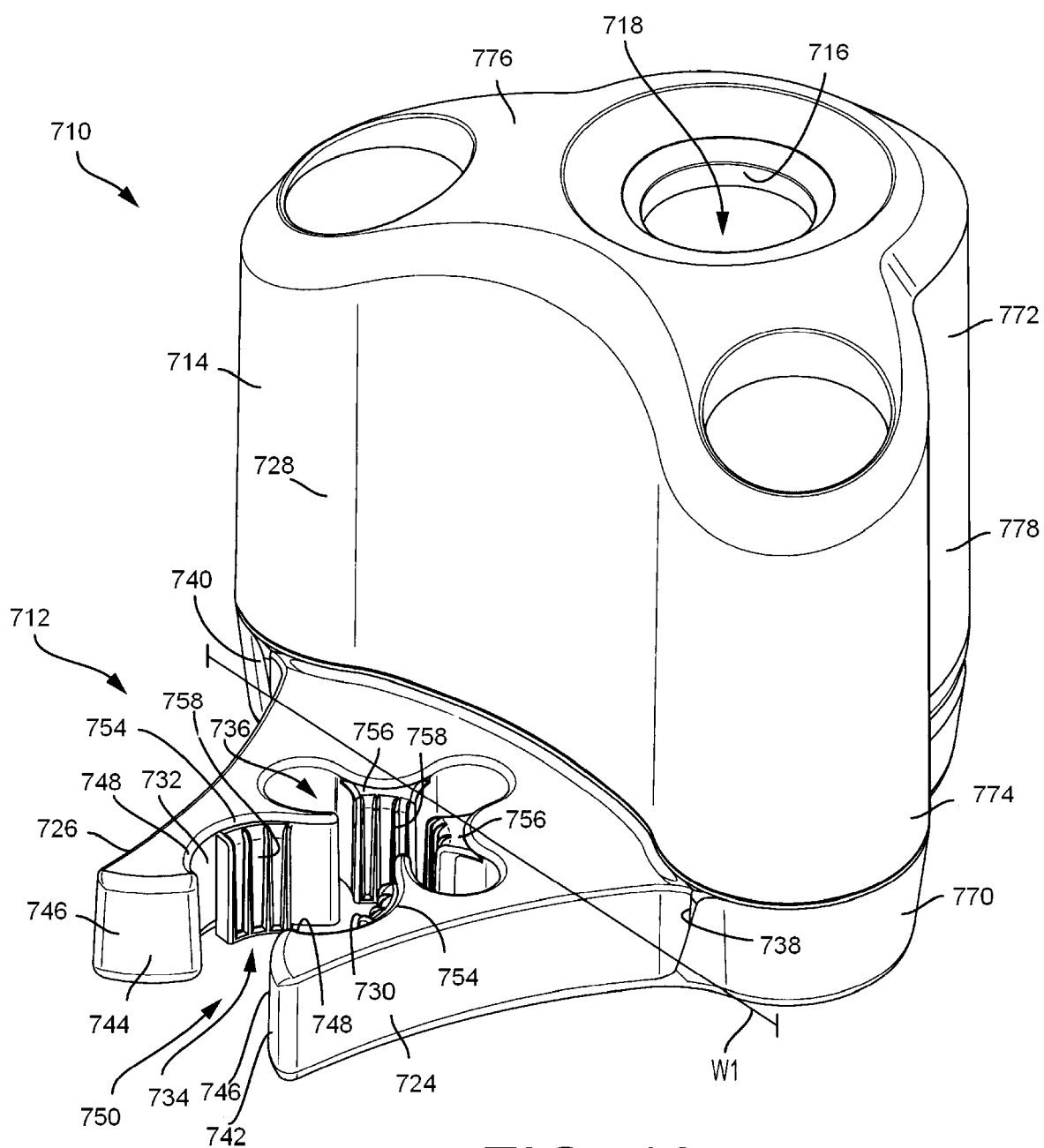
FIG. 13 is a perspective view of another exemplification of a scope cleaning device according to an aspect of the present disclosure.
Figure 14:
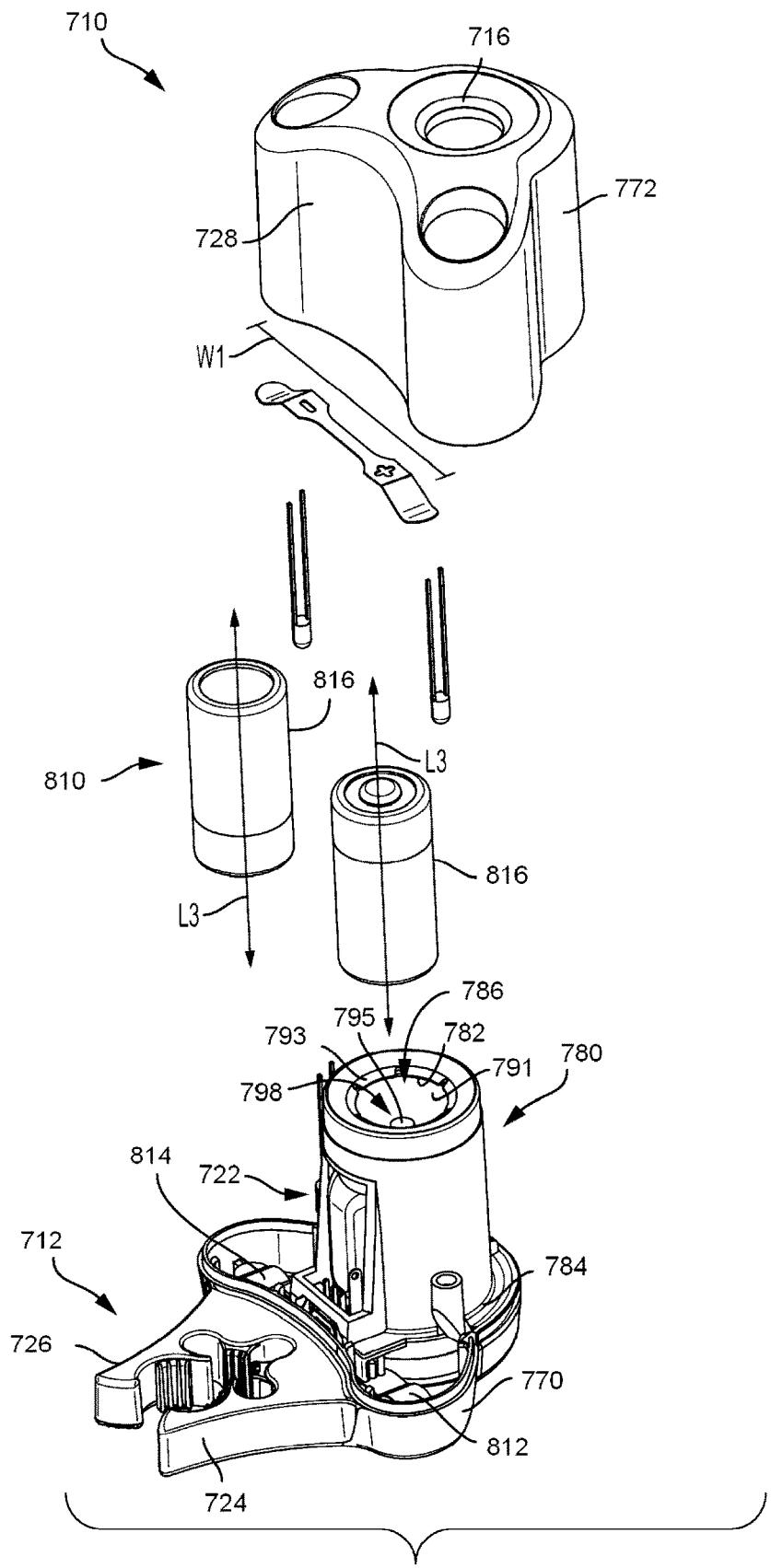
FIG. 14 is an exploded perspective view of the scope cleaning device of FIG. 13.

With reference again to FIGS. 13-15, in some examples, the housing 714 is formed from multiple individually formed or molded pieces joined together to form an enclosure. For example, the housing 714 can include a base 770 integrally formed with the connector 712. The housing 714 can also include a cover 772, such as a dome shaped cover, having an open bottom portion 774, a partially closed top portion 776, and an annular sidewall 778 extending therebetween. As shown in FIGS. 13 and 14, the at least one opening 716 for accessing the interior 718 of the housing 714 can be positioned on the top portion 776 of the cover 772. As described herein, additional structures formed from other materials can be attached to the base 770 and/or connector 712 using a suitable adhesive or molding process. For example, as described herein, the textured or high friction surface 758 of the connector 712 can be formed by overmolding a textured or high friction material to the connector 712 to enhance the frictional engagement between the connector 712 and trocar.

Figure 15:
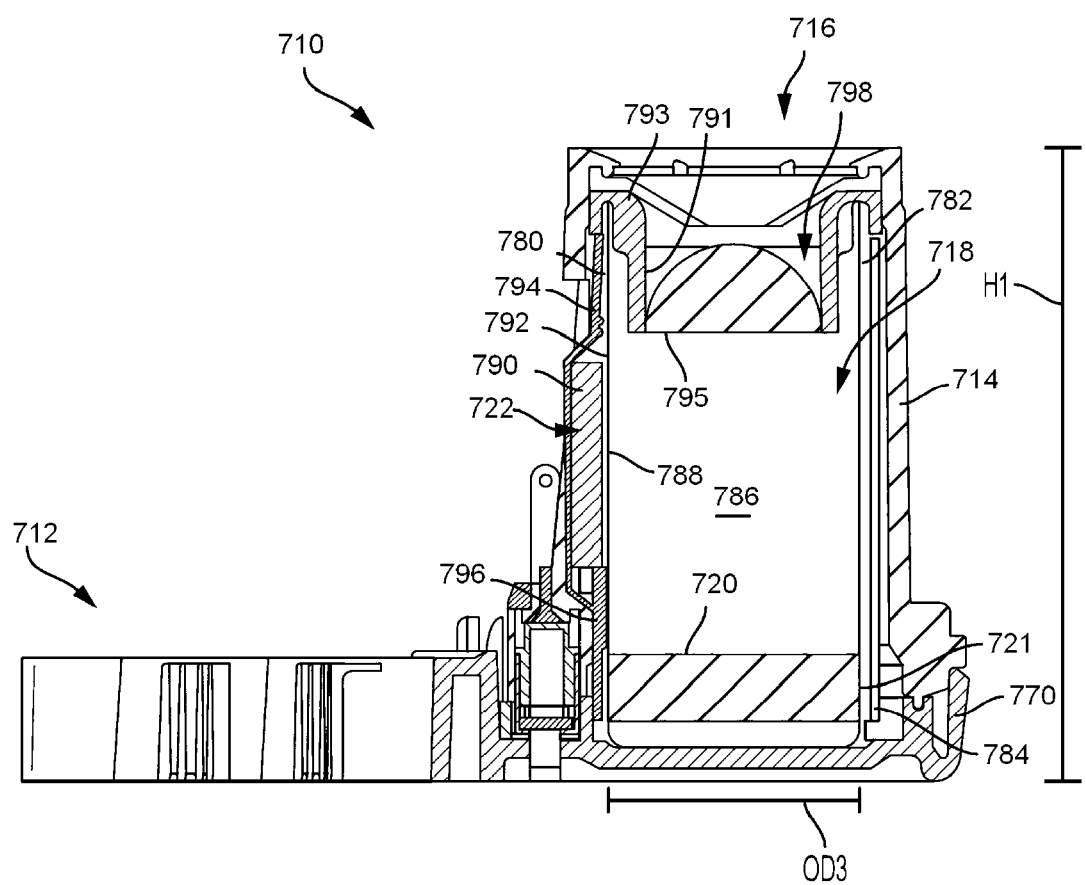
FIG. 15 is a cross-sectional view of the base and the fluid reservoir of the scope cleaning device of FIG. 13.
Figure 16:
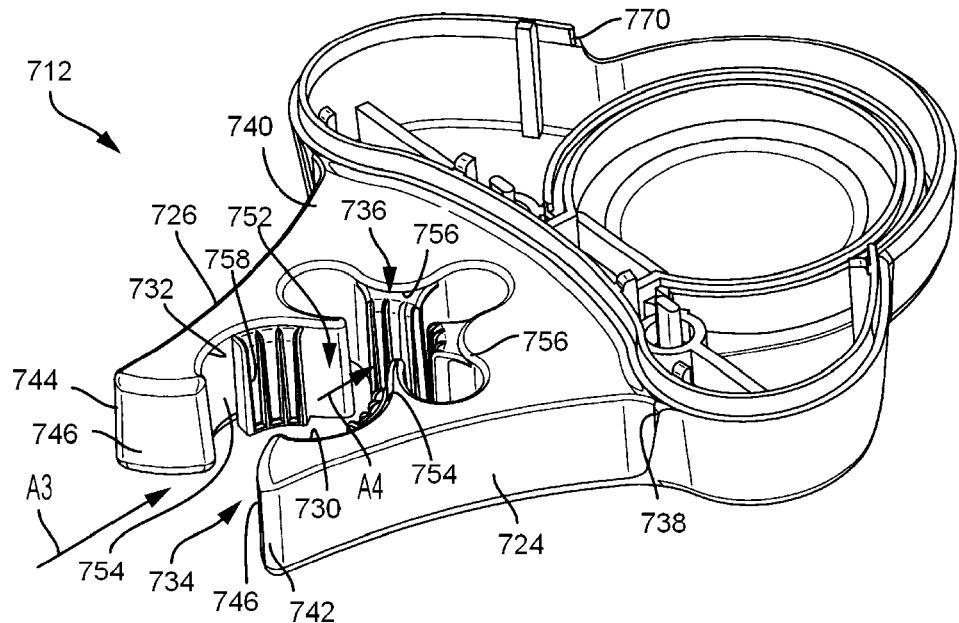
FIG. 16 is a perspective view of the base of the scope cleaning device of FIG. 13.
Figure 17:
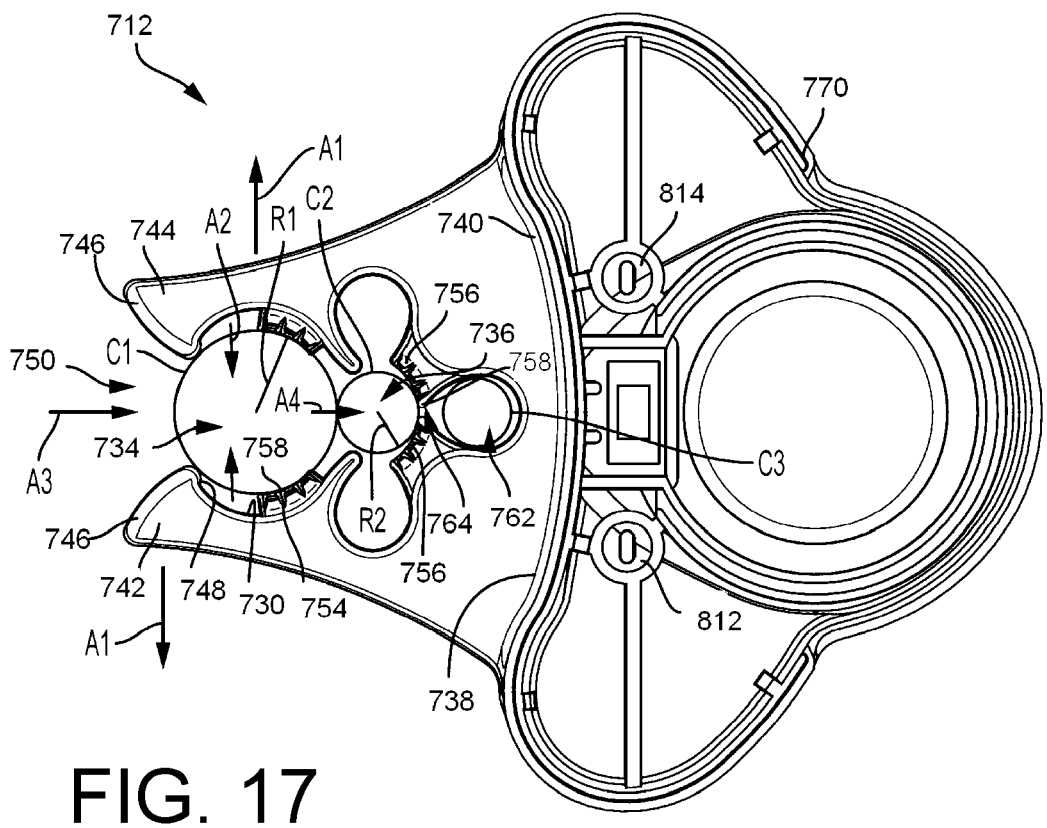
FIG. 17 is a top view of the base of the scope cleaning device of FIG. 13.

With reference to FIGS. 14 and 15, in some examples, the housing 714 further includes a tubular fluid reservoir 780 enclosed by the cover 772 and/or the base 770. The tubular reservoir 780 is sized to receive a portion of the scope for cleaning and defogging the scope. In some examples, the reservoir is about 35 mm to 45 mm tall and has an outer diameter of about 15 mm to 25 mm. The fluid reservoir 780 can include an open top 782 accessible through the at least one opening 716 of the cover 772 and a closed bottom 784 mounted to the base 770. The fluid reservoir 780 defines an interior 786, configured to receive cleaning solution to clean the scope. The at least one sponge 720 can be inserted into the interior 786 of the fluid reservoir 780. The sponge 720 can be a circular shape and sized such that a peripheral edge 721 of the sponge 720 engages an inner surface 788 of the fluid reservoir 780 by a frictional engagement to hold the sponge 720 in place in the fluid reservoir 780.

As in previous exemplifications, the heater assembly 722 is positioned in proximity to the fluid reservoir 780 and is configured to heat fluid and the sponge 720 contained therein. By heating the fluid and sponge to an appropriate temperature, the fluid effectively defogs a lens of the surgical scope, which improves a quality of images captured by the scope during a surgical procedure. Particularly, warming the lens of the scope to approximately body temperature reduces a likelihood that a lens of the scope will fog when it is inserted into the patient's body.

In some examples, the heater assembly 722 includes a conductive film 790 wrapped around at least a portion of an outer surface 792 of the fluid reservoir 780. The conductive film 790 can be any suitable conductive material, which increases in temperature when an electric current passes through the conductive film 790. Exemplary conductive materials include metallic films, such as films formed from copper, zinc, and similar materials. The conductive film 790 may also be a film formed from a conductive polymer material and/or a polymer film impregnated with conductive metallic particles. In other examples, the conductive film 790 can be replaced by other electrical circuitry for generating sufficient heat to warm the fluid reservoir 780 and surgical scope. For example, the heater assembly can include conductive wires, coils, foils, tape, or similar materials electrically connected to a power source for generating heat.

In some examples, the heater assembly 722 further includes an insulator 794 positioned around at least a portion of the conductive film 790 and the outer surface 792 of the fluid reservoir 780. For example, the insulator 794 can be an annular sleeve formed from an insulating material, such as silicone, neoprene, fiberglass, cotton, felt, or other insulating materials as are known in the art. In some examples, the insulator 794 can be molded or coated over the conductive film to provide protection for the film. In other examples, the insulator 794 is a separate sheet or sleeve wrapped around or positioned over the conductive film.

In some examples, the heater assembly 722 also includes a thermostat 796 electrically connected to a power source 810. The thermostat 796 can be configured to selectively apply power from the power source 810 to the conductive film 790, thereby causing the conductive film 790 to increase or decrease in temperature. The thermostat 796 can be mounted to other portions of the fluid reservoir 780 or at any other convenient location within the housing 714. In some examples, the thermostat 796 is configured to disconnect the power source 810 from the conductive film 790 when the thermostat 796 measures that the conductive film 790 and/or portions of the fluid reservoir 780 are above a target temperature value.

In some examples, the power source 810 includes battery terminals, such as a first battery terminal 812 and a second battery terminal 814, sized to receive one or more batteries 816. The batteries 816 can be conventional commercially available batteries, such as one or more of single A batteries, AA batteries, and/or a AAA batteries. For example, as shown in FIG. 14, the scope cleaner device 710 including two AA batteries 816. The battery terminals 812, 814 can be mounted to the base 770 of the housing 714 and configured to hold the batteries 816 in a position, in which a longitudinal axis L3 (shown in FIG. 14) of the battery 816 is parallel or is substantially parallel to a central longitudinal axis L1 (shown in FIG. 18) of a portion of the trocar received by the connector 712.

In some examples, the fluid reservoir 780 also includes an annular seal 798 connected to the open top 782 of the fluid reservoir 780. The annular seal 798 can be an elastomeric seal sized to receive the surgical device, such as the surgical scope, and to seal against a portion of the device to prevent fluid, such as defogging solution, from leaking from the interior 786 of the fluid reservoir 780. In some examples, the annular seal 798 includes a conical outer surface 791 extending radially inwardly from a peripheral edge 793 of the seal 798 to a narrow central opening 795. The annular seal 798 serves several purposes. First, it helps to maintain fluid in the fluid reservoir 780 by, for example, wiping excess fluid from the scope cleaner. The seal 798 also helps to prevent fluid from spilling out of the fluid reservoir 780 if the trocar, to which the cleaning device 710 is attached, is bumped, jostled, or moved. The seal 798 and central opening 795 can also be sized to facilitate filling the fluid reservoir 780 with defogging fluid. For example, a tip of a fluid bottle can be inserted into the interior 786 of the fluid reservoir 780 through the narrow opening 795. A top portion of the fluid bottle could rest against the conical surface 791 as the fluid reservoir 780 is being filled.

It is to be understood that the present application may assume various alternative variations, except where expressly specified to the contrary. It is also to be understood that the specific devices illustrated in the attached drawings, and described in the specification, are simply exemplary exemplifications of the present application. Although the present application has been described in detail for the purpose of illustration based on what is currently considered to be the most practical and possible exemplifications, it is to be understood that such detail is solely for that purpose and that the present application is not limited to the disclosed exemplifications, but, on the contrary, is intended to cover modifications and equivalent arrangements that are within the spirit and scope thereof. For example, it is to be understood that the present application contemplates that, to the extent possible, one or more features of any exemplification can be combined with one or more features of any other exemplification. The exemplifications of the present application described herein above in the context of the possible exemplifications are not to be taken as limiting the exemplifications of the present application to all of the provided details thereof, since modifications and variations thereof may be made without departing from the spirit and scope of the exemplifications of the present application.

Figure 20:
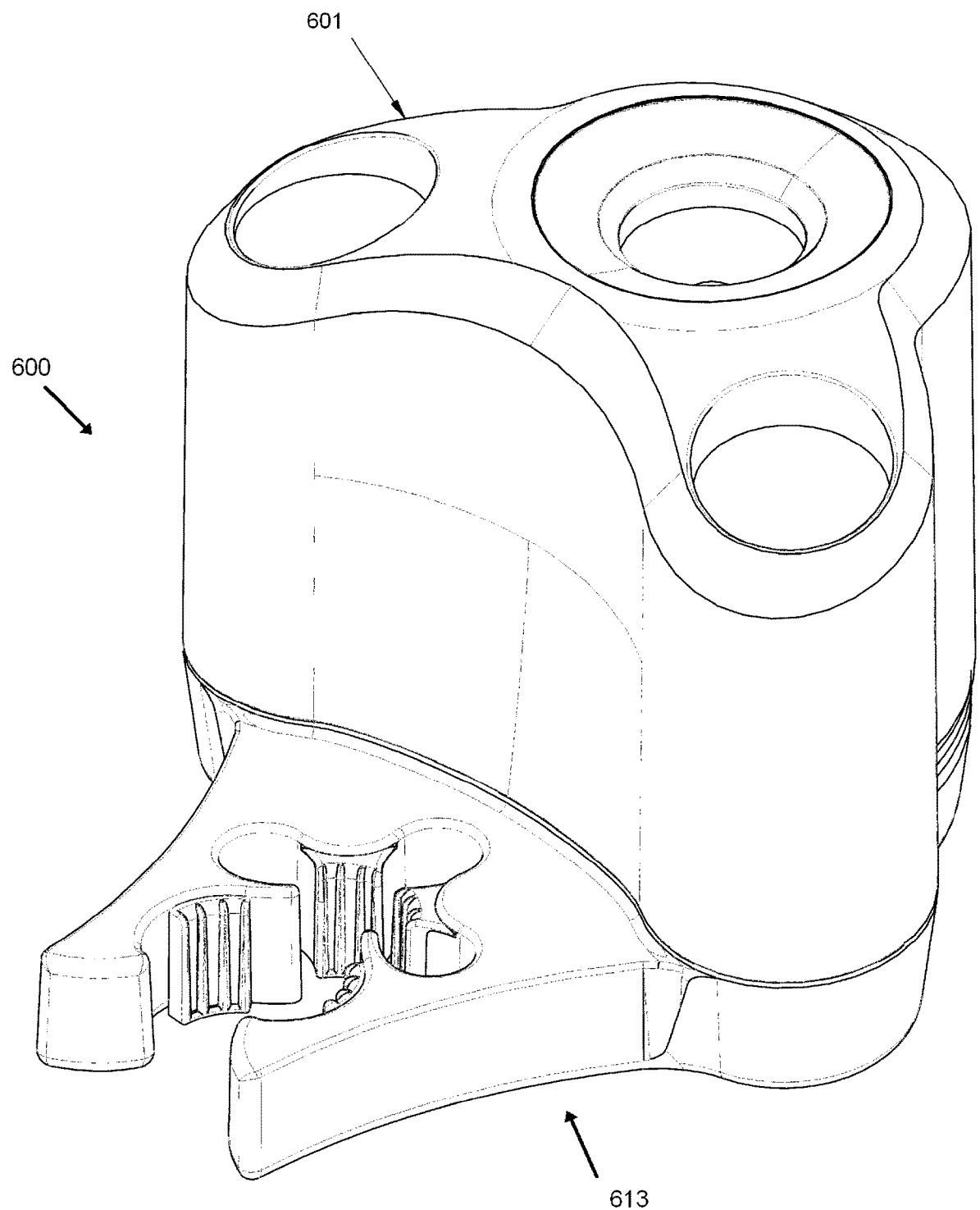
FIG. 20 is perspective view of a device.

FIG. 20 is perspective view of a device 600, which comprises a top housing assembly 601 and an assembled bottom assembly 613.

Figure 21:
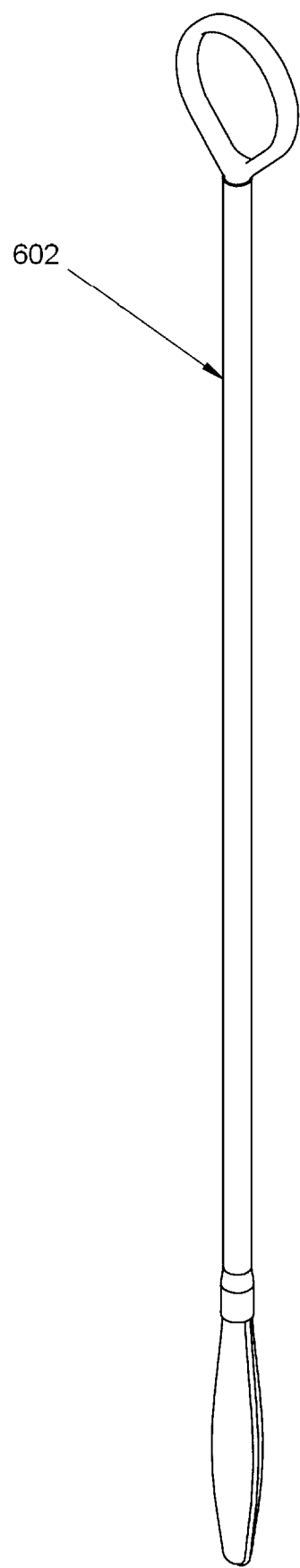
FIG. 21 shows a five millimeter wiping wand.

FIG. 21 shows a five millimeter wiping wand 602.

Figure 22:
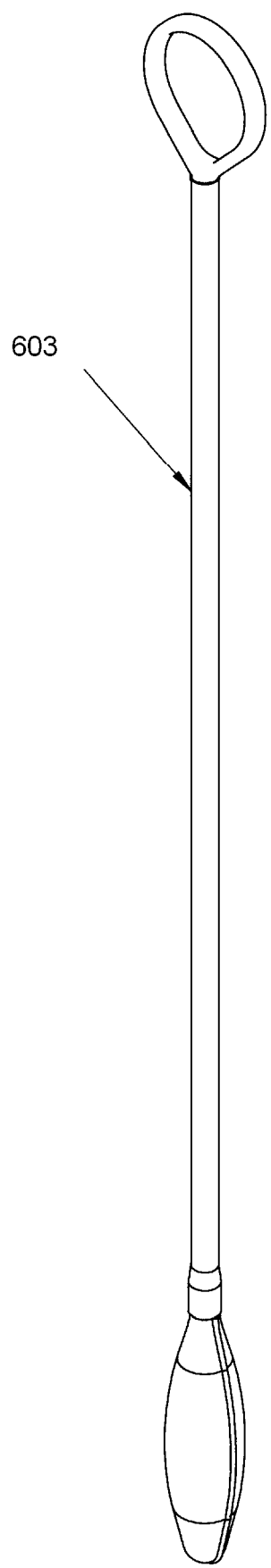
FIG. 22 shows a twelve millimeter wiping wand.

FIG. 22 shows a twelve millimeter wiping wand 603.

Figure 23:
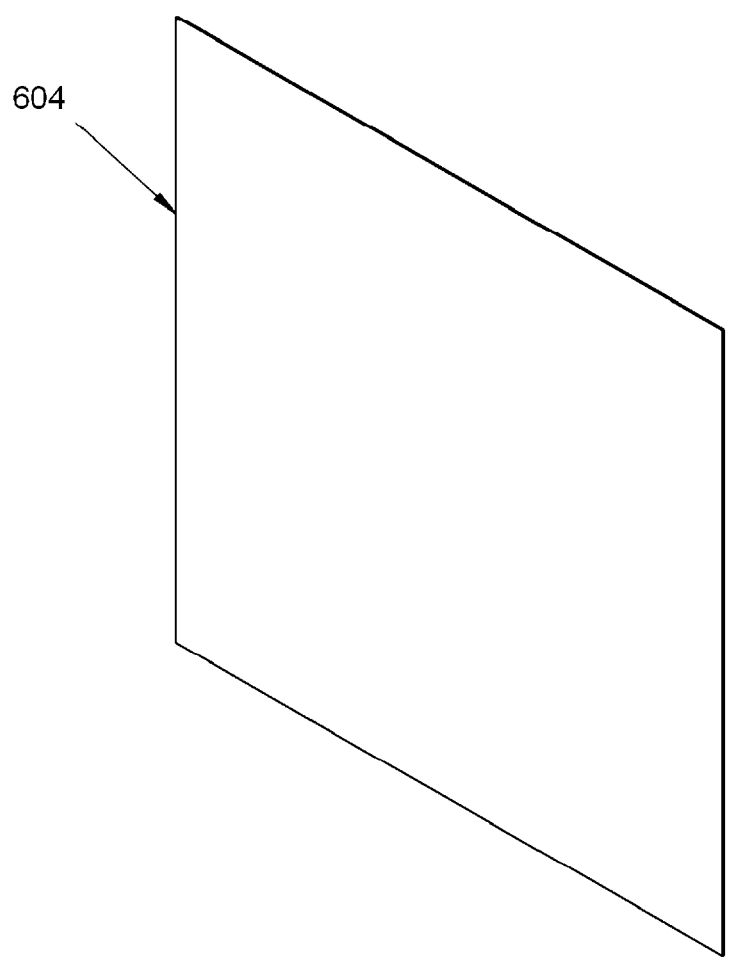
FIG. 23 shows a microfiber cloth.

FIG. 23 shows a microfiber cloth 604.

Figure 24:
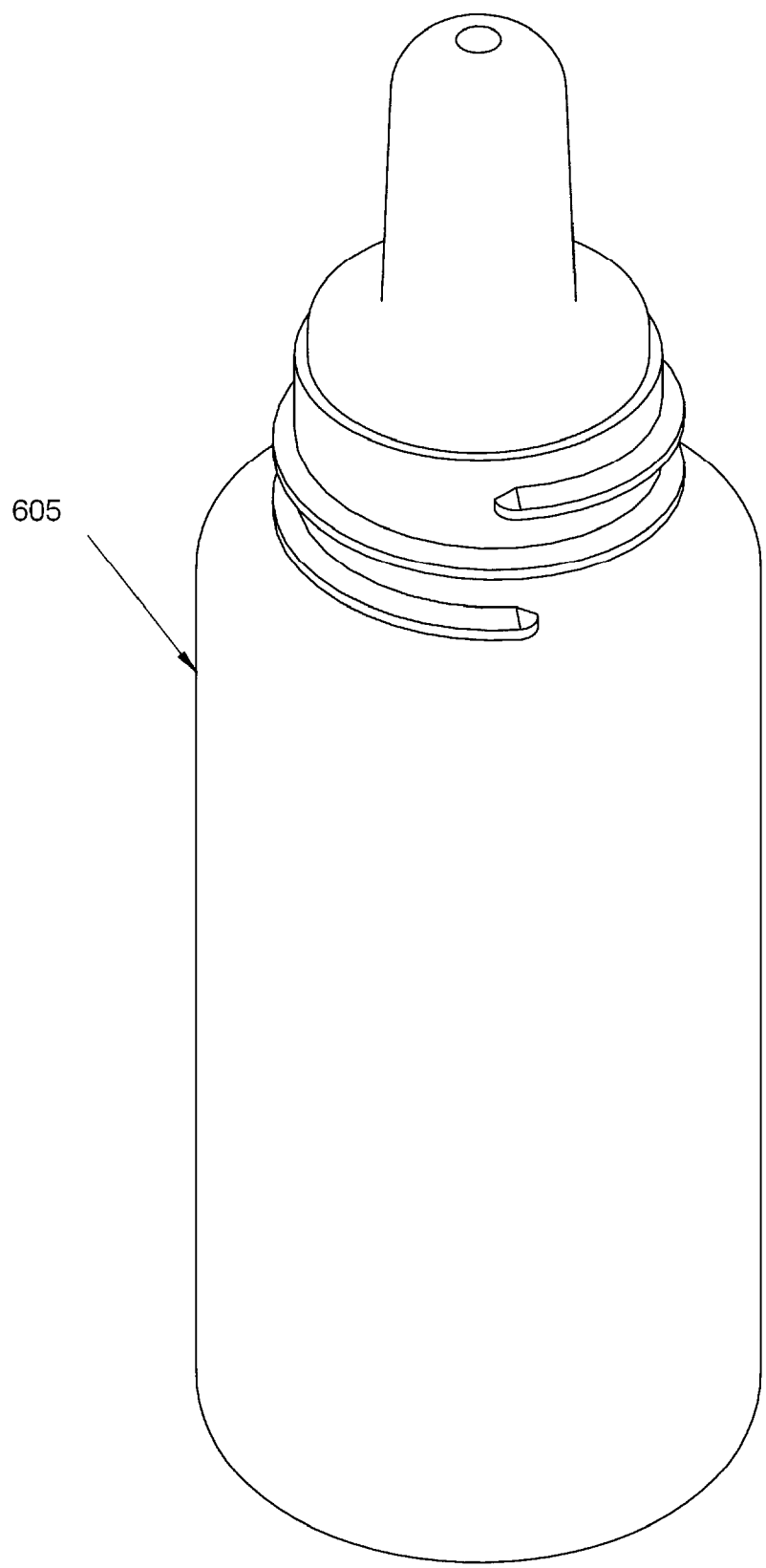
FIG. 24 shows a bottle of anti-fog solution.

FIG. 24 shows a bottle of anti-fog solution 605.

Figure 25:
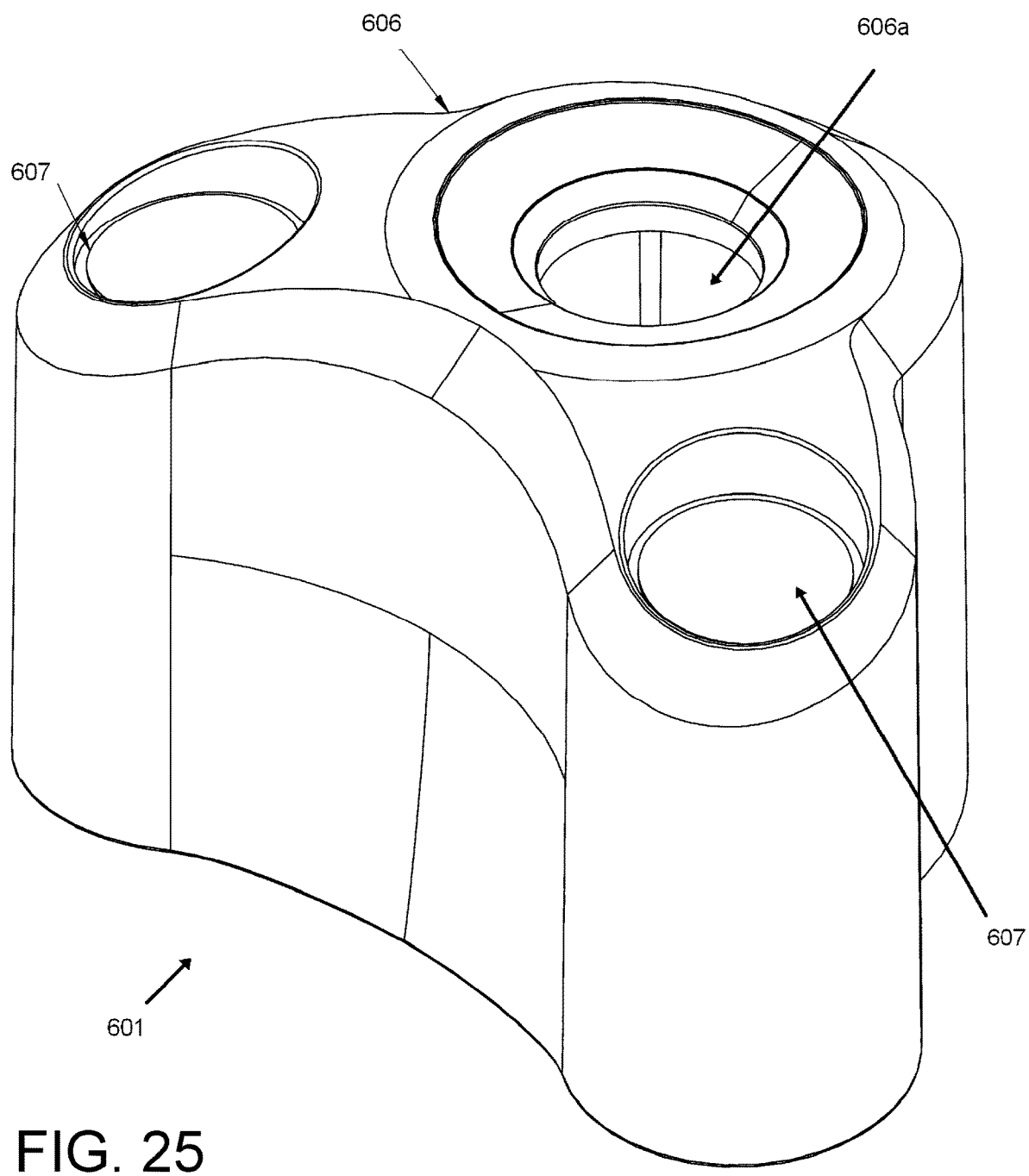
FIG. 25 shows a housing top.

FIG. 25 shows a housing top 606, a hole 606*a*, and two microfiber patches 607.

Figure 26:
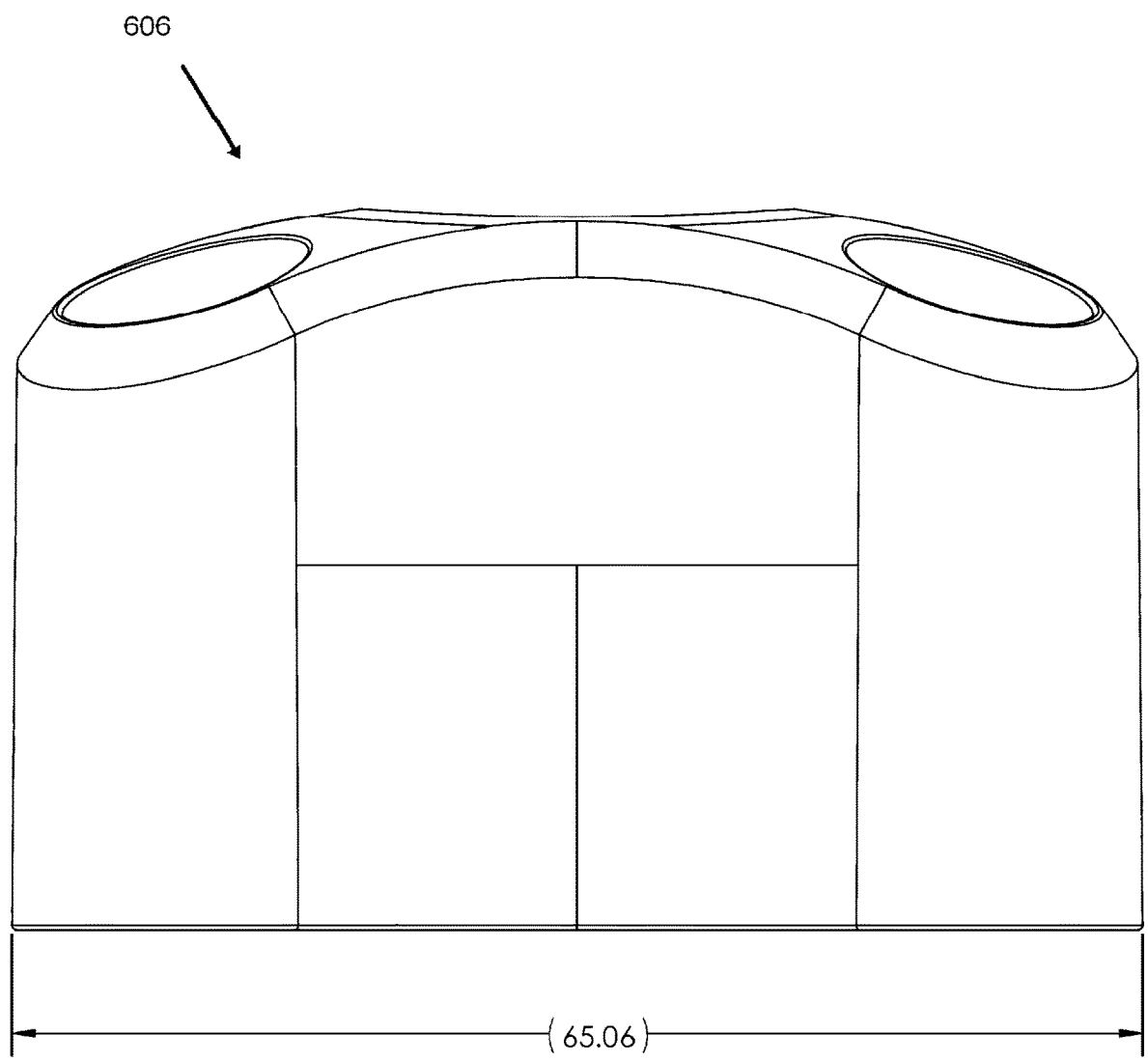
FIG. 26 shows a side view of the housing top.

FIG. 26 shows a side view of the housing top 606. The housing top 606 has a possible width of 65.06 millimeters.

Figure 27:
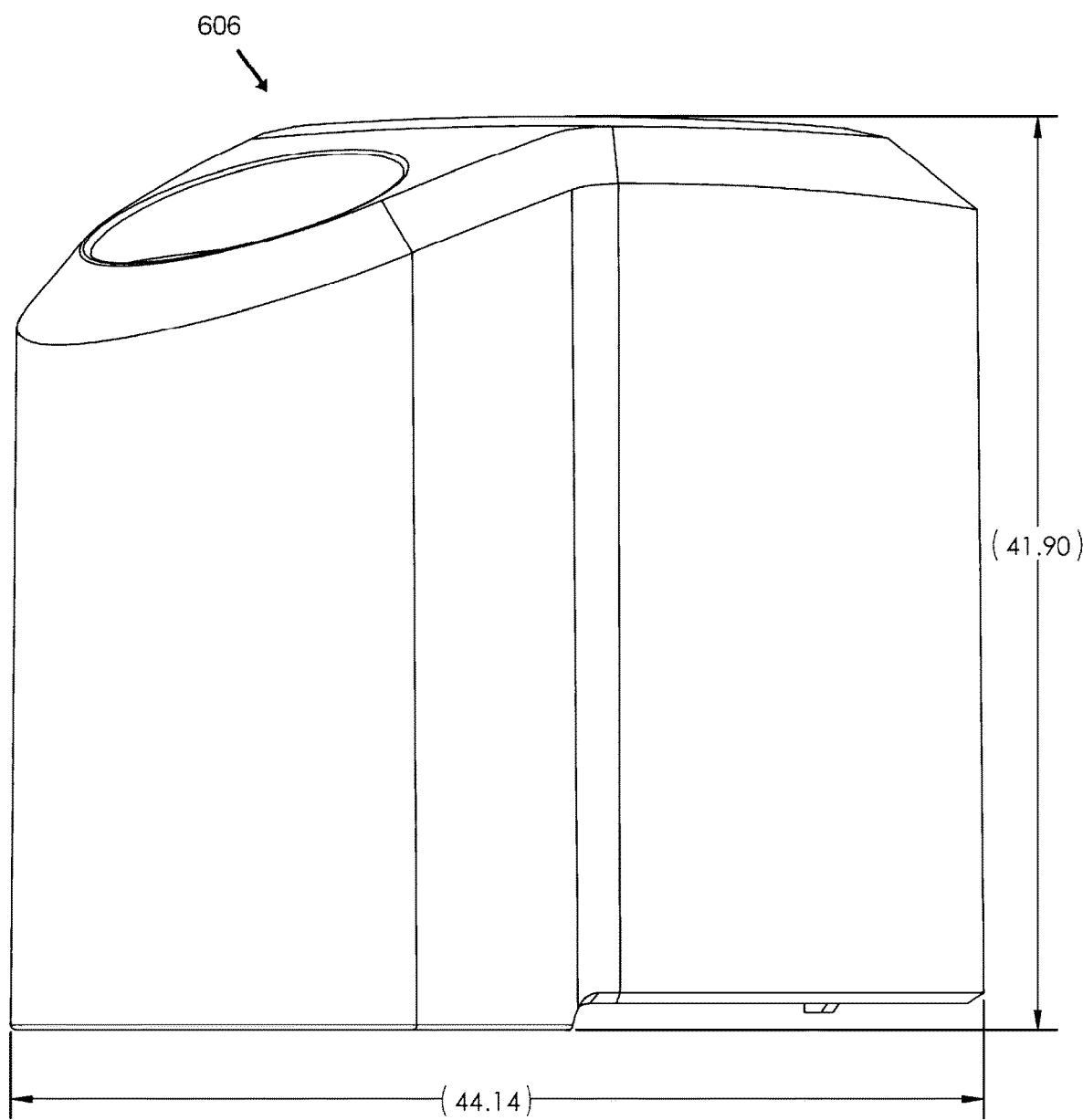
FIG. 27 shows an additional side view of the housing top.

FIG. 27 shows an additional side view of the housing top 606. The housing assembly 606 has a possible length of 44.14 millimeters and a possible height of 41.9 millimeters.

Figure 28:
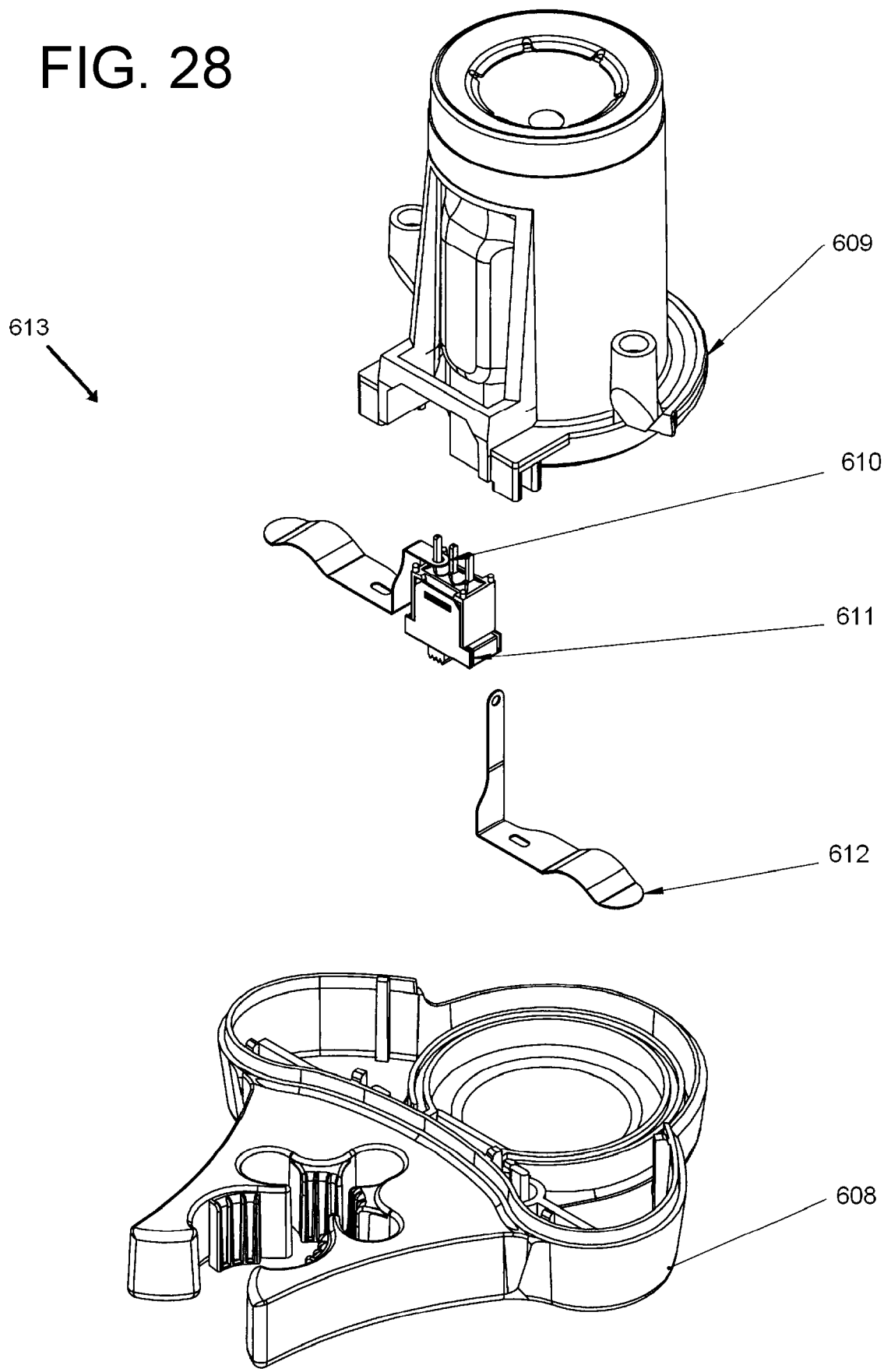
FIG. 28 is a perspective view of an expanded subassembly of the bottom of a housing assembly.

FIG. 28 is a perspective view of an expanded subassembly of the bottom 613 of a housing assembly 601, showing individual components including a housing bottom 608, a reservoir subassembly 609, a battery contact B 610, an e-switch 500ASSPM2E 611, and a battery contact C 612. The e-switch 500ASSPM2E 611 and battery contact C 612 are configured to be ultrasonically welded together.

Figure 29:
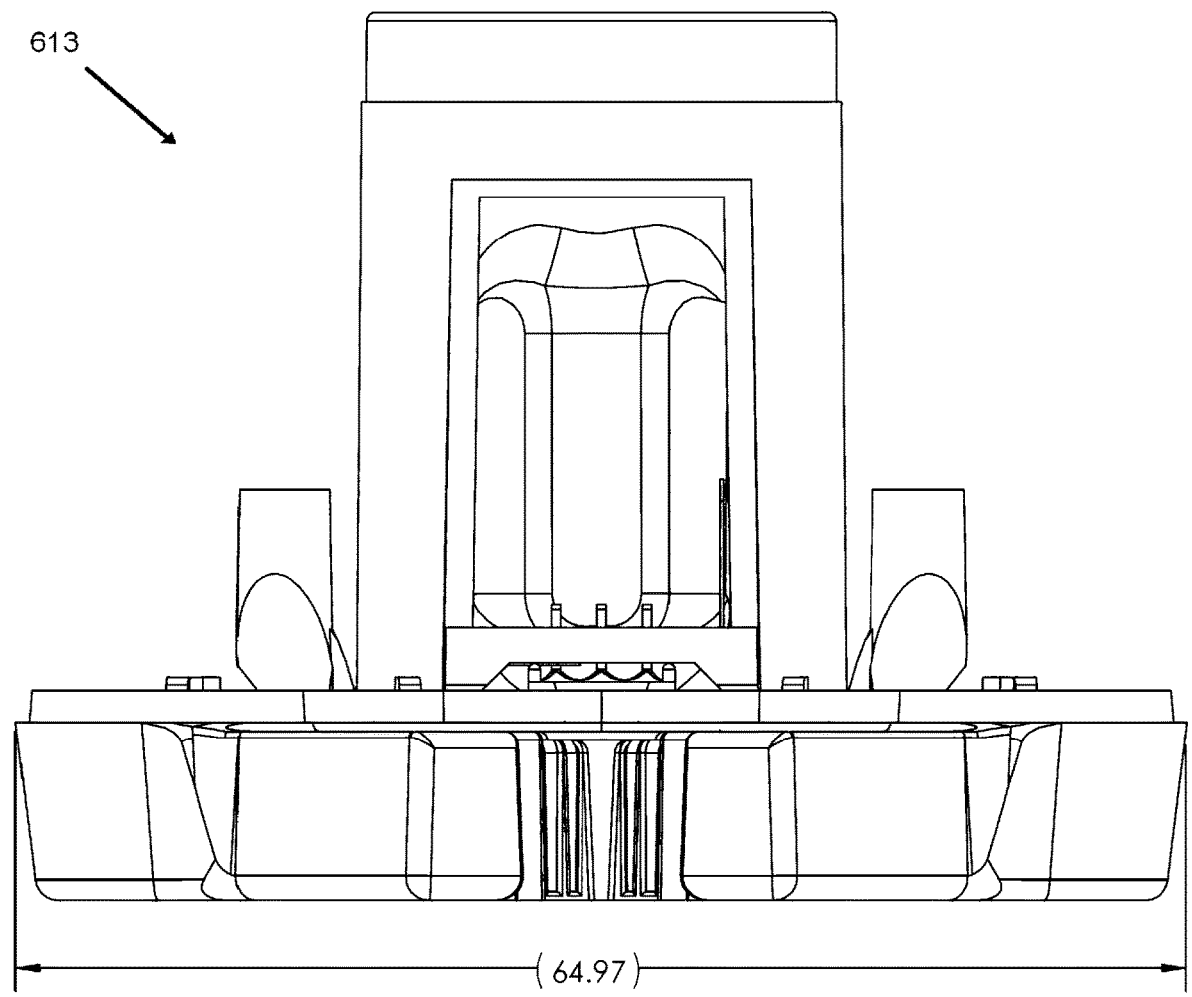
FIG. 29 shows a side view of the assembled bottom assembly.

FIG. 29 shows a side view of the assembled bottom assembly 613. The housing bottom 613 has a possible width of 64.97 millimeters.

Figure 30:
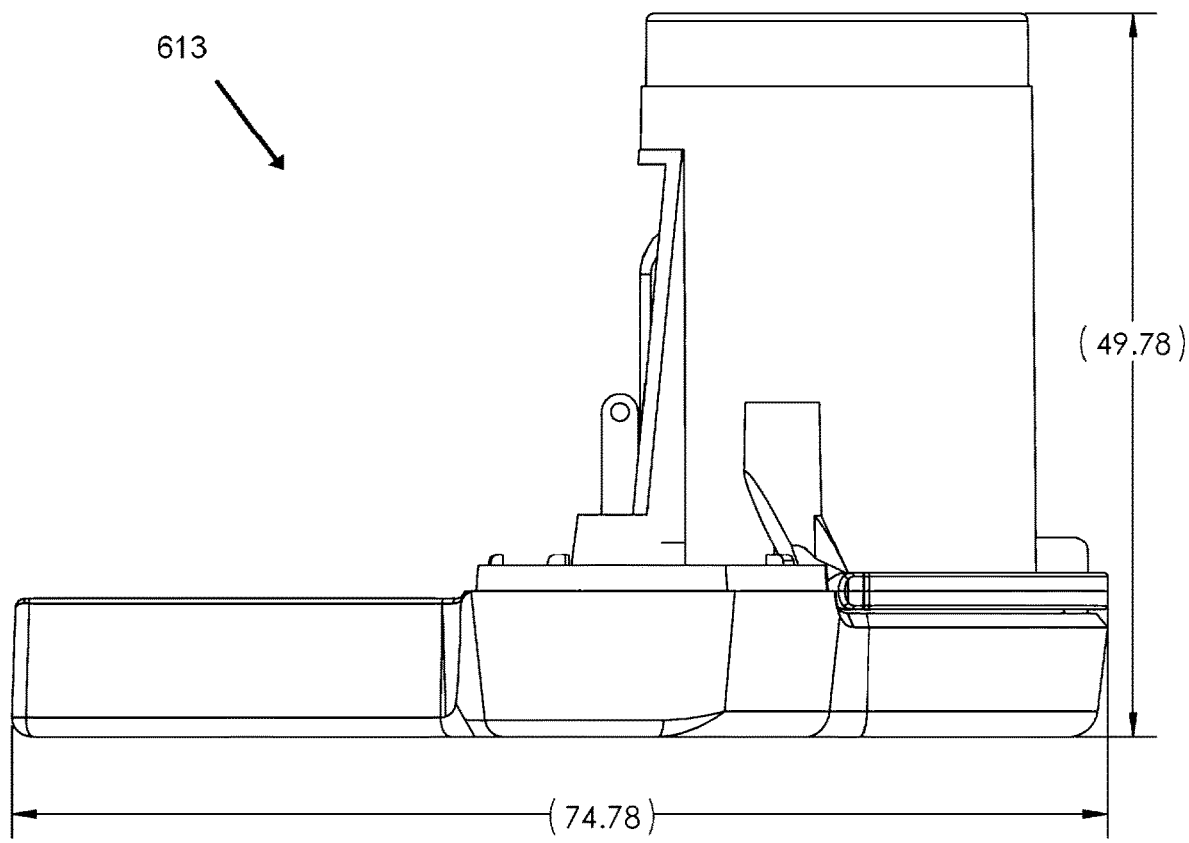
FIG. 30 shows an additional side view of the housing bottom assembly.

FIG. 30 shows an additional side view of the housing bottom assembly 613. The housing bottom 613 has a possible length of 74.78 millimeters and a possible height of 49.78 millimeters.

Figure 31:
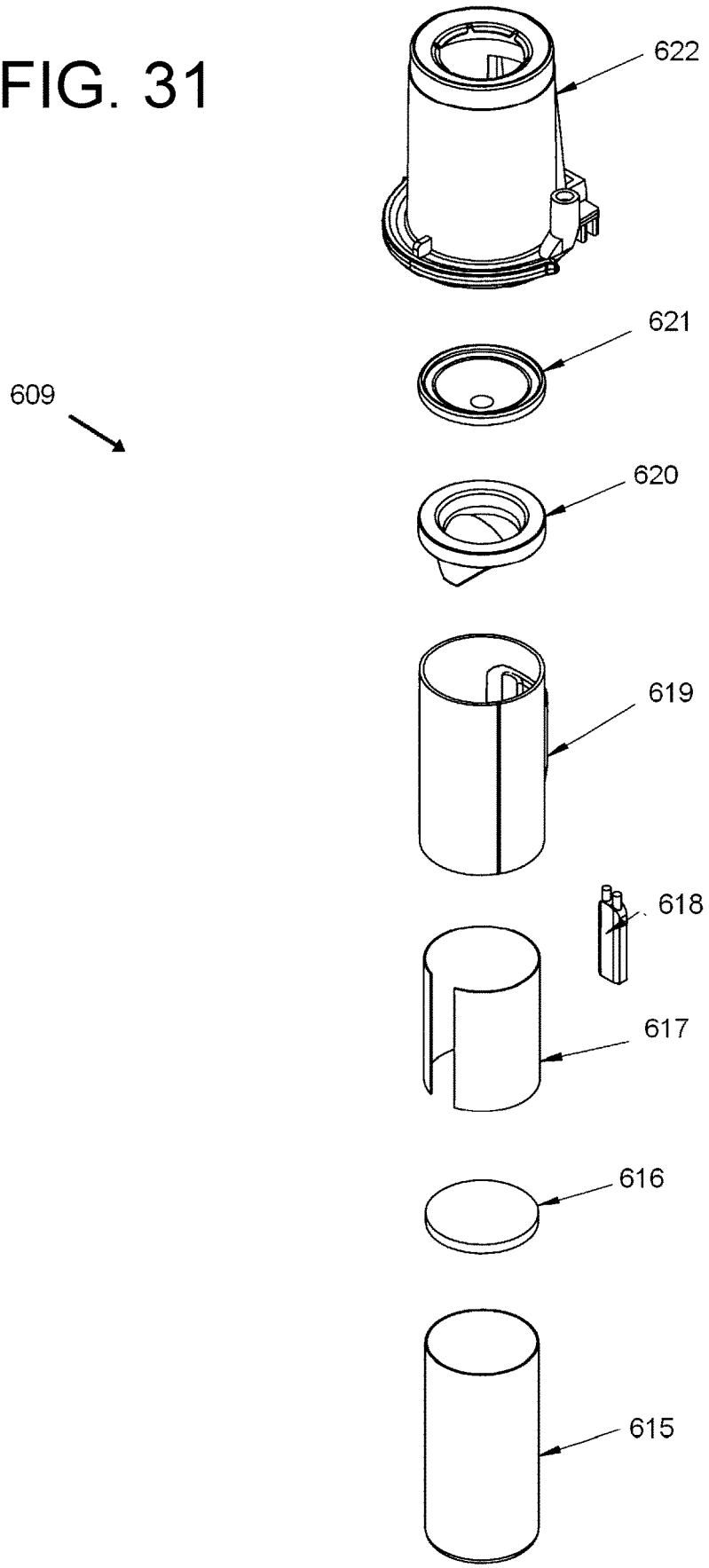
FIG. 31 is a perspective view of an expanded subassembly of a reservoir assembly.

FIG. 31 is a perspective view of an expanded subassembly of a reservoir assembly 609, showing individual components including a reservoir 615, a reservoir sponge 616, a heater 617, a thermostat TB02-BB8D-055 618, a reservoir insulation 619, an inner seal 620, an outer seal 621, and a reservoir retainer 622. The reservoir sponge 616 is configured to be pressed into the bottom of the reservoir 615.

Figure 32:
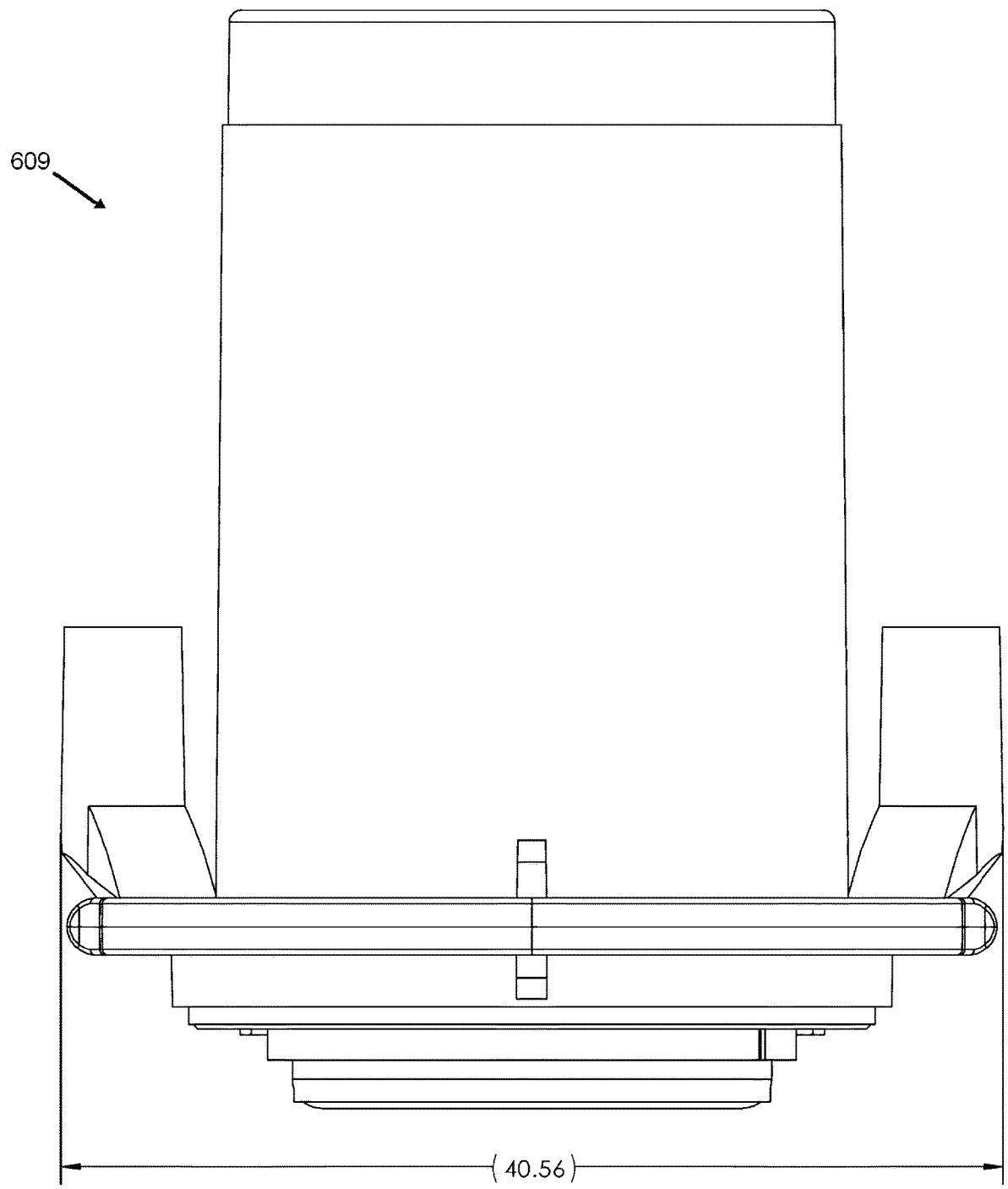
FIG. 32 shows a side view of the assembled reservoir subassembly.

FIG. 32 shows a side view of the assembled reservoir subassembly 609. The reservoir assembly 609 has a possible width of 40.56 millimeters.

Figure 33:
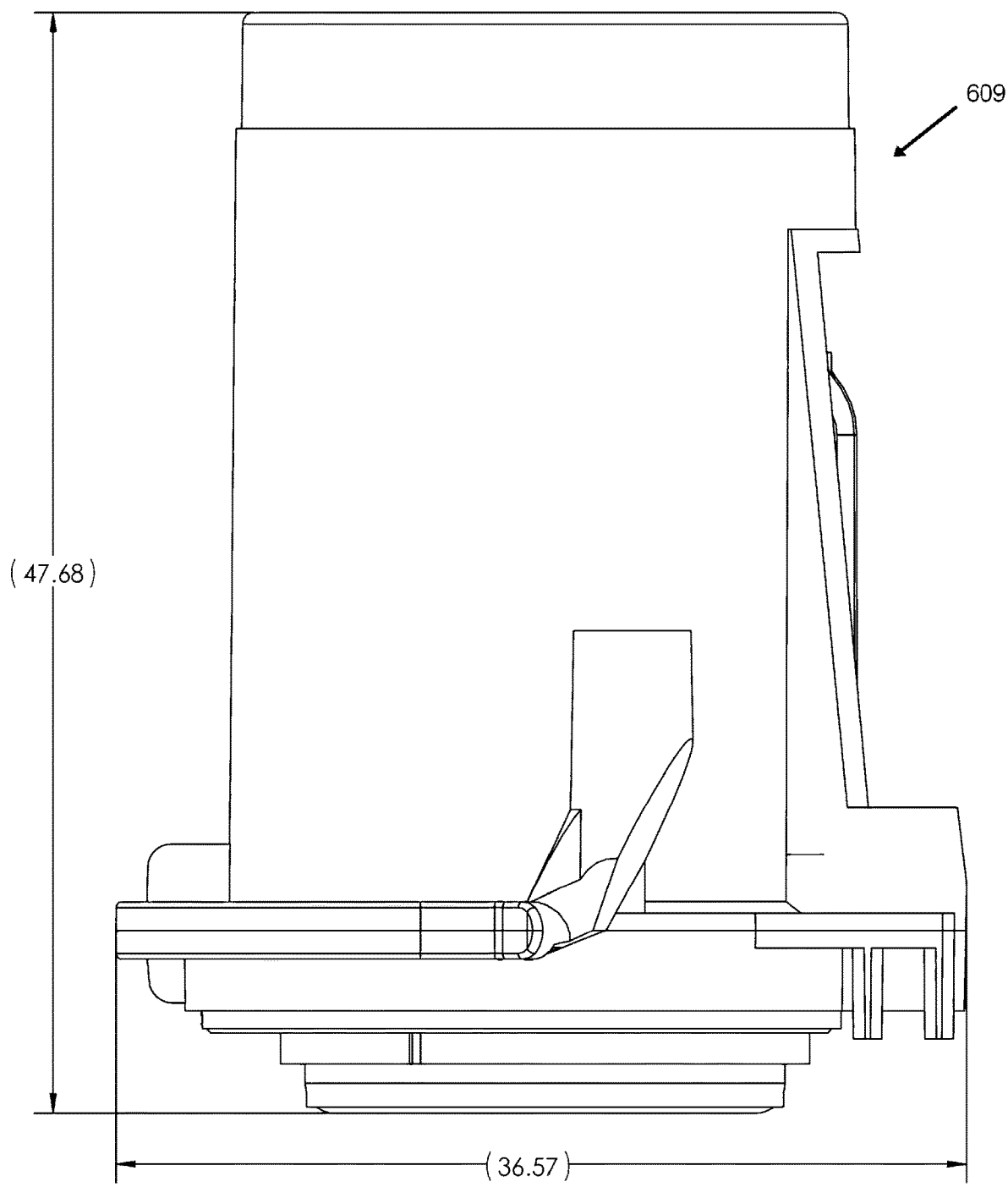
FIG. 33 shows an additional side view of the assembled reservoir subassembly.

FIG. 33 shows an additional side view of the assembled reservoir subassembly 609. The reservoir assembly 609 has a possible length of 36.57 millimeters and a possible height of 47.68 millimeters.

Figure 34:
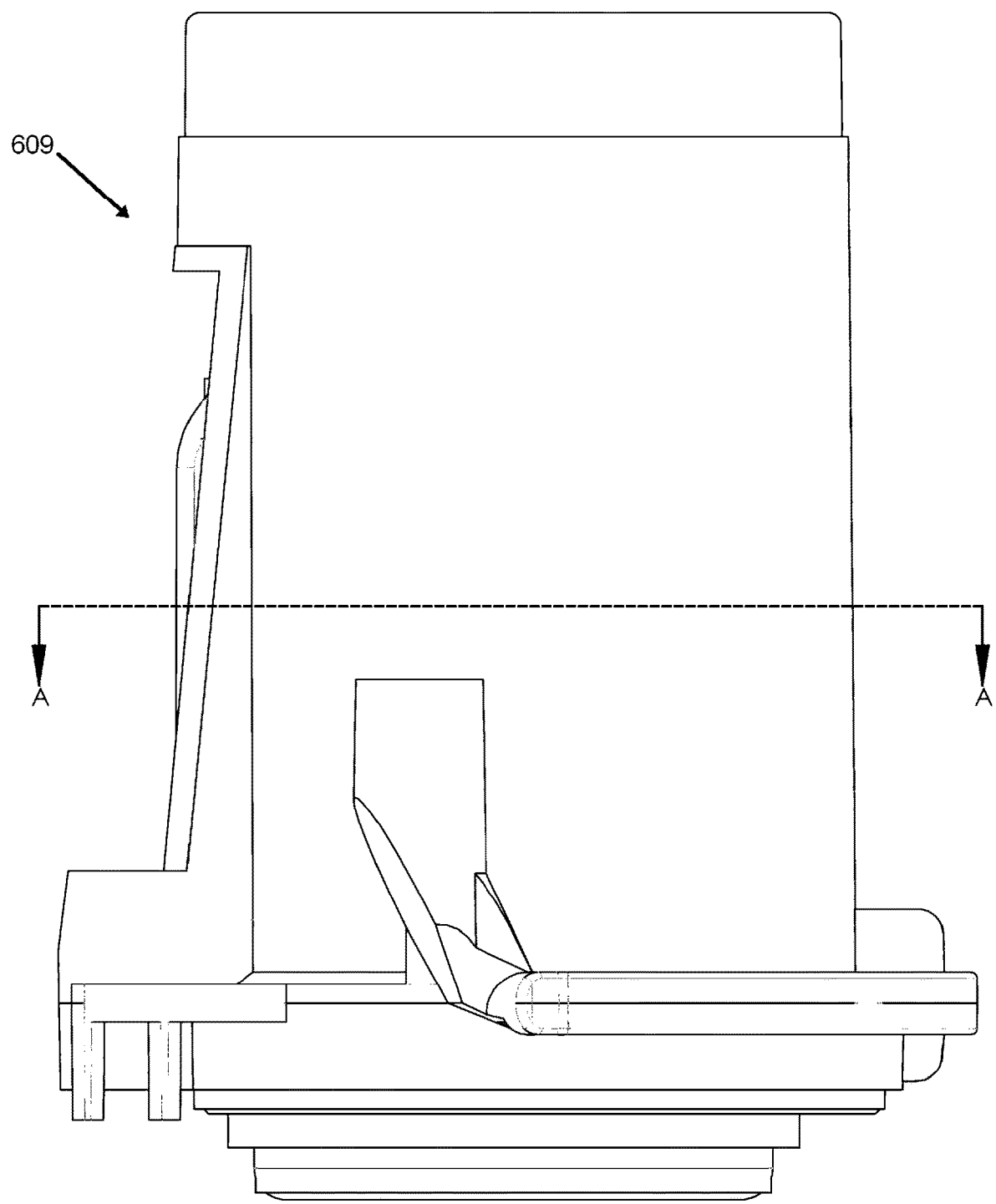
FIG. 34 shows an assembled reservoir subassembly.

FIG. 34 shows an assembled reservoir subassembly 609 with a line A-A to show where a cross-sectional cut is being taken.

Figure 35:
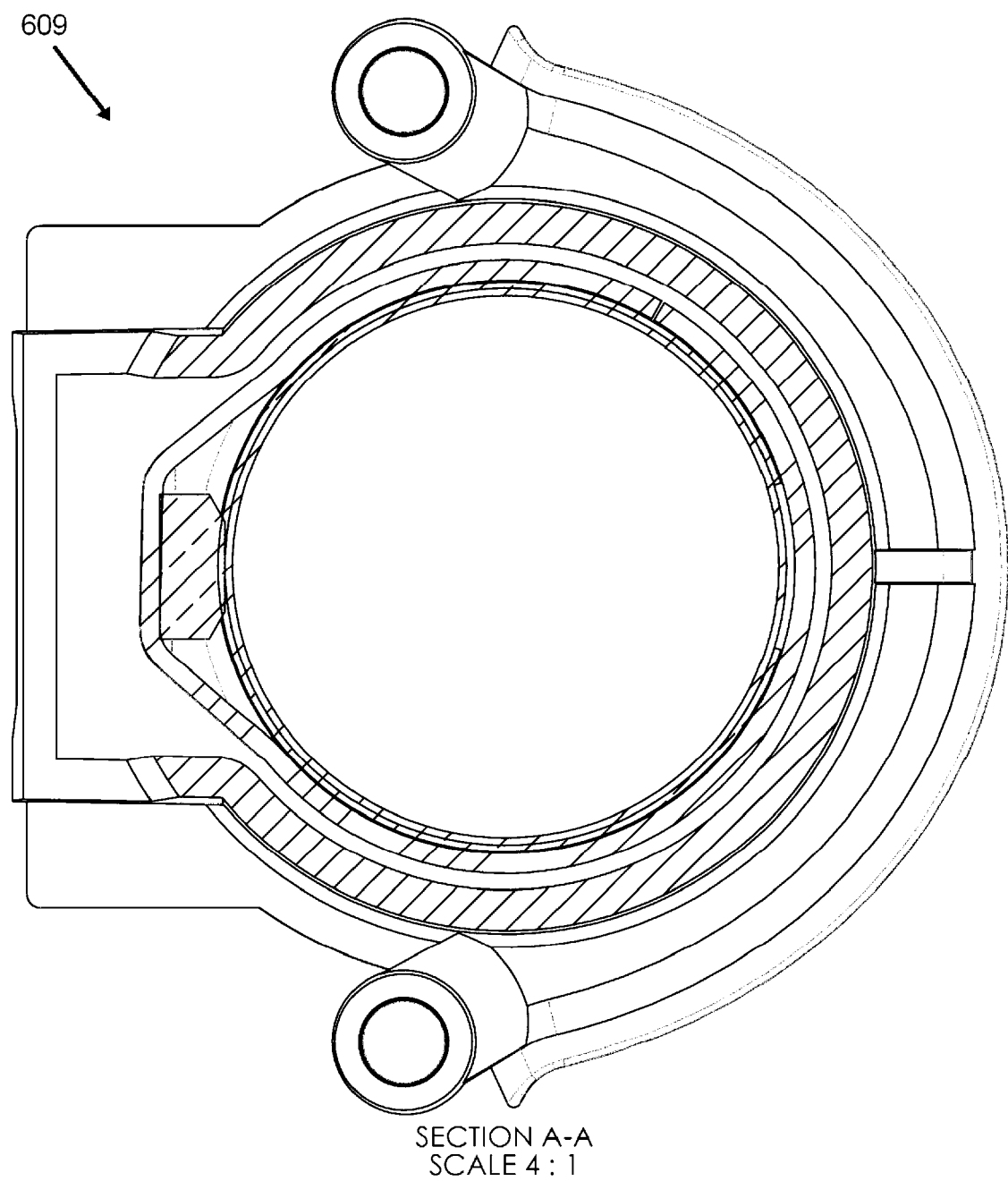
FIG. 35 shows a cross-section of the assembled reservoir subassembly.

FIG. 35 shows the cross-section of the assembled reservoir subassembly 609 as shown in FIG. 34. The heater 617 should be attached to the reservoir 615 before the thermostat 618. The thermostat 618 should be attached to the outer surface of the heater 617, centered between the ends with the wire leads pointed toward the reservoir opening. The thermostat 618 should be adhered to the heater 617 with thermally conductive adhesive. The thermostat 618 should be wrapped with insulation 619, with the insulation split not located over the thermostat 618. The insulated reservoir should be aligned with the thermostat 618 centered in the vertical opening in the retainer housing.

Figure 36:
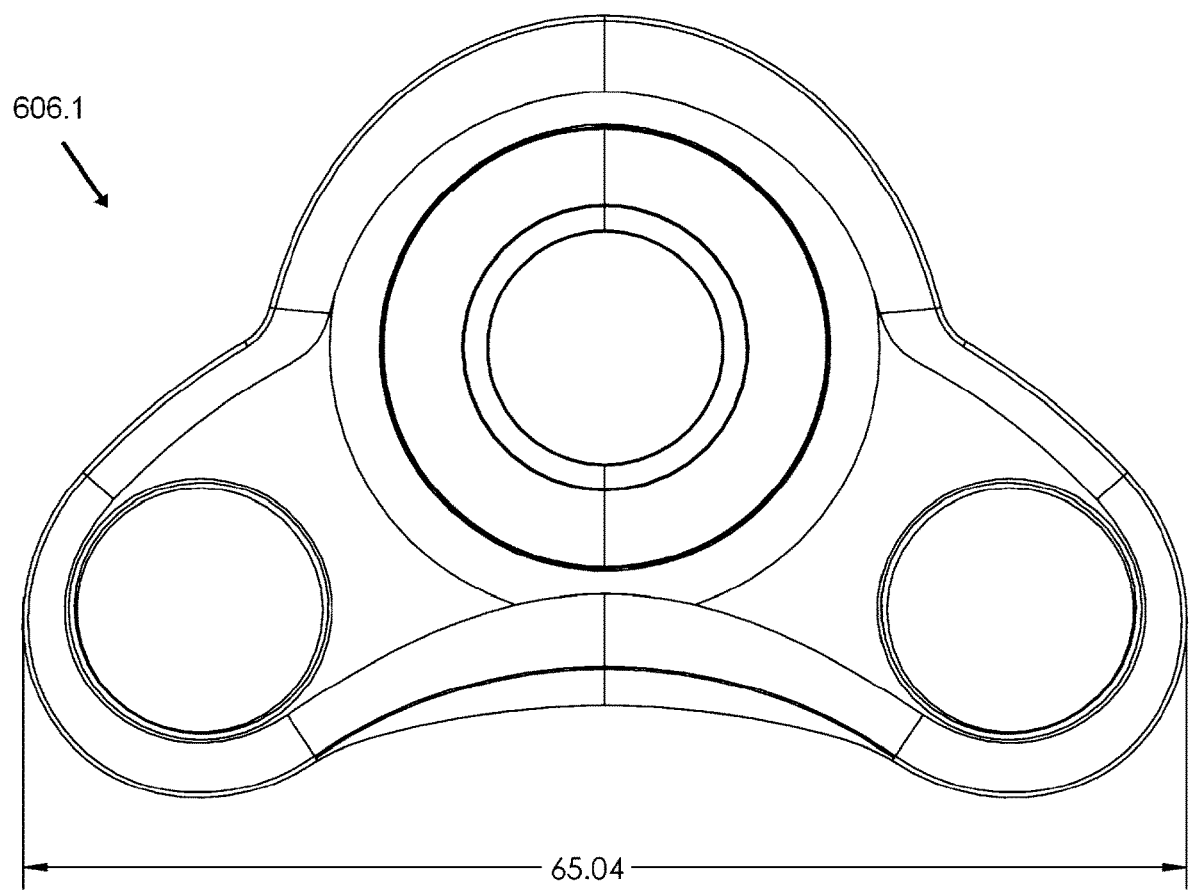
FIG. 36 shows a top view of a possible exemplification of a housing top.

FIG. 36 shows a top view of a possible exemplification of a housing top 606.1. The housing top 606.1 has a possible width of 65.04 millimeters.

Figure 37:
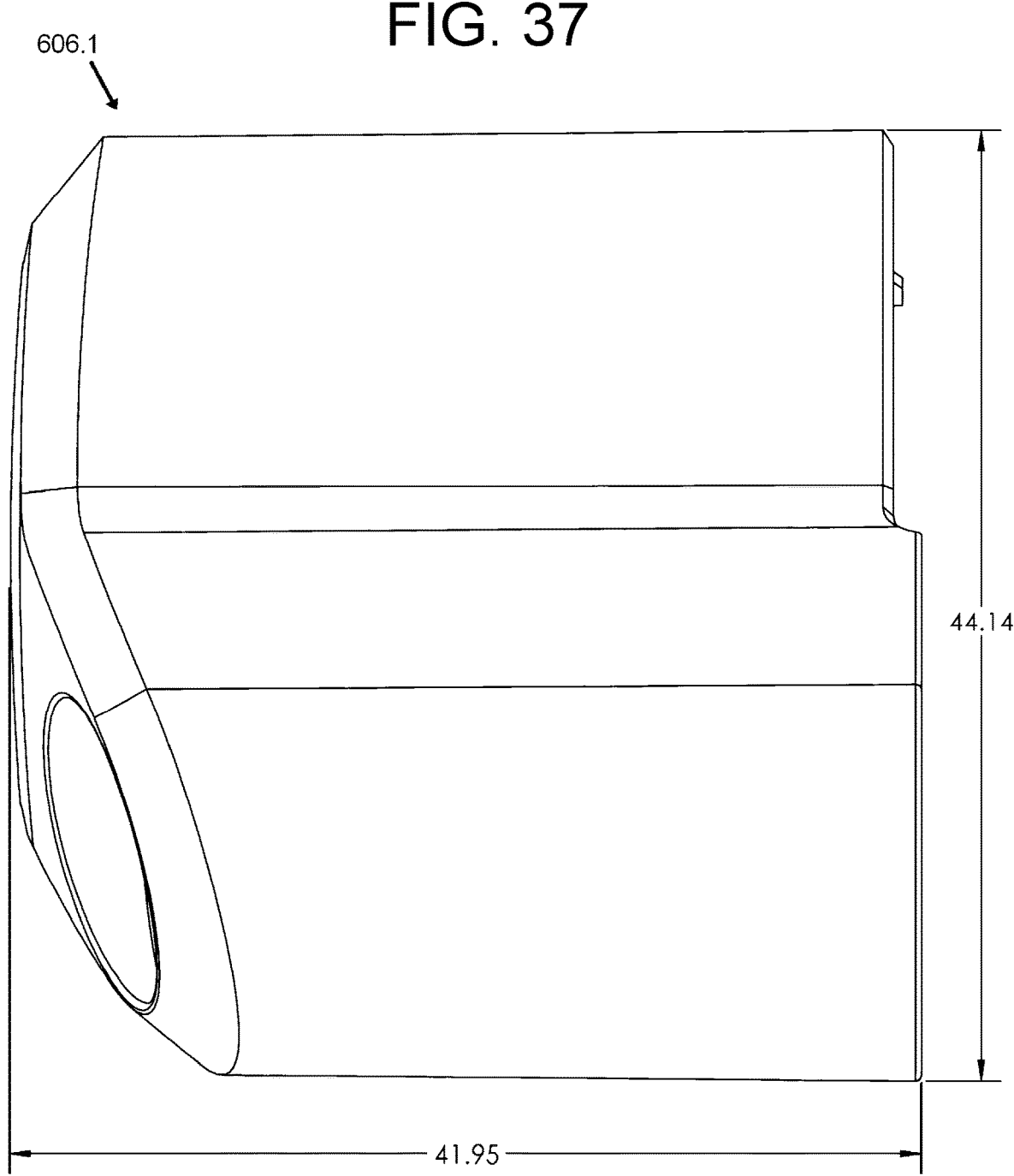
FIG. 37 shows a side view of the possible exemplification of the housing top.

FIG. 37 shows a side view of the possible exemplification of the housing top 606.1, including a possible length of 41.95 millimeters and a possible height of 44.14 millimeters.

Figure 38:
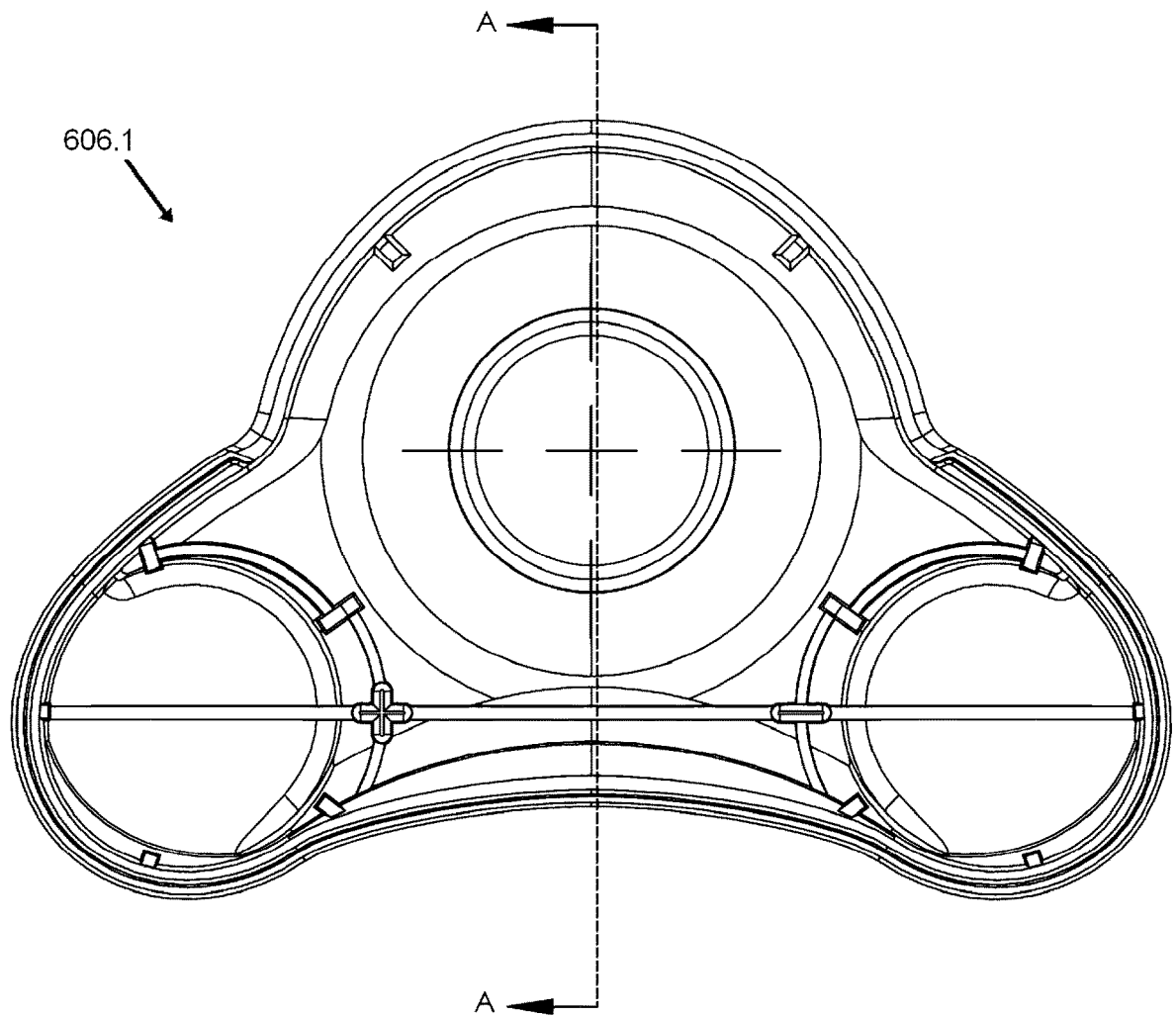
FIG. 38 shows a housing top.

FIG. 38 shows a housing top 606.1 with a line A-A to show where a cross-sectional cut is being taken.

Figure 39:
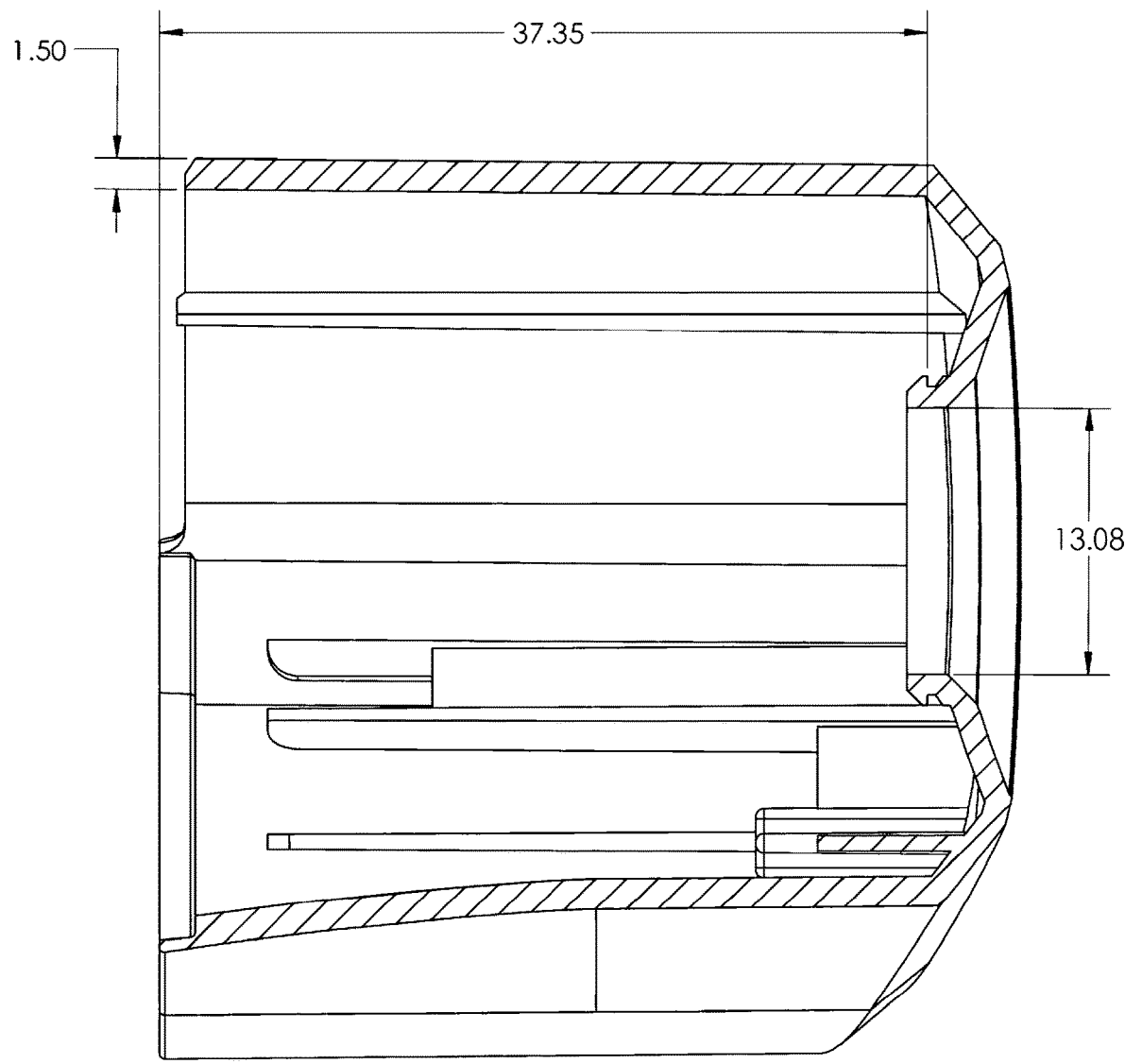
FIG. 39 shows a cross-section of the housing top.

FIG. 39 shows the cross-section of the housing top 606.1 as shown in FIG. 38.

Figure 40:
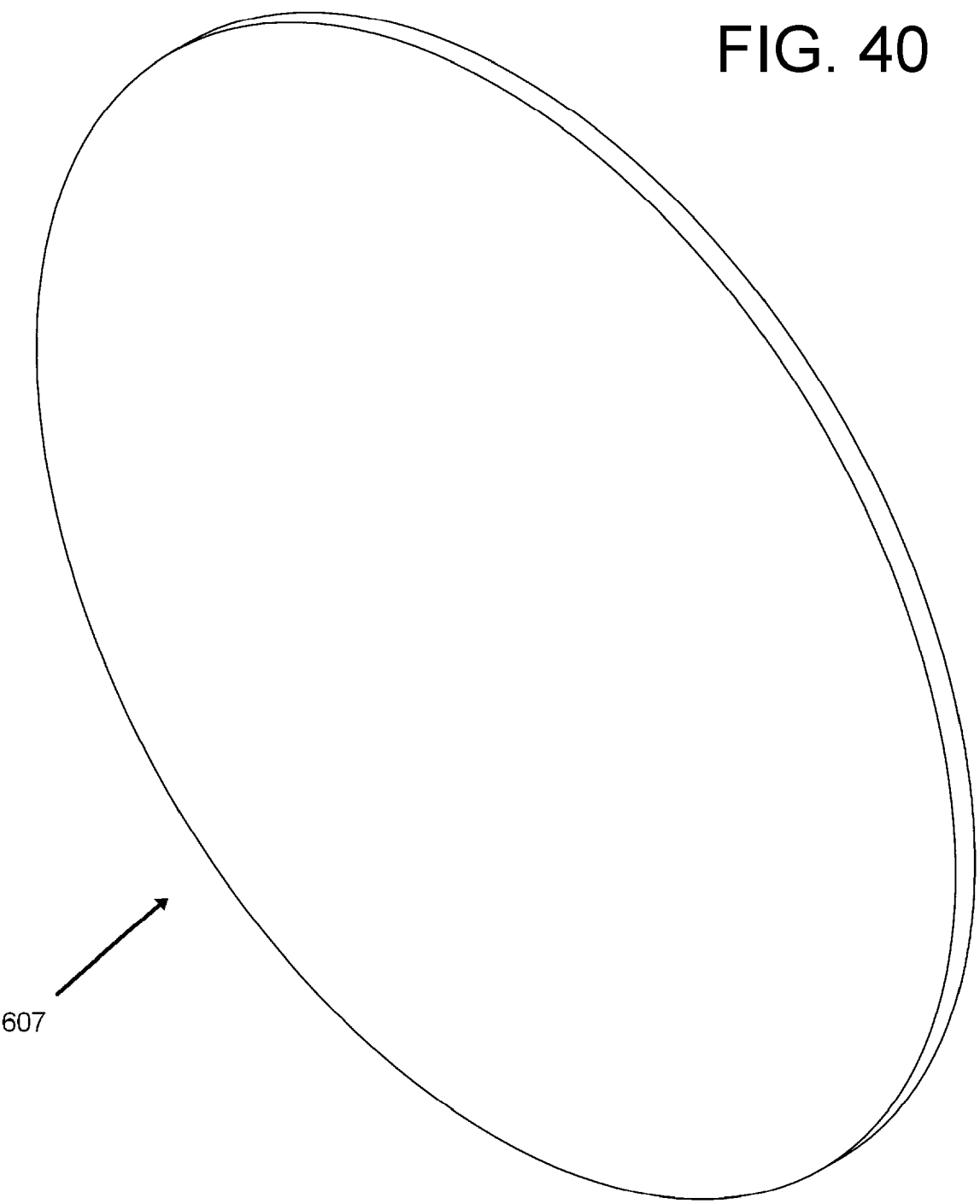
FIG. 40 is a perspective view of one possible exemplification of a microfiber patch.

FIG. 40 is a perspective view of one possible exemplification of a microfiber patch 607 that may be adhered to a housing top of the present application.

Figure 41:
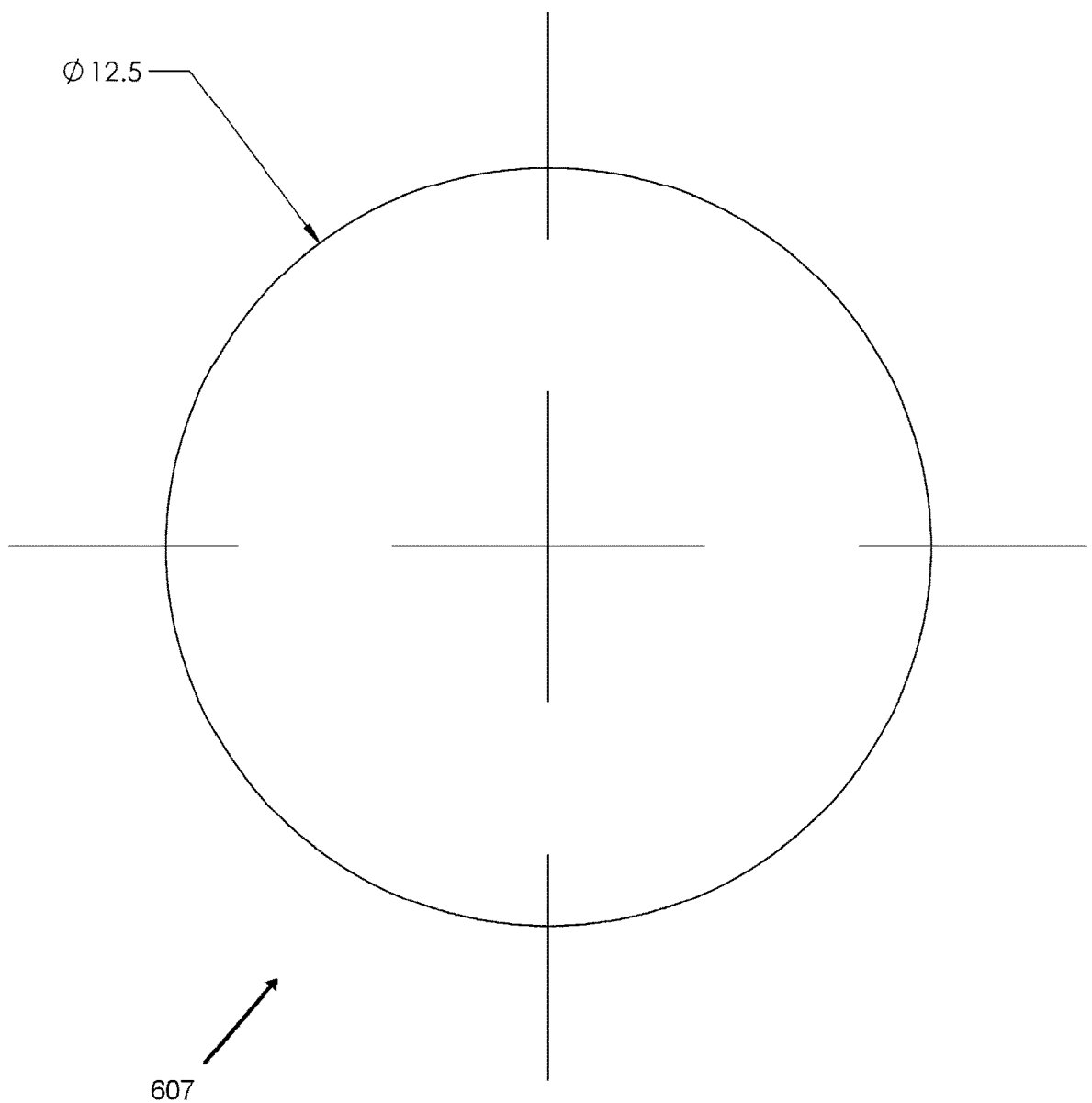
FIG. 41 shows a front view of the microfiber patch.

FIG. 41 shows a front view of the microfiber patch 607.

Figure 42:
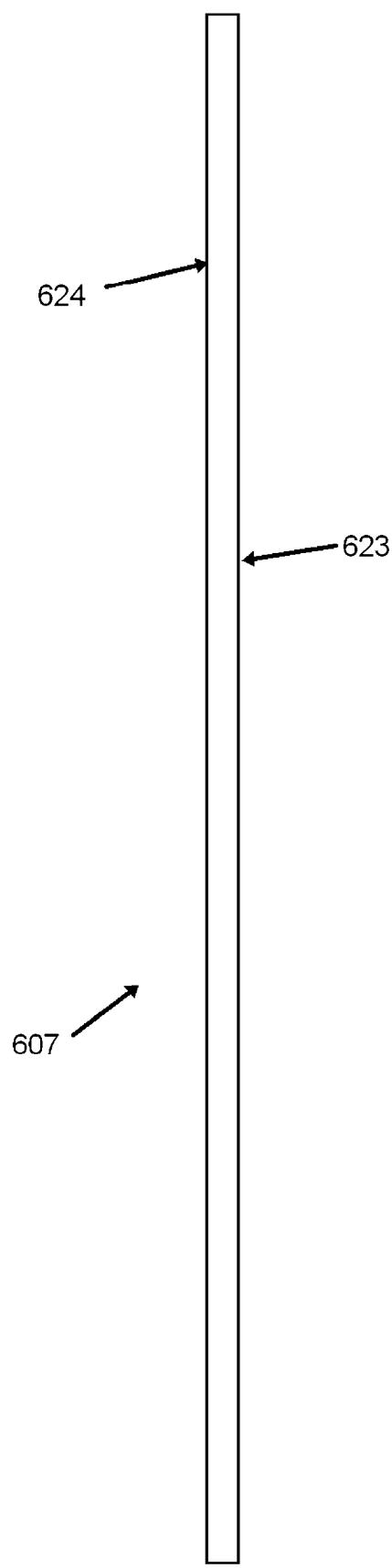
FIG. 42 shows a side view of the microfiber patch.

FIG. 42 shows a side view of the microfiber patch 607. The microfiber patch 607 comprises two sides. One side 623 is configured to be adhered to the housing top, and the opposite site 624 is configured to be exposed.

Figure 43:
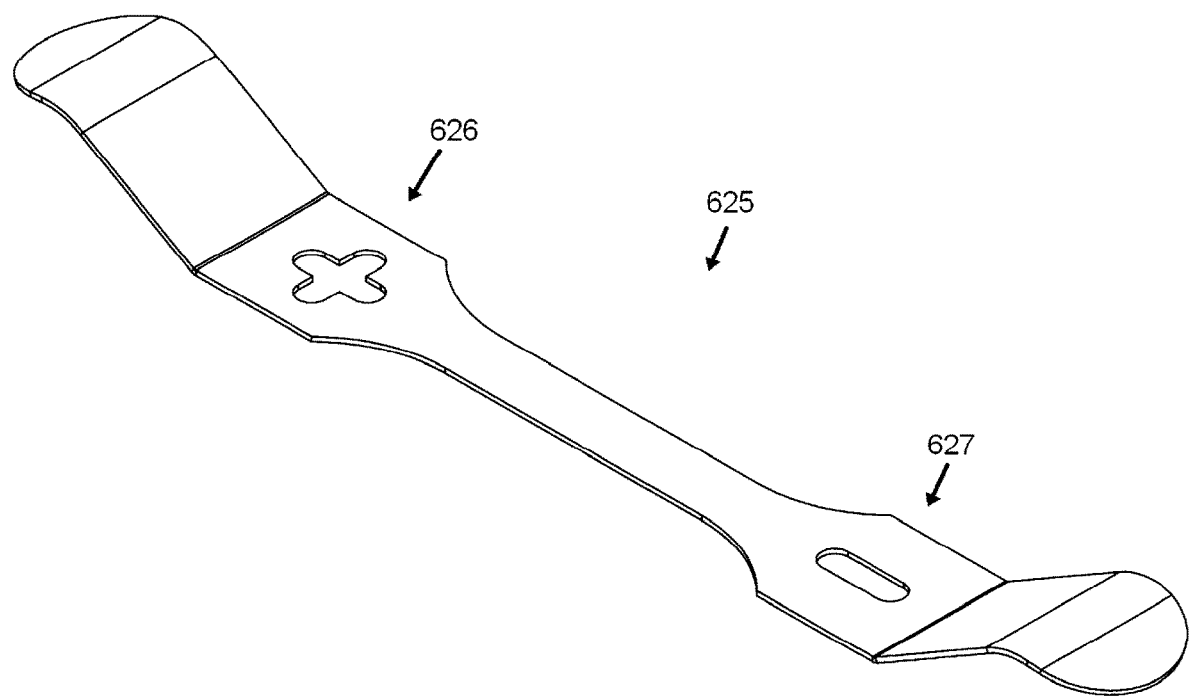
FIG. 43 shows a first battery contact.

FIG. 43 shows a first battery contact 625. The battery contact 625 may be comprised of beryllium copper C172 alloy, ½-hard heat transfer after forming to ½ HT temper, with a finish of electroless nickel plate. The battery contact 625 has a positive contact point 626 and a negative contact point 627, so that it will contact two batteries during use.

Figure 44:
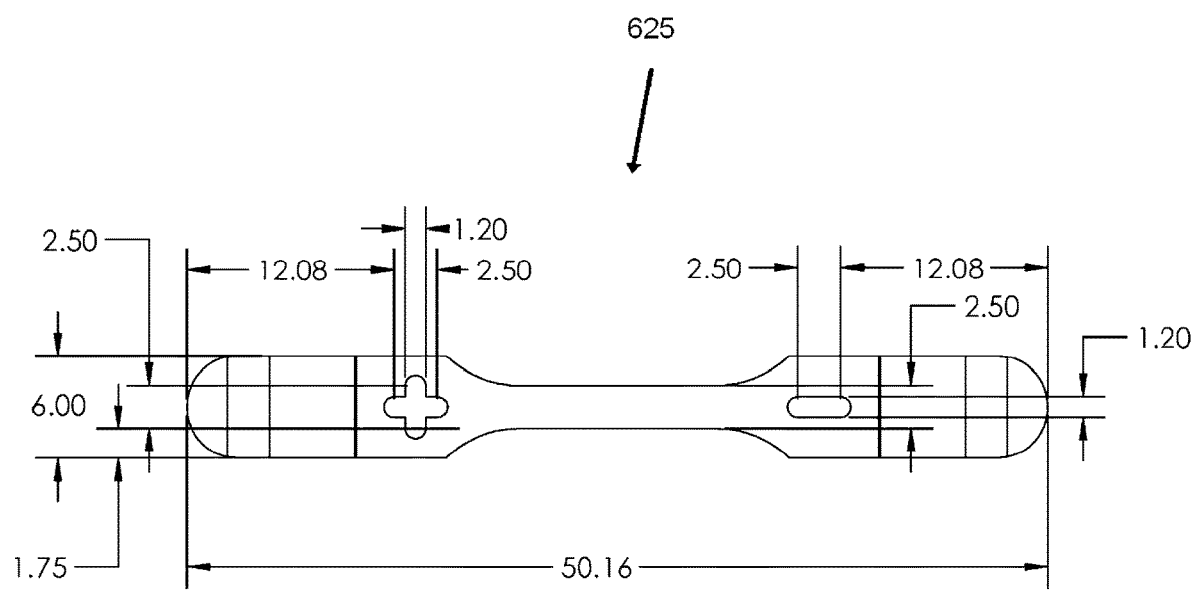
FIG. 44 is a top view of the first battery contact.

FIG. 44 is a top view of the battery contact 625.

Figure 45:
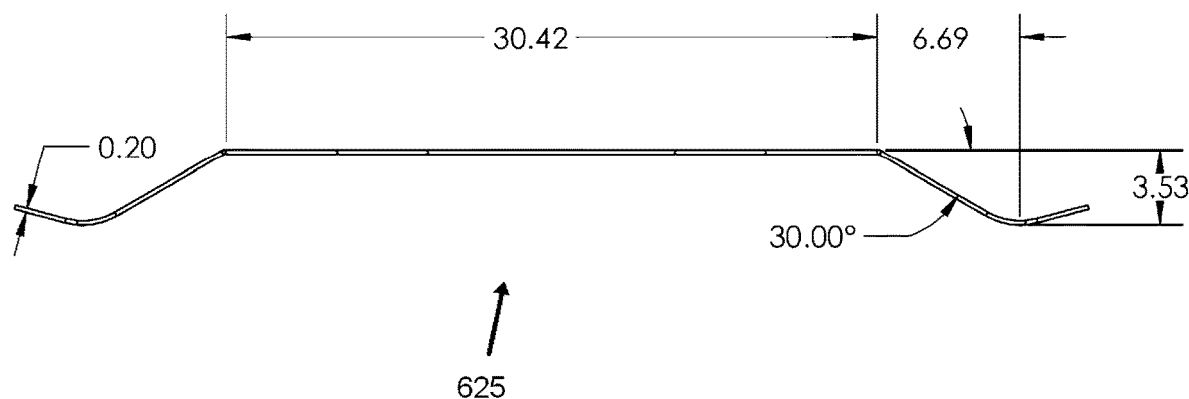
FIG. 45 is a side view of the first battery contact.

FIG. 45 is a side view of the battery contact 625.

Figure 46:
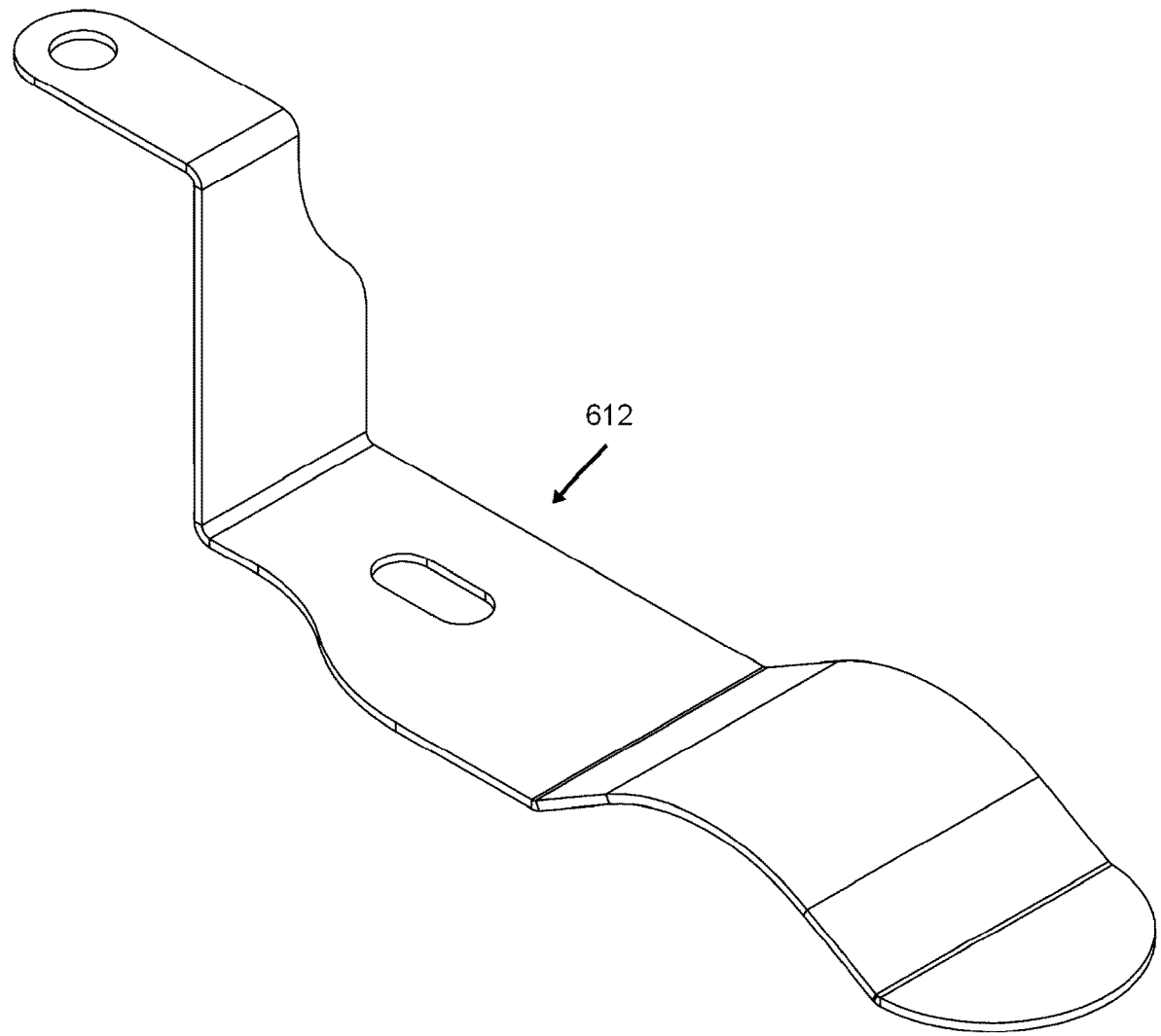
FIG. 46 shows a perspective view of a second battery contact.

FIG. 46 shows a perspective view of battery contact 612. The battery contact 612 may be comprised of beryllium copper C172 alloy, ½-hard heat transfer after forming to ½ HT temper, with a finish of electroless nickel plate.

Figure 47:
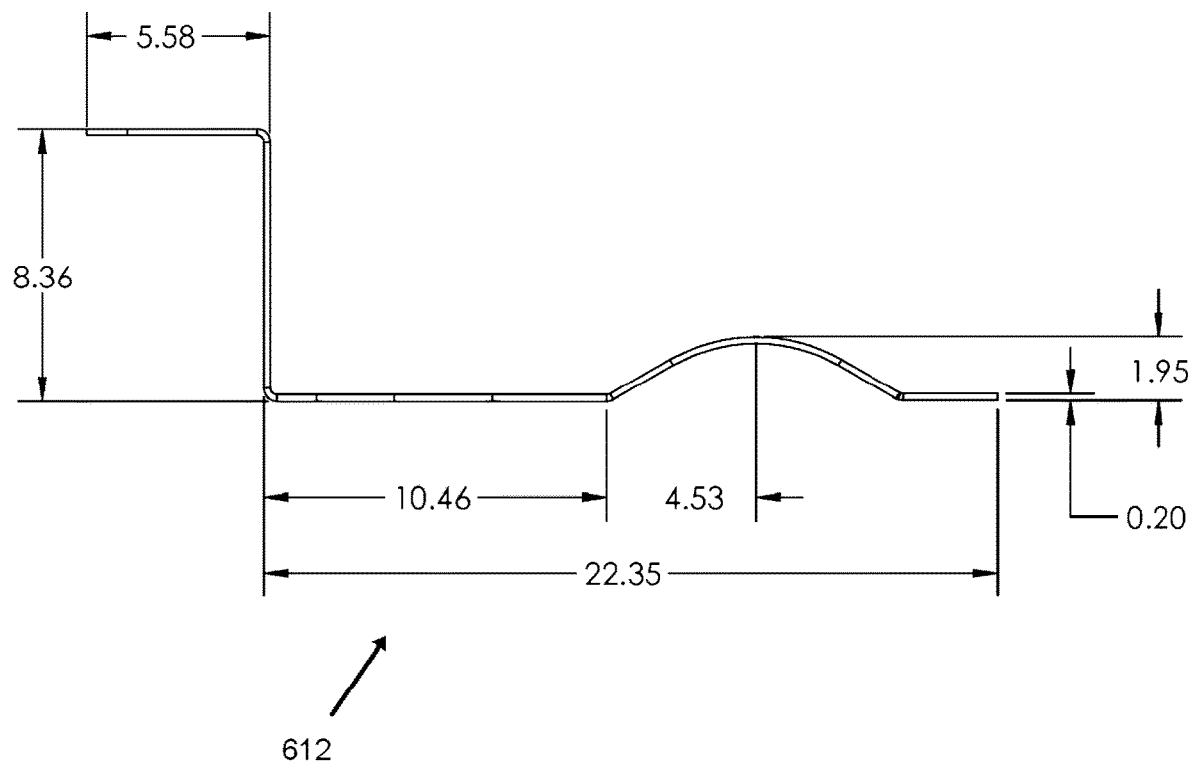
FIG. 47 shows a side view of the second battery contact.

FIG. 47 shows a side view of the battery contact 612.

Figure 48:
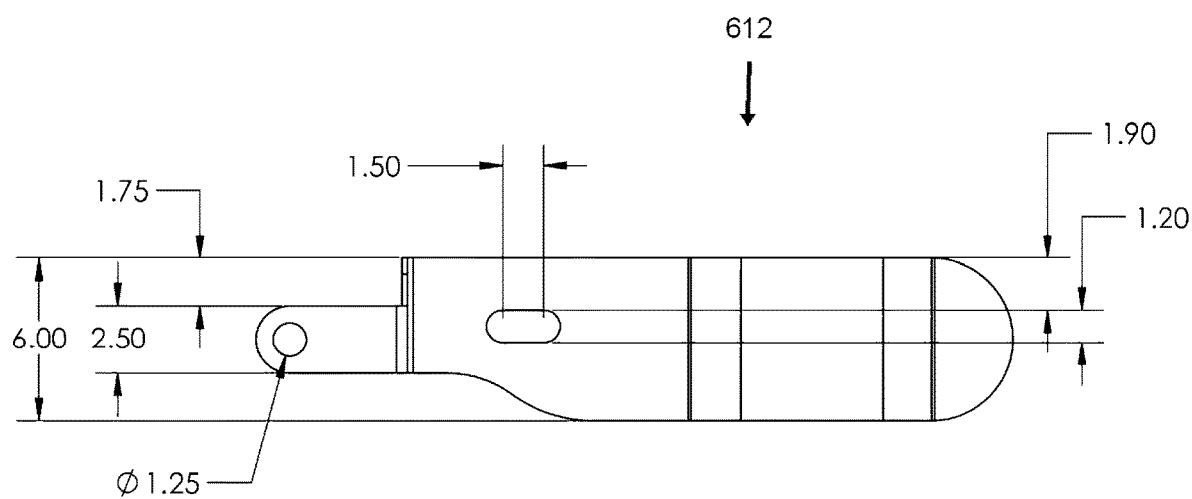
FIG. 48 shows a top view of the second battery contact.

FIG. 48 shows a top view of the battery contact 612.

Figure 49:
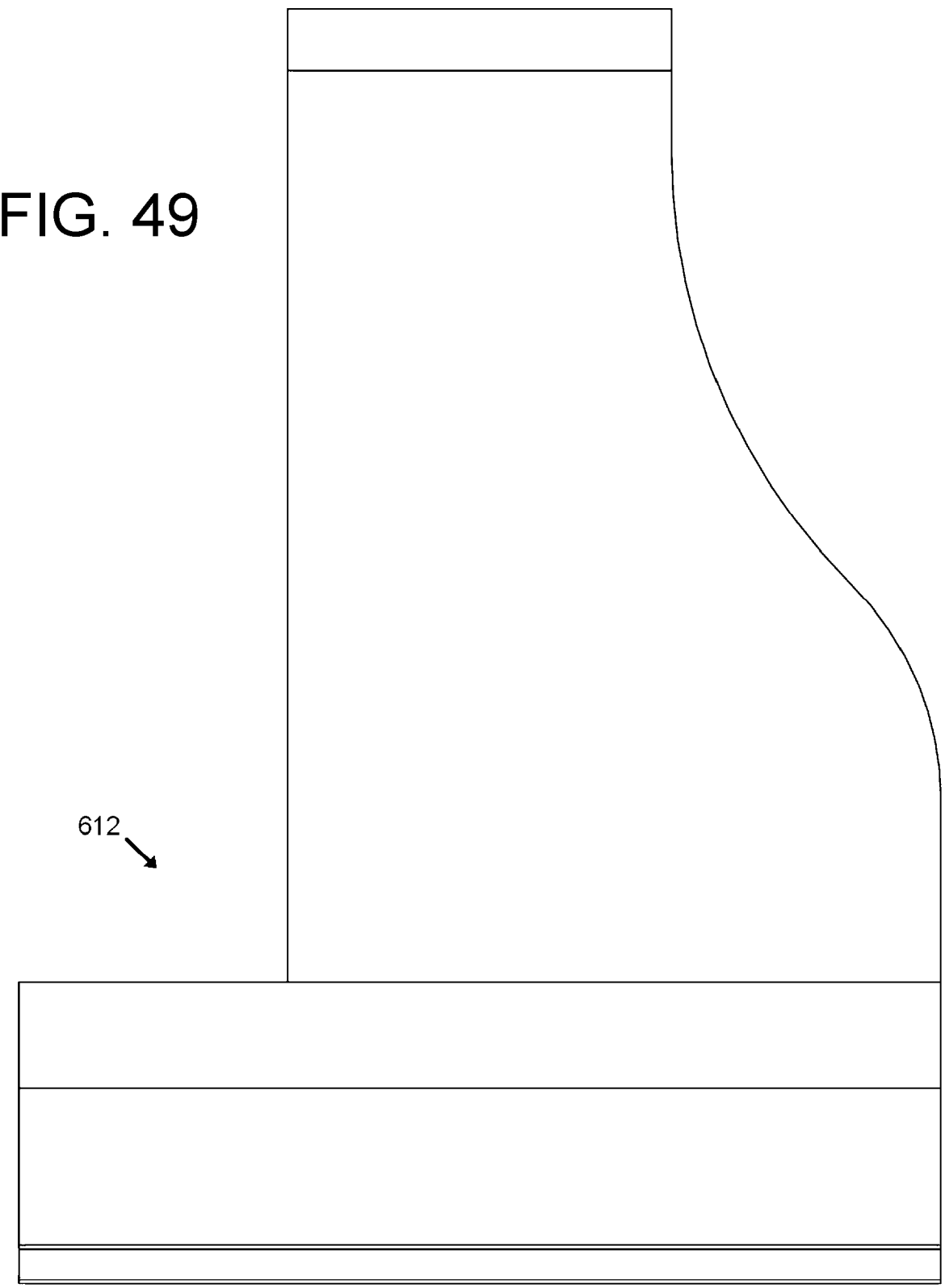
FIG. 49 shows a different side view of the second battery contact.

FIG. 49 shows a different side view of the battery contact 612.

Figure 50:
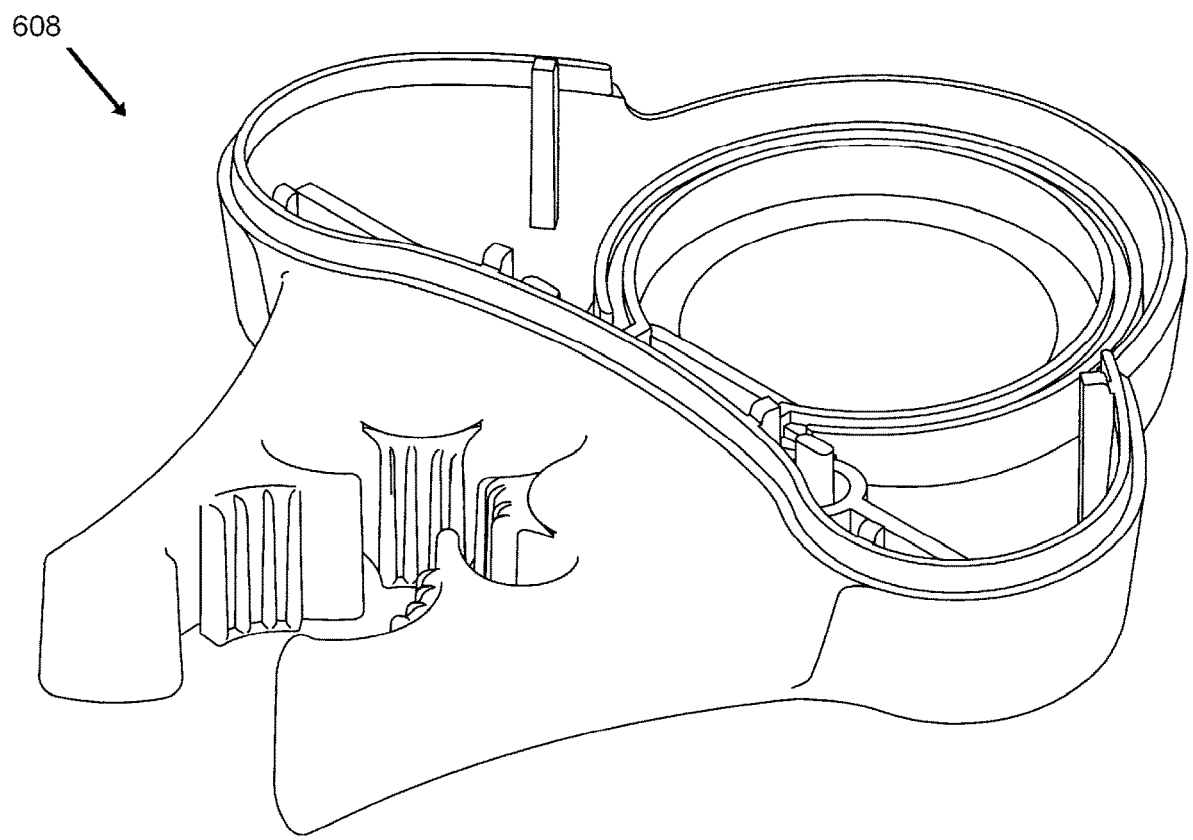
FIG. 50 shows a perspective view of a housing bottom.

FIG. 50 shows a perspective view of a housing bottom 608.

Figure 51:
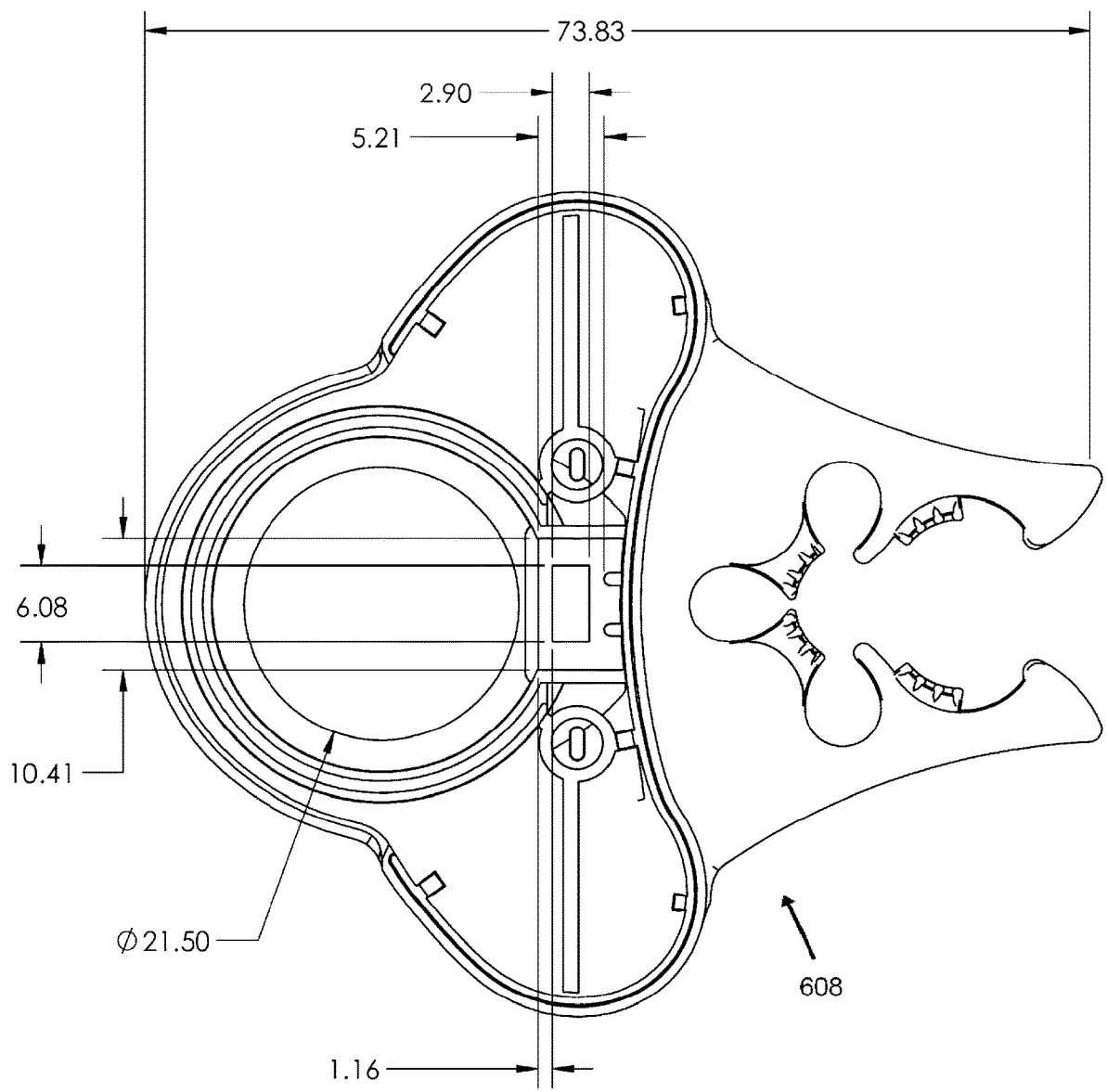
FIG. 51 shows a top view of the housing bottom.

FIG. 51 shows a top view of the housing bottom 608. Some areas of the housing bottom 608 may be overmolded with textin Rx170A.

Figure 52:
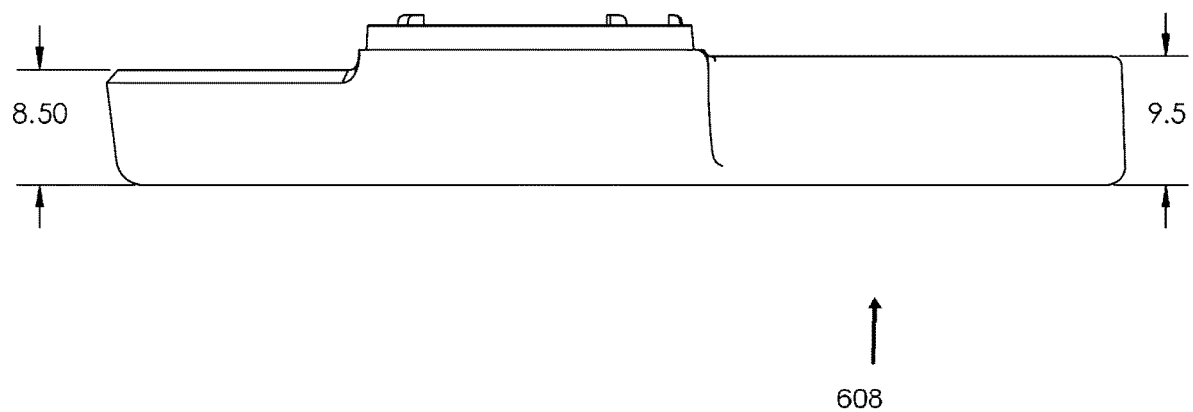
FIG. 52 shows a side view of the housing bottom.

FIG. 52 shows a side view of the housing bottom 608.

Figure 53:
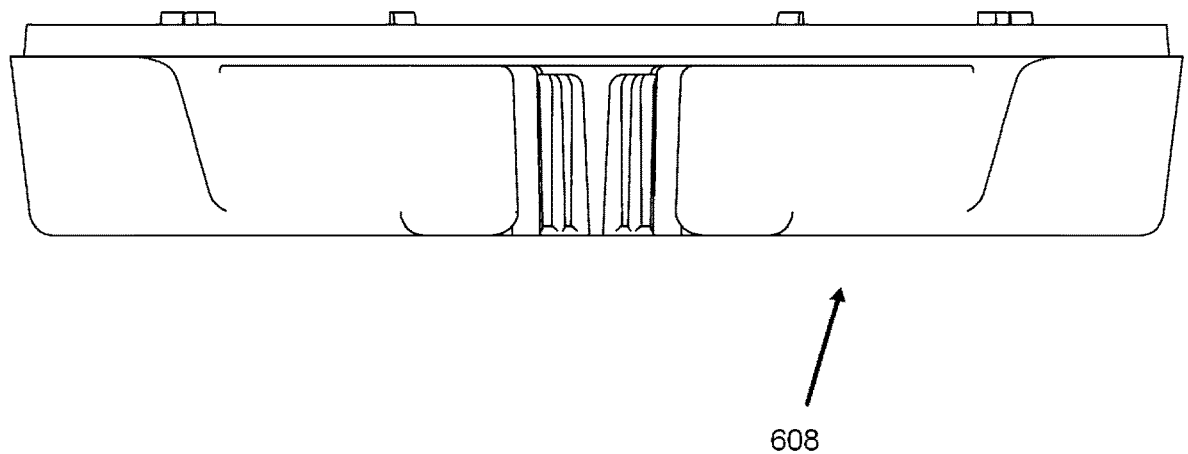
FIG. 53 shows a different side view of the housing bottom.

FIG. 53 shows a different side view of the housing bottom 608.

Figure 54:
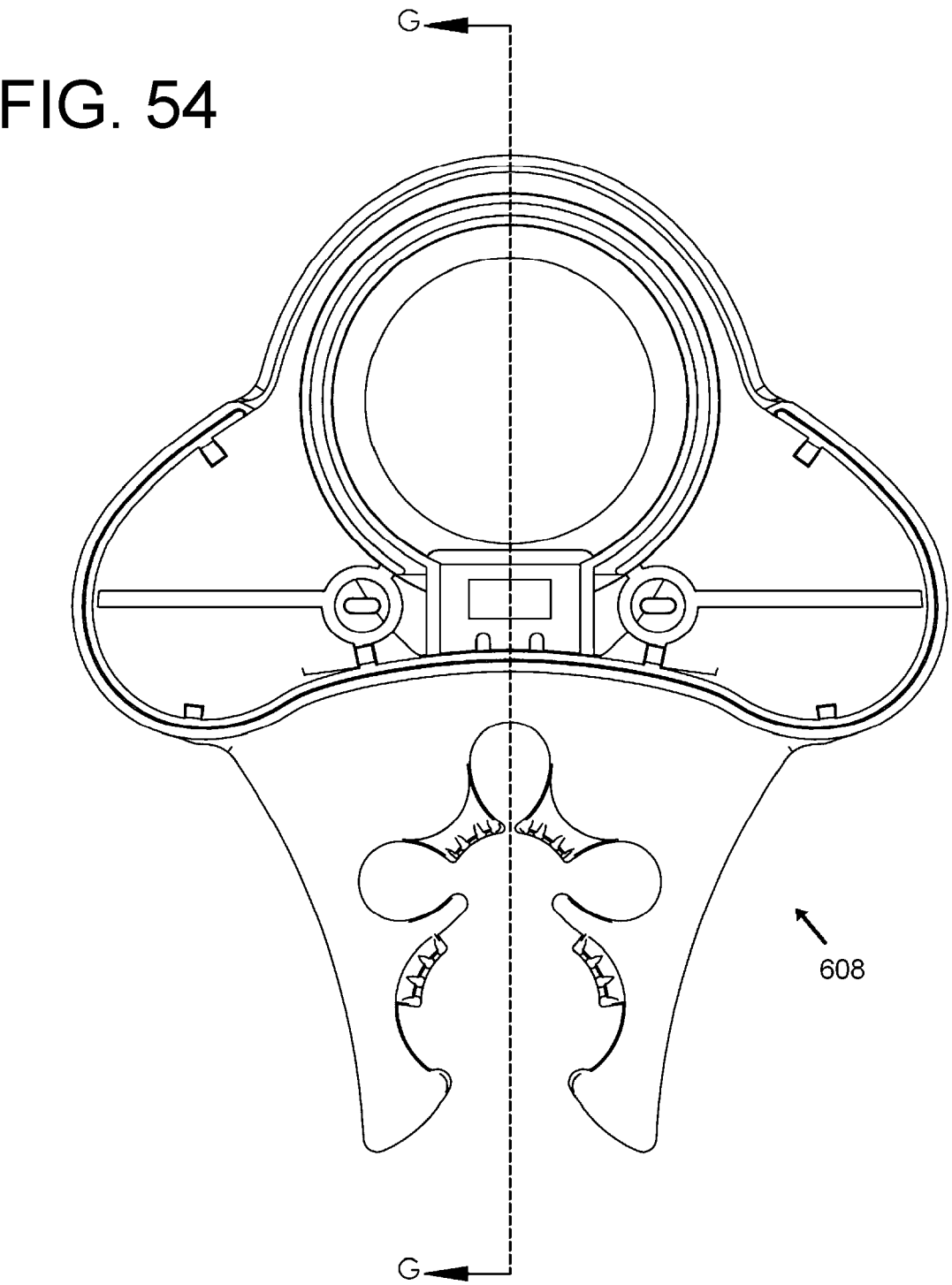
FIG. 54 shows a top view of the housing bottom.

FIG. 54 shows a top view of the housing bottom 608 with a line G-G to show where a cross-sectional cut is being taken.

Figure 55:
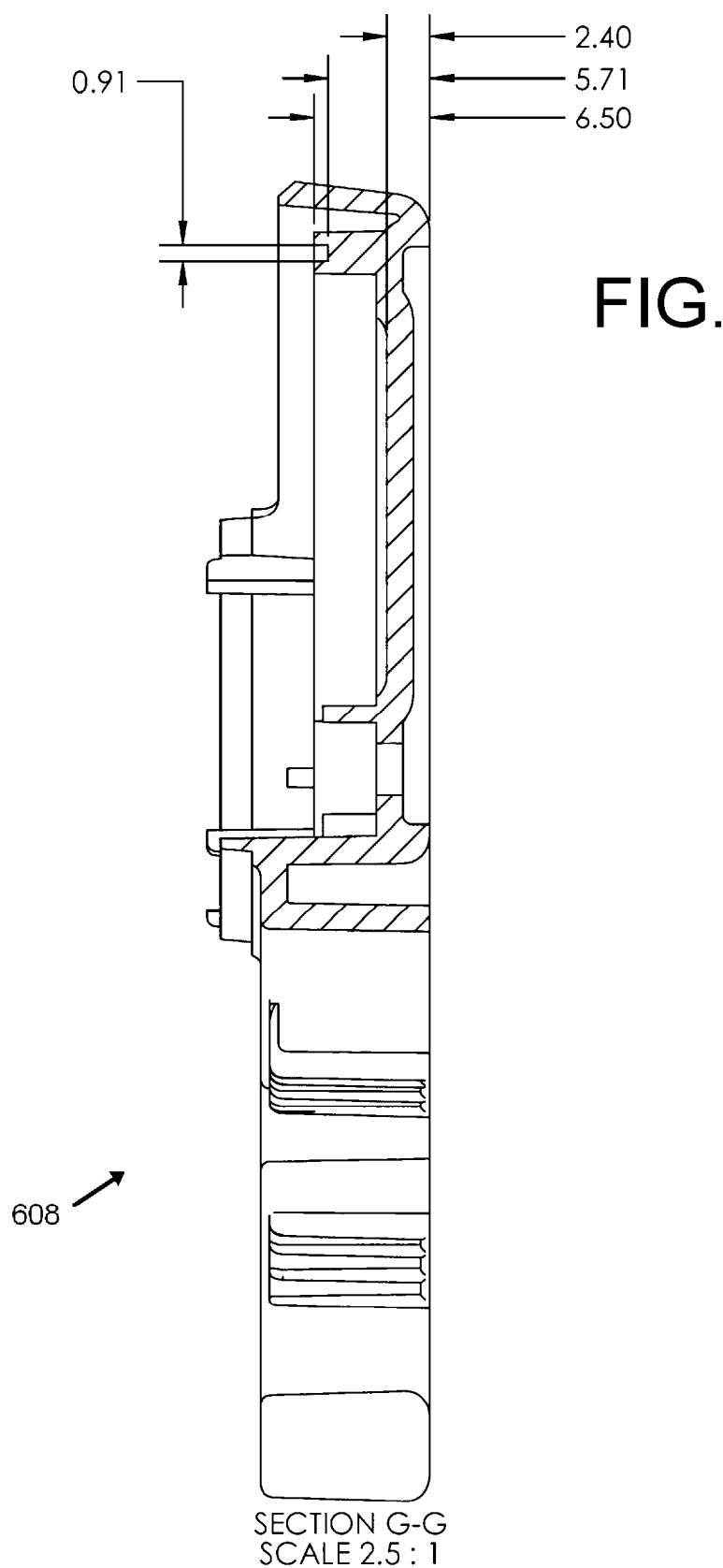
FIG. 55 shows a cross-section of the housing bottom.

FIG. 55 shows the cross-section of the housing bottom 608 as shown in FIG. 54.

Figure 56:
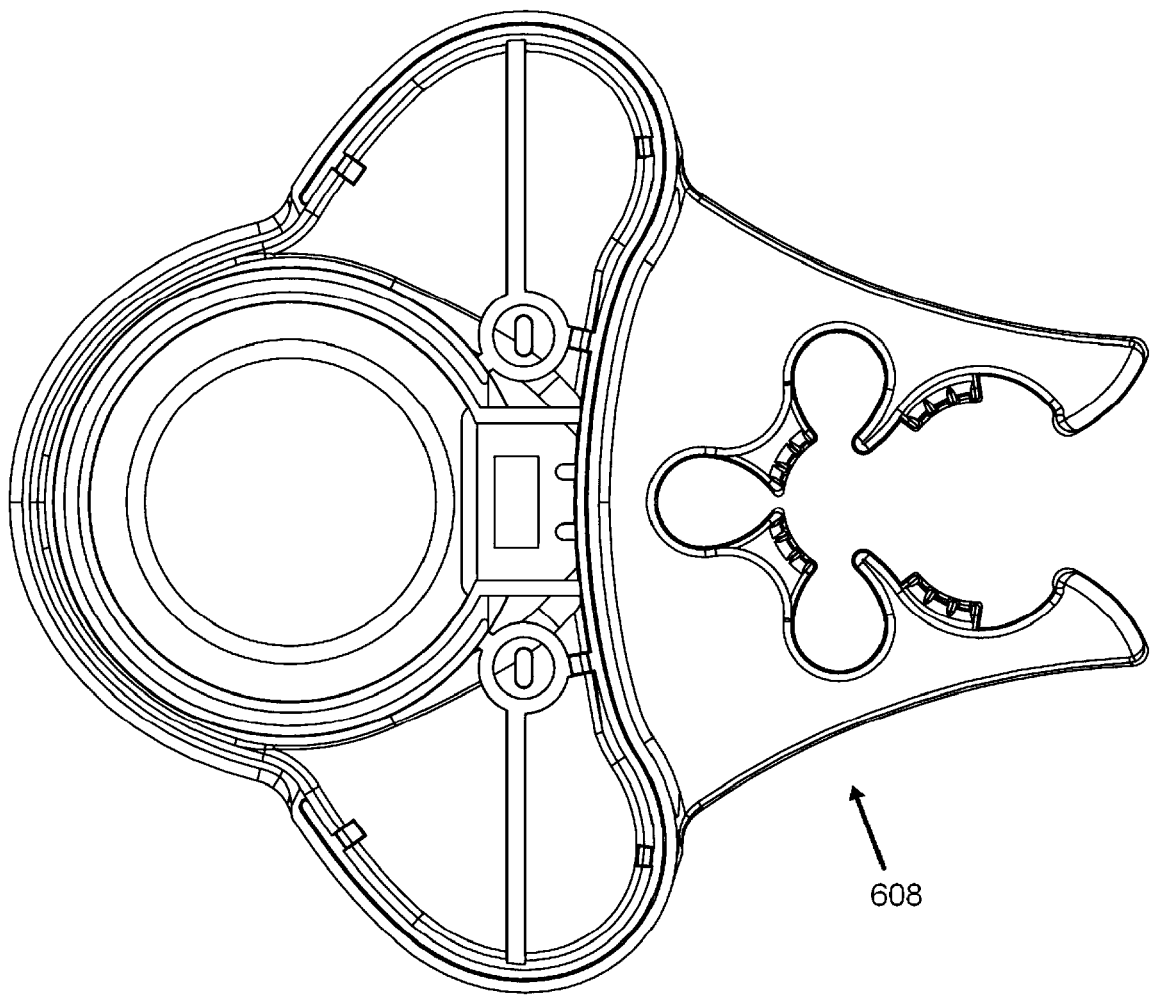
FIG. 56 shows another top view of the housing bottom.

FIG. 56 shows another top view of the housing bottom 608.

Figure 57:
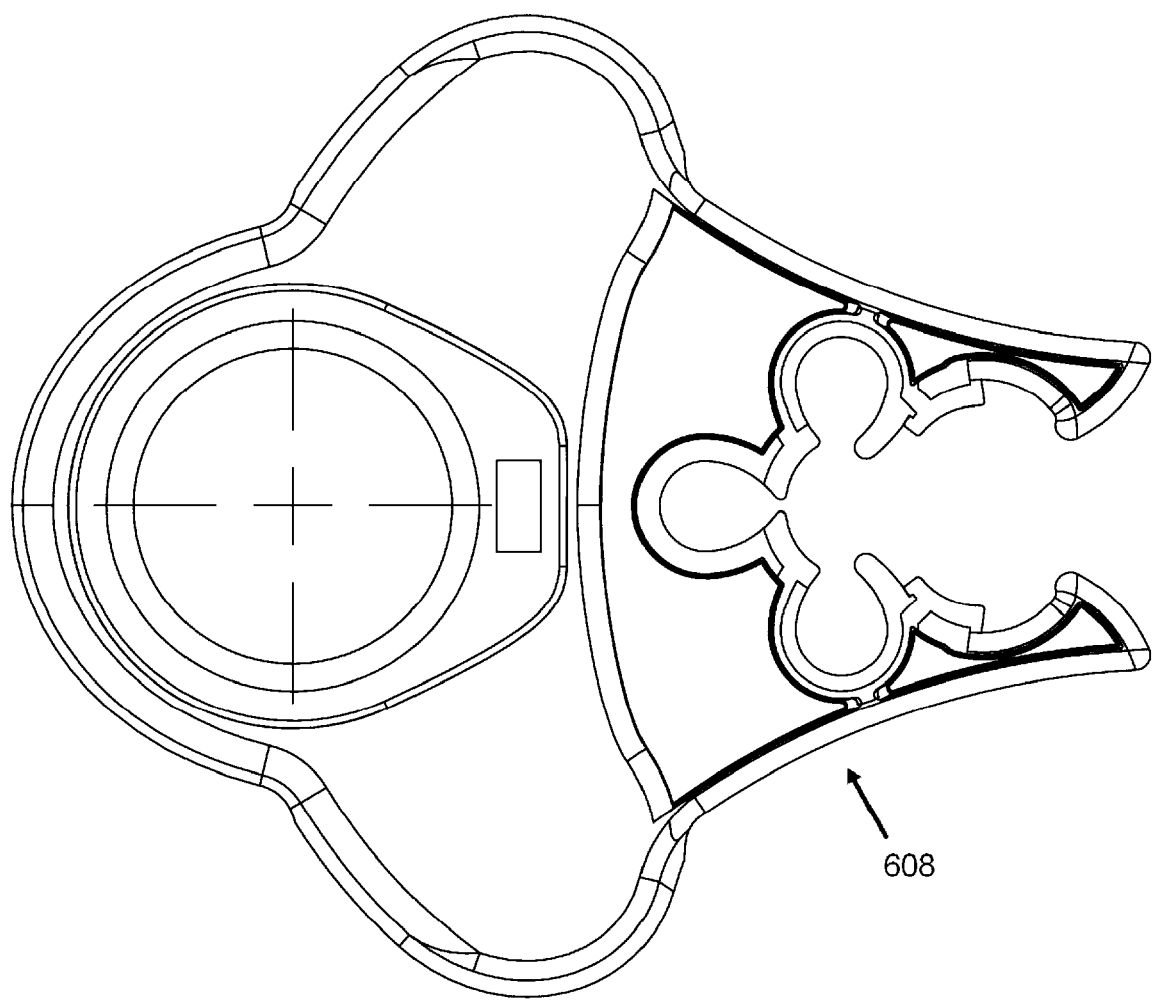
FIG. 57 shows the bottom view of the housing bottom.

FIG. 57 shows the bottom view of the housing bottom 608.

Figure 58:
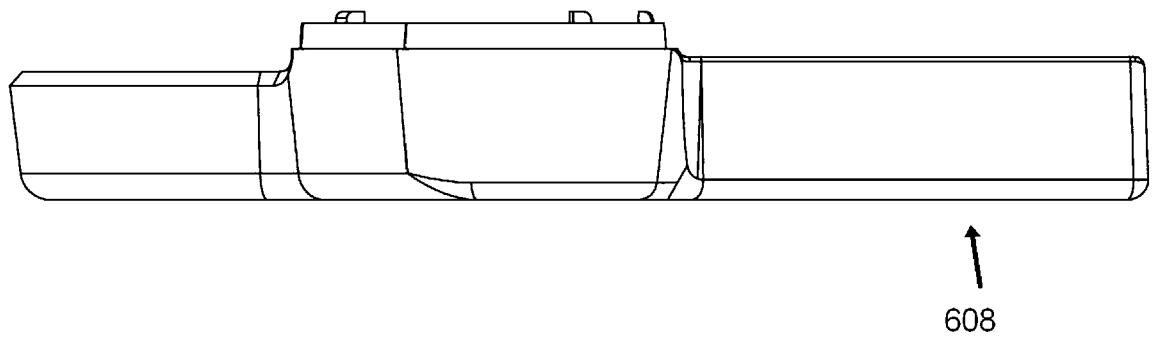
FIG. 58 shows a side view of the housing bottom.

FIG. 58 shows a side view of the housing bottom 608.

Figure 59:
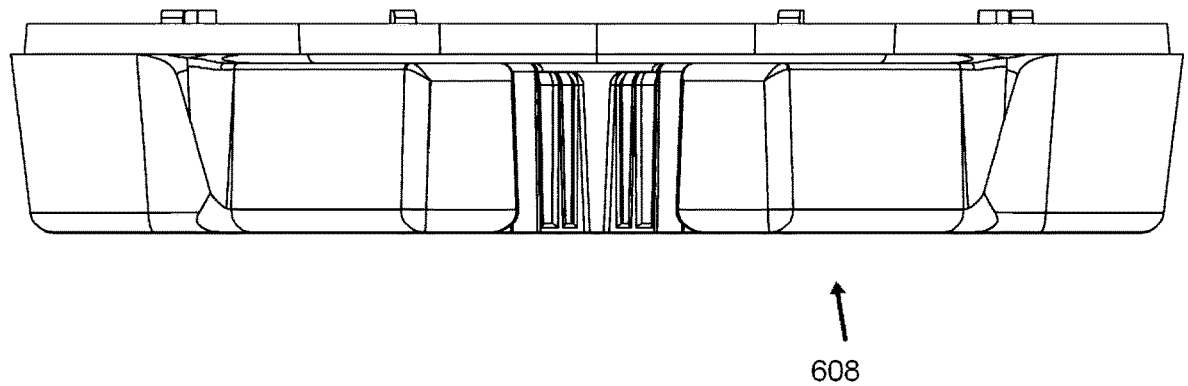
FIG. 59 shows a front view of the housing bottom.

FIG. 59 shows a front view of the housing bottom 608.

Figure 60:
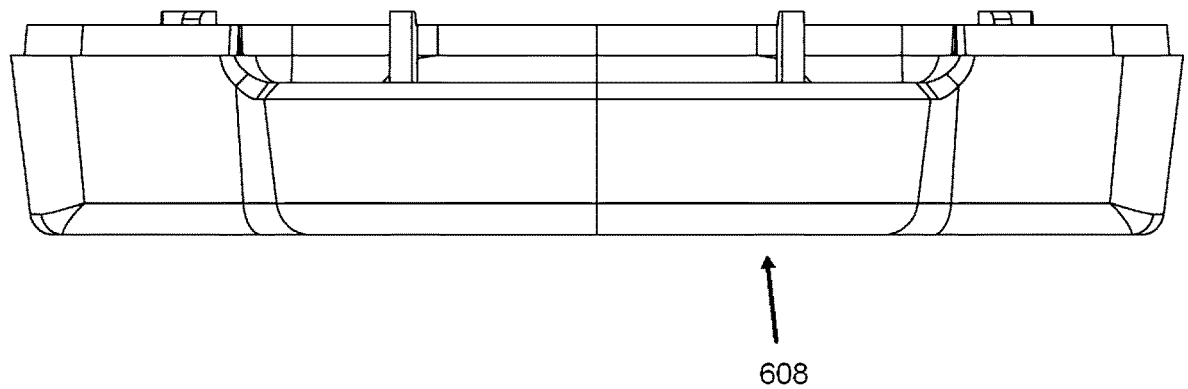
FIG. 60 shows a back view of the housing bottom.

FIG. 60 shows a back view of the housing bottom 608.

Figure 61:
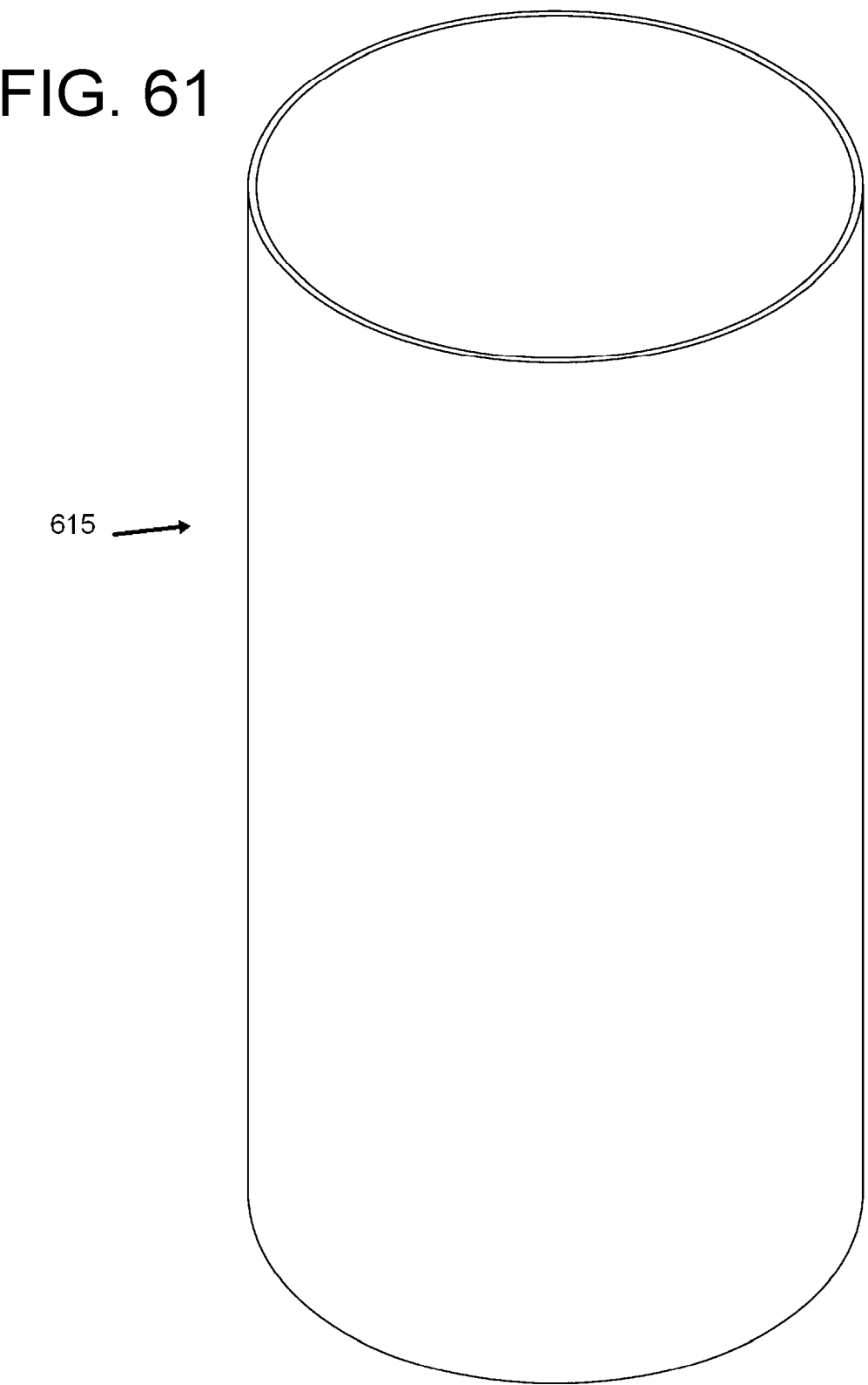
FIG. 61 shows a perspective view of a reservoir.

FIG. 61 shows a perspective view of a reservoir 615.

Figure 62:
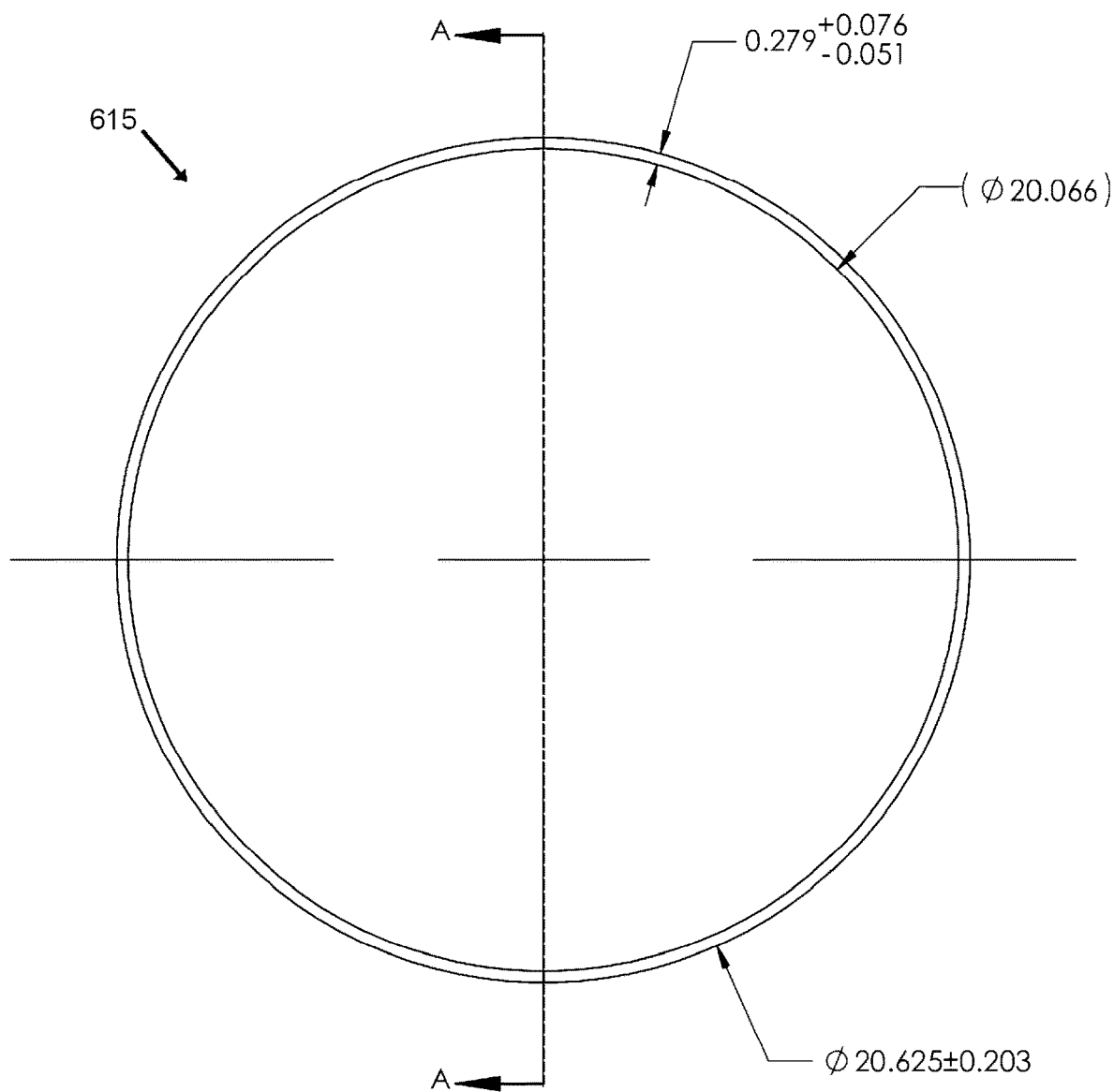
FIG. 62 shows a top view of the reservoir.

FIG. 62 shows a top view of the reservoir 615 with a line A-A to show where a cross-sectional cut is being taken.

Figure 63:
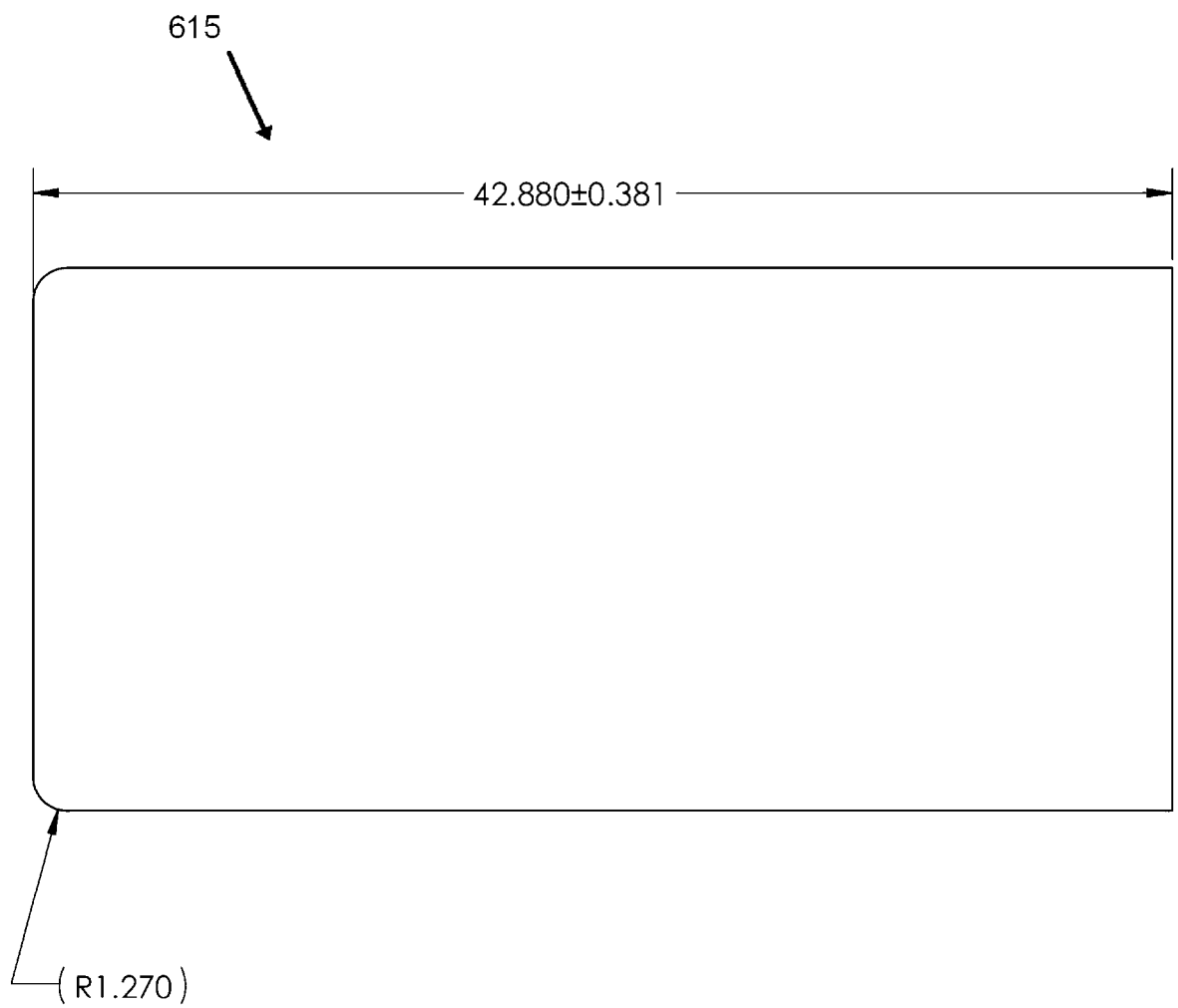
FIG. 63 shows a side view of the reservoir.

FIG. 63 shows a side view of the reservoir 615.

Figure 64:
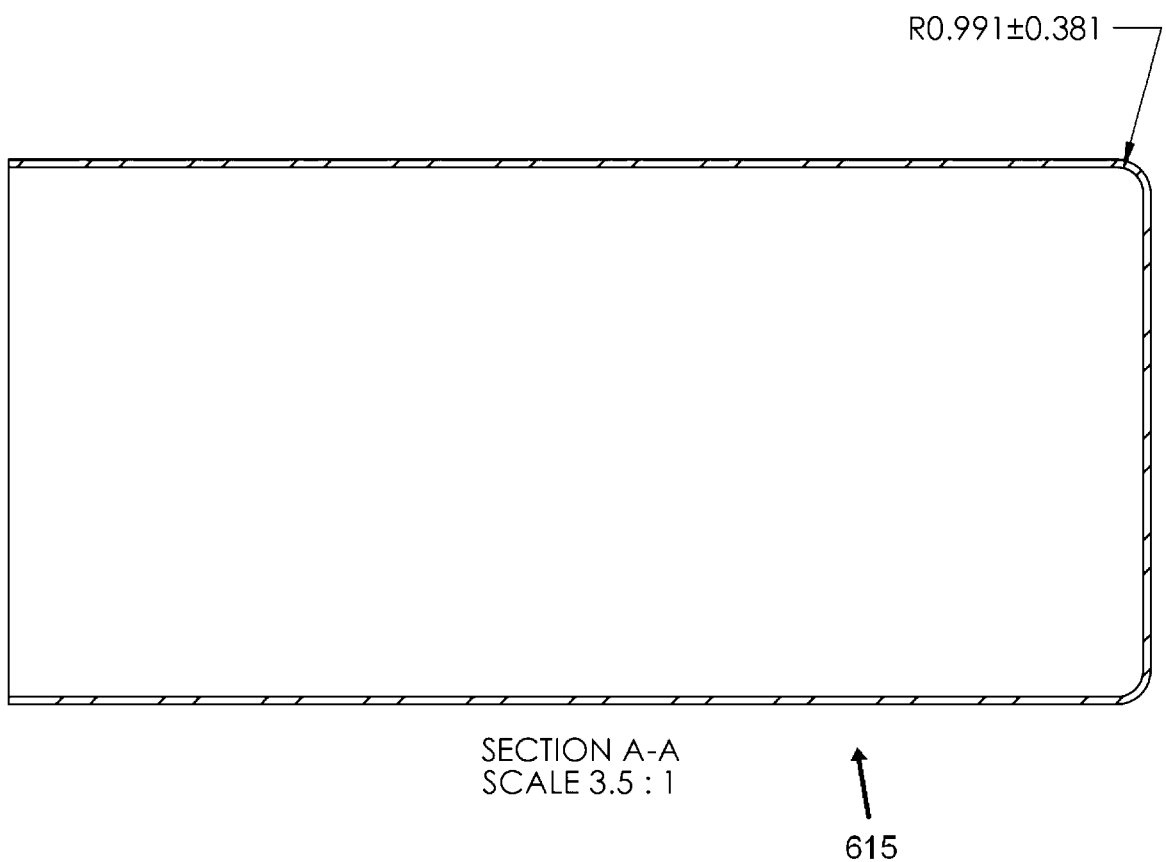
FIG. 64 shows a cross-section of the reservoir.

FIG. 64 shows a cross-section of the reservoir 615 as shown in FIG. 62.

Figure 65:
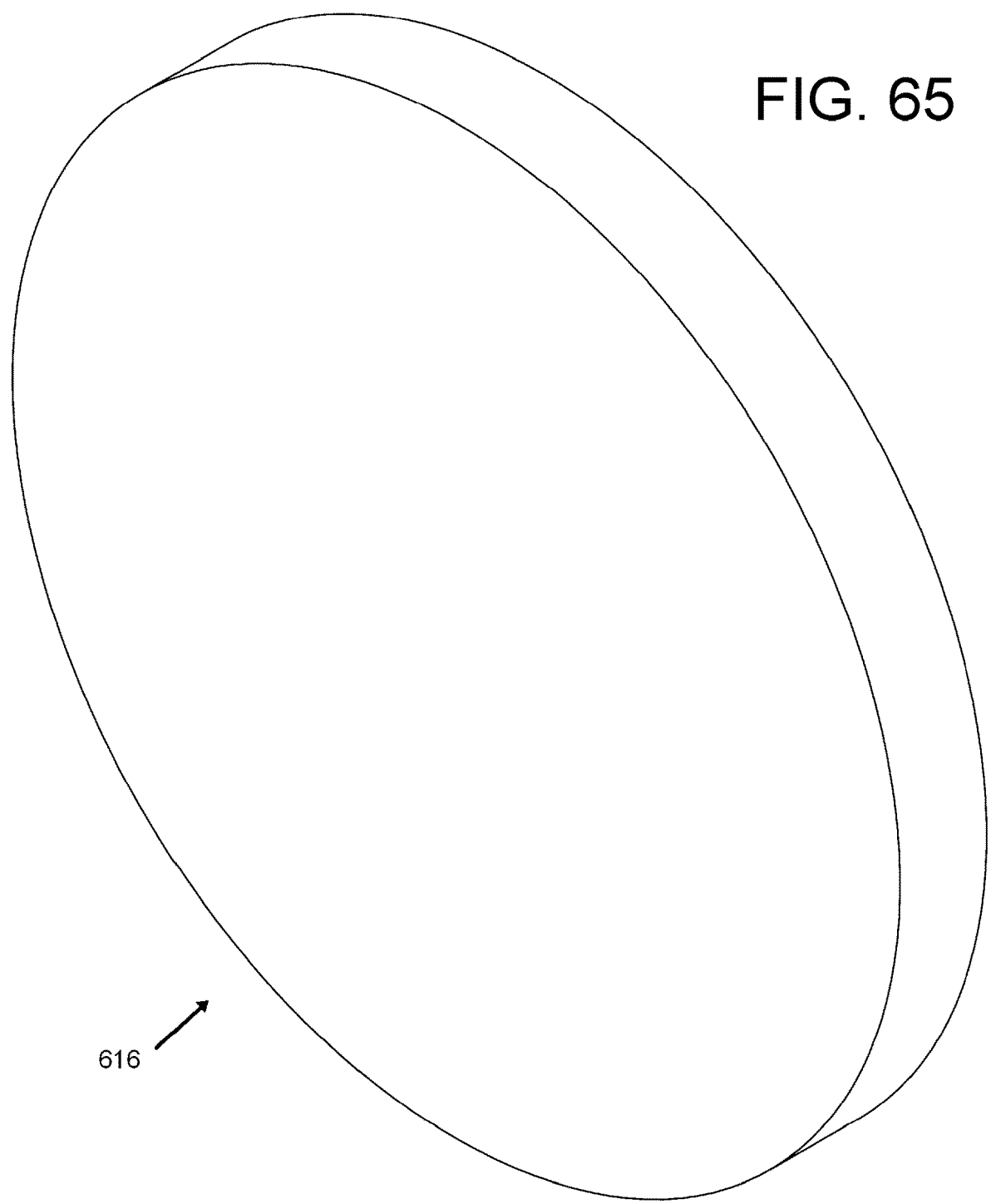
FIG. 65 is a perspective view of a reservoir sponge.

FIG. 65 is a perspective view of a reservoir sponge 616.

Figure 66:
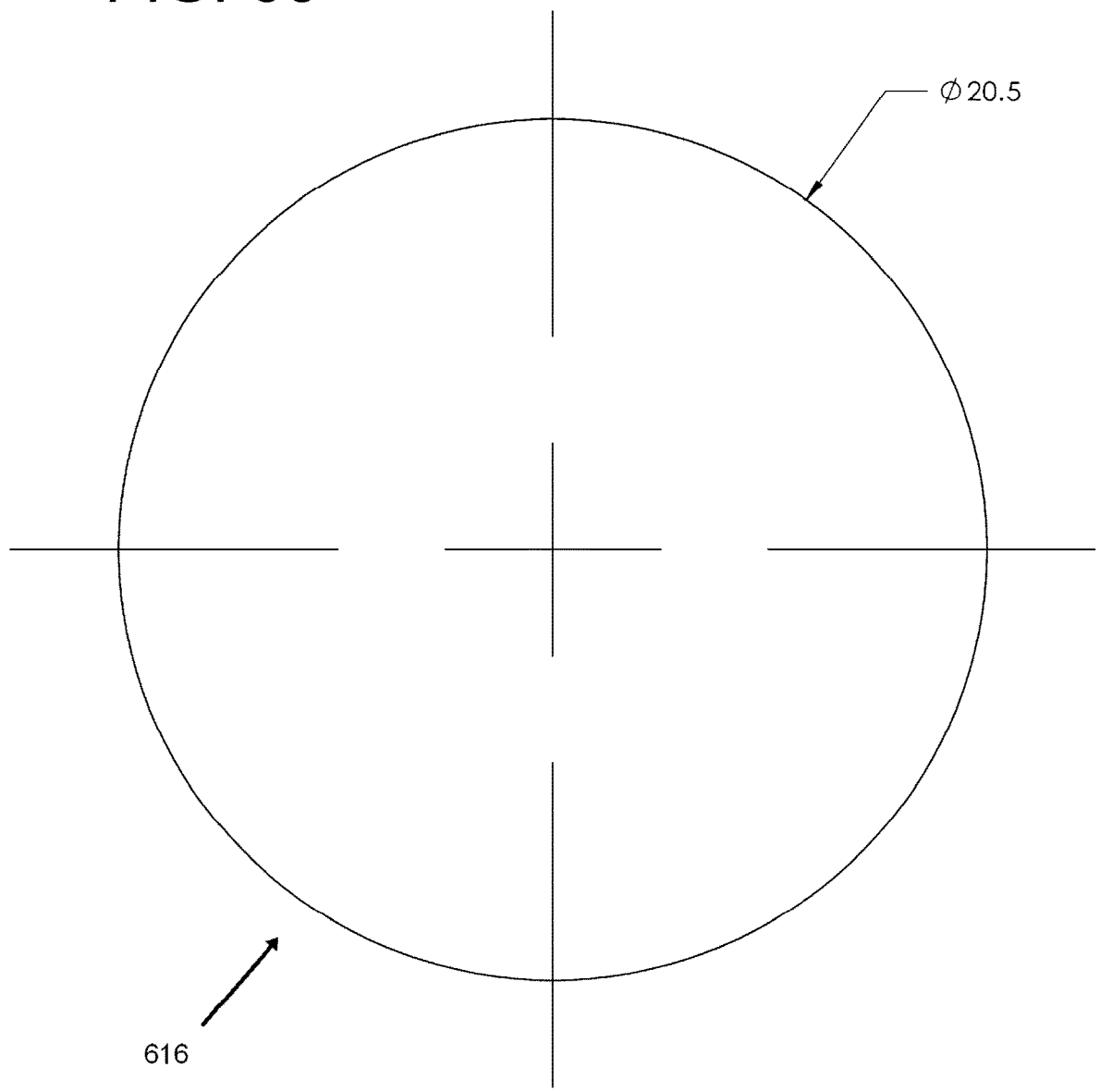
FIG. 66 shows a front view of the reservoir sponge.

FIG. 66 shows a front view of the reservoir sponge 616.

Figure 67:
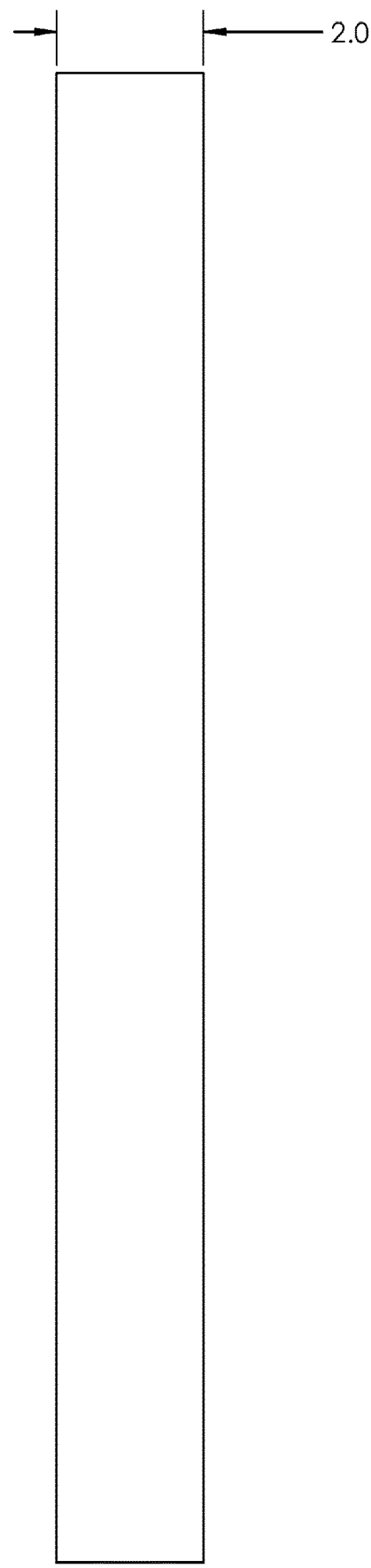
FIG. 67 shows a side view of the reservoir sponge.

FIG. 67 shows a side view of the reservoir sponge 616.

Figure 68:
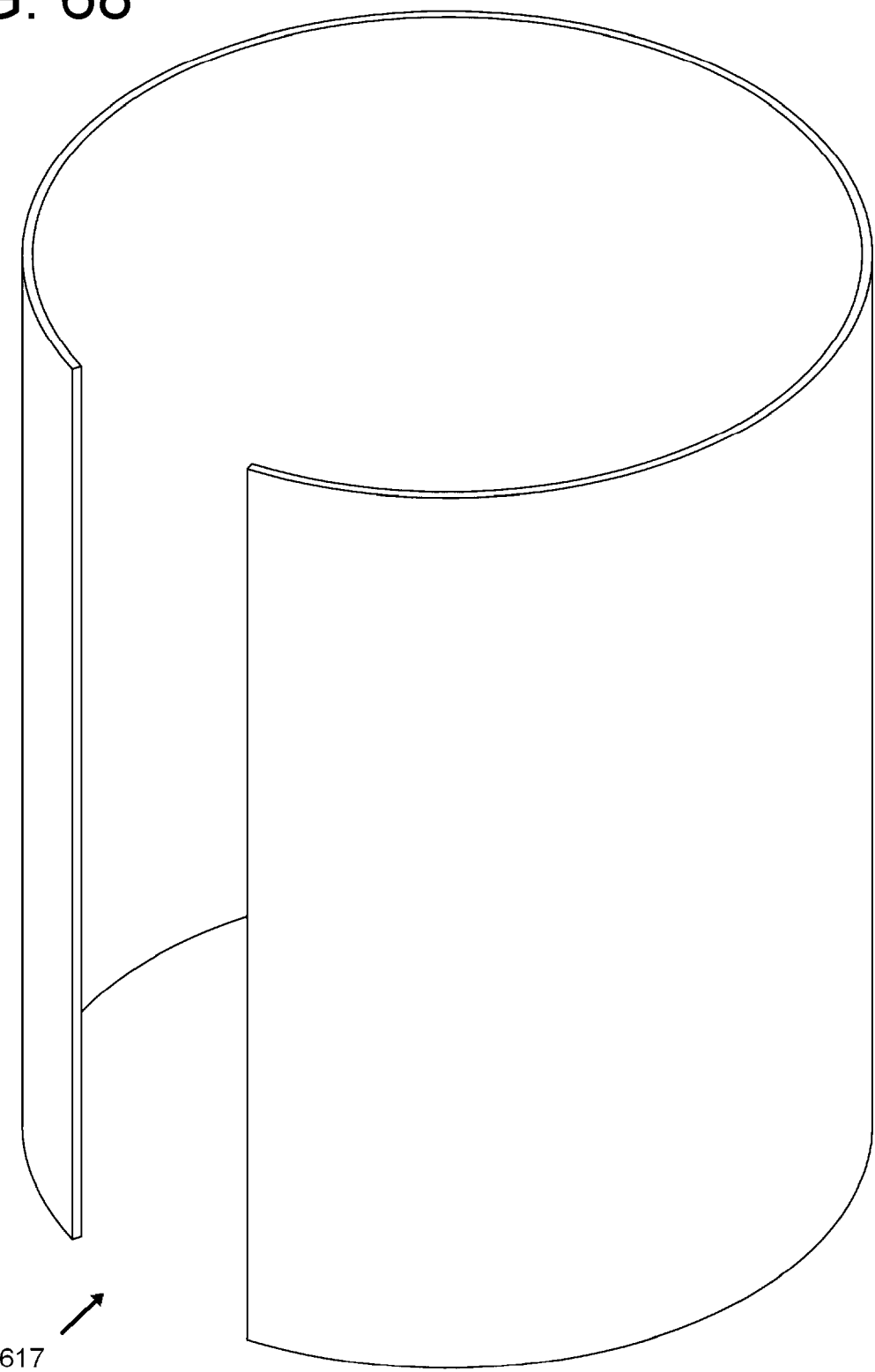
FIG. 68 shows a perspective view of a heater.

FIG. 68 shows a perspective view of a heater 617.

Figure 69:
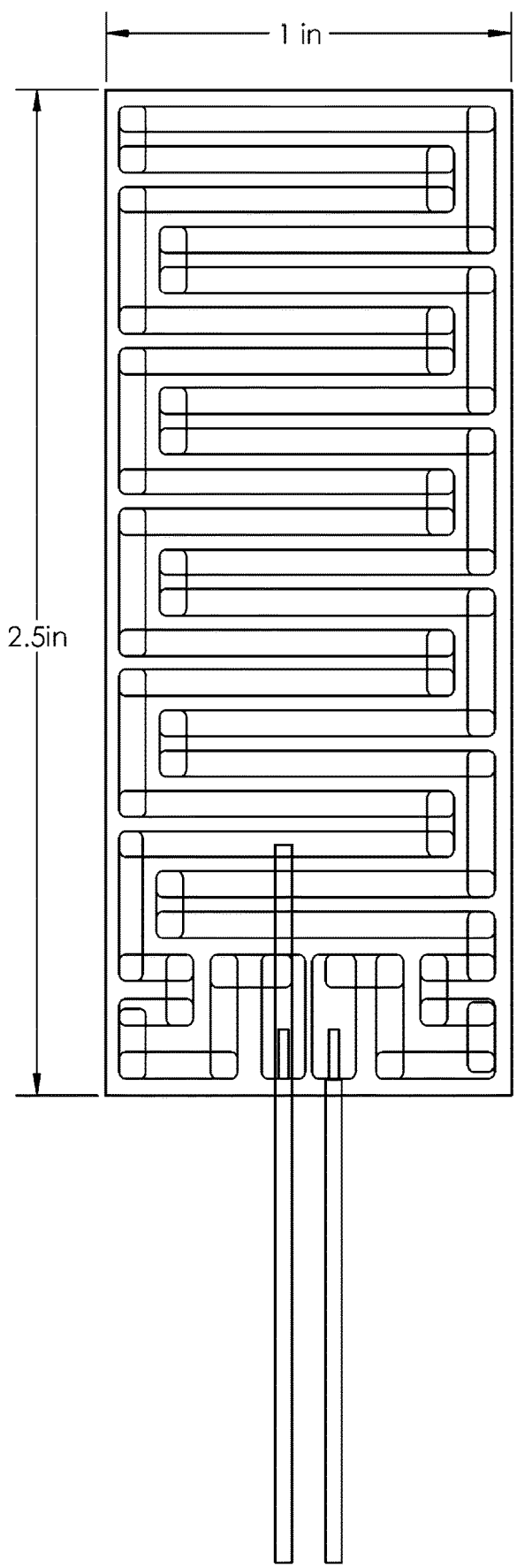
FIG. 69 shows circuitry for the heater.

FIG. 69 shows the circuitry inside the heater 617.

Figure 70:
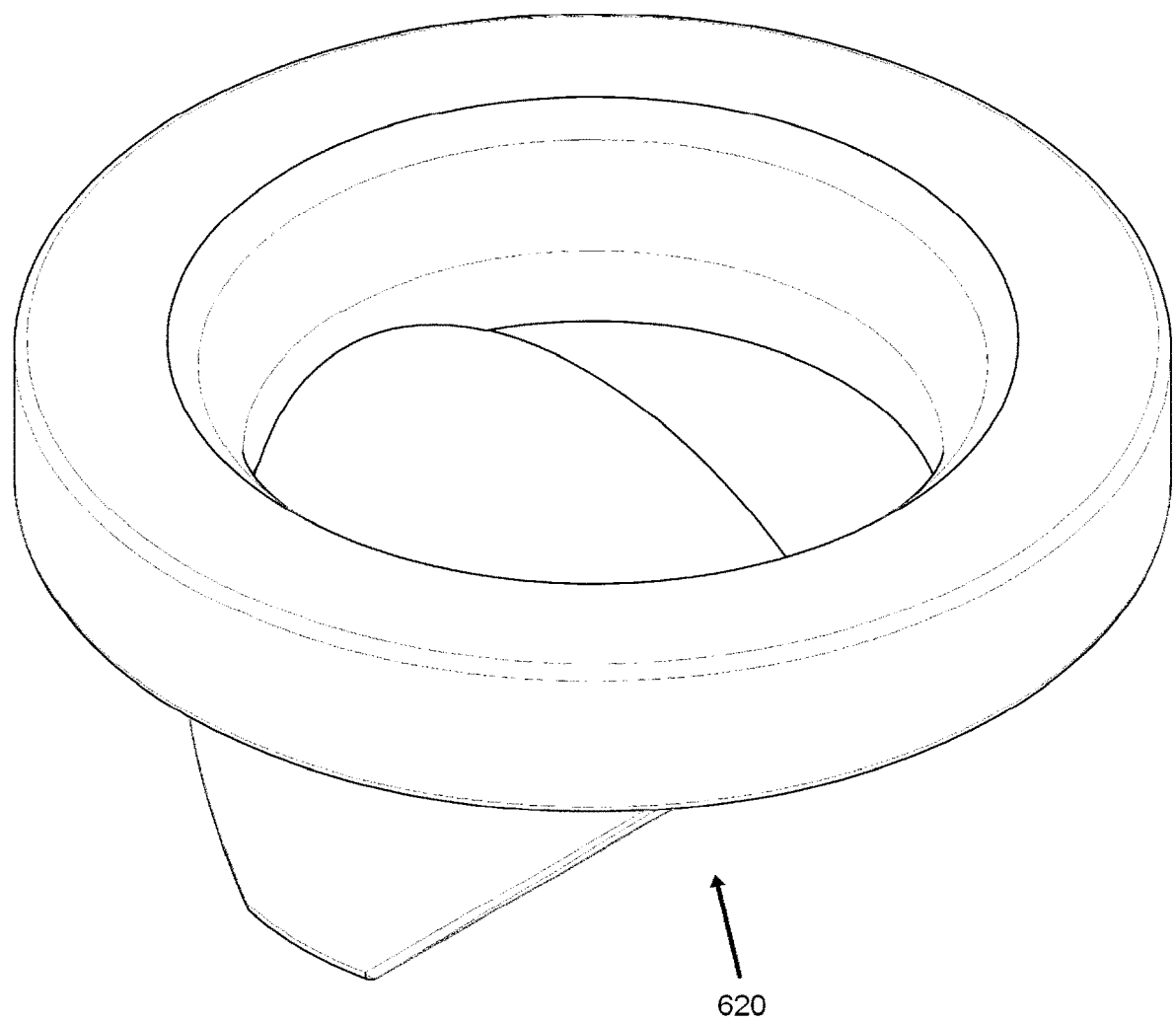
FIG. 70 is a perspective view of an inner seal.

FIG. 70 is a perspective view of an inner seal 620.

Figure 71:
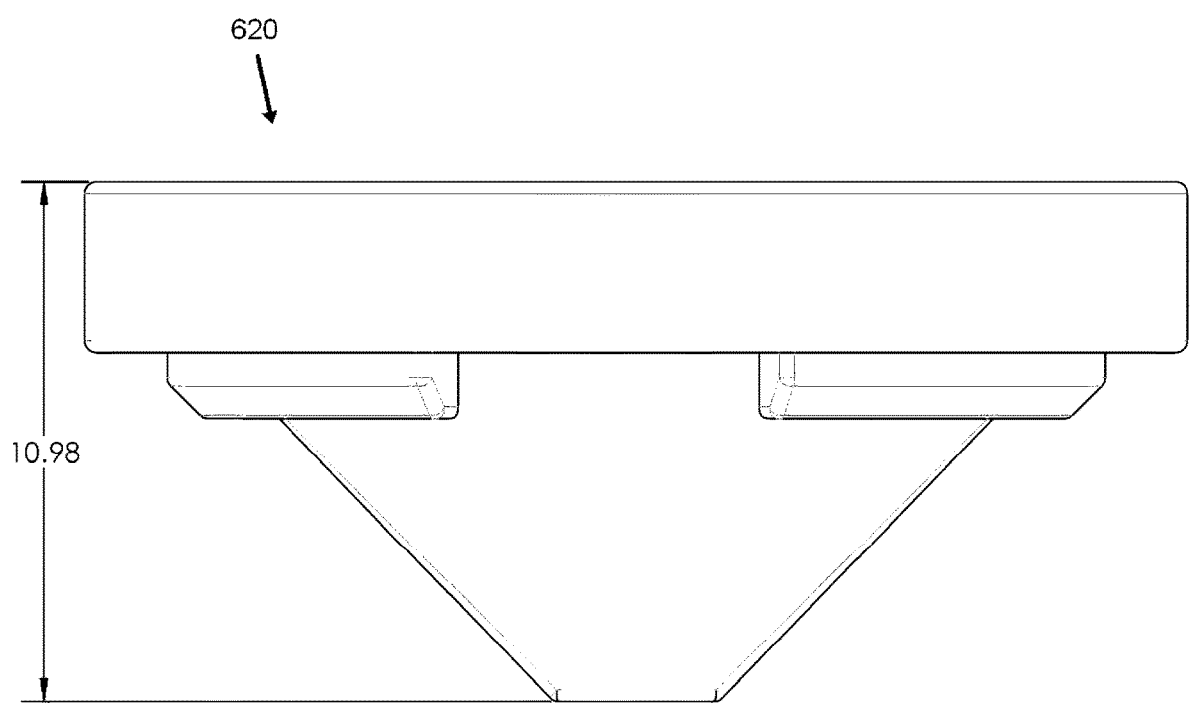
FIG. 71 shows a side view of the inner seal.

FIG. 71 shows a side view of the inner seal 620.

Figure 72:
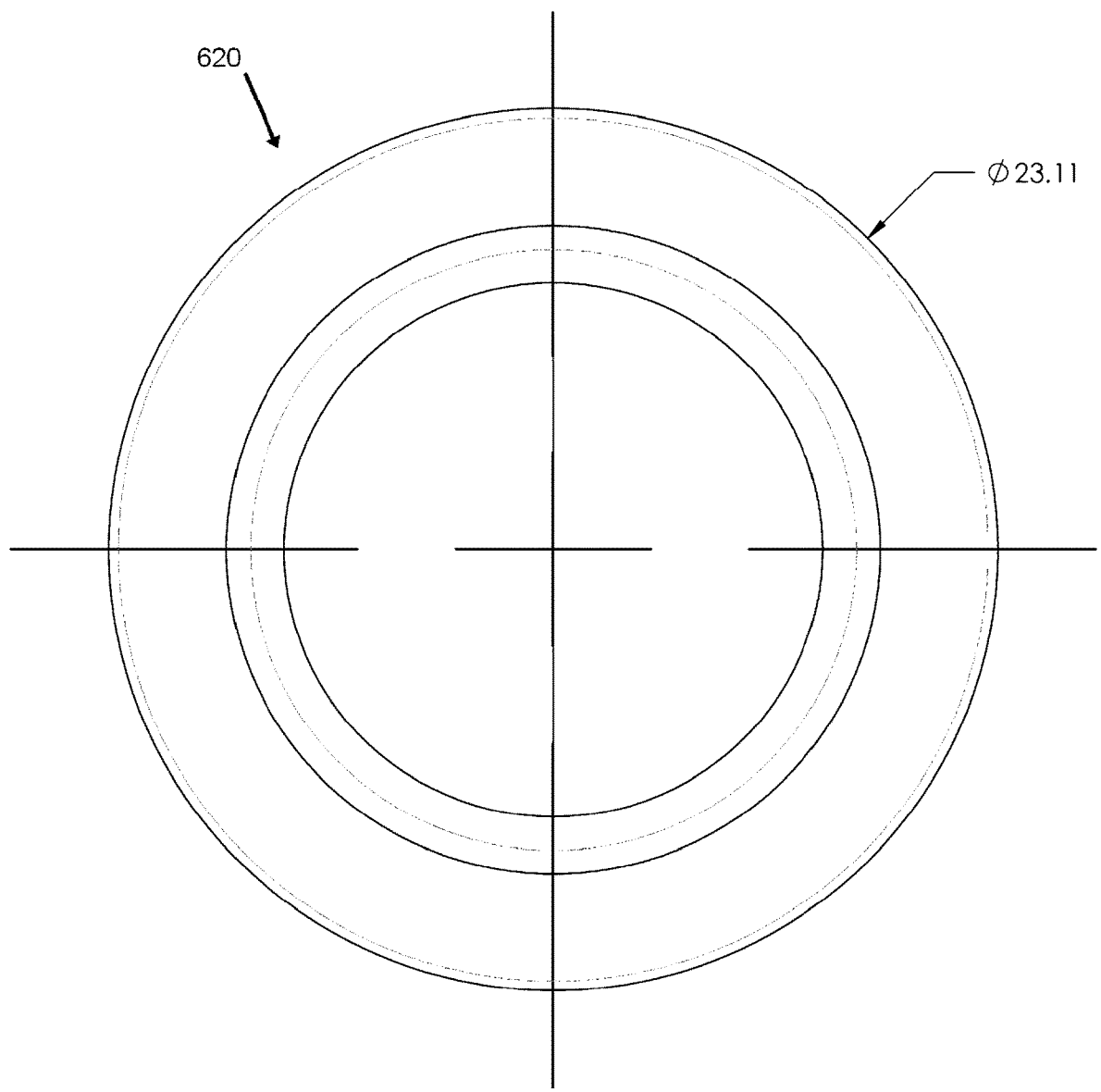
FIG. 72 shows a top view of the inner seal.

FIG. 72 shows a top view of the inner seal 620.

Figure 73:
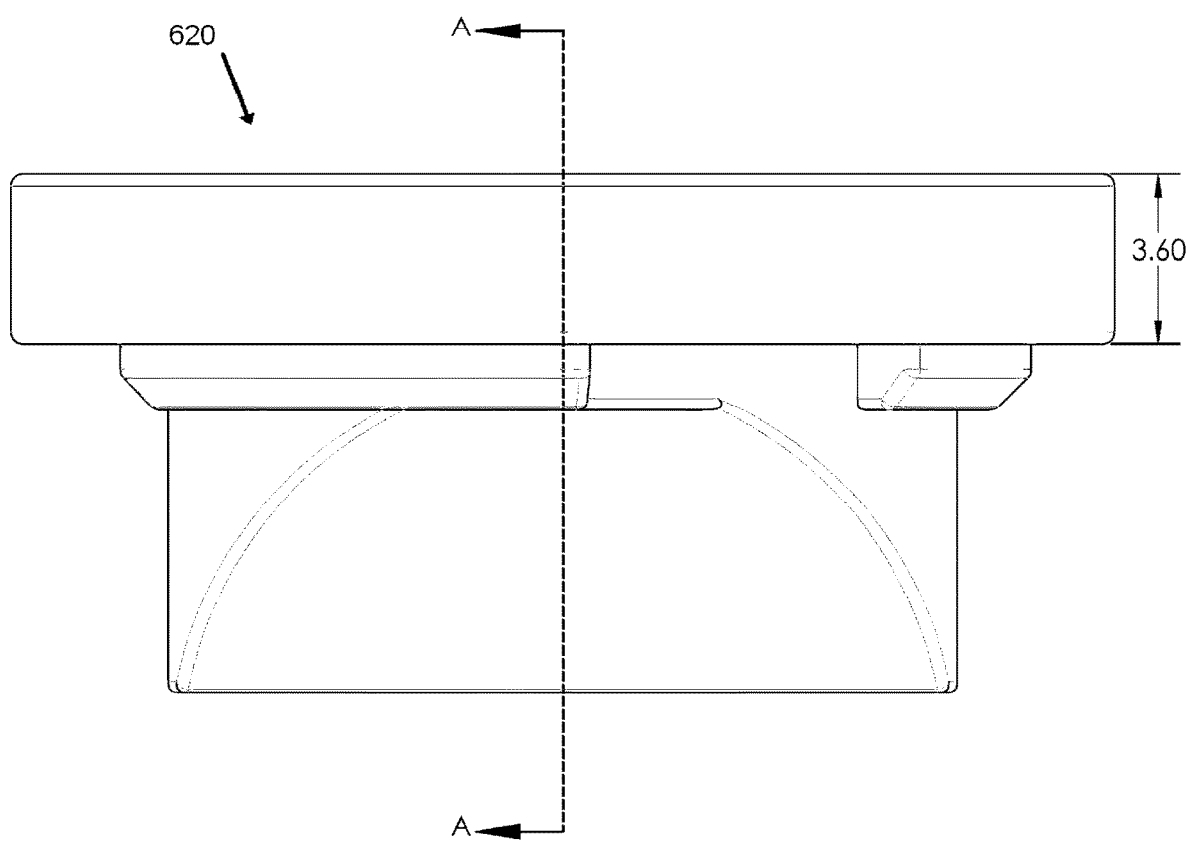
FIG. 73 shows another side view of the inner seal.

FIG. 73 shows another side view of the inner seal 620. With a line A-A to show where a cross-sectional cut is being taken.

Figure 74:
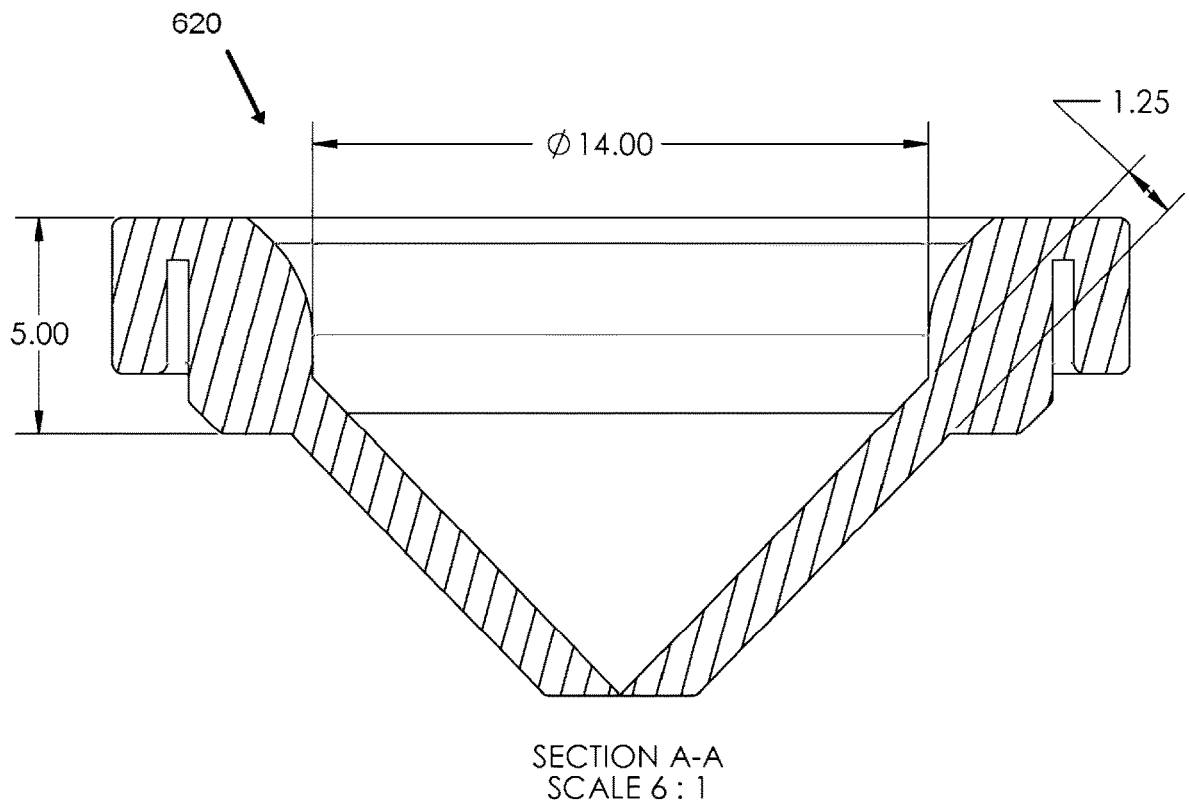
FIG. 74 shows a cross-section of the inner seal.

FIG. 74 shows a cross-section of the inner seal 620 as shown in FIG. 73.

Figure 75:
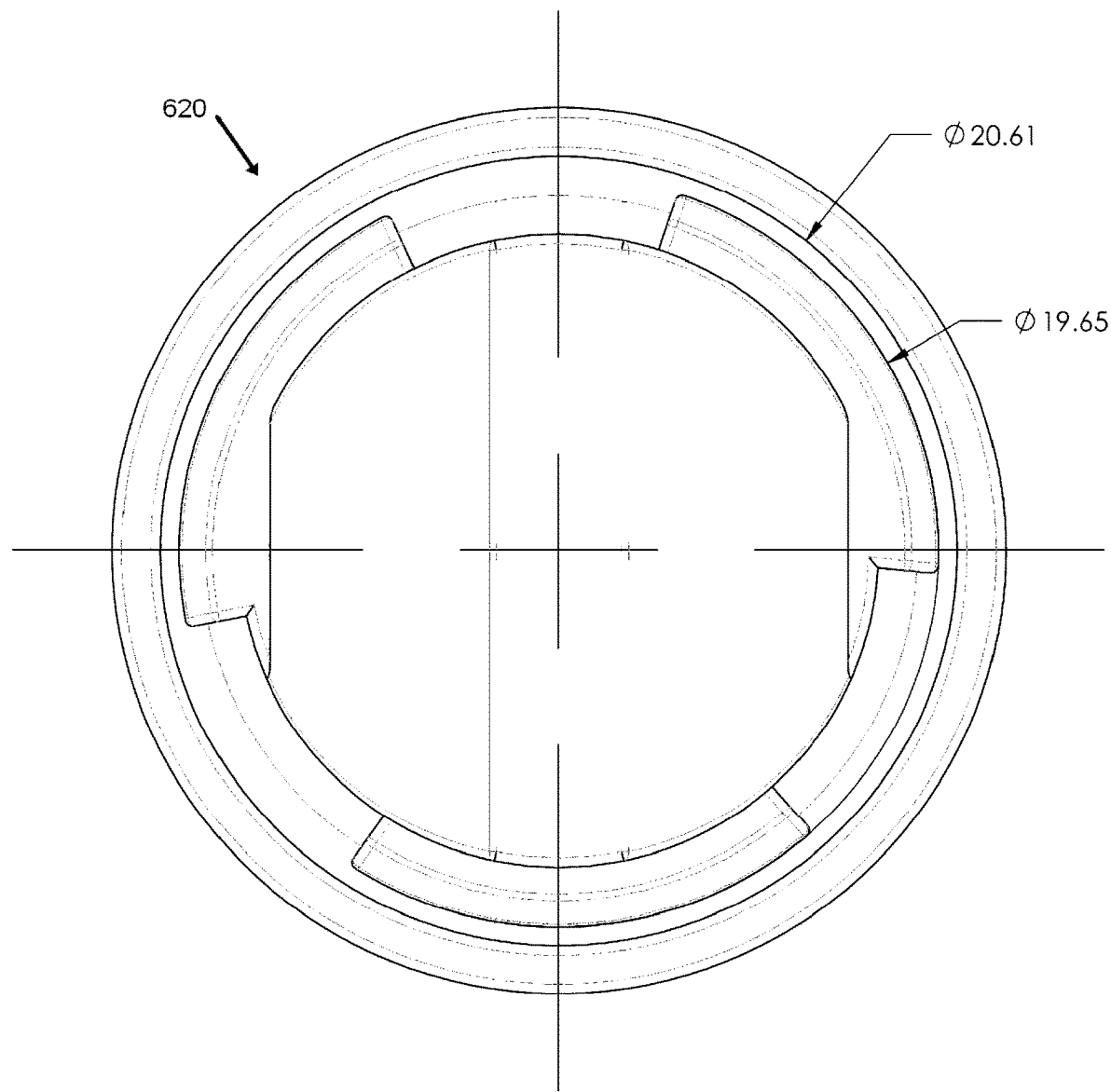
FIG. 75 shows a bottom view of the inner seal.

FIG. 75 shows a bottom view of the inner seal 620.

Figure 76:
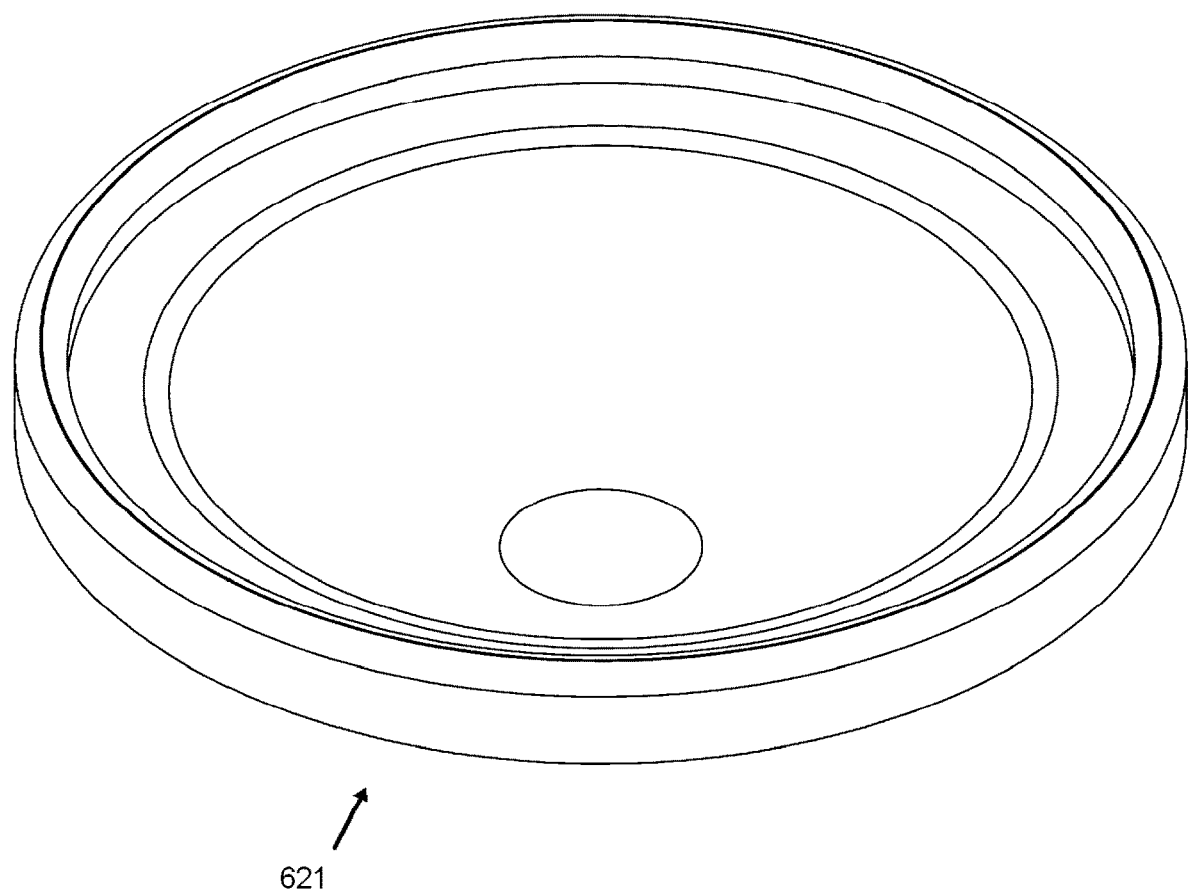
FIG. 76 is a perspective view of an outer seal.

FIG. 76 is a perspective view of an outer seal 621.

Figure 77:
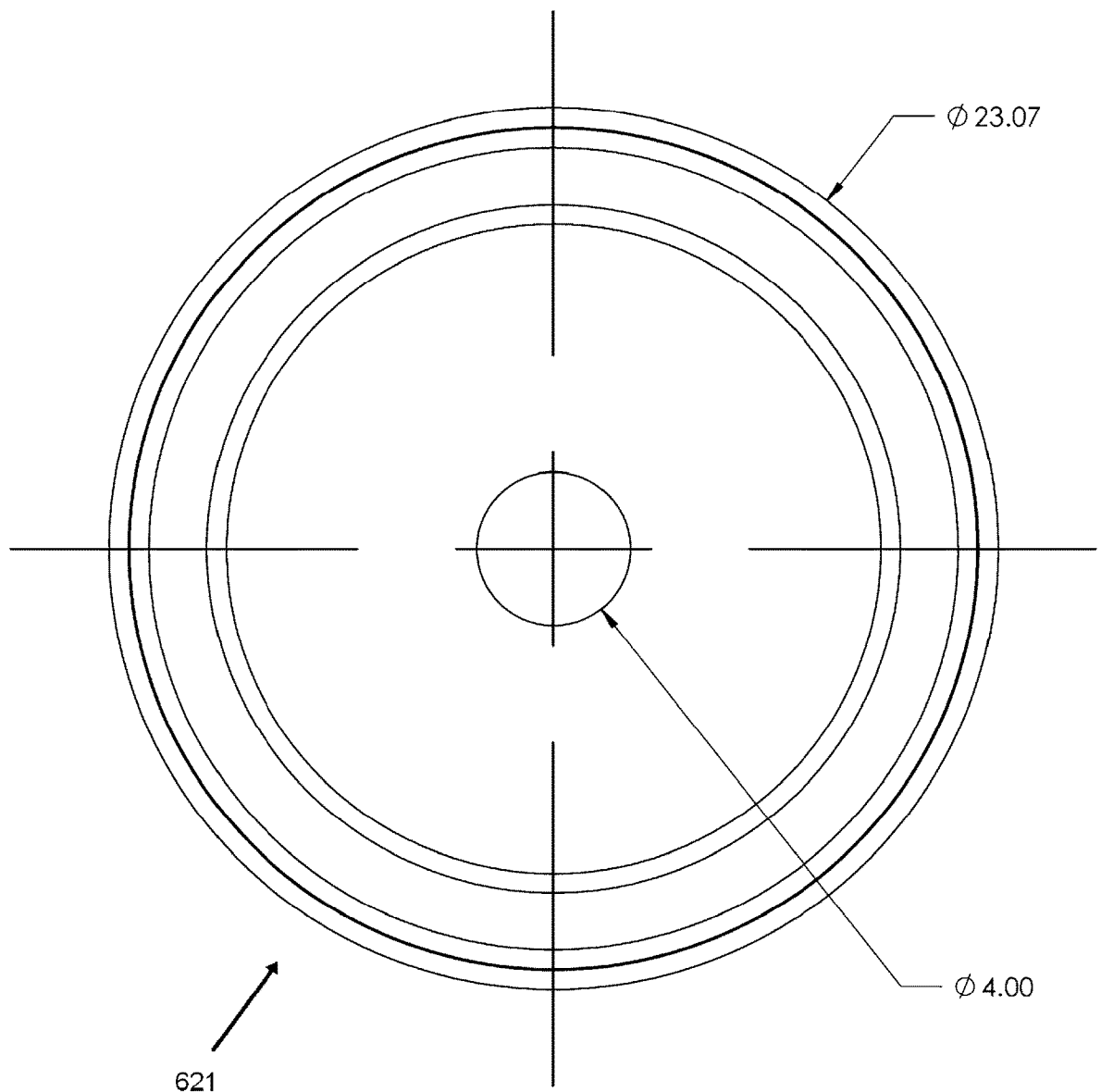
FIG. 77 shows a top view of the outer seal.

FIG. 77 shows a top view of the outer seal 621.

Figure 78:
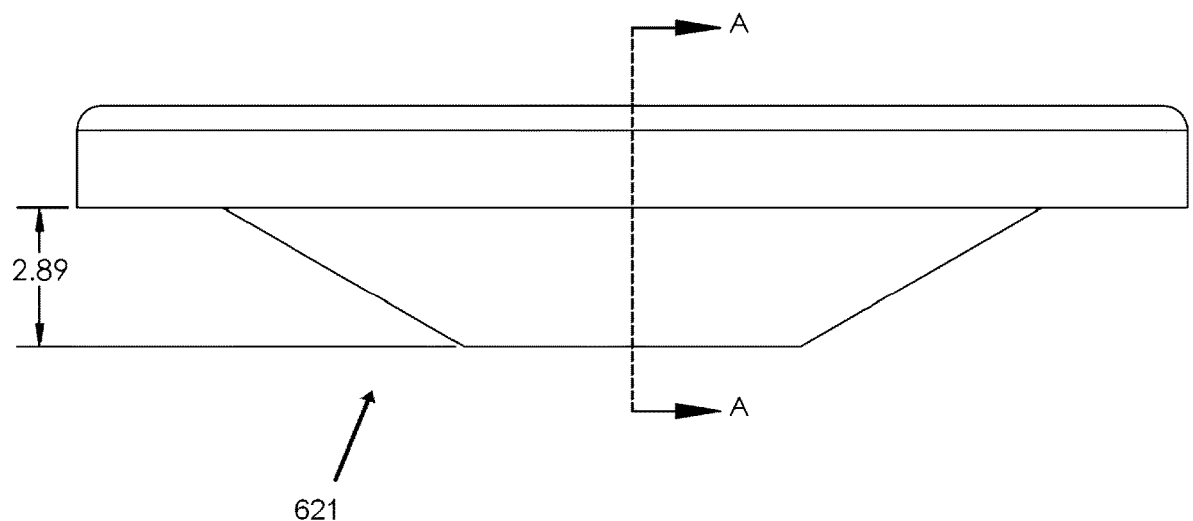
FIG. 78 shows a side view of the outer seal.

FIG. 78 shows a side view of the outer seal 621, with a line A-A to show where a cross section is taken.

Figure 79:
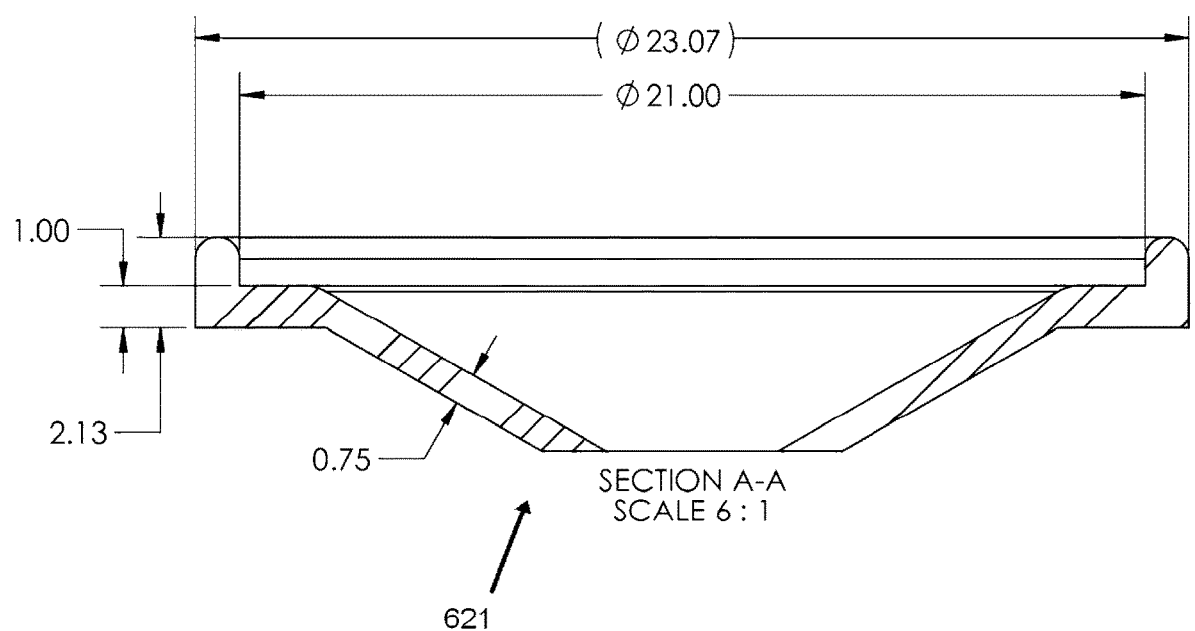
FIG. 79 shows a cross section of the outer seal.

FIG. 79 shows the cross section of the outer seal 621, as shown in FIG. 78.

Figure 80:
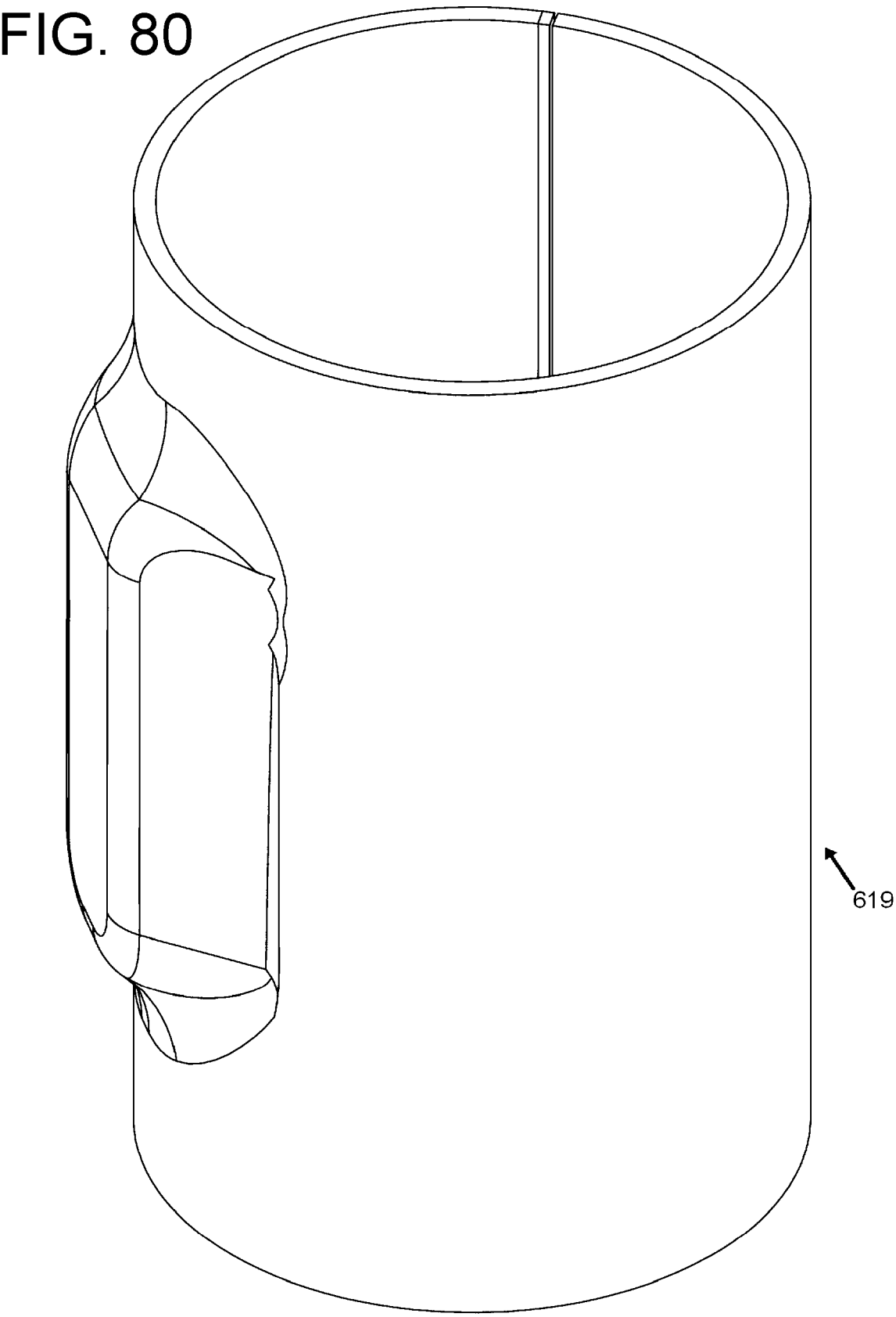
FIG. 80 is a perspective view of a reservoir installation.

FIG. 80 is a perspective view of a reservoir installation 628, that is, an installed configuration 628. The material, in one possible exemplification a silicone tape, may lay over the thermostat 618.

Figure 81:
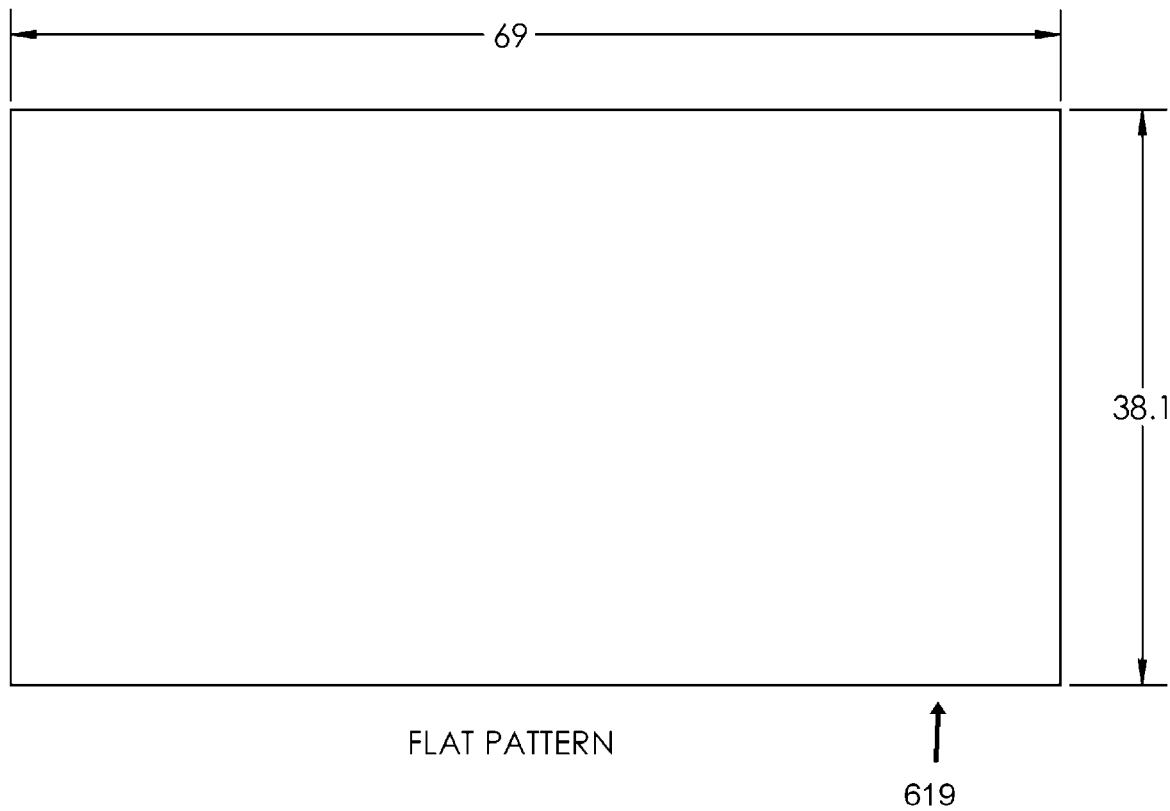
FIG. 81 shows a top view of reservoir insulation in a flat pattern.

FIG. 81 shows a top view of reservoir insulation 619 in a flat pattern. Adhesive may be on one side of the reservoir insulation 619. The reservoir insulation 619 may have a width of 69 millimeters and a height of 38.1 millimeters.

Figure 82:
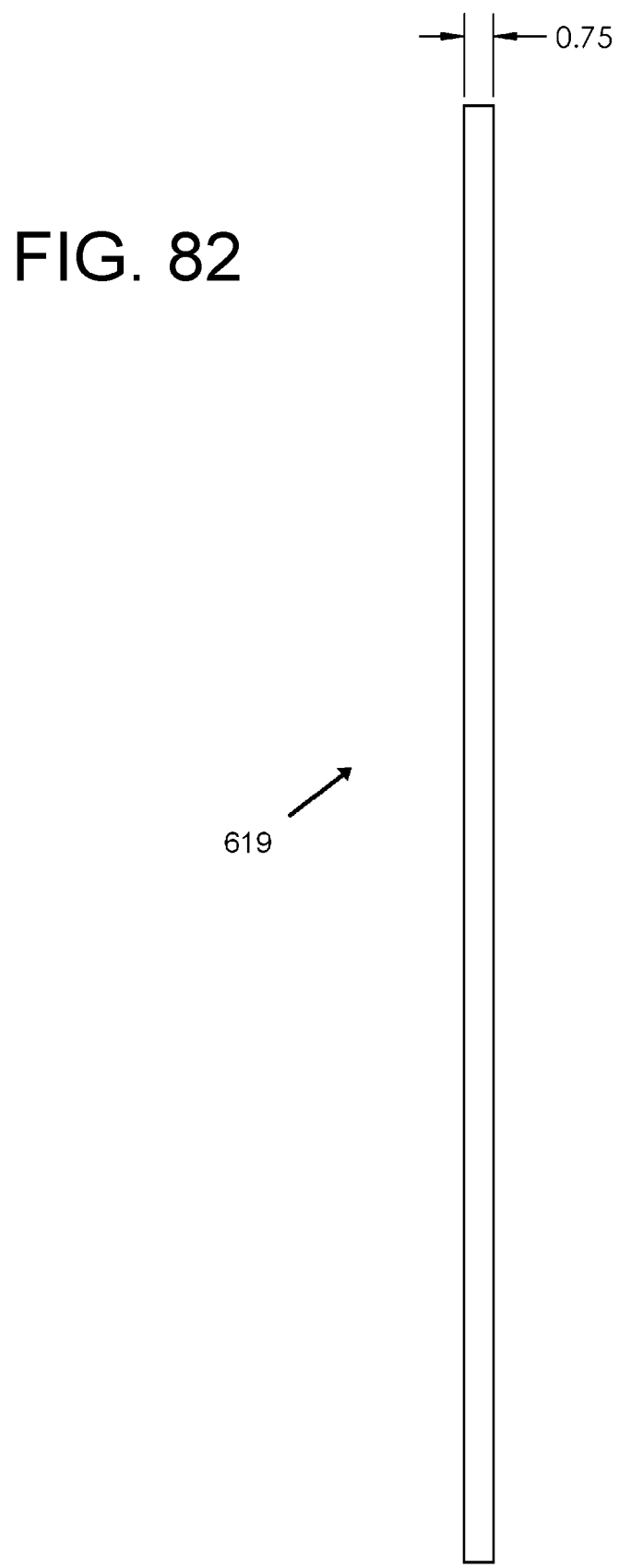
FIG. 82 shows a side view of the reservoir insulation.

FIG. 82 shows a side view of the reservoir insulation 619. The reservoir insulation 619 may have a thickness of 0.75 millimeters.

Figure 83:
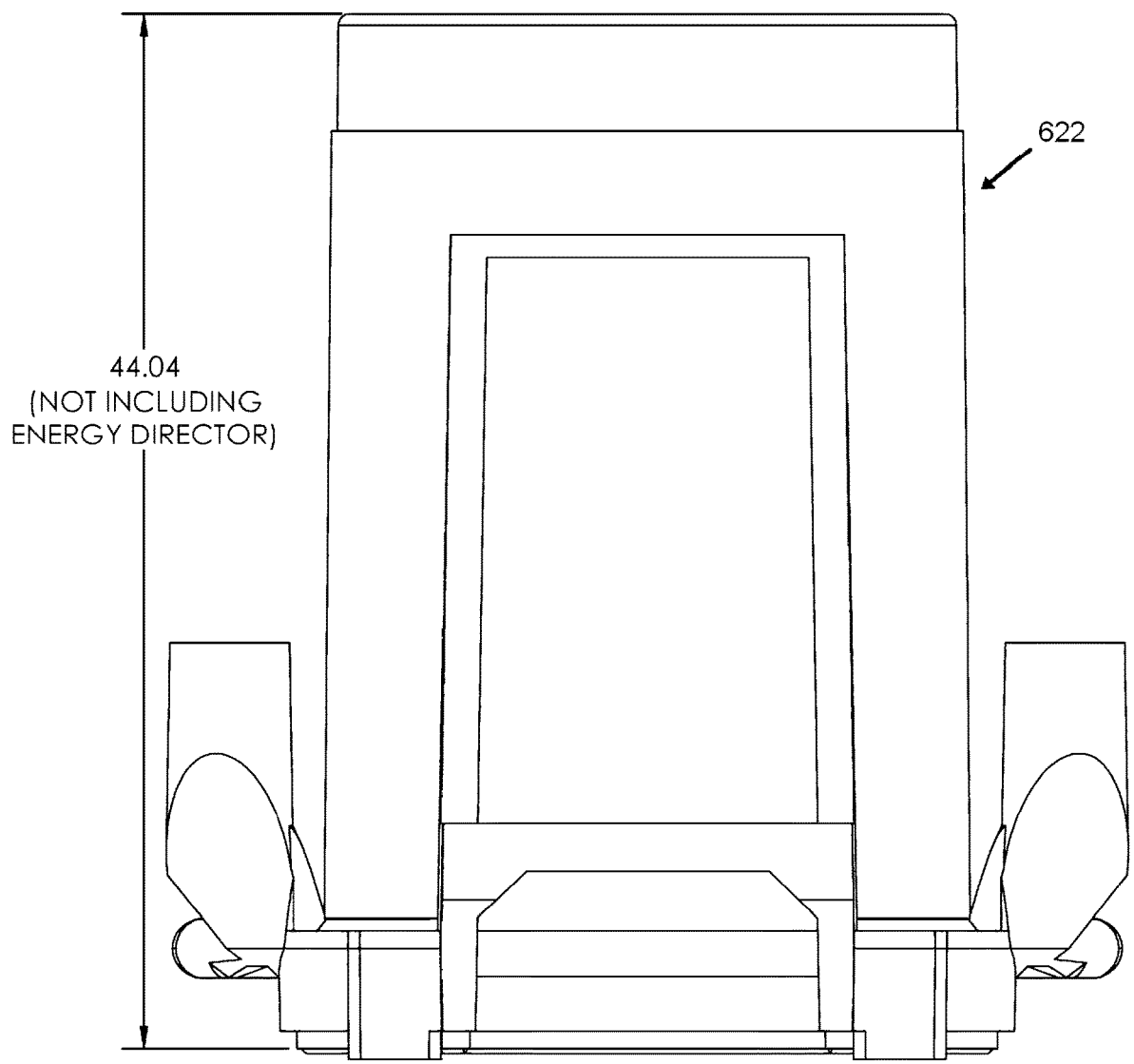
FIG. 83 shows one possible side view of a reservoir retainer.

FIG. 83 shows one possible side view of a reservoir retainer 622.

Figure 84:
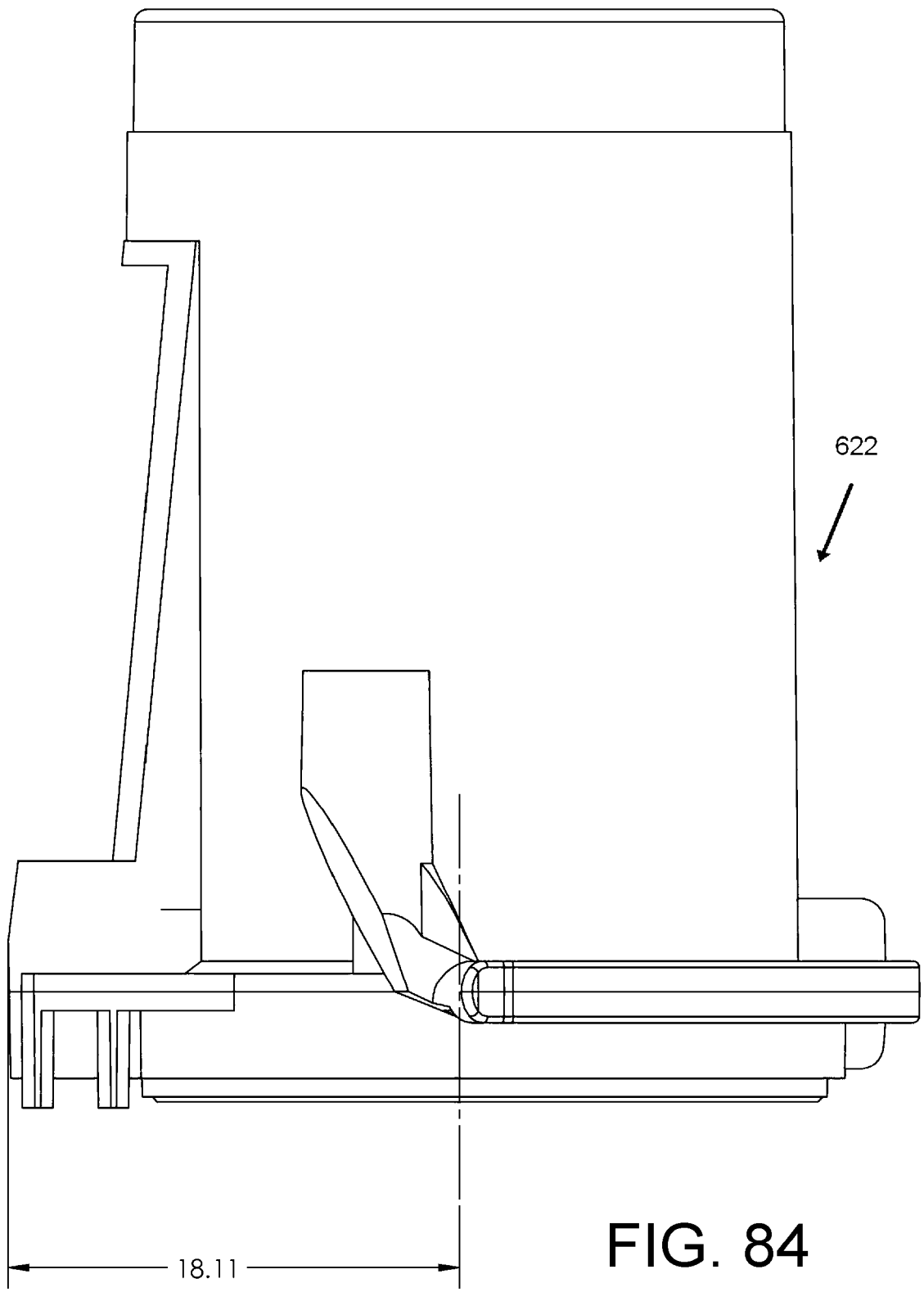
FIG. 84 shows another possible side view of the reservoir retainer.

FIG. 84 shows another possible side view of the reservoir retainer 622.

Figure 85:
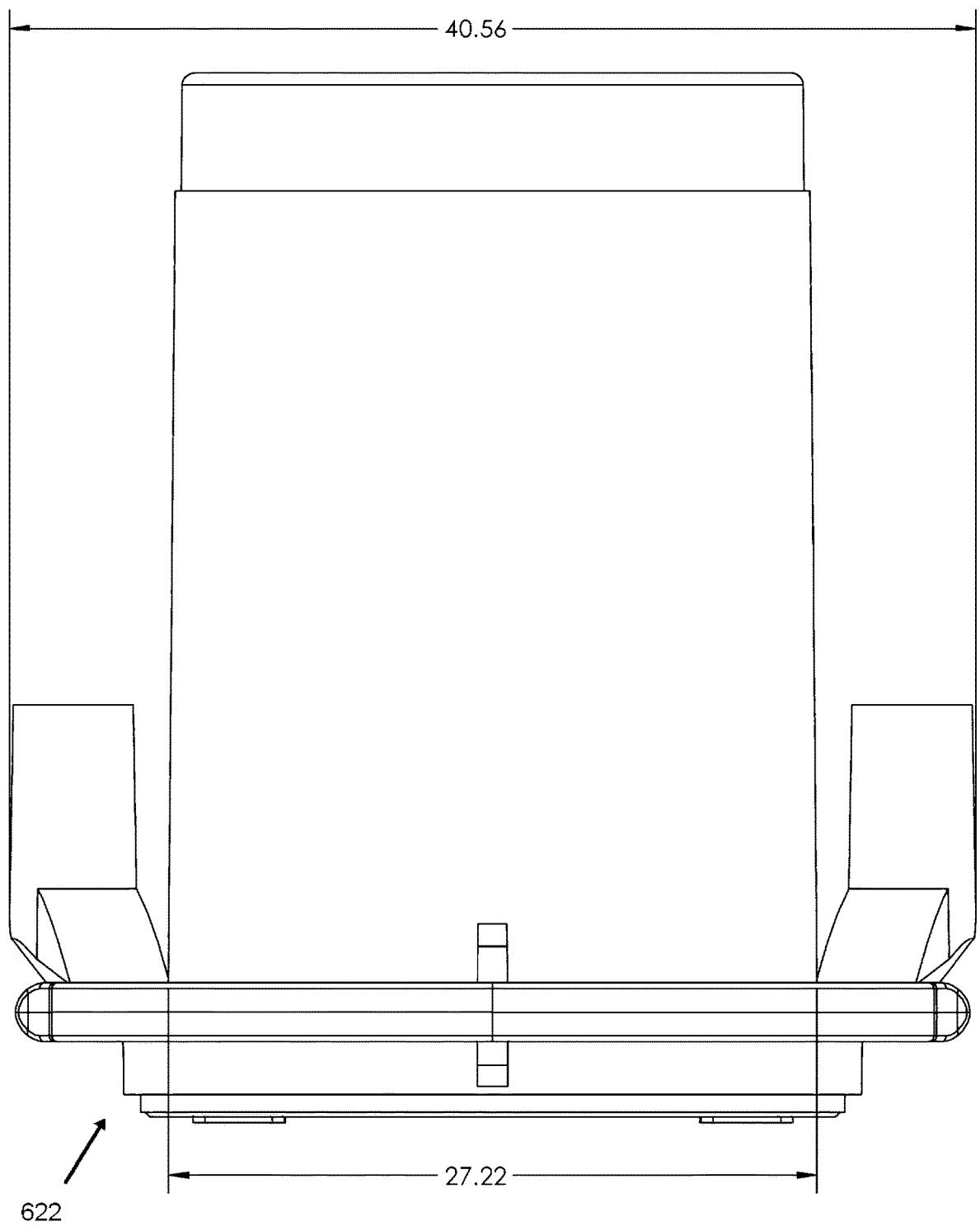
FIG. 85 shows another possible side view of the reservoir retainer.

FIG. 85 shows another possible side view of the reservoir retainer 622.

Figure 86:
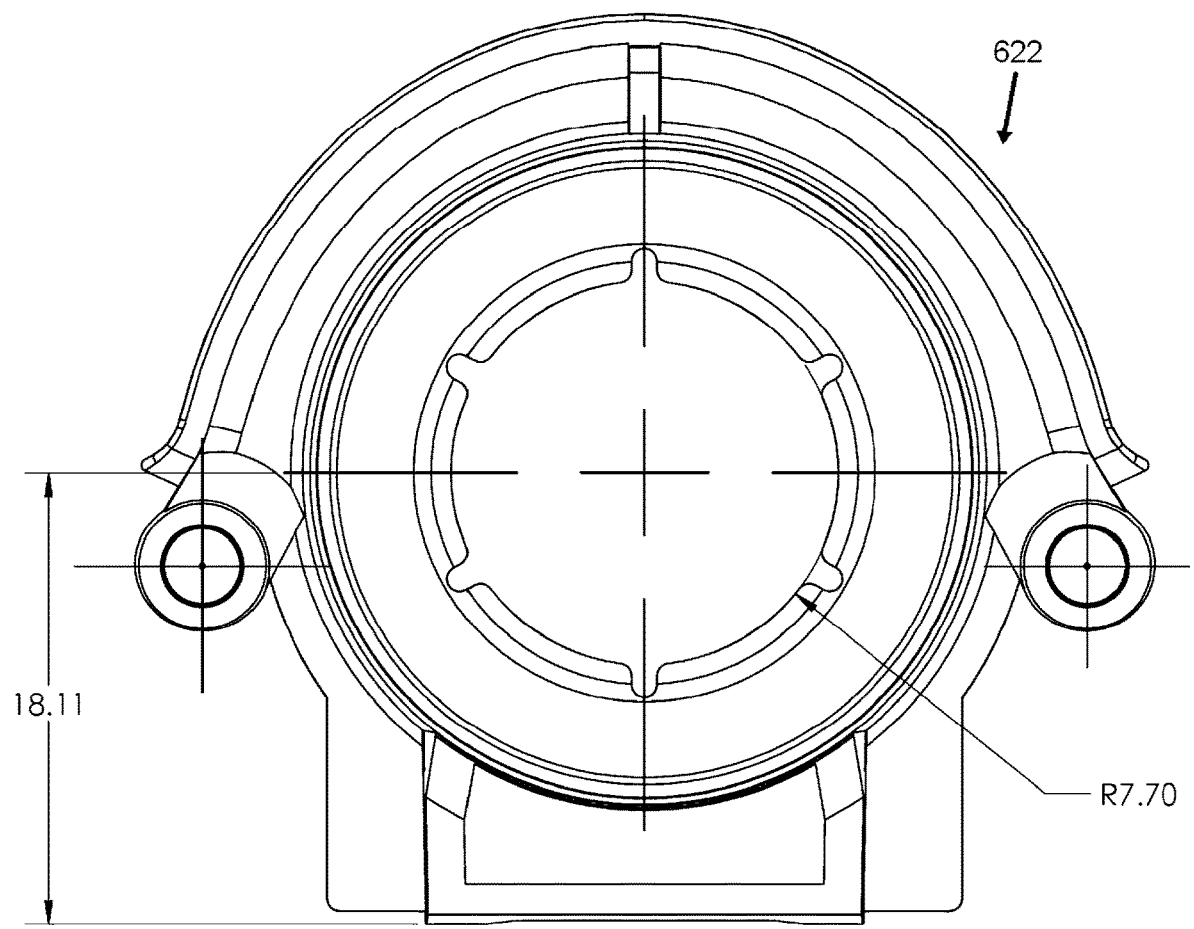
FIG. 86 shows a top view of the reservoir retainer.

FIG. 86 shows a top/bottom view of the reservoir retainer 622.

Figure 87:
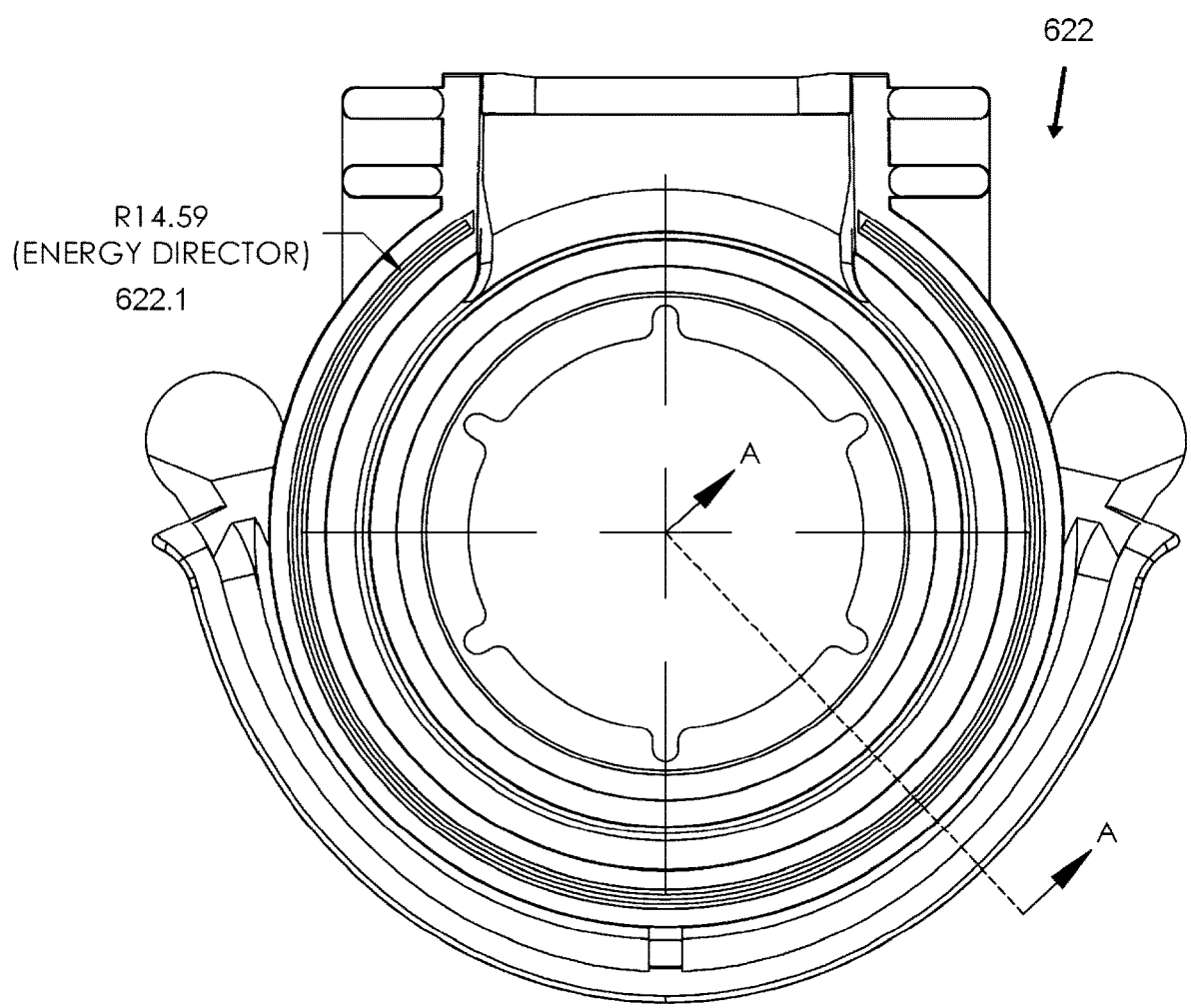
FIG. 87 shows a bottom view of the reservoir retainer including an energy director.

FIG. 87 shows a top/bottom view of the reservoir retainer 622 including an energy director 622.1, with a line A-A to show where a cross section is taken.

Figure 88:
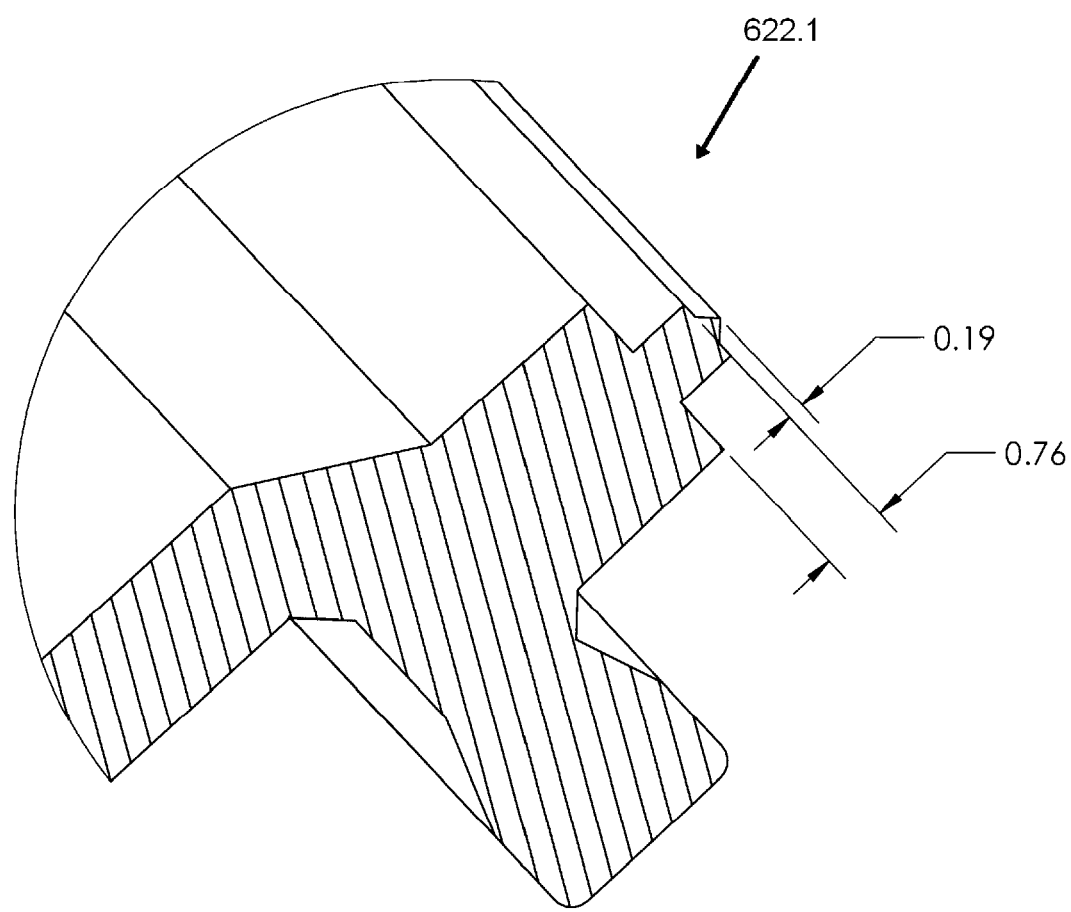
FIG. 88 shows a cross section of the energy director of the reservoir retainer.

FIG. 88 shows the cross section of the energy director 622.1 of the reservoir retainer 622 as shown in FIG. 87.

Figure 89:
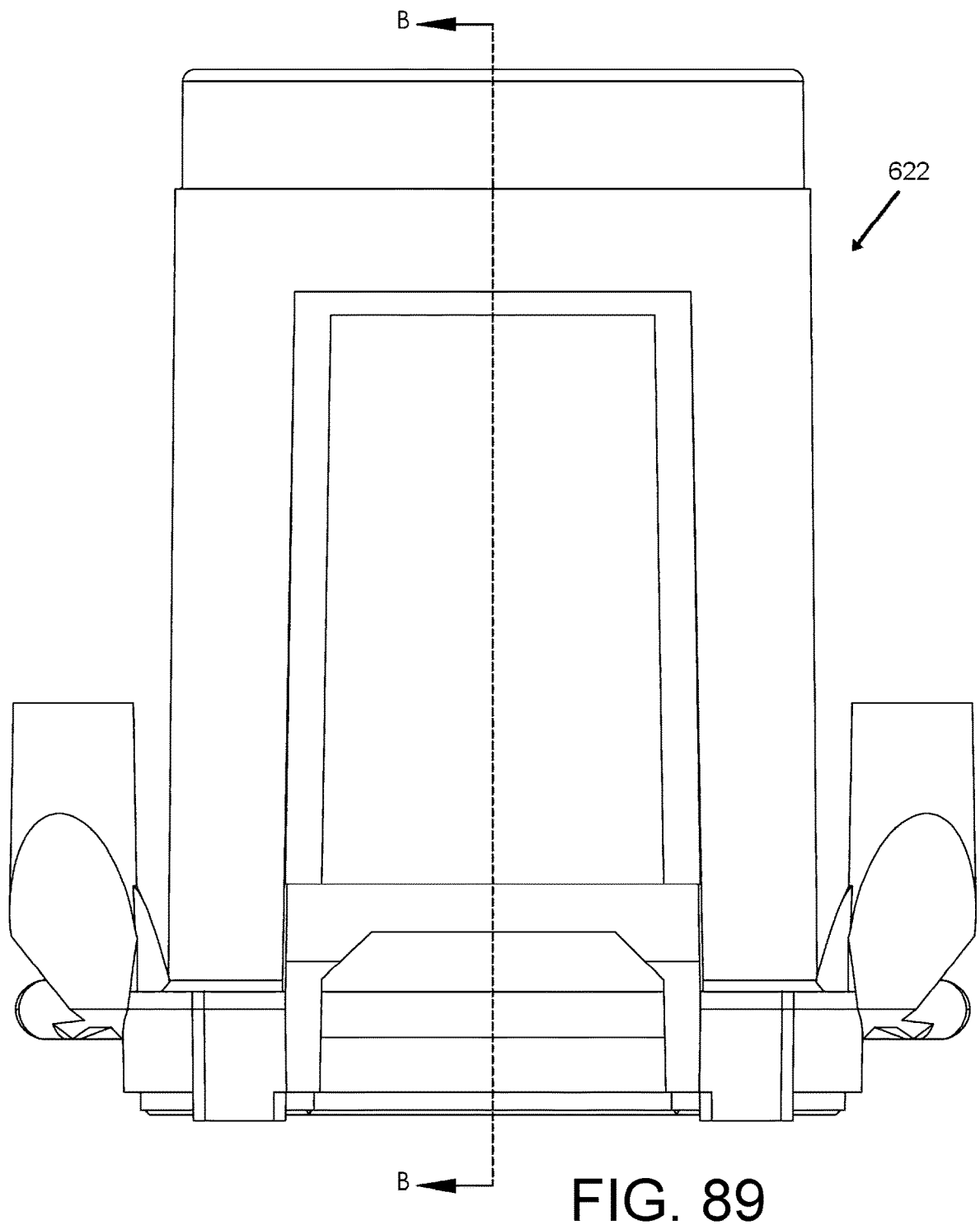
FIG. 89 shows the reservoir retainer.

FIG. 89 shows the reservoir retainer 622 of FIG. 83, including a line B-B to show where a cross section is being taken.

Figure 90:
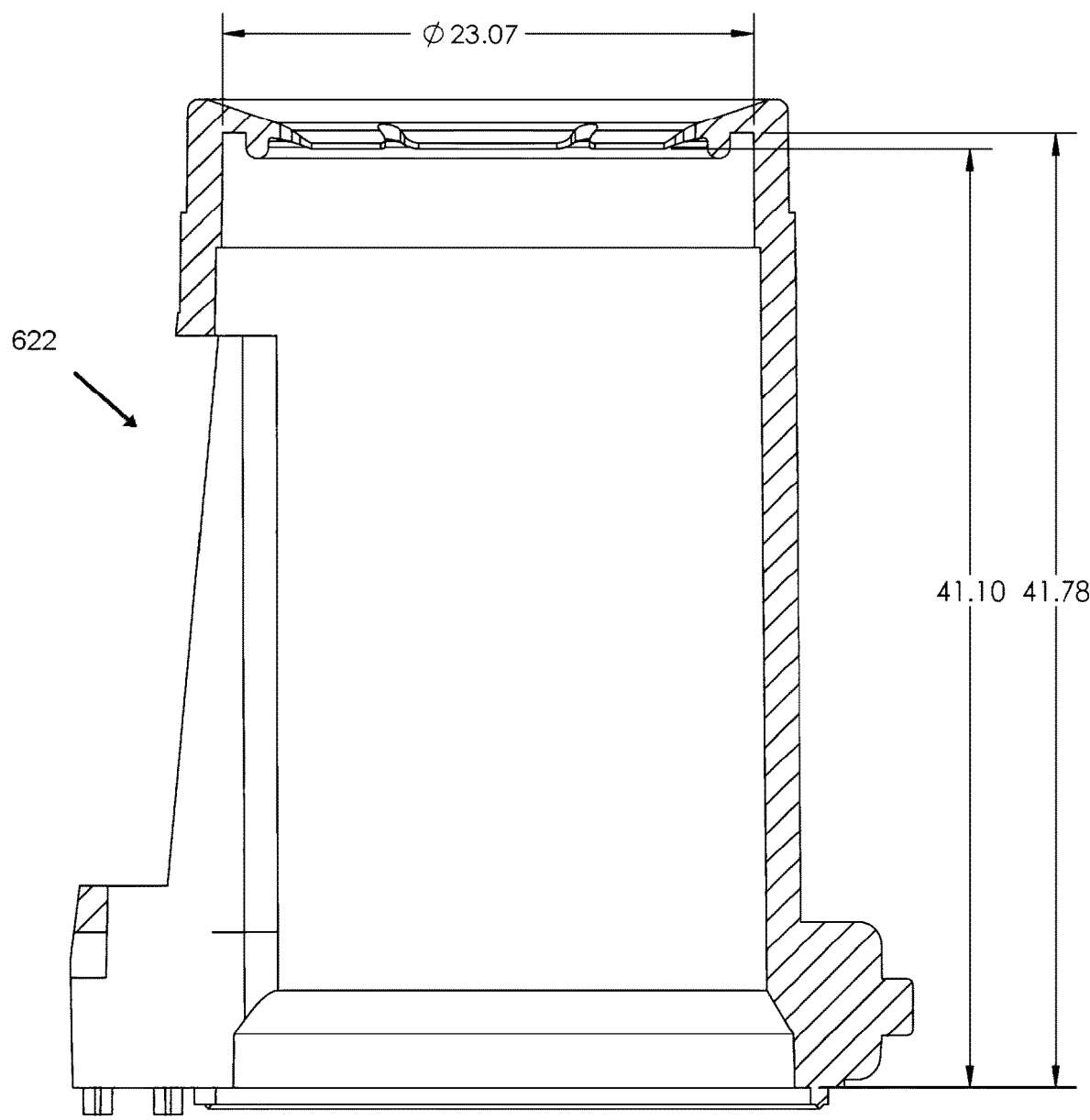
FIG. 90 shows a cross section of the reservoir retainer.

FIG. 90 shows the cross section of the reservoir retainer 622 as shown in FIG. 89.

Figure 91:
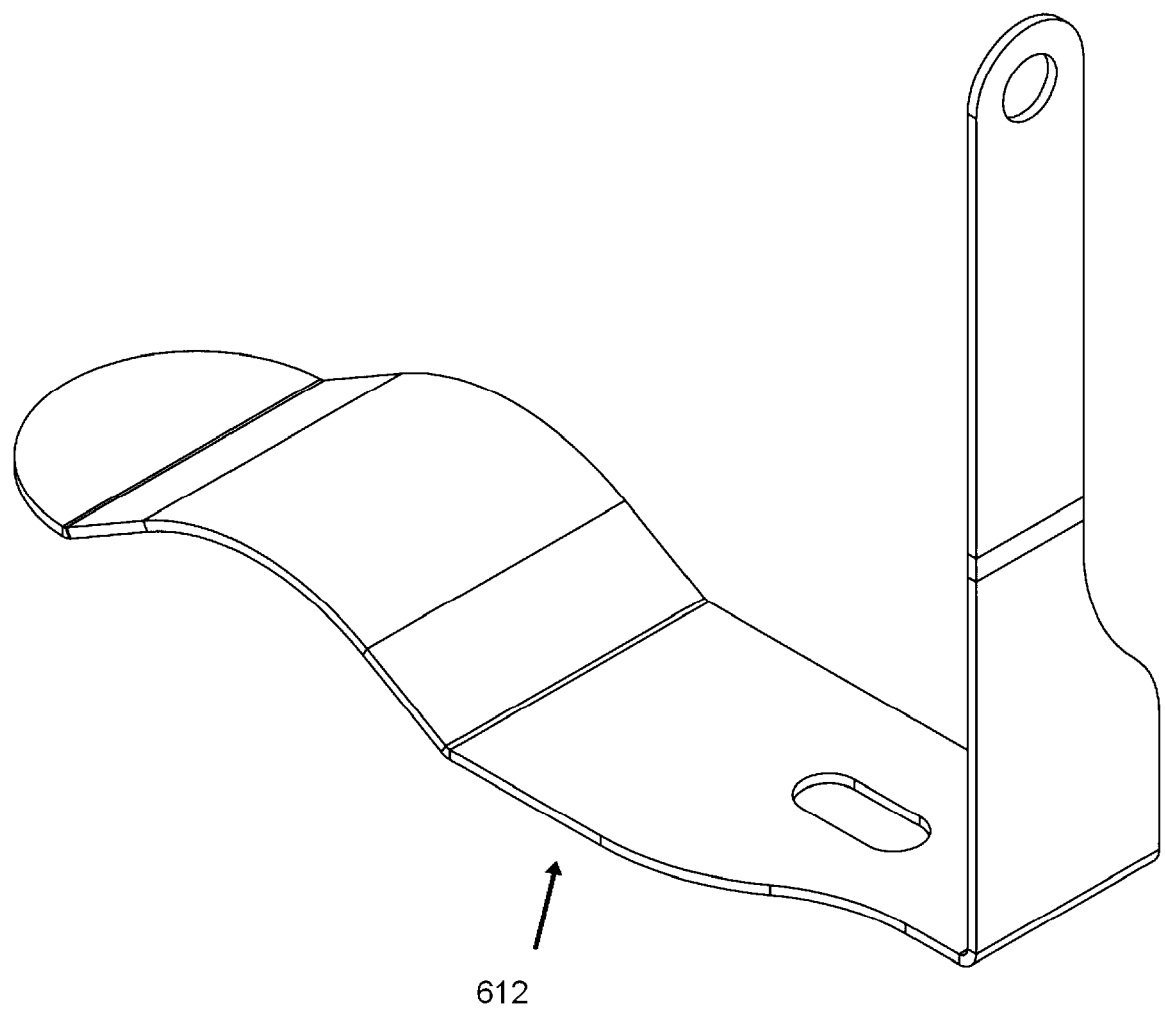
FIG. 91 shows a perspective view of a third battery contact.

FIG. 91 shows a perspective view of battery contact C 612.

Figure 92:
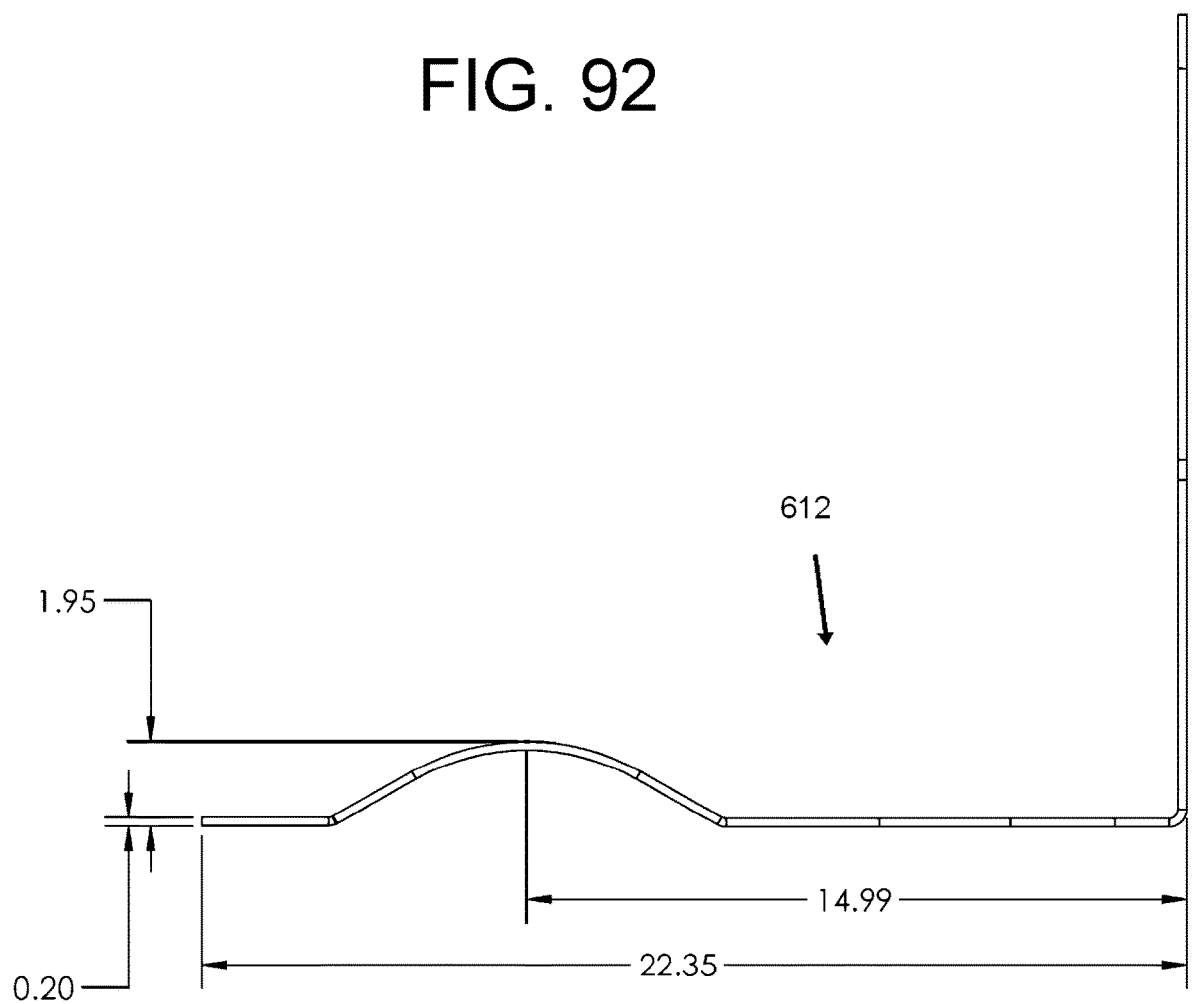
FIG. 92 shows a side view of the third battery contact.

FIG. 92 shows a side view of battery contact 612.

Figure 93:
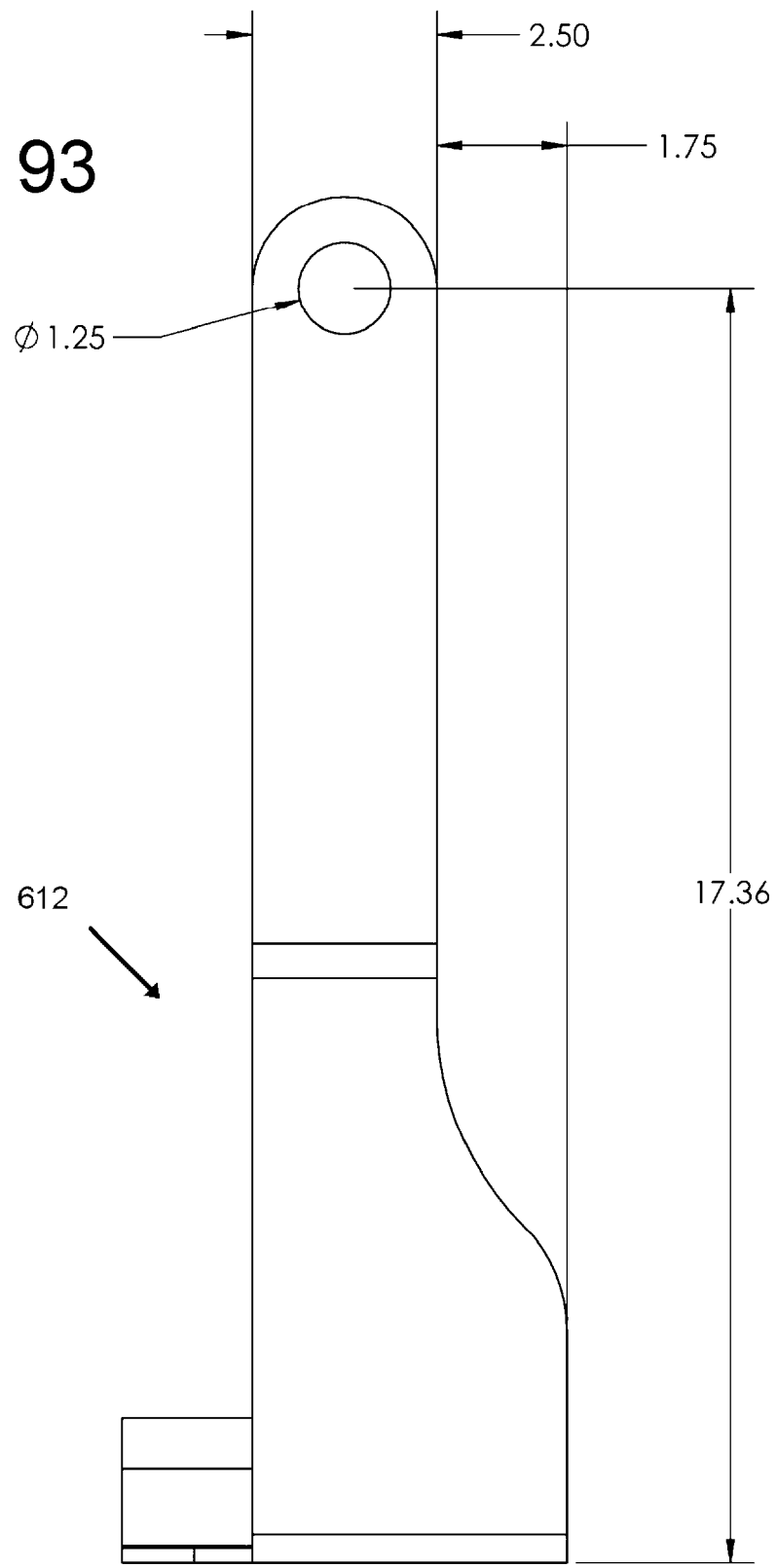
FIG. 93 shows another side view of the third battery contact.

FIG. 93 shows another side view of battery contact 612.

Figure 94:
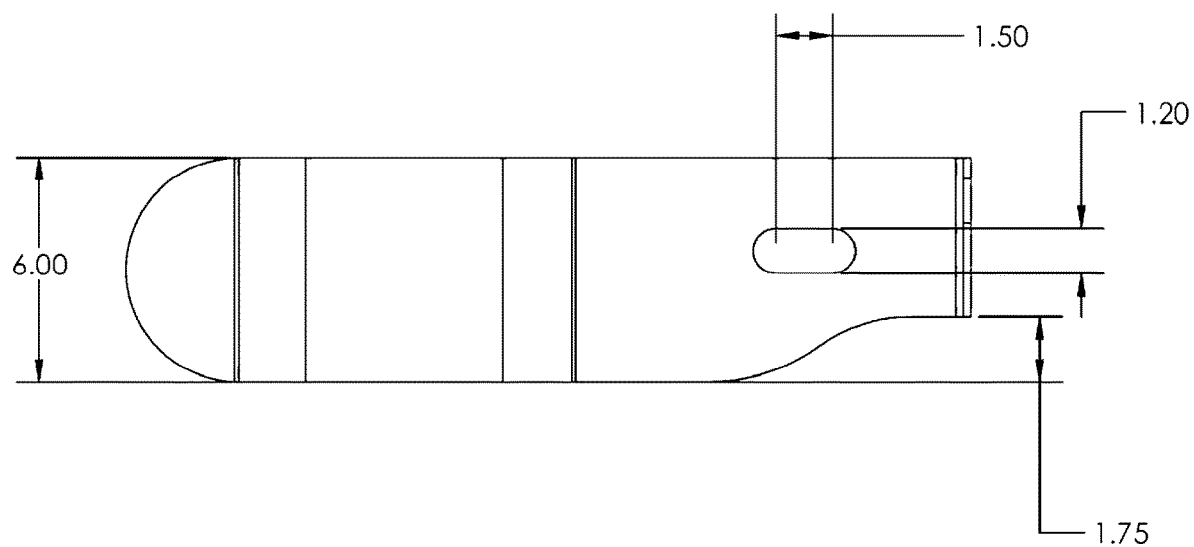
FIG. 94 shows a top view of the third battery contact.

FIG. 94 shows a top view of battery contact 612.

Figure 95:
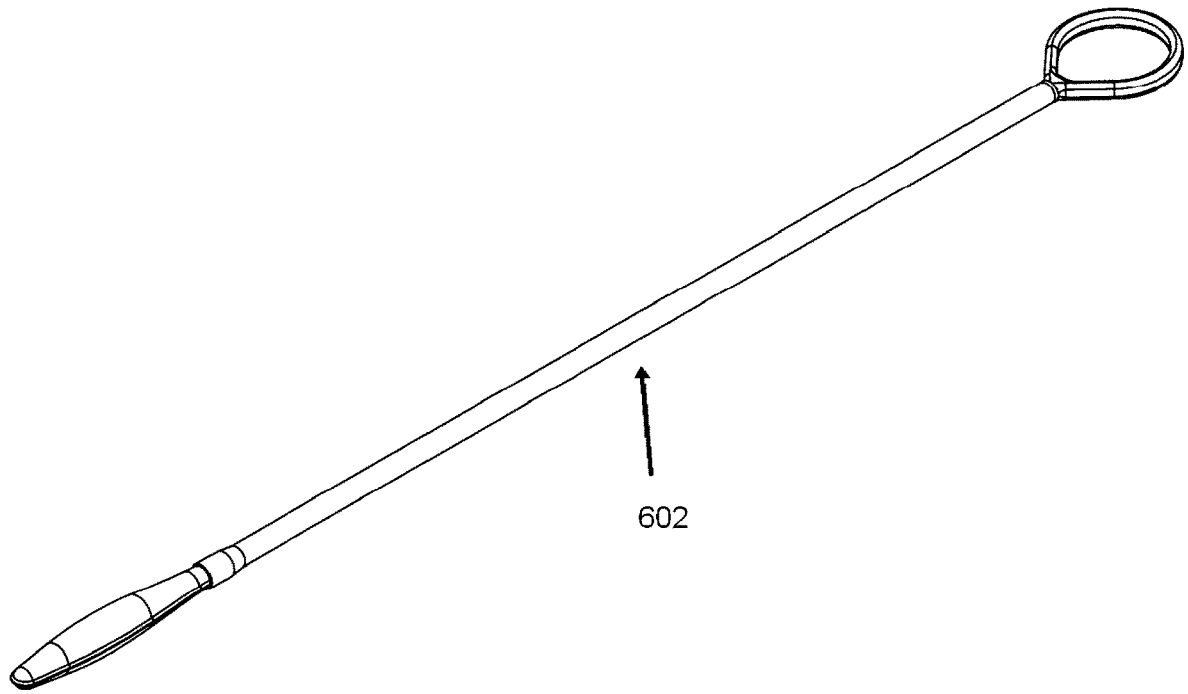
FIG. 95 shows a perspective view of a five millimeter wiping wand.

FIG. 95 shows a perspective view of a five millimeter wiping wand 602.

Figure 96:
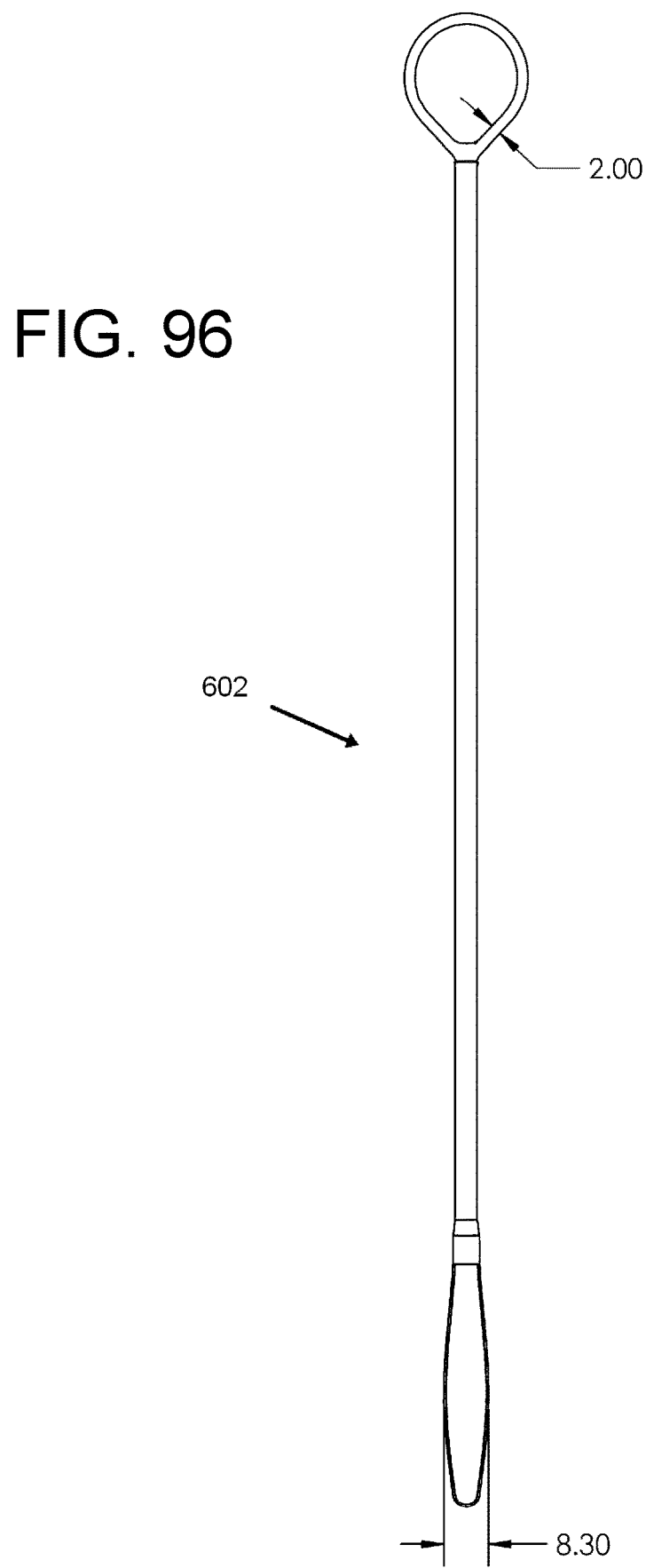
FIG. 96 shows a side view of the five millimeter wiping wand.

FIG. 96 shows a side view of the five millimeter wiping wand 602.

Figure 97:
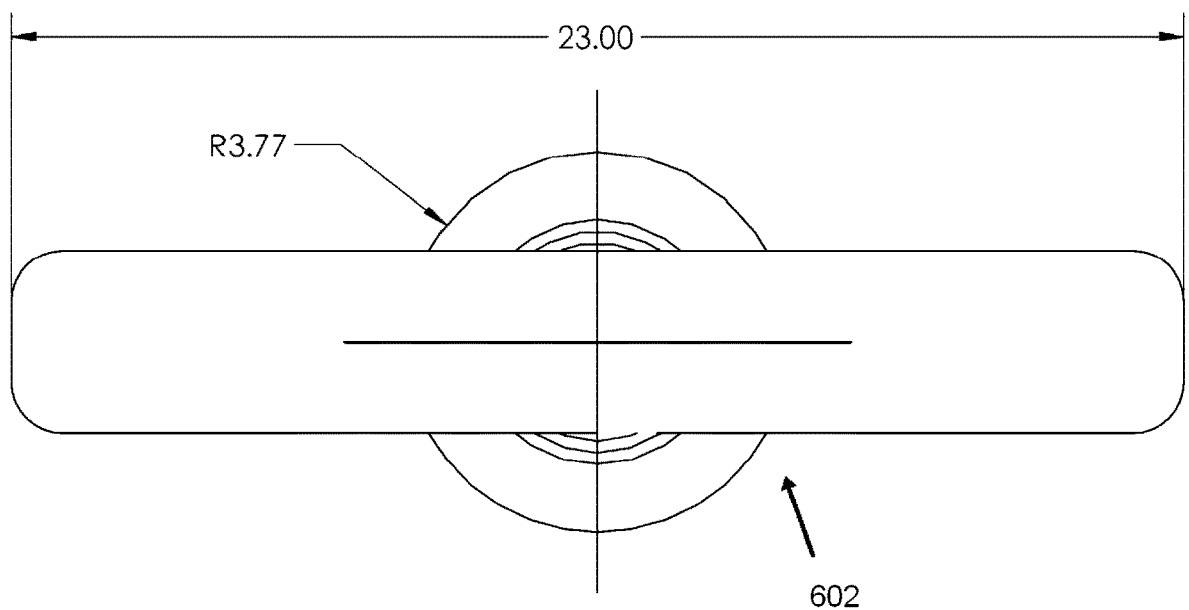
FIG. 97 shows an end view of the five millimeter wiping wand.

FIG. 97 shows an end view of the five millimeter wiping wand 602.

Figure 98:
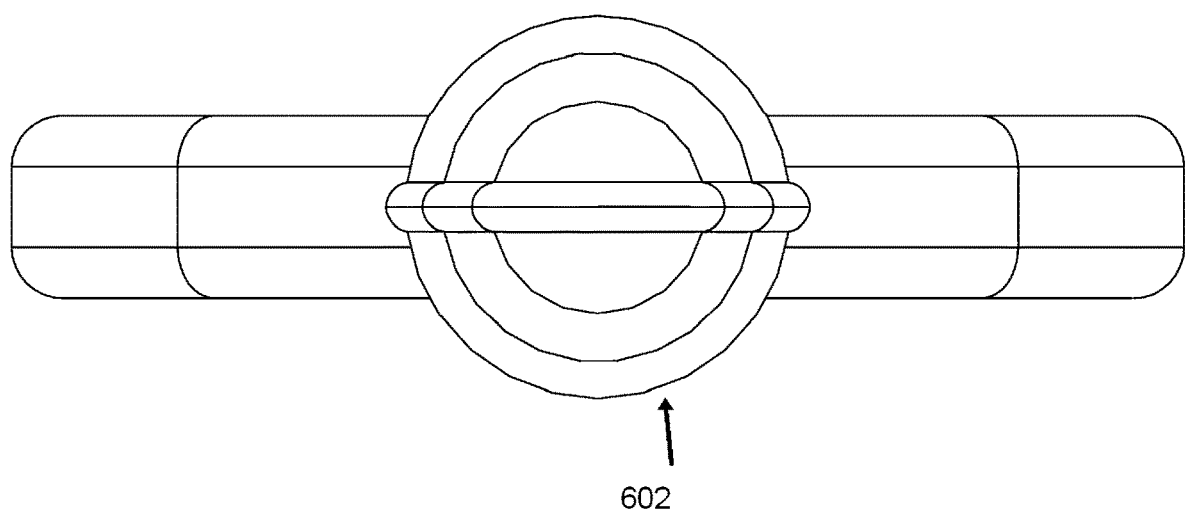
FIG. 98 shows an end view, opposite of the end shown in FIG. 97, of the five millimeter wiping wand.

FIG. 98 shows an end view, opposite of the end shown in FIG. 97, of the five millimeter wiping wand 602.

Figure 99:
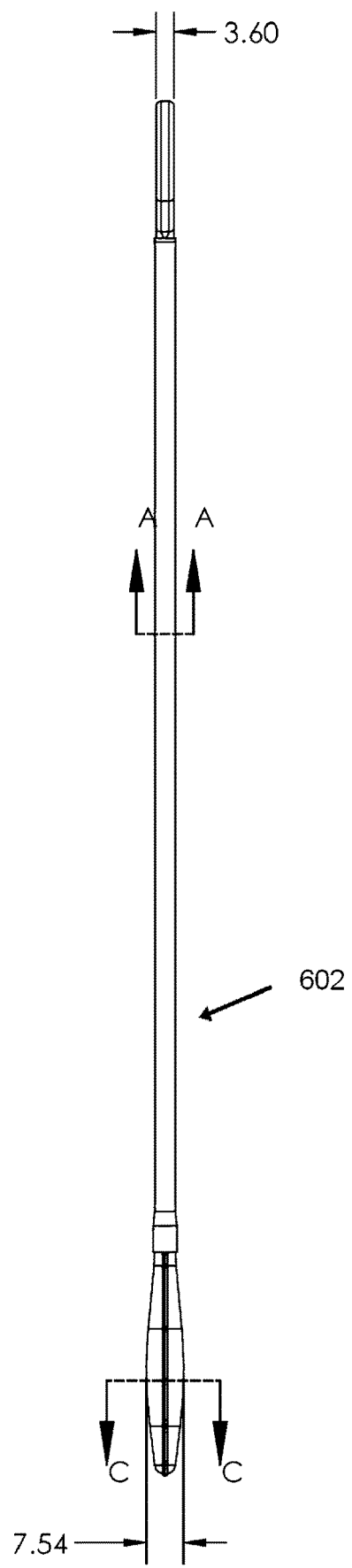
FIG. 99 shows the side view of the five millimeter wiping wand as shown in FIG. 96.

FIG. 99 shows the side view of the five millimeter wiping wand 602 as shown in FIG. 96, with a line A-A to show where a cross section is being taken and a line C-C to show where a different cross section is being taken.

Figure 100:
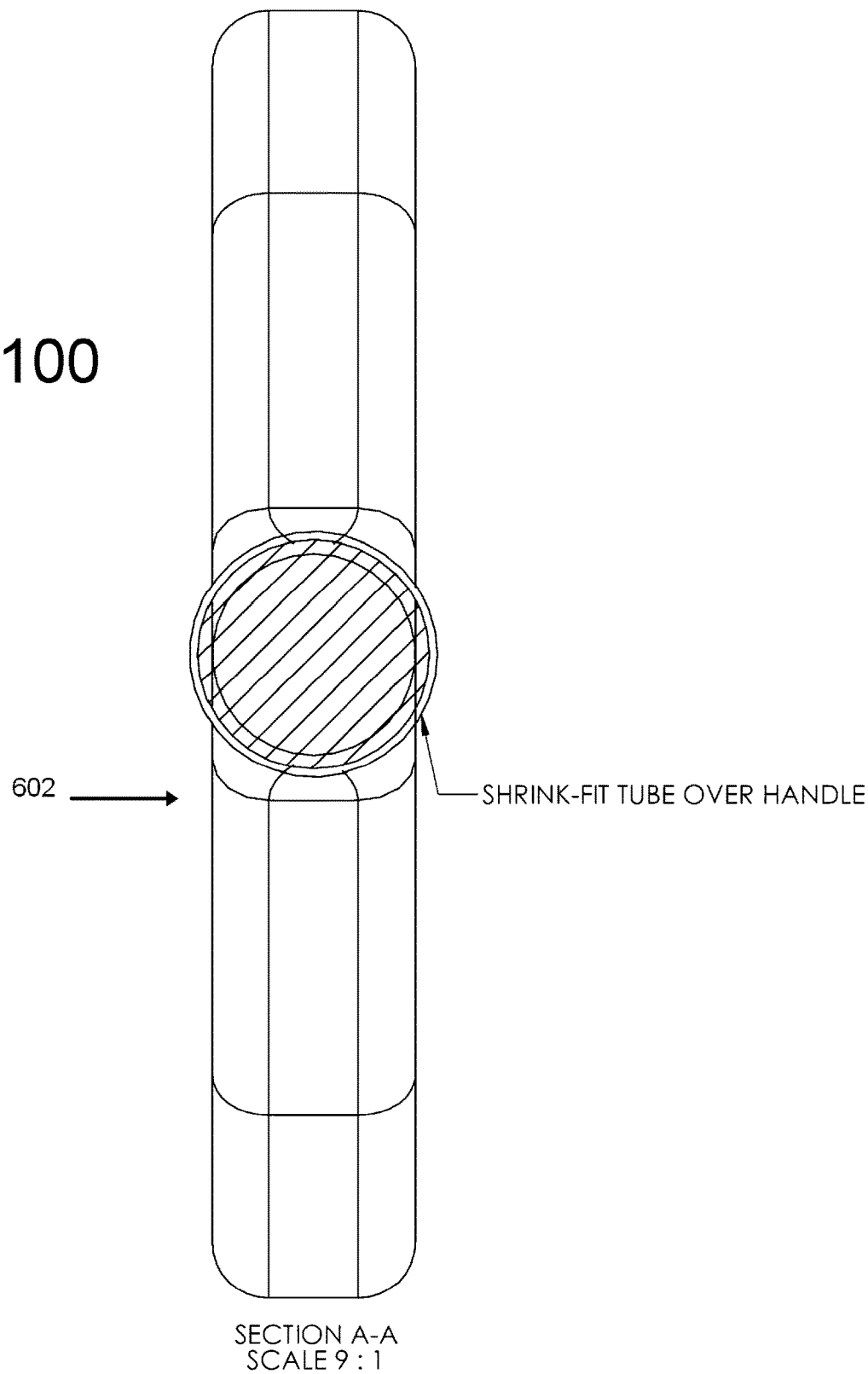
FIG. 100 shows a cross section of the five millimeter wiping wand.

FIG. 100 shows the cross section of the five millimeter wiping wand 602 as shown by the line A-A in FIG. 99.

Figure 101:
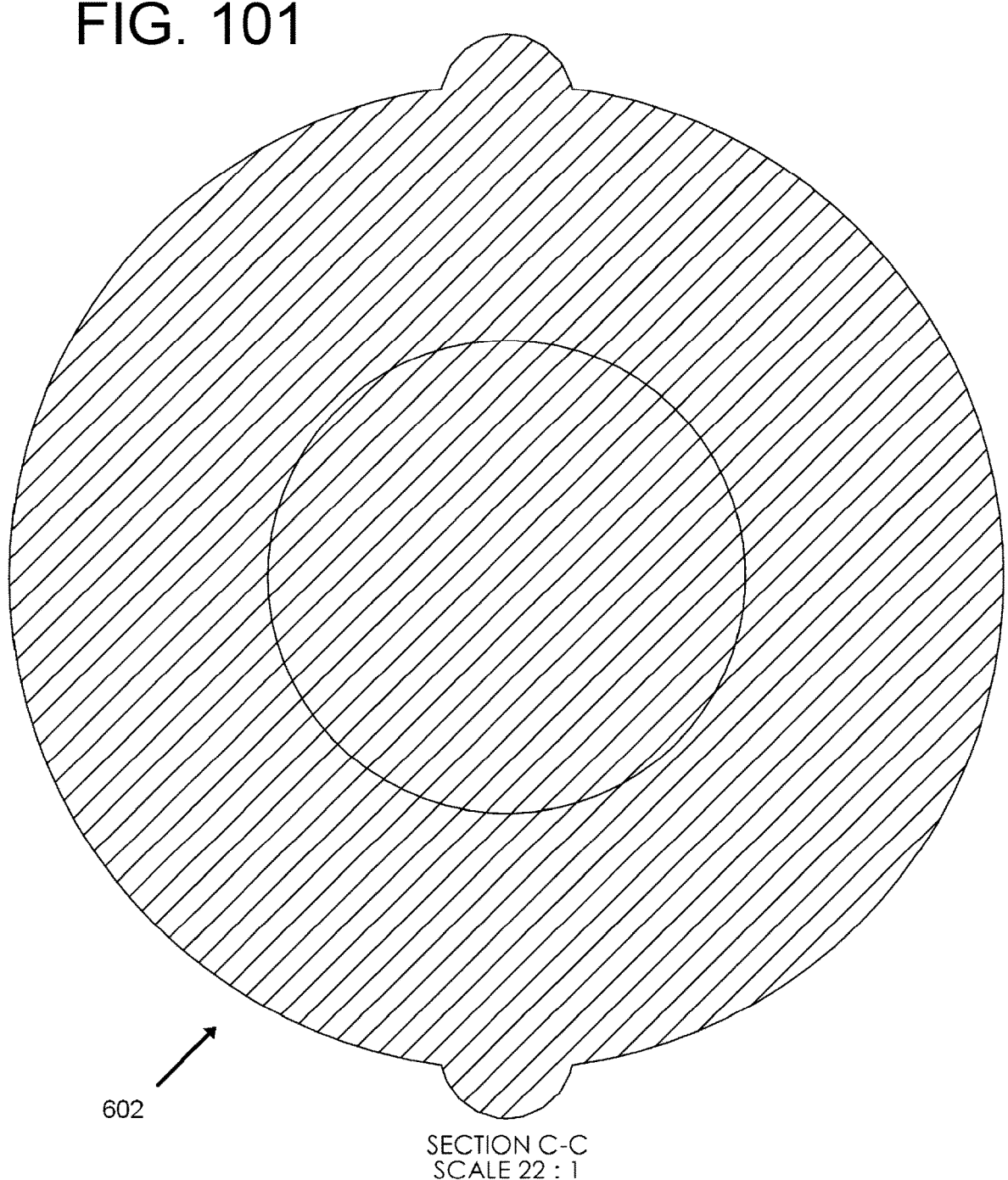
FIG. 101 shows a different cross section of the five millimeter wiping wand.

FIG. 101 shows the cross section of the five millimeter wiping wand 602 as shown by the line C-C in FIG. 99.

Figure 102:
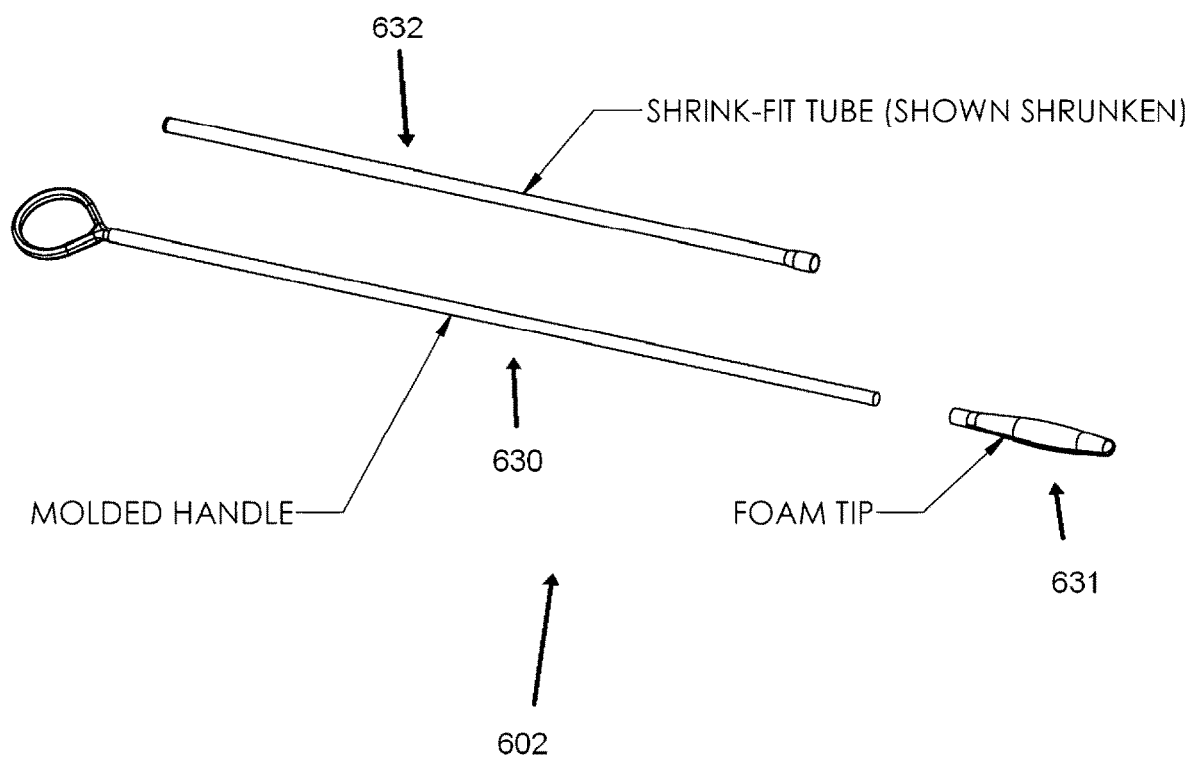
FIG. 102 shows a perspective view of the components of the five millimeter wiping wand.

FIG. 102 shows a perspective view of the components of the five millimeter wiping wand 602, including a molded handle 630, a foam tip 631, and a shrink-fit tube 632 (shown shrunken).

Figure 103:
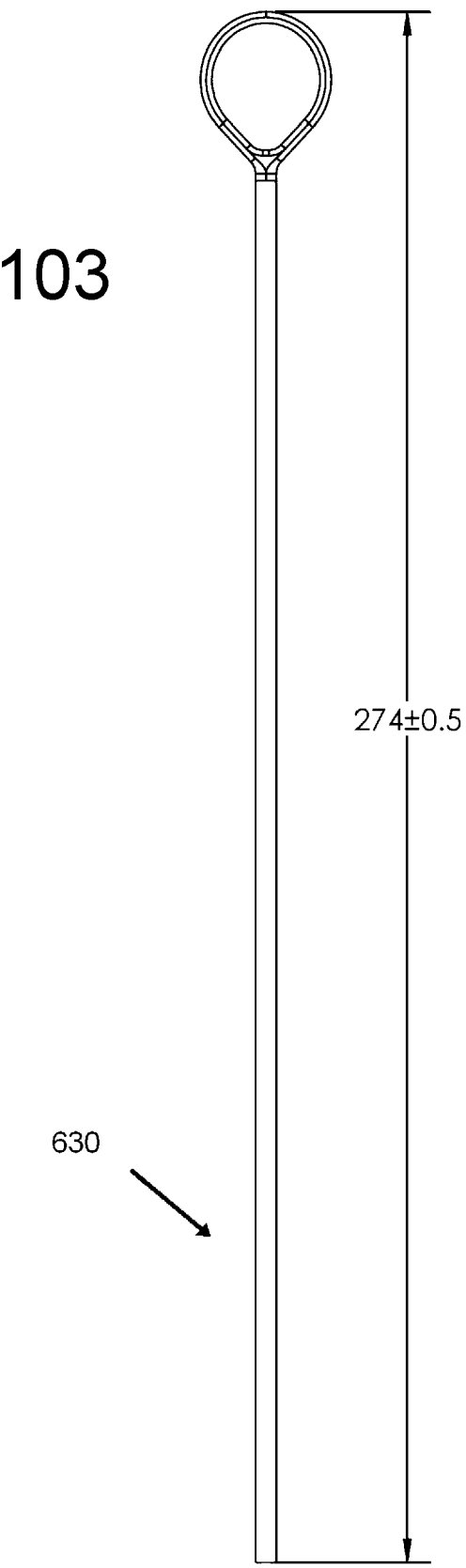
FIG. 103 shows a side view of a molded handle.

FIG. 103 shows a side view of the molded handle 630.

Figure 104:
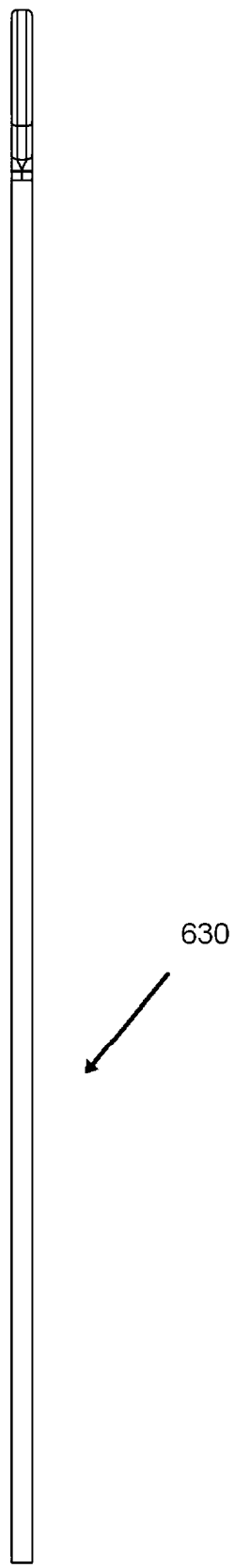
FIG. 104 shows an additional side view of the molded handle.

FIG. 104 shows an additional side view of the molded handle 630.

Figure 105:
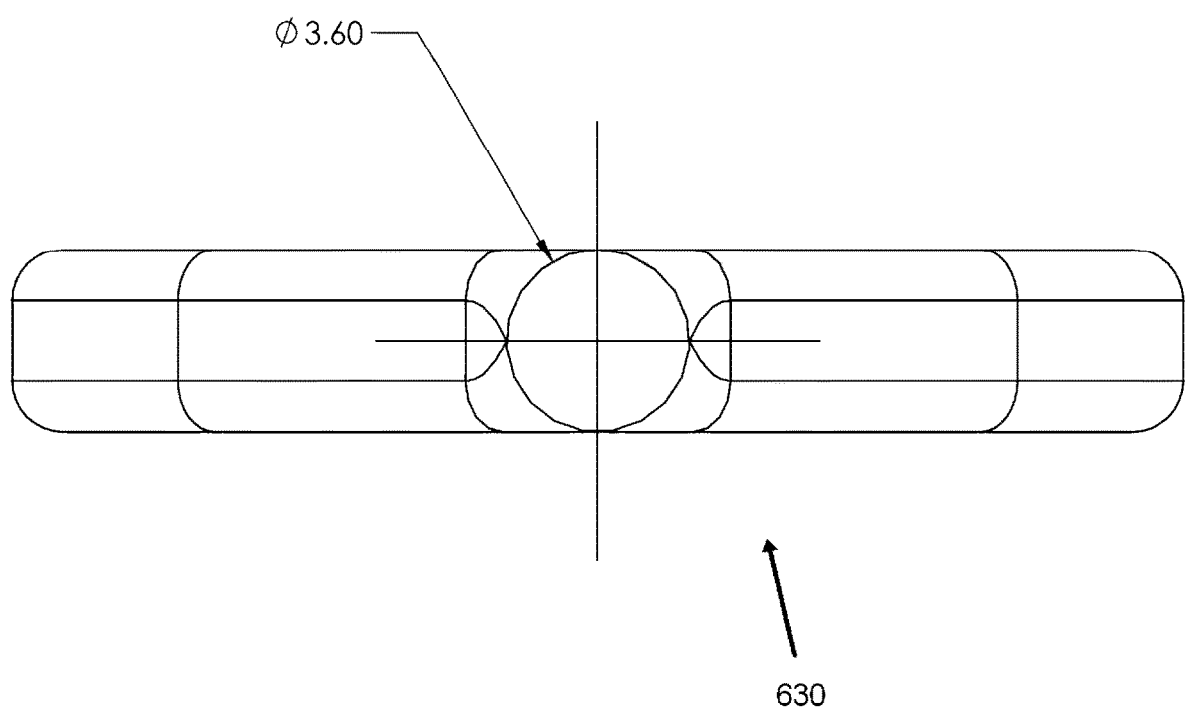
FIG. 105 shows a top view of the molded handle.

FIG. 105 shows a top view of the molded handle 630.

Figure 106:
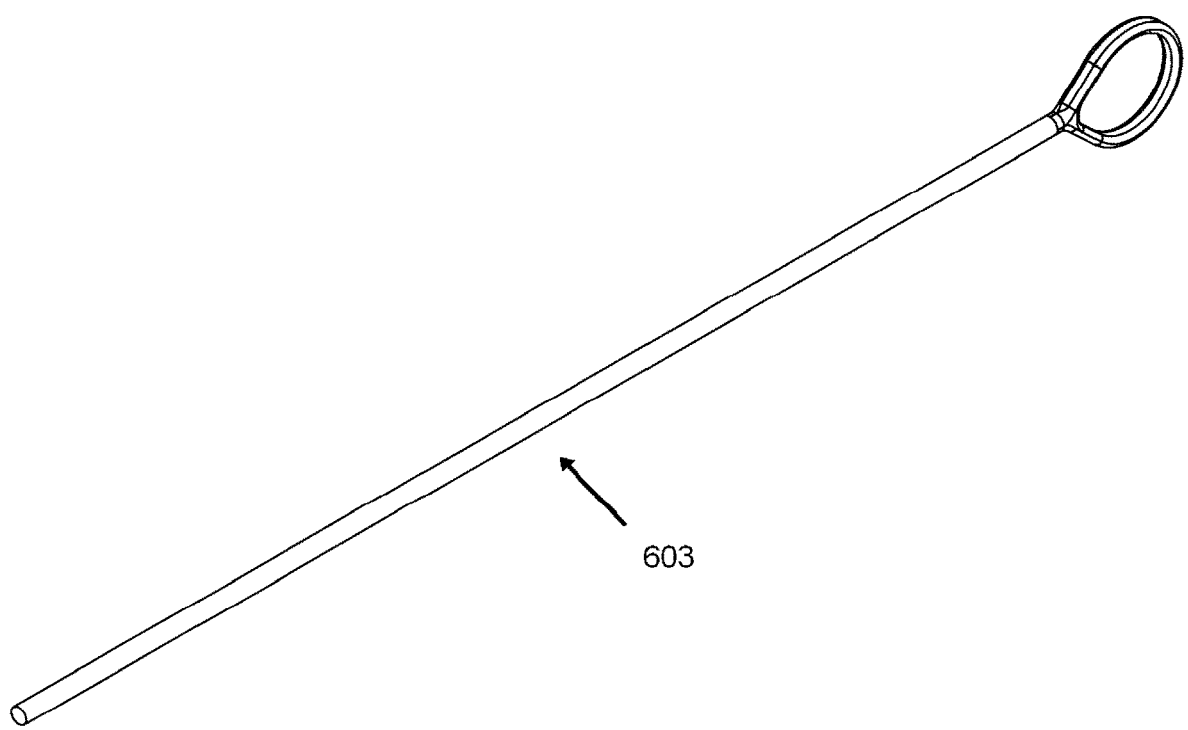
FIG. 106 shows a perspective view of a twelve millimeter wiping wand.

FIG. 106 shows a perspective view of a twelve millimeter wiping wand 603.

Figure 107:
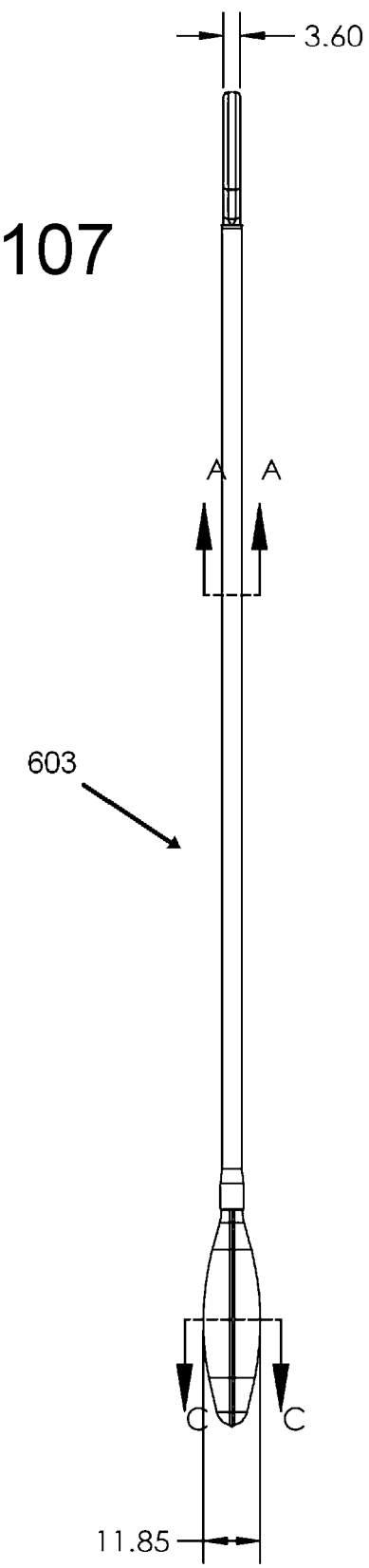
FIG. 107 shows a side view of the twelve millimeter wiping wand.

FIG. 107 shows a side view of the twelve millimeter wiping wand 603, with a line A-A to show where a cross section is being taken and a line C-C to show where a different cross section is being taken.

Figure 108:
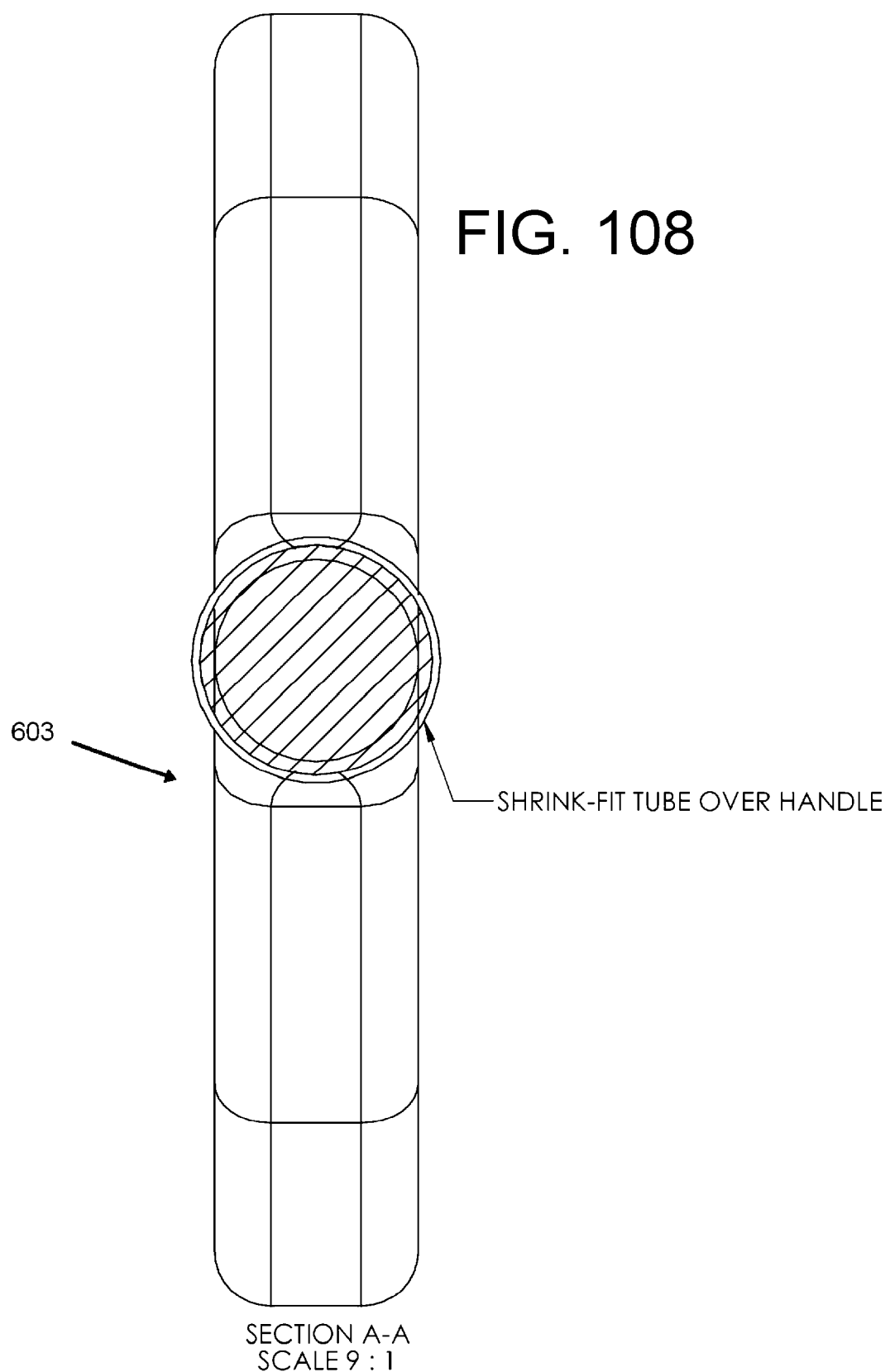
FIG. 108 shows a cross section of the twelve millimeter wiping wand.

FIG. 108 shows the cross section of the twelve millimeter wiping wand 603 as shown by the line A-A in FIG. 107.

Figure 109:
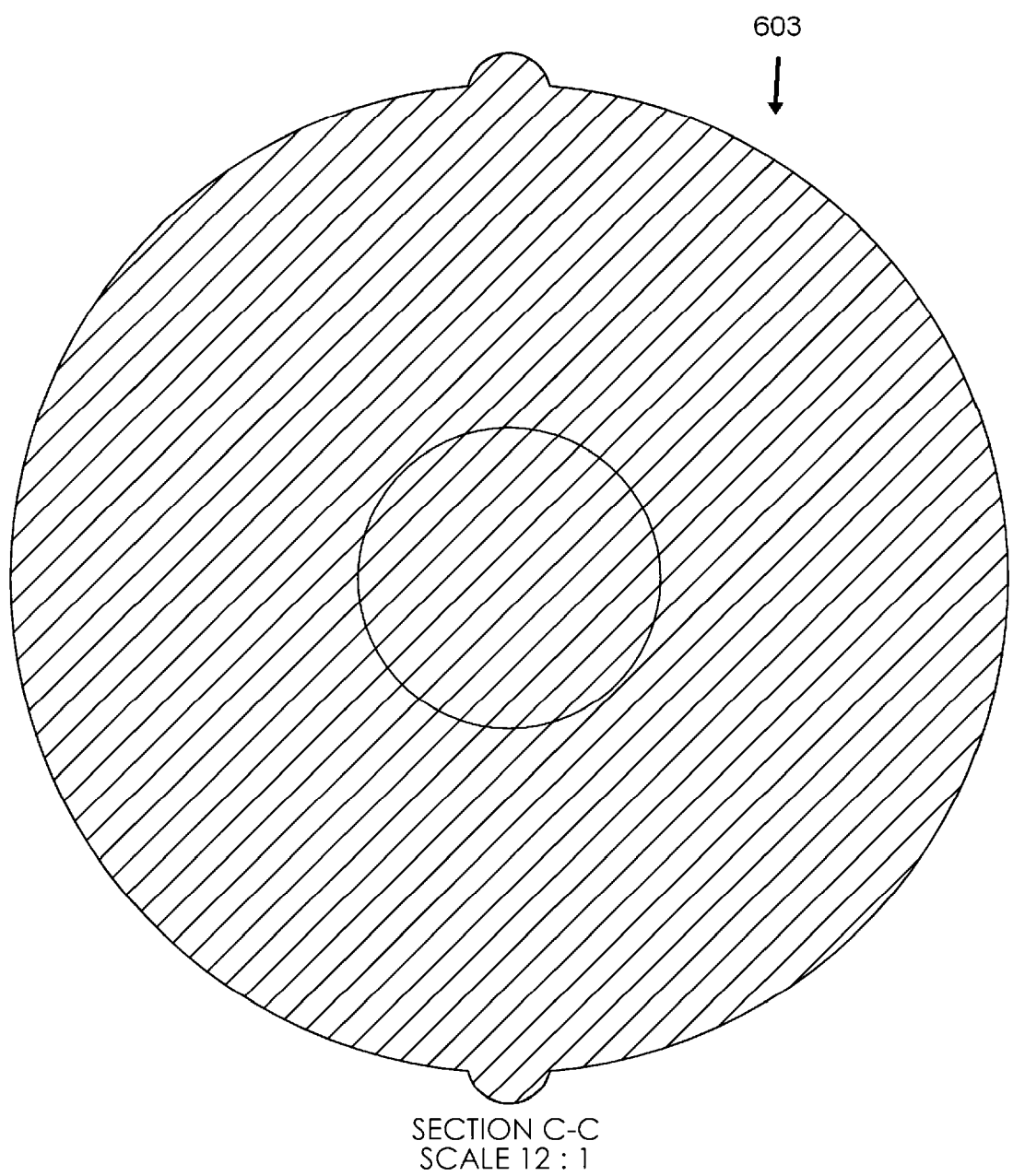
FIG. 109 shows a different cross section of the twelve millimeter wiping wand.

FIG. 109 shows the cross section of the twelve millimeter wiping wand 603 as shown by the line C-C in FIG. 107.

Figure 110:
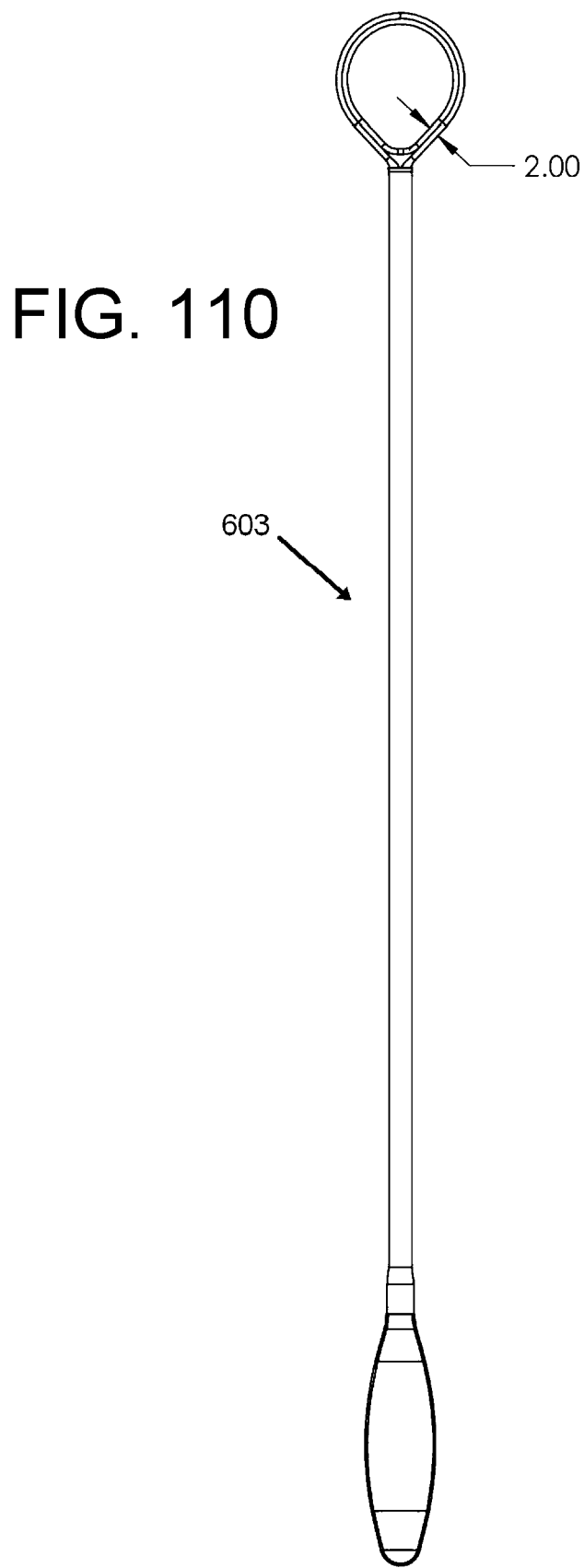
FIG. 110 shows a side view of the twelve millimeter wiping wand.

FIG. 110 shows a side view of the twelve millimeter wiping wand 603.

Figure 111:
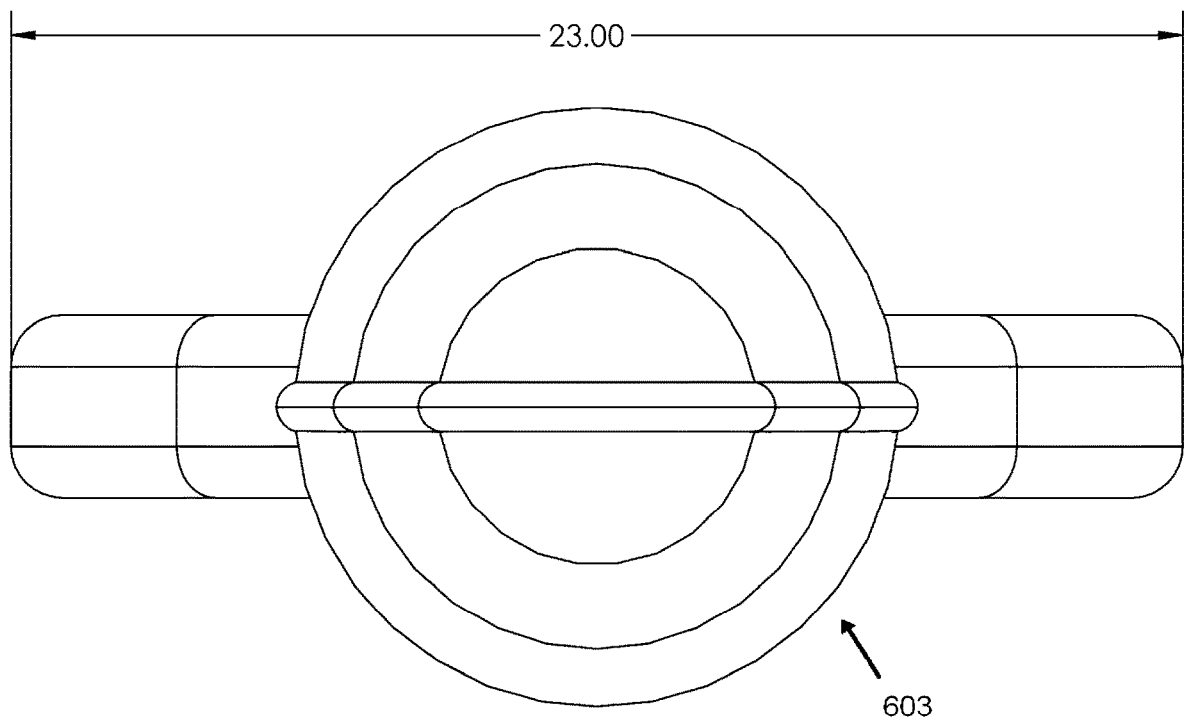
FIG. 111 shows an end view of the twelve millimeter wiping wand.

FIG. 111 shows an end view of the twelve millimeter wiping wand 603.

Figure 112:
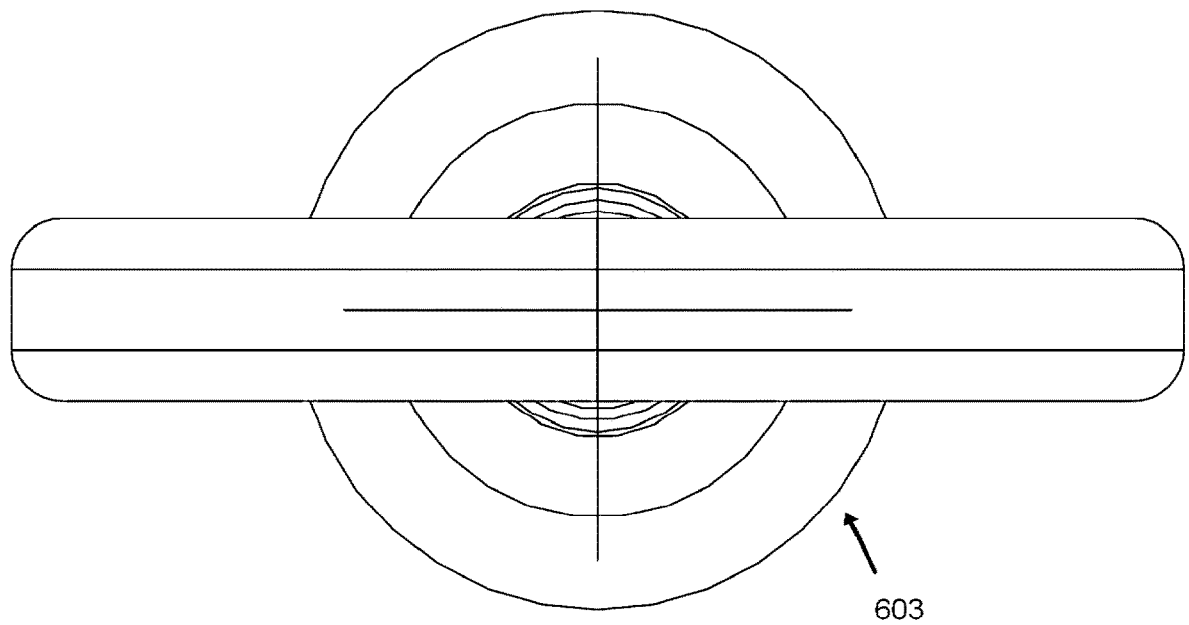
FIG. 112 shows an end view, opposite of the end shown in FIG. 111, of the twelve millimeter wiping wand.

FIG. 112 shows an end view, opposite of the end shown in FIG. 111, of the twelve millimeter wiping wand 603.

Figure 113:
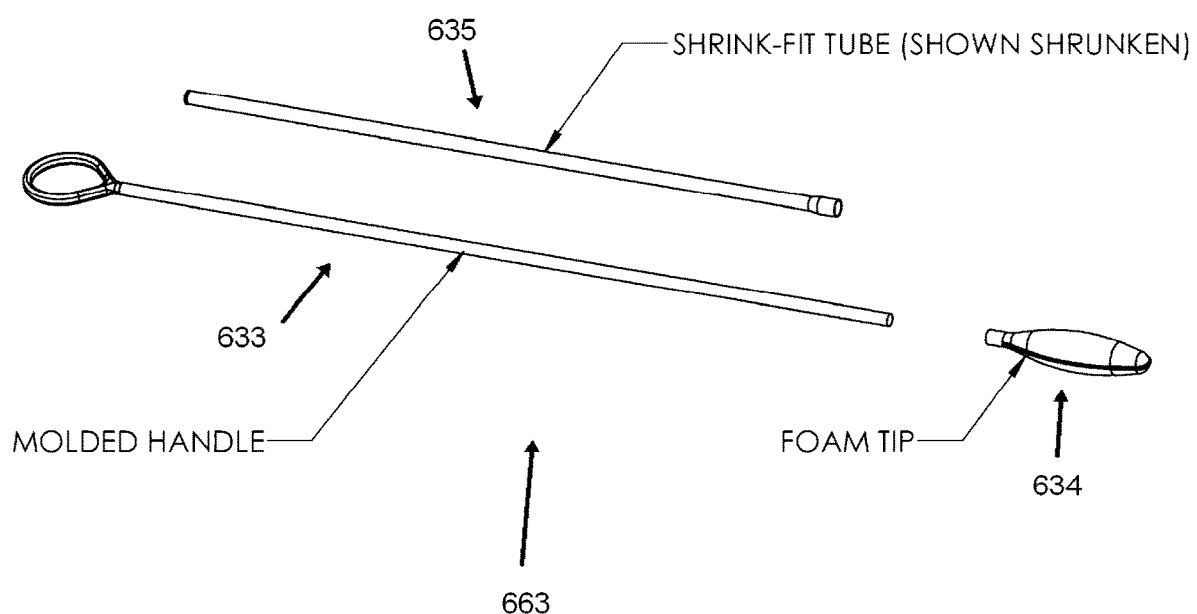
FIG. 113 shows a perspective view of the components of the twelve millimeter wiping wand.

FIG. 113 shows a perspective view of the components of the twelve millimeter wiping wand 603, including a molded handle 633, a foam tip 634, and a shrink-fit tube 635 (shown shrunken).

Figure 114:
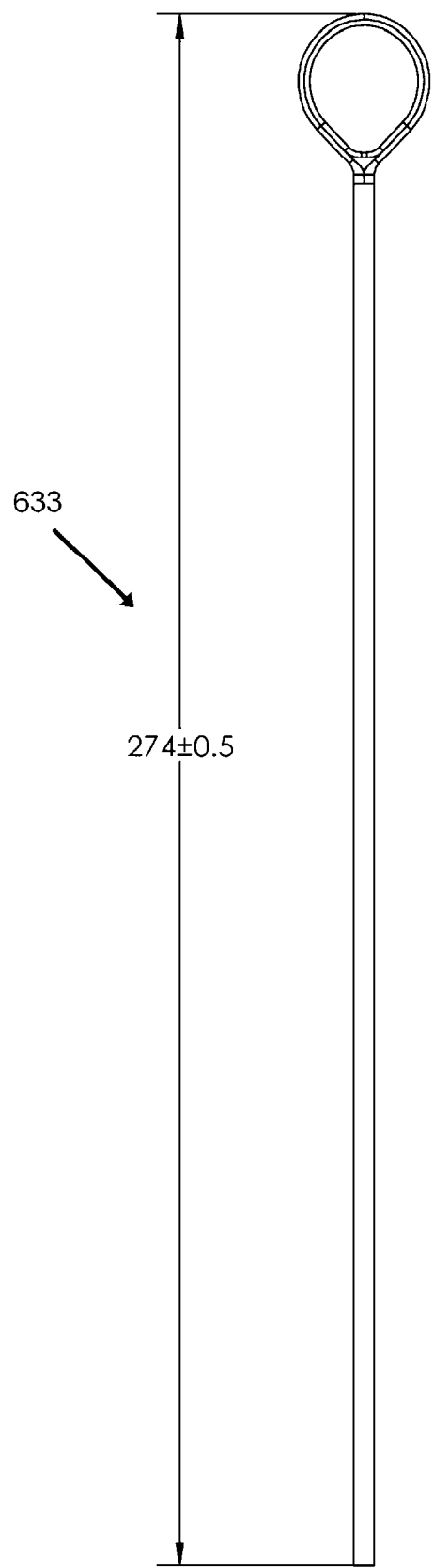
FIG. 114 shows a side view of a molded handle.

FIG. 114 shows a side view of the molded handle 633.

Figure 115:
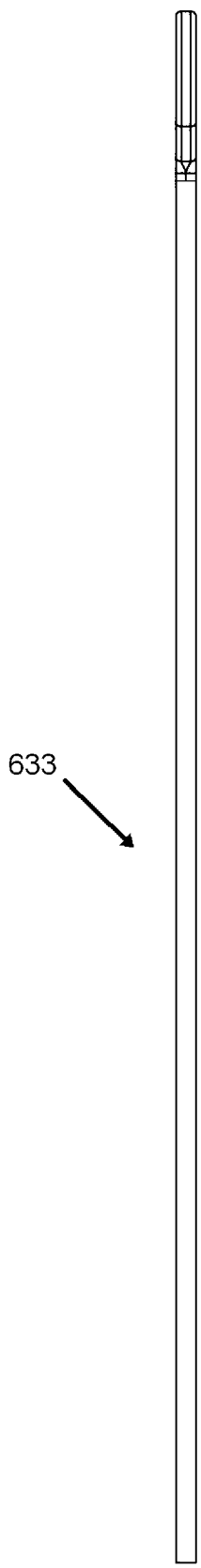
FIG. 115 shows an additional side view of the molded handle.

FIG. 115 shows an additional side view of the molded handle 633.

Figure 116:
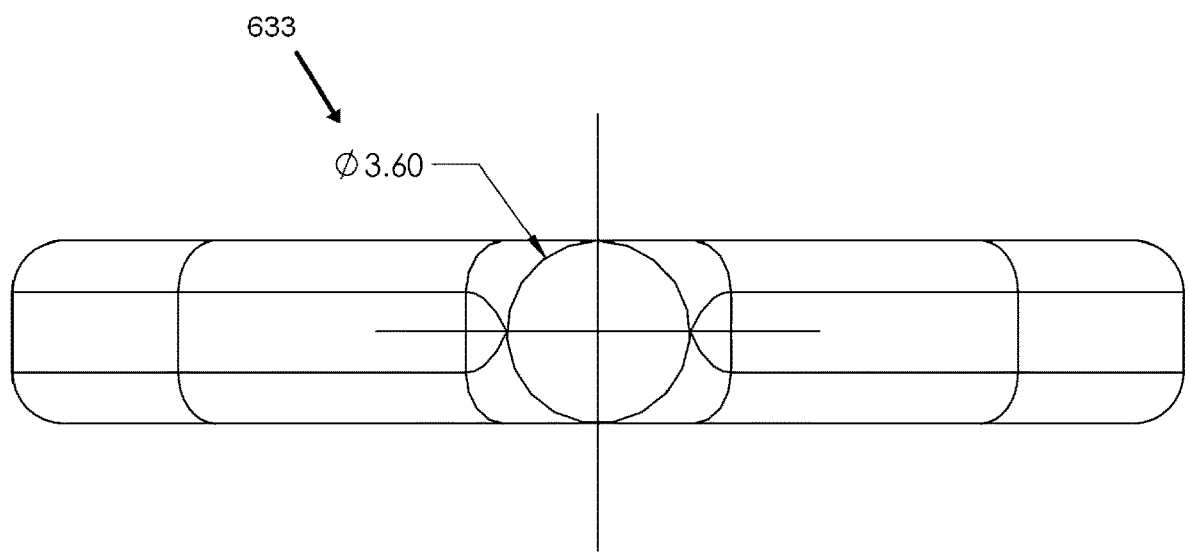
FIG. 116 shows a top view of the molded handle.

FIG. 116 shows a top view of the molded handle 633.

Figure 117:
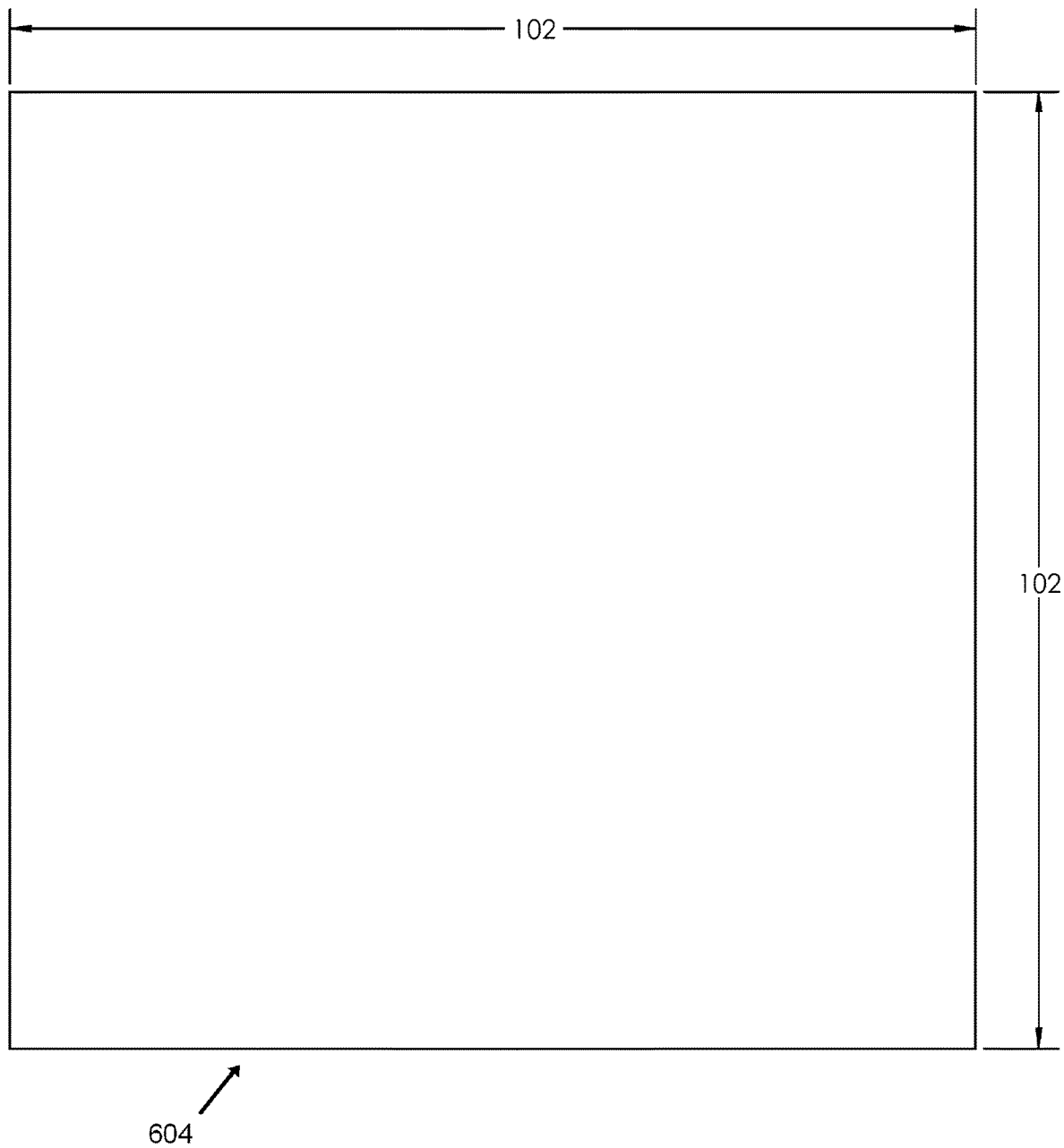
FIG. 117 shows a top view of a microfiber cloth.

FIG. 117 shows a top view of a microfiber cloth 604. The microfiber cloth 604 has a possible width of 102 millimeters and a possible length of 102 millimeters.

Figure 118:
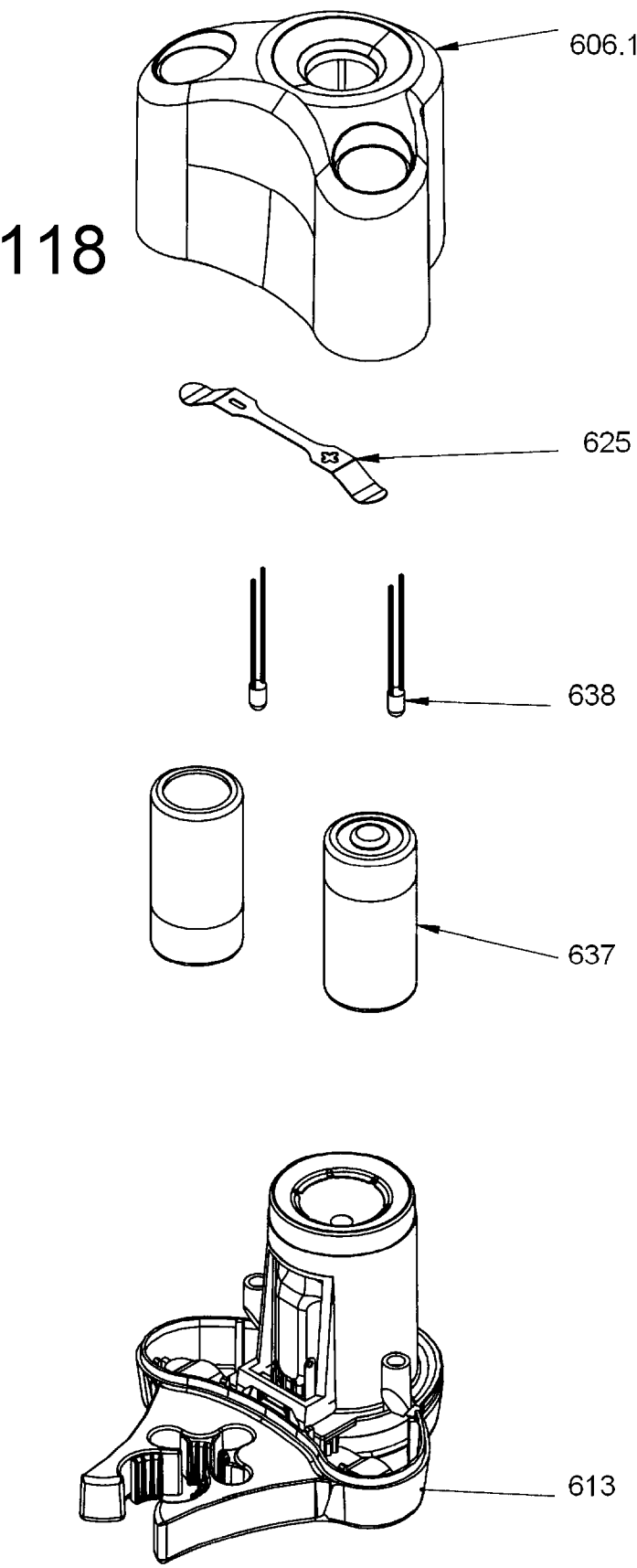
FIG. 118 shows an expanded view of the device and its components.

FIG. 118 shows an expanded view of the device 600, including the housing top 606.1, the battery contact A 625, two 123 lithium batteries 637, two LED TT OVLBG4C7 638, and the assembled bottom assembly 613.

Figure 119:
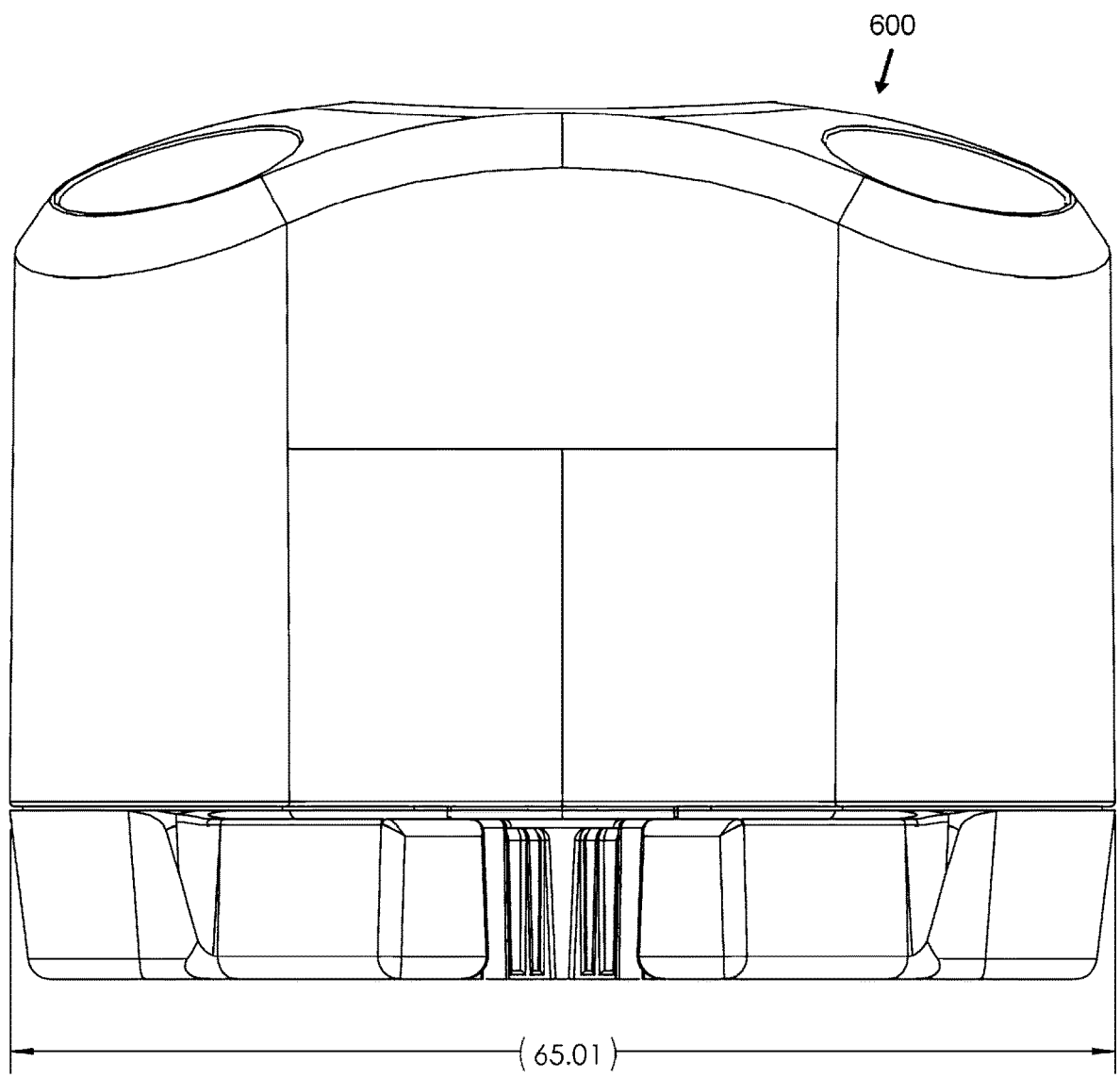
FIG. 119 shows a side view of the completed assembly.

FIG. 119 shows a side view of the completed assembly 600.

Figure 120:
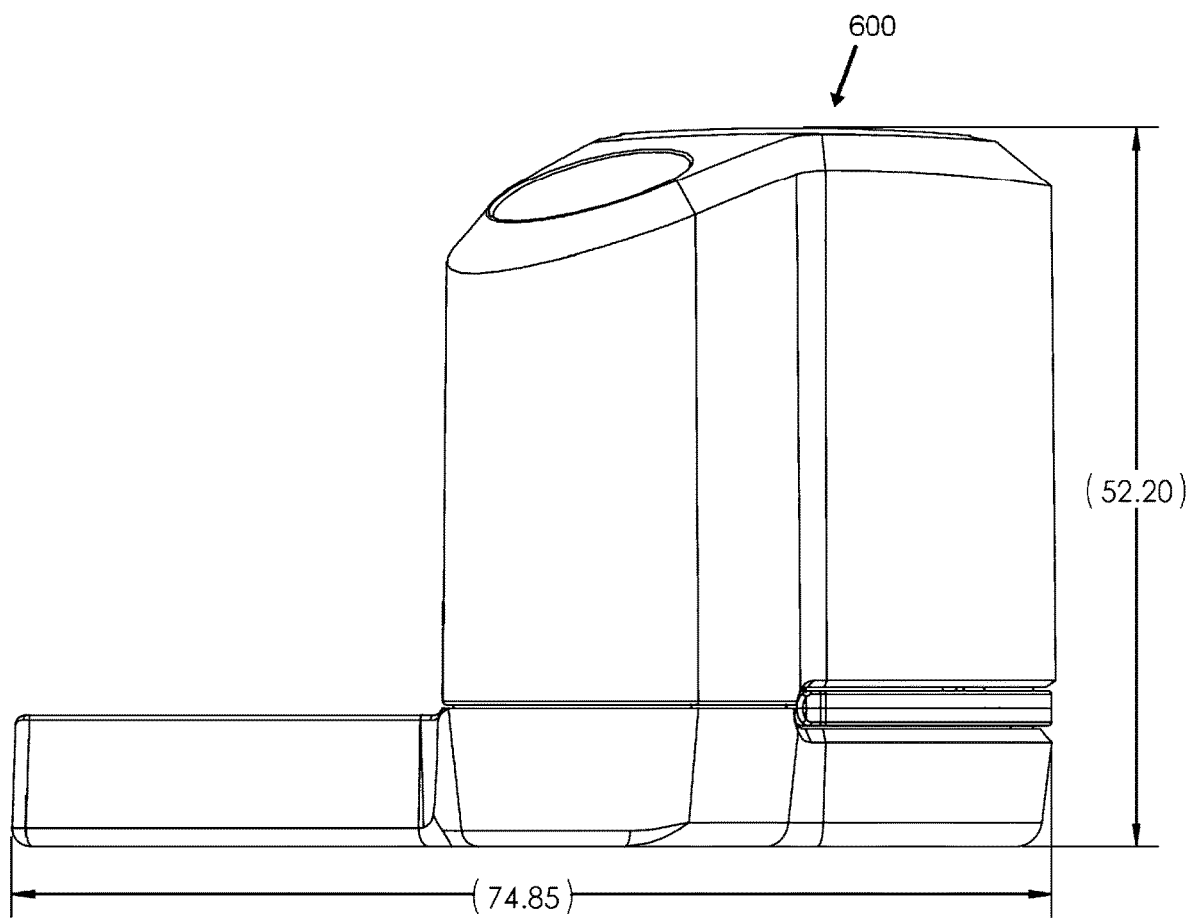
FIG. 120 shows another side view of the completed assembly of the device.

FIG. 120 shows another side view of the completed assembly of the device 600.

U.S. patent application Ser. No. 16/110,035, filed on Aug. 23, 2018, is hereby incorporated by reference as if set forth in its entirety herein except for the exceptions indicated herein.

U.S. patent application Ser. No. 16/164,420, filed on Oct. 18, 2018, is hereby incorporated by reference as if set forth in its entirety herein except for the exceptions indicated herein.

The following patents and patent publications are hereby incorporated by reference: U.S. Patent Application Publication No. 2012/0184897, having the title "INTEGRATED SYSTEMS AND METHODS FOR MAINTENANCE AND MANASGEMENT OF AN INTRAABDOMINAL GAS ENVIRONMENT DURING LAPAROSCOPIC SURGERY," published Jul. 19, 2012; U.S. Patent Application Publication No. 2012/0197084, having the title "SYSTEMS AND METHODS FOR OPTIMIZING AND MAINTAINING VISUALIZATION OF A SURGICAL FIELD DURING THE USE OF SURGICAL SCOPES," published Aug. 2, 2012; U.S. Patent Application Publication No. 2013/0060086, having the title "IMAGING SENSOR PROVIDING IMPROVED VISUALIZATION FOR SURGICAL SCOPES," published on Mar. 7, 2013; U.S. Patent Application Publication No. 2010/0168520, having the title "VIEW OPTIMIZER AND STABILIZER FOR USE WITH SURGICAL SCOPES," published Jul. 1, 2010; U.S. Pat. No. 8,535,220, having the title "LAPAROSCOPE CLEANING SYSTEM," issued Sep. 17, 2013; U.S. Pat. No. 4,392,485, having the title "ENDOSCOPE," issued on Jul. 12, 1983; U.S. Pat. No. 8,152,717, entitled "DEVICE FOR WHITE BALANCING AND APPLYING AN ANTI-FOG AGENT TO MEDICAL VIDEOSCOPES PRIOR TO MEDICAL PROCEDURES," issued on Apr. 10, 2012; U.S. Pat. No. 7,803,109, entitled "METHOD AND APPARATUS FOR PROTECTING THE DISTAL LENS OF ENDOSCOPES," issued on Sep. 28, 2010; U.S. Pat. No. 7,311,660, entitled "METHOD AND APPARATUS FOR HEATING AND APPLYING WARM ANTIFOG SOLUTION TO ENDOSCOPES AS WELL AS A DISTAL LENS PROTECTOR," issued on Dec. 25, 2007; U.S. Pat. No. 7,080,641, entitled "METHOD AND APPARATUS FOR HEATING STERILE SOLUTIONS DURING MEDICAL PROCEDURES," issued on Jul. 25, 2006; U.S. Pat. No. 8,870,752, entitled "MEDICAL DEVICE SHEATH," issued on Oct. 28, 2014; U.S. Pat. No. 8,727,969, entitled "ENDOSCOPE," issued on May 20, 2014; U.S. Pat. No. 8,696,552, entitled "SELF-CONTAINED STERILIZABLE SURGICAL SYSTEM," issued on Apr. 15, 2014; U.S. Pat. No. 8,540,745, entitled "BALLOON DISSECTOR WITH CANNULA," issued on Sep. 24, 2013; U.S. Pat. No. 8,517,918, entitled "OPTICAL TROCAR WITH SCOPE HOLDING ASSEMBLY," issued on Aug. 27, 2013; U.S. Pat. No. 8,467,589, entitled "HYBRID REGISTRATION METHOD," issued on Jun. 18, 2013; U.S. Pat. No. 8,454,645, entitled "BALLOON DISSECTOR WITH CANNULA," issued on Jun. 4, 2013; U.S. Pat. No. 8,452,068, entitled "HYBRID REGISTRATION METHOD," issued on May 28, 2013; U.S. Pat. No. 7,955,330, entitled "MULTI-PORT SIDE-FIRE COAGULATOR," issued Jun. 7, 2011; and U.S. Pat. No. 7,927,330, entitled "MULTI-PORT SIDE-FIRE COAGULATOR," issued Apr. 19, 2011.

Words relating to the opinions and judgments of the author of all patents, patent applications, patent publications, and other documents cited herein and not directly relating to the technical details of the description of the embodiments therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, patent publications, and other documents, are not considered to be incorporated by reference herein for any of the patents, patent applications, patent publications, and other documents cited herein.

One feature or aspect of an embodiment is believed at the time of the filing of this patent application to possibly reside broadly in a system configured to comprise: a cleaning device configured to clean a scope during a medical procedure; said device comprising further: a casing housing a sponge and a heating element; and an attachment element connected to an outer surface of said casing and configured to removably attach said casing to a surgical implement; said surgical implement being configured to be operatively attachable to a patient; wherein said casing is configured to allow a lens of said scope to access said sponge and said heating element; and said pad provides an air flow sufficient to provide substantial air flow at at least a portion of a contact area of a patient, and prevent or minimize pressure injury to a patient.

One feature or aspect of an embodiment is believed at the time of the filing of this patent application to possibly reside broadly in a cleaning device configured for cleaning a scope during use, said cleaning device comprising: a casing housing a sponge and a heating element; and an attachment element connected to an outer surface of said casing and configured to removably attach said casing to a structure, wherein said casing is configured to permit a lens of said scope to access said sponge and said heating element.

Another feature or aspect of an embodiment is believed at the time of the filing of this patent application to possibly reside broadly in the cleaning device, wherein: said casing comprises a first depression formed in an upper surface of said casing and configured to receive said sponge therein and a second depression formed in said upper surface of said casing and configured to receive said heating element therein.

Yet another feature or aspect of an embodiment is believed at the time of the filing of this patent application to possibly reside broadly in the cleaning device, further comprising: a cover and a wiping element, wherein said cover is disposed over said second depression, wherein said cover comprises a first hole; wherein said wiping element comprises a second hole; and wherein said wiping element is disposed over said cover so that said first hole and said second hole are oriented to allow said scope to access said heating element.

Still another feature or aspect of an embodiment is believed at the time of the filing of this patent application to possibly reside broadly in the cleaning device, wherein said wiping element comprises a microfiber material.

A further feature or aspect of an embodiment is believed at the time of the filing of this patent application to possibly reside broadly in the cleaning device, wherein said sponge is impregnated with a cleaning medium.

Another feature or aspect of an embodiment is believed at the time of the filing of this patent application to possibly reside broadly in the cleaning device, wherein: said heating element comprises a heating coil and at least one battery operatively connected to said heating coil; said heating coil being configured to warm said lens of said scope when said scope is positioned in proximity to said heating coil.

Yet another feature or aspect of an embodiment is believed at the time of the filing of this patent application to possibly reside broadly in the cleaning device, further comprising one or more lights operatively connected to at least one battery.

Still feature or aspect of an embodiment is believed at the time of the filing of this patent application to possibly reside broadly in the cleaning device, wherein said heating element comprises a chemical pack.

A further feature or aspect of an embodiment is believed at the time of the filing of this patent application to possibly reside broadly in the cleaning device, wherein said attachment element comprises a snap member, said snap member being configured to removably attach said casing to said structure.

One feature or aspect of an embodiment is believed at the time of the filing of this patent application to possibly reside broadly in a cleaning kit for use a procedure, said cleaning kit comprising: a container housing said sponge configured to removably attach to said structure; a cover comprising a scope access hole configured to permit said scope to access said sponge; said cover positioned on an upper surface of said container; and a cleaner comprising an elongated body comprising a first end comprising a cleaning tip disposed thereon and a second end; said cleaner configured to be removably supported by at least one of said containers and said cover when not in use; wherein said cleaner being configured for insertion in said structure; and said cleaning tip being configured to contact cannula said structure upon said cleaner being inserted into said structure.

Another feature or aspect of an embodiment is believed at the time of the filing of this patent application to possibly reside broadly in the cleaning kit, wherein said elongated body of said cleaner further comprises: a solution container configured to receive a cleaning medium; and a valve disposed on said second end of said elongated body, with said valve being configured to dispense said cleaning medium during use.

Yet another feature or aspect of an embodiment is believed at the time of the filing of this patent application to possibly reside broadly in the cleaning kit, further comprising: at least one wiping element disposed on said cover; with said at least one wiping element being configured to allow said scope to access said sponge through said scope access hole.

Still another feature or aspect of an embodiment is believed at the time of the filing of this patent application to possibly reside broadly in the cleaning kit, further comprising: a heater disposed in said container; with said heater being configured to warm said scope inserted through said scope access hole.

A further feature or aspect of an embodiment is believed at the time of the filing of this patent application to possibly reside broadly in the cleaning kit, with said heater being configured to border a substantial portion of a perimeter of said sponge.

Another feature or aspect of an embodiment is believed at the time of the filing of this patent application to possibly reside broadly in the cleaning kit, wherein: said heater comprises a heating coil; at least one battery operatively connected to said heating coil; and with said heating coil being configured to warm said lens of said scope during use.

Yet another feature or aspect of an embodiment is believed at the time of the filing of this patent application to possibly reside broadly in the cleaning kit, further comprising one or more lights operatively connected to said at least one battery.

Still another feature or aspect of an embodiment is believed at the time of the filing of this patent application to possibly reside broadly in the cleaning kit, wherein said heater comprises a chemical pack.

A further feature or aspect of an embodiment is believed at the time of the filing of this patent application to possibly reside broadly in the cleaning kit, further comprising a snap member configured to attach said container to said structure.

One feature or aspect of an embodiment is believed at the time of the filing of this patent application to possibly reside broadly in a method of cleaning a scope during use comprising: inserting said structure into a patient; attaching said cleaning device to said structure; heating said heating element of said cleaning device to a desired temperature; inserting said scope into said structure; removing said scope from said structure; wiping said lens of said scope on said wiping element; and heating said lens of said scope with said heating element.

Another feature or aspect of an embodiment is believed at the time of the filing of this patent application to possibly reside broadly in the method, further comprising wiping said lens on said sponge.

One feature or aspect of an embodiment is believed at the time of the filing of this patent application to possibly reside broadly in a cleaning device configured for cleaning a surgical scope during minimally invasive surgery comprising: a casing defining an interior, the casing comprising an upper surface comprising at least one opening for accessing the interior, a bottom surface, and a sidewall extending therebetween; a sponge and a heating element disposed in the interior of the casing; and an attachment element comprising a snap member integrally molded with and extending from the casing, the snap member comprising a first arm and a second arm extending from a sidewall of the casing defining a cavity having a partially circular cross section configured to receive and engage an outer surface of a tubular portion of a trocar to removably attach the casing to the trocar in a position in which a central longitudinal axis of the trocar is spaced apart from the interior of the casing, wherein the attachment element supports the casing, so that a line normal to the bottom surface and passing through the opening of the casing is parallel to and a fixed distance from the central longitudinal axis of the trocar, and wherein the casing is configured to allow a lens of the surgical scope to access the sponge and the heating element.

Another feature or aspect of an embodiment is believed at the time of the filing of this patent application to possibly reside broadly in the cleaning device, wherein: the interior of the casing comprises a first chamber, the sponge being disposed therein, and a second chamber separate from the first chamber, wherein the heating element is disposed in the second chamber.

Yet another feature or aspect of an embodiment is believed at the time of the filing of this patent application to possibly reside broadly in the cleaning device, wherein the upper surface of the casing further comprises at least one recess, the device further comprising a wiping element disposed in the at least one recess.

Still another feature or aspect of an embodiment is believed at the time of the filing of this patent application to possibly reside broadly in the cleaning device, wherein the wiping element is comprised of a microfiber material.

A further feature or aspect of an embodiment is believed at the time of the filing of this patent application to possibly reside broadly in the cleaning device, wherein the sponge is impregnated with a cleaning medium.

Another feature or aspect of an embodiment is believed at the time of the filing of this patent application to possibly reside broadly in the cleaning device, wherein: the heating element is comprised of a heating coil and at least one battery operatively connected to the heating coil, wherein the heating coil is configured to warm the lens of the surgical scope when the surgical scope is positioned in proximity to the heating coil.

Yet another feature or aspect of an embodiment is believed at the time of the filing of this patent application to possibly reside broadly in the cleaning device, further comprising one or more lights operatively connected to the at least one battery.

Still another feature or aspect of an embodiment is believed at the time of the filing of this patent application to possibly reside broadly in the cleaning device, wherein the heating element is comprised of a chemical pack.

One feature or aspect of an embodiment is believed at the time of the filing of this patent application to possibly reside broadly in a cleaning kit for use during minimally invasive surgery comprising: a container housing a sponge configured to removably attach to a trocar; a cover comprising a scope access hole configured to permit a surgical scope to access the sponge, the cover positioned on an upper surface of the container; and a cannula cleaner comprising an elongated body having a first end having a cleaning tip disposed thereon and a second end, the cannula cleaner configured to be removably supported by at least one of the container and the cover when not in use, wherein the cannula cleaner is configured for insertion in a cannula of the trocar and the cleaning tip is configured to contact the cannula when the cannula cleaner is inserted into the cannula.

Another feature or aspect of an embodiment is believed at the time of the filing of this patent application to possibly reside broadly in the cleaning kit, wherein the elongated body of the cannula cleaner further comprises: a solution container configured to receive a cleaning medium; and a valve disposed on the second end of the elongated body, wherein the valve is configured to dispense the cleaning medium during surgery.

Yet another feature or aspect of an embodiment is believed at the time of the filing of this patent application to possibly reside broadly in the cleaning kit, further comprising: at least one wiping element disposed on the cover, wherein the at least one wiping element is configured to allow the surgical scope to access the sponge through the scope access hole.

Still another feature or aspect of an embodiment is believed at the time of the filing of this patent application to possibly reside broadly in the cleaning kit, further comprising: a heater disposed in the container, wherein the heater is configured to warm the surgical scope inserted through the scope access hole.

A further feature or aspect of an embodiment is believed at the time of the filing of this patent application to possibly reside broadly in the cleaning kit, wherein the heater is configured to border a substantial portion of a perimeter of the sponge.

Another feature or aspect of an embodiment is believed at the time of the filing of this patent application to possibly reside broadly in the cleaning kit, wherein the heater comprises a heating coil and at least one battery operatively connected to the heating coil, and wherein the heating coil is configured to warm a lens of the surgical scope during surgery.

Yet another feature or aspect of an embodiment is believed at the time of the filing of this patent application to possibly reside broadly in the cleaning kit, further comprising one or more lights operatively connected to the at least one battery.

Still another feature or aspect of an embodiment is believed at the time of the filing of this patent application to possibly reside broadly in the cleaning kit, wherein the heater comprises a chemical pack.

A further feature or aspect of an embodiment is believed at the time of the filing of this patent application to possibly reside broadly in the cleaning kit, further comprising a snap member configured to attach the container to the trocar.

One feature or aspect of an embodiment is believed at the time of the filing of this patent application to possibly reside broadly in a trocar assembly for introducing a surgical scope to a body during a minimally invasive surgery, the assembly comprising: a trocar comprising a tubular portion comprising an outer surface; and a cleaning device mounted to the trocar configured for cleaning the surgical scope, the cleaning device comprising: a casing defining an interior, the casing comprising an upper surface comprising at least one opening for accessing the interior, a bottom surface, and a sidewall extending therebetween; a sponge and a heating element disposed in the interior of the casing; and an attachment element comprising a snap member integrally molded with and extending from the casing, the snap member comprising a first arm and a second arm extending from a sidewall of the casing defining a cavity having a partially circular cross section configured to receive and engage the outer surface of the tubular portion of the trocar to removably attach the casing to the trocar in a position in which a central longitudinal axis of the trocar is spaced apart from the interior of the casing, wherein the attachment element supports the casing, so that a line normal to the bottom surface and passing through the opening of the casing is parallel to and a fixed distance from the central longitudinal axis of the trocar, and wherein the casing is configured to allow a lens of the surgical scope to access the sponge and the heating element.

Another feature or aspect of an embodiment is believed at the time of the filing of this patent application to possibly reside broadly in the trocar assembly, wherein the interior of the casing comprises a first chamber, the sponge being disposed therein, and a second chamber separate from the first chamber, wherein the heating element is disposed in the second chamber.

Yet another feature or aspect of an embodiment is believed at the time of the filing of this patent application to possibly reside broadly in the system, wherein the heating element comprises a heating coil and at least one battery operatively connected to the heating coil, and wherein the heating coil is configured to warm the lens of the surgical scope when the surgical scope is positioned in proximity to the heating coil.

Still another feature or aspect of an embodiment is believed at the time of the filing of this patent application to possibly reside broadly in the cleaning device, wherein each arm of the snap member comprises an inwardly directed protrusion extending into the cavity for engaging the trocar to maintain the trocar within the cavity.

A further feature or aspect of an embodiment is believed at the time of the filing of this patent application to possibly reside broadly in the cleaning device, wherein the attachment element maintains the casing in an upright orientation relative to the trocar, such that a longitudinal axis of the casing is parallel to the central longitudinal axis of at least a portion of the trocar engaged to the attachment extension.

One feature or aspect of an embodiment is believed at the time of the filing of this patent application to possibly reside broadly in a cleaning device configured for cleaning a surgical scope during minimally invasive surgery comprising: a casing housing a sponge and a heating element; and an attachment element connected to an outer surface of the casing and configured to removably attach the casing to a trocar, wherein the casing is configured to allow a lens of the surgical scope to access the sponge and the heating element.

Another feature or aspect of an embodiment is believed at the time of the filing of this patent application to possibly reside broadly in the cleaning device, wherein: the casing comprises a first depression formed in an upper surface of the casing and configured to receive the sponge therein and a second depression formed in an upper surface of the casing and configured to receive the heating element therein.

Yet another feature or aspect of an embodiment is believed at the time of the filing of this patent application to possibly reside broadly in the cleaning device, further comprising: a cover and a wiping element, wherein the cover is disposed over the second depression, wherein the cover comprises a first hole; wherein the wiping element comprises a second hole; and wherein the wiping element is disposed over the cover so that the first hole and the second hole are oriented to allow the surgical scope to access the heating element.

Still another feature or aspect of an embodiment is believed at the time of the filing of this patent application to possibly reside broadly in the cleaning device, wherein the wiping element is comprised of a microfiber material.

A further feature or aspect of an embodiment is believed at the time of the filing of this patent application to possibly reside broadly in the cleaning device, wherein the sponge is impregnated with a cleaning medium.

Another feature or aspect of an embodiment is believed at the time of the filing of this patent application to possibly reside broadly in the cleaning device, wherein: the heating element is comprised of a heating coil and at least one battery operatively connected to the heating coil, wherein the heating coil is configured to warm the lens of the surgical scope when the surgical scope is positioned in proximity to the heating coil.

Yet another feature or aspect of an embodiment is believed at the time of the filing of this patent application to possibly reside broadly in the cleaning device, further comprising one or more lights operatively connected to the at least one battery.

Still another feature or aspect of an embodiment is believed at the time of the filing of this patent application to possibly reside broadly in the cleaning device, wherein the heating element is comprised of a chemical pack.

A further feature or aspect of an embodiment is believed at the time of the filing of this patent application to possibly reside broadly in the cleaning device, wherein the attachment element is a snap member, the snap member being configured to removably attach the casing to the trocar.

One feature or aspect of an embodiment is believed at the time of the filing of this patent application to possibly reside broadly in a cleaning kit for use during minimally invasive surgery comprising: a container housing a sponge configured to removably attach to a trocar; a cover comprising a scope access hole configured to permit a surgical scope to access the sponge, the cover positioned on an upper surface of the container; and a cannula cleaner comprising an elongated body having a first end having a cleaning tip disposed thereon and a second end, the cannula cleaner configured to be removably supported by at least one of the container and the cover when not in use, wherein the cannula cleaner is configured for insertion in a cannula of the trocar and the cleaning tip is configured to contact the cannula when the cannula cleaner is inserted into the cannula.

Another feature or aspect of an embodiment is believed at the time of the filing of this patent application to possibly reside broadly in the cleaning kit, wherein the elongated body of the cannula cleaner further comprises: a solution container configured to receive a cleaning medium; and a valve disposed on the second end of the elongated body, wherein the valve is configured to dispense the cleaning medium during surgery.

Yet another feature or aspect of an embodiment is believed at the time of the filing of this patent application to possibly reside broadly in the cleaning kit, further comprising: at least one wiping element disposed on the cover, wherein the at least one wiping element is configured to allow the surgical scope to access the sponge through the scope access hole.

Still another feature or aspect of an embodiment is believed at the time of the filing of this patent application to possibly reside broadly in the cleaning kit, further comprising: a heater disposed in the container; wherein the heater is configured to warm the surgical scope inserted through the scope access hole.

A further feature or aspect of an embodiment is believed at the time of the filing of this patent application to possibly reside broadly in the cleaning kit, wherein the heater is configured to border a substantial portion of a perimeter of the sponge.

Another feature or aspect of an embodiment is believed at the time of the filing of this patent application to possibly reside broadly in the cleaning kit, wherein the heater comprises a heating coil and at least one battery operatively connected to the heating coil, and wherein the heating coil is configured to warm a lens of the surgical scope during surgery.

Yet another feature or aspect of an embodiment is believed at the time of the filing of this patent application to possibly reside broadly in the cleaning kit, further comprising one or more lights operatively connected to the at least one battery.

Still another feature or aspect of an embodiment is believed at the time of the filing of this patent application to possibly reside broadly in the cleaning kit, wherein the heater comprises a chemical pack.

A further feature or aspect of an embodiment is believed at the time of the filing of this patent application to possibly reside broadly in the cleaning kit, further comprising a snap member configured to attach the container to the trocar.

One feature or aspect of an embodiment is believed at the time of the filing of this patent application to possibly reside broadly in a method of cleaning a surgical scope during minimally invasive surgery comprising: inserting a trocar into a patient; attaching a cleaning device according to the present application to the trocar; heating a heating element of the cleaning device to a desired temperature; inserting the surgical scope from the trocar; wiping a lens of the surgical scope on the wiping element; and heating the lens of the surgical scope with the heating element.

Another feature or aspect of an embodiment is believed at the time of the filing of this patent application to possibly reside broadly in the method, further comprising wiping the lens on the sponge.

The appended drawings in their entirety, including all dimensions, proportions and/or shapes in at least one embodiment of the invention, are accurate and are hereby included by reference into this specification.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A surgical scope cleaning device comprising:
a body portion;
an attachment portion being connected to said body portion and configured to support said body portion on a trocar;
said body portion comprising a casing;
said body portion comprising a cleaning element and a heating element, each being disposed inside said casing;
said casing comprising an opening therein to permit insertion of a portion of a surgical scope to be treated by said cleaning element and/or said heating element;
said attachment portion comprising a first arm and a second arm being disposed to extend away from a body portion;
said first arm and said second arm being configured to together hold a portion of a trocar in a receiving space therebetween to removably attach said body portion to a trocar; and
said first arm and said second arm being configured to together form at least three receiving spaces of different sizes to permit attachment of said attachment portion to any one of at least three trocars of different diameters.

2. The surgical scope cleaning device according to claim 1, wherein said first and second arms are sufficiently resilient to permit said first and second arms to be temporarily pushed apart during insertion of a trocar therebetween, and to return to an initial position upon insertion of a trocar in a corresponding one of said at least two receiving spaces.

3. The surgical scope cleaning device according to claim 2, wherein, for each of said at least two receiving spaces, each of said first and second arms comprises a protrusion, such that the space between said protrusions is less than the diameter of its corresponding receiving space and a diameter of a trocar corresponding to its corresponding receiving space.

4. The surgical scope cleaning device according to claim 3, wherein the thicknesses of each of said first and second arms at said protrusions is greater than the thicknesses of said first and second arms at portions thereof connected to said protrusions, such that said first and second arms are flexible to permit temporary deformation thereof during insertion of a trocar.

5. The surgical scope cleaning device according to claim 4 wherein:
said casing comprises an upper surface portion, a bottom surface portion, and a side surface portion disposed between and substantially transverse to said upper surface portion and said bottom surface portion; and
said upper surface portion is substantially convex and said bottom surface is substantially flat.

6. The surgical scope cleaning device according to Claim 5, wherein said side surface portion comprises a contoured, ergonomic shape to permit gripping of said body portion by a hand of a user.

7. The surgical scope cleaning device according to claim 6, wherein:
said side surface portion comprises a substantially concave Surface portion configured to be engaged by a thumb of a hand of a user; and
said side surface portion comprises a projecting, substantially convex surface portion configured to be engaged by at least a finger of a hand of a user.

8. The surgical scope cleaning device according to claim 7, wherein:
each of said first arm and said second arm comprises inner surfaces disposed about said receiving space;
at least one of said first arm and said second arm comprises at least one gripping surface disposed on a portion of said inner surfaces and configured to increase a holding force on an outer surface of a trocar held by said first arm and said second arm;

said at least one gripping surface comprises a textured or high friction surface;

said at least one gripping surface comprises a plurality of ribs extending from said inner surfaces; and said ribs comprise a high friction material attached to said inner surfaces, which inner surfaces comprise a material different than said high friction material.

9. The surgical scope cleaning device according to claim 1, wherein said side surface portion comprises a contoured, ergonomic shape to permit gripping of said body portion by a hand of a user.

10. The surgical scope cleaning device according to claim 9, wherein:

each of said first arm and said second arm comprises inner surfaces disposed about said receiving space; and at least one of said first arm and said second arm comprises at least one gripping surface disposed on a portion of said inner surfaces and configured to increase a holding force on an outer surface of a trocar held by said first arm and said second arm.

11. The surgical scope cleaning device according to claim 10, wherein said side surface portion comprises a substantially concave surface portion configured to be engaged by a thumb of a hand of a user.

12. The surgical scope cleaning device according to claim 11, wherein said side surface portion comprises a projecting, substantially convex surface portion configured to be engaged by at least a finger of a hand of a user.

13. The surgical scope cleaning device according to claim 1, wherein:

each of said first arm and said second arm comprises inner Surfaces disposed about said receiving space; and at least one of said first arm and said second arm comprises at least one gripping surface disposed on a portion of said inner surfaces and configured to increase a holding force on an outer surface of a trocar held by said first arm and said second arm.

14. The surgical scope cleaning device according to claim 13, wherein said at least one gripping surface comprises a textured or high friction surface.

15. The surgical scope cleaning device according to claim 14, wherein:

said at least one gripping surface comprises a plurality of ribs extending from said inner surfaces; and said ribs comprise a high friction material attached to said inner surfaces, which inner surfaces comprise a material different than said high friction material.

\* \* \* \* \*